US007781226B2

(12) United States Patent
McDevitt et al.

(10) Patent No.: US 7,781,226 B2
(45) Date of Patent: Aug. 24, 2010

(54) PARTICLE ON MEMBRANE ASSAY SYSTEM

(75) Inventors: John T. McDevitt, Austin, TX (US);
Nick Christodoulides, Austin, TX (US);
Pierre Floriano, Austin, TX (US); Karri L. Ballard, Pflugerville, TX (US); Bruce Bernard, Austin, TX (US); Glenn Simmons, Austin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 403 days.

(21) Appl. No.: 11/021,123

(22) Filed: Dec. 22, 2004

(65) Prior Publication Data

US 2005/0191620 A1 Sep. 1, 2005

Related U.S. Application Data

(60) Provisional application No. 60/548,613, filed on Feb. 27, 2004, provisional application No. 60/548,601, filed on Feb. 27, 2004, provisional application No. 60/548,190, filed on Feb. 27, 2004.

(51) Int. Cl.
*G01N 15/06* (2006.01)
*G01N 21/00* (2006.01)
*G01N 27/00* (2006.01)
*G01N 21/64* (2006.01)
*G01N 33/53* (2006.01)
*G01N 33/566* (2006.01)
*G01N 33/543* (2006.01)
*G01N 33/551* (2006.01)
*G01N 1/00* (2006.01)
*C12M 1/34* (2006.01)
*C12M 3/00* (2006.01)

(52) U.S. Cl. .................. 436/518; 422/68.1; 422/81; 422/82.01; 422/82.05; 422/82.06; 422/82.07; 422/82.08; 422/82.09; 435/287.1; 435/287.2; 435/288.4; 435/288.7; 435/808; 436/501; 436/524; 436/164; 436/523; 436/800; 436/805; 356/38

(58) Field of Classification Search ................ 422/68.1, 422/81, 82.01, 82.05–82.09; 435/287.1, 435/287.2, 288.4, 288.7, 808; 436/501, 518, 436/524, 164, 523, 800, 805; 356/38
See application file for complete search history.

(56) References Cited

U.S. PATENT DOCUMENTS 4,360,611 A  11/1982  Wakimoto et al.

(Continued)

FOREIGN PATENT DOCUMENTS

EP          0 518 557 B1    12/1992

(Continued)

OTHER PUBLICATIONS

U.S. Appl. No. 11/022,219, filed Dec. 2004, McDevitt et al.*
Lavigne et al., "Solution-Based Analysis of Multiple Analytes by a Sensor Array: Toward the Development of an Electronic Tongue," J. Am. Chem. Soc., vol. 120, No. 25, Jun. 11, 1998, pp. 6429-6430.

(Continued)

*Primary Examiner*—Gailene R Gabel
*Assistant Examiner*—Jacqueline Diramio
(74) *Attorney, Agent, or Firm*—Fulbright & Jaworski L.L.P.

(57) ABSTRACT

Described herein is an analyte detection device and method related to a portable instrument suitable for point-of-care analyses. In some embodiments, a portable instrument may include a disposable cartridge, an optical detector, a sample collection device and/or sample reservoir, reagent delivery systems, fluid delivery systems, one or more channels, and/or waste reservoirs. Use of a portable instrument may reduce the hazard to an operator by reducing an operator's contact with a sample for analysis. The device is capable of obtaining diagnostic information using cellular- and/or particle-based analyses and may be used in conjunction with membrane- and/or particle-based analysis cartridges. Analytes, including proteins and cells and/or microbes may be detected using the membrane and/or particle based analysis system.

15 Claims, 72 Drawing Sheets

U.S. PATENT DOCUMENTS

| | | | |
|---|---|---|---|
| 4,459,361 A | 7/1984 | Gefter | 436/523 |
| 4,493,815 A | 1/1985 | Fernwood et al. | |
| 4,874,499 A | 10/1989 | Smith et al. | |
| 4,988,618 A | 1/1991 | Li et al. | |
| 5,126,276 A | 6/1992 | Fish et al. | |
| 5,137,833 A | 8/1992 | Russell | |
| 5,156,810 A | 10/1992 | Ribi | |
| 5,156,972 A | 10/1992 | Issachar | |
| 5,223,393 A | 6/1993 | Khanna et al. | |
| 5,235,028 A | 8/1993 | Barany et al. | |
| 5,248,742 A | 9/1993 | McGarry et al. | |
| 5,252,294 A | 10/1993 | Kroy et al. | |
| 5,262,127 A | 11/1993 | Wise et al. | |
| 5,296,375 A | 3/1994 | Kricka et al. | |
| 5,321,545 A | 6/1994 | Bisconte | 359/391 |
| 5,385,709 A | 1/1995 | Wise et al. | |
| 5,391,272 A | 2/1995 | O'Daly et al. | |
| 5,472,672 A | 12/1995 | Brennan | |
| 5,541,057 A | 7/1996 | Bogart et al. | |
| 5,547,682 A | 8/1996 | Chagnon et al. | |
| 5,550,373 A | 8/1996 | Cole et al. | |
| 5,583,054 A | 12/1996 | Ito et al. | |
| 5,587,128 A | 12/1996 | Wilding et al. | |
| 5,616,790 A | 4/1997 | Arnold et al. | |
| 5,681,484 A | 10/1997 | Zanzucchi et al. | |
| 5,690,807 A | 11/1997 | Clark, Jr. et al. | |
| 5,714,122 A | 2/1998 | Bretscher et al. | |
| 5,747,349 A | 5/1998 | Van Den Engh et al. | |
| 5,770,370 A | 6/1998 | Kumar | |
| 5,773,307 A | 6/1998 | Colin et al. | |
| 5,779,907 A | 7/1998 | Yu | |
| 5,788,814 A | 8/1998 | Sun et al. | |
| 5,827,748 A | 10/1998 | Golden | |
| 5,837,552 A | 11/1998 | Cotton et al. | |
| 5,840,256 A | 11/1998 | Demers et al. | |
| 5,843,767 A | 12/1998 | Beattie | |
| 5,846,396 A | 12/1998 | Zanzucchi et al. | |
| 5,846,708 A | 12/1998 | Hollis et al. | |
| 5,854,684 A | 12/1998 | Stabile et al. | |
| 5,856,174 A | 1/1999 | Lipshutz et al. | |
| 5,863,957 A | 1/1999 | Li et al. | |
| 5,866,099 A | 2/1999 | Owen et al. | |
| 5,872,623 A | 2/1999 | Stabile et al. | |
| 5,922,617 A | 7/1999 | Wang et al. | |
| 5,942,443 A | 8/1999 | Parce et al. | |
| 5,972,721 A | 10/1999 | Bruno et al. | 436/526 |
| 5,980,704 A | 11/1999 | Cherukuri et al. | |
| 5,985,120 A | 11/1999 | Cholli et al. | |
| 6,023,540 A | 2/2000 | Walt et al. | |
| 6,074,616 A | 6/2000 | Buechler et al. | |
| 6,083,761 A | 7/2000 | Kedar et al. | |
| 6,083,763 A | 7/2000 | Balch | |
| 6,103,479 A | 8/2000 | Taylor | |
| 6,127,139 A | 10/2000 | Te Koppele et al. | |
| 6,151,973 A | 11/2000 | Geysen et al. | |
| 6,168,948 B1 | 1/2001 | Anderson et al. | |
| 6,171,489 B1 | 1/2001 | Ballard et al. | |
| 6,171,780 B1 | 1/2001 | Pham et al. | |
| 6,210,910 B1 | 4/2001 | Walt et al. | |
| 6,219,566 B1 | 4/2001 | Weersink et al. | |
| 6,245,296 B1 | 6/2001 | Ligler et al. | |
| 6,268,222 B1 | 7/2001 | Chandler et al. | |
| 6,288,220 B1 | 9/2001 | Kambara et al. | |
| 6,331,441 B1 | 12/2001 | Balch et al. | |
| 6,355,491 B1 | 3/2002 | Zhou et al. | |
| 6,485,690 B1 | 11/2002 | Pfost et al. | |
| 6,514,415 B2 | 2/2003 | Hatch | |
| 6,566,079 B2 * | 5/2003 | Hefti | 435/7.1 |
| 6,591,124 B2 | 7/2003 | Sherman et al. | |
| 6,601,613 B2 | 8/2003 | McNeely et al. | |
| 6,682,649 B1 | 1/2004 | Petersen et al. | |
| 6,692,696 B1 | 2/2004 | Alberte | |
| 6,808,937 B2 | 10/2004 | Liger et al. | 436/518 |
| 6,905,885 B2 | 6/2005 | Colston et al. | 436/518 |
| 2003/0008339 A1 | 1/2003 | Massey et al. | 435/14 |
| 2003/0232328 A1 * | 12/2003 | Houghton et al. | 435/5 |
| 2004/0029259 A1 | 2/2004 | McDevitt et al. | 506/70 |
| 2004/0038318 A1 * | 2/2004 | Bell | 435/7.4 |
| 2004/0060867 A1 * | 4/2004 | Kriksunov et al. | 210/650 |
| 2004/0096991 A1 * | 5/2004 | Zhang | 436/518 |
| 2005/0079507 A1 * | 4/2005 | Fang | 435/6 |
| 2005/0164404 A1 * | 7/2005 | Marlborugh et al. | 436/514 |
| 2006/0073585 A1 * | 4/2006 | McDevitt et al. | 435/288.7 |
| 2006/0079000 A1 * | 4/2006 | Floriano et al. | 436/164 |

FOREIGN PATENT DOCUMENTS

| | | | |
|---|---|---|---|
| GB | 2 315 131 A | | 1/1998 |
| WO | 98/17383 | | 4/1998 |
| WO | 98/53300 | | 11/1998 |
| WO | 99/18434 | | 4/1999 |
| WO | WO 2004/009840 | * | 1/2004 |

OTHER PUBLICATIONS

White et al., "Rapid Analyte Recognition in a Device Based on Optical Sensors and the Olfactory System," *Analytical Chemistry*, vol. 68, No. 13, Jul. 1, 1996, pp. 2191-2202.

Cho et al., "An Unnatural Biopolymer," *Science*, 1993, 261, p. 1303-1305.

Lauritzen et al., "Peptide Dot Immunoassay and Iimmunoblotting: Electroblotting from Aluminum Thin-layer Chromatography Plates and Isoelectric Focusing Gels to Activated Nitrocellulose," *Electrophoresis*, 1993, 14, p. 852-859.

Schutz et al., "Direct Observation of Ligand Colocalization on Individual Receptor Molecules," *Biophysical Journal*, 1998, 74, 2223-2226.

Michael et al., "Making Sensors out of Disarray: Optical Sensor Microarray" *SPIE*, 1998, vol. 3270, pp. 34-41.

Dickinson et al., "Convergent, Self-Encoded Bead Sensor Arrays in the Design of an Artificial Nose", *Anal. Chem.*, Jun. 1, 1999, vol. 71, No. 11, pp. 2192-2198.

Office Communication, issued in European Application No. 05723785, dated Jun. 17, 2008.

Office Communication, issued in European Patent Application No. 05 723 785, dated Dec. 30, 2009.

* cited by examiner

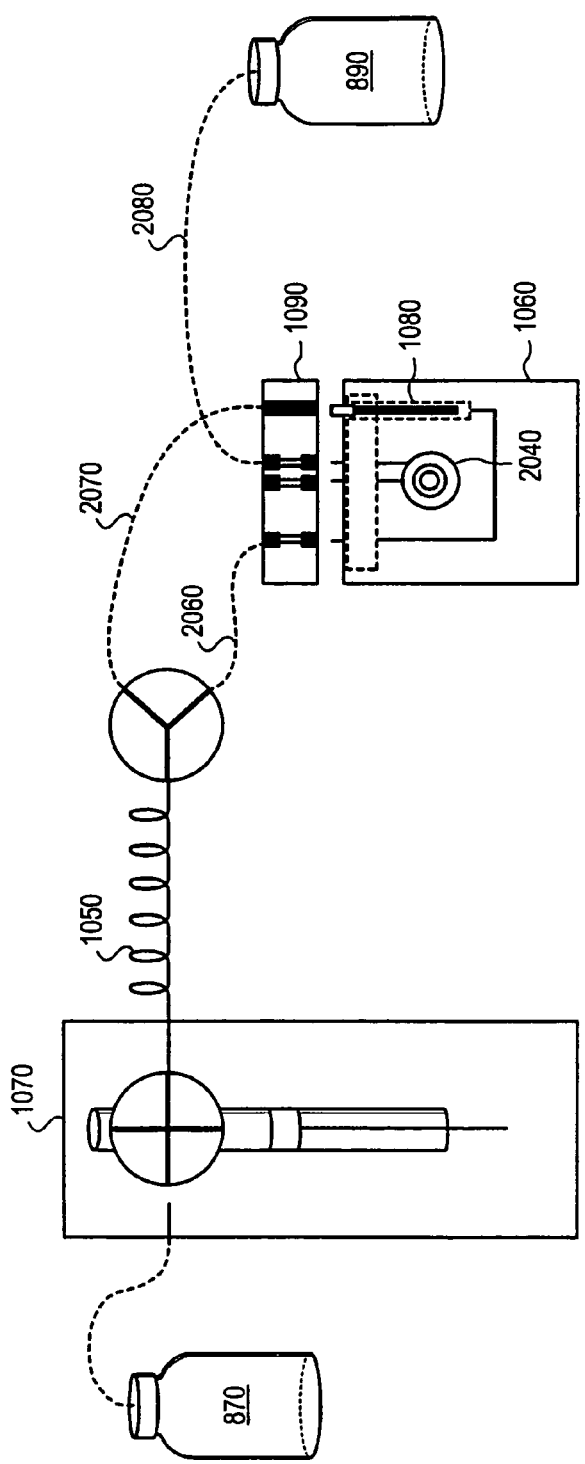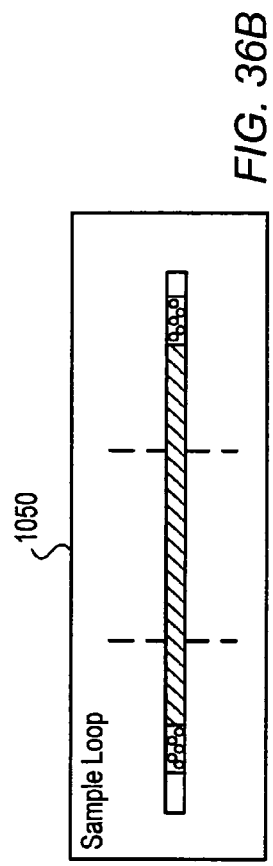

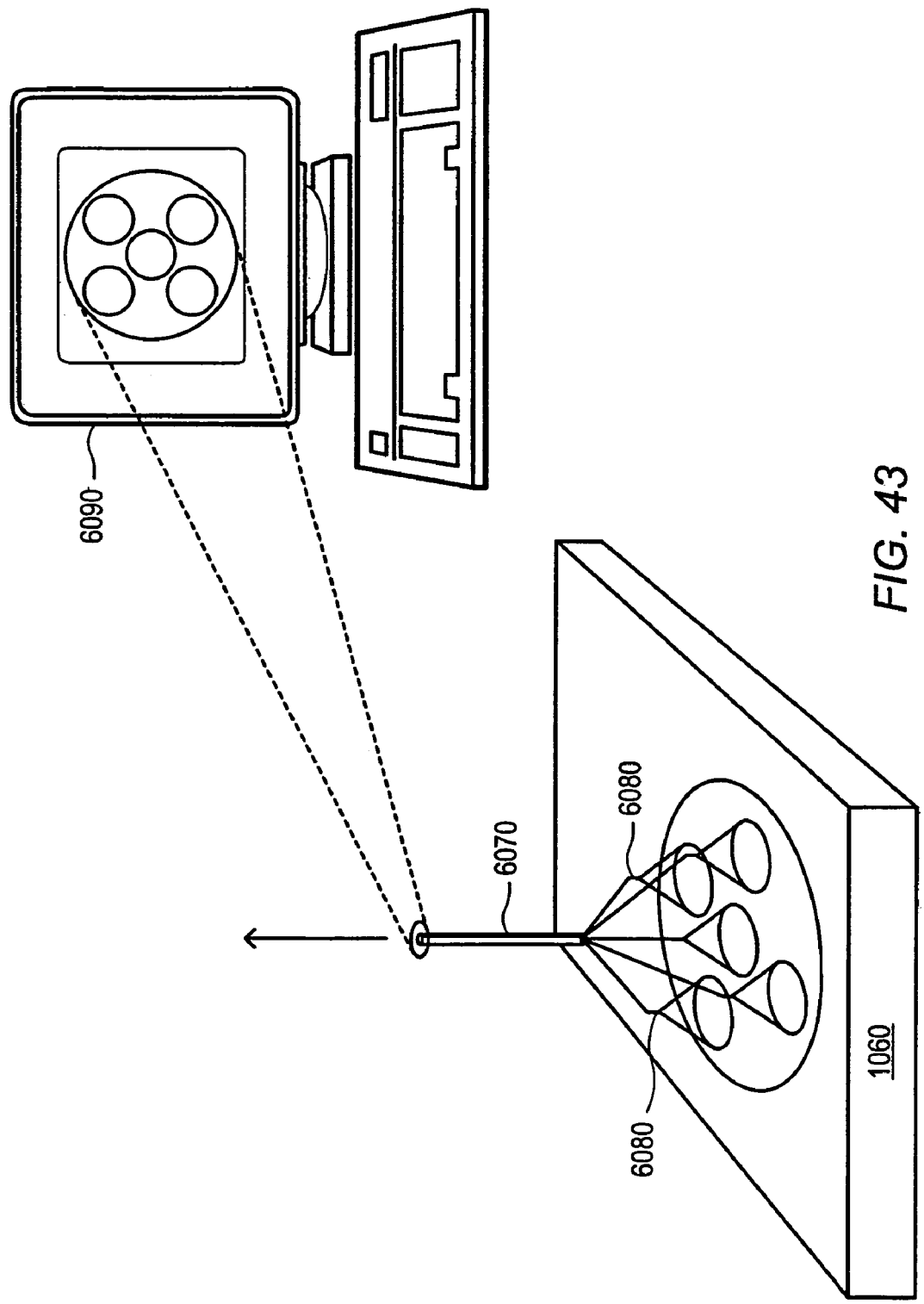

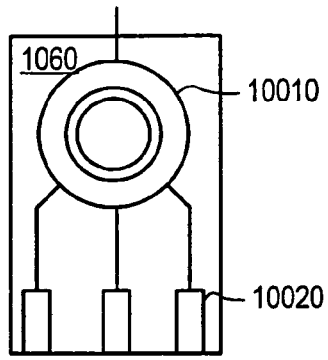
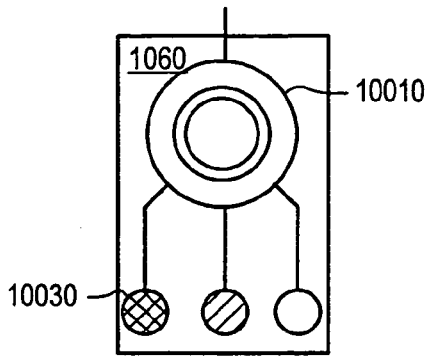
FIG. 55A
FIG. 55B
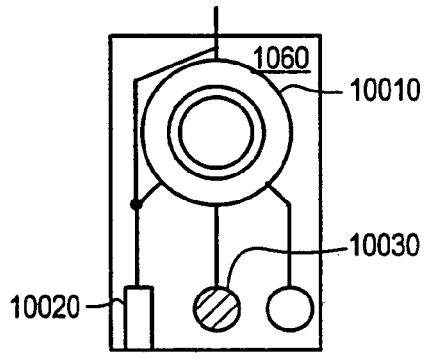
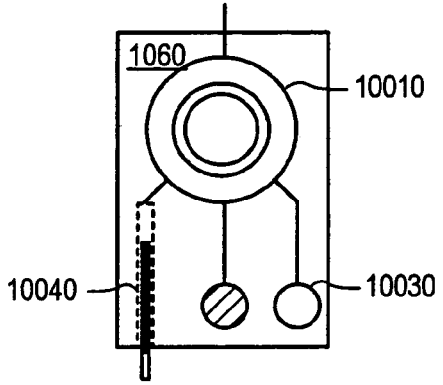
FIG. 55C
FIG. 55D
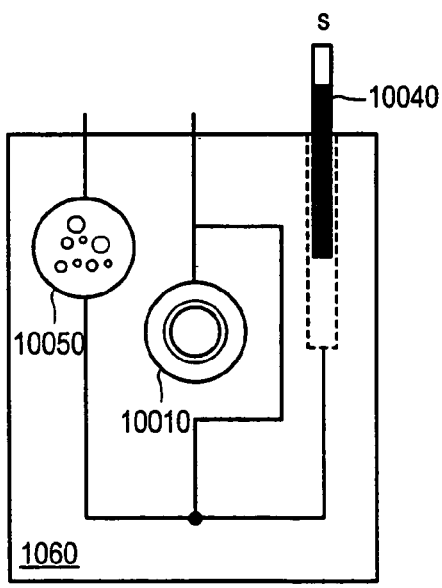
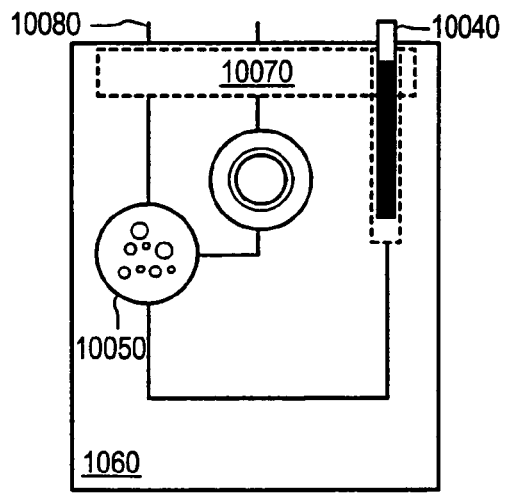
FIG. 56A
FIG. 56B

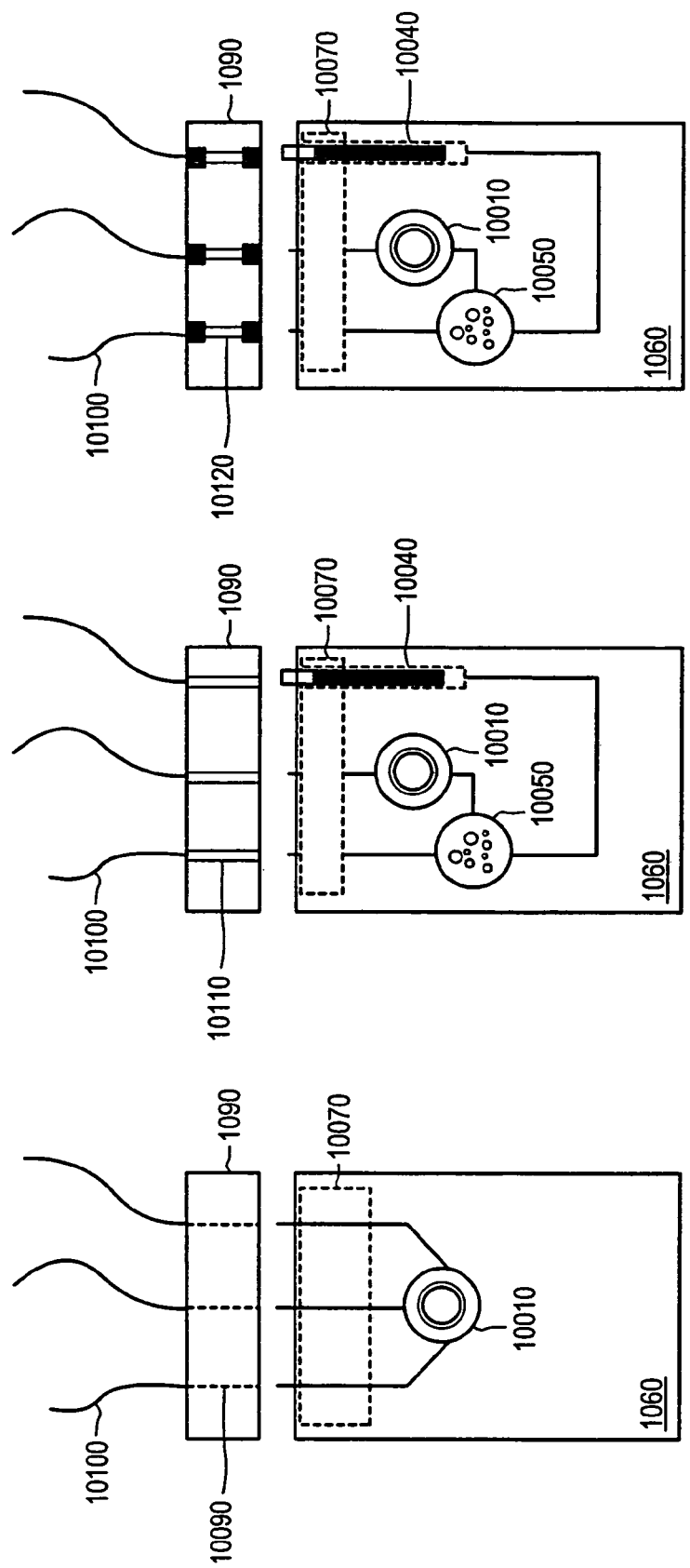

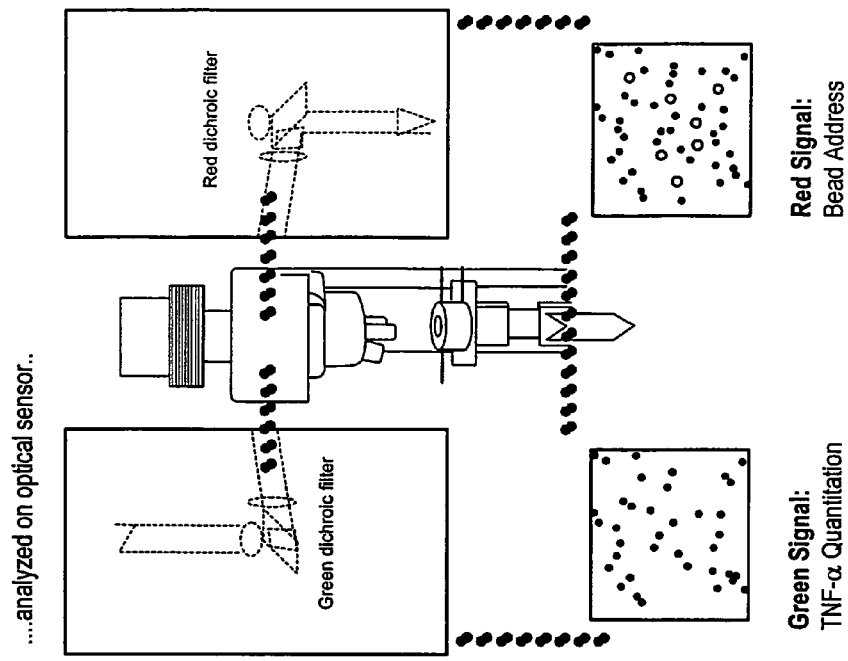
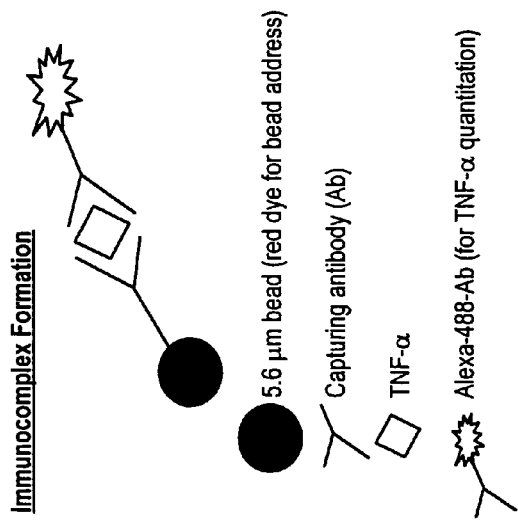
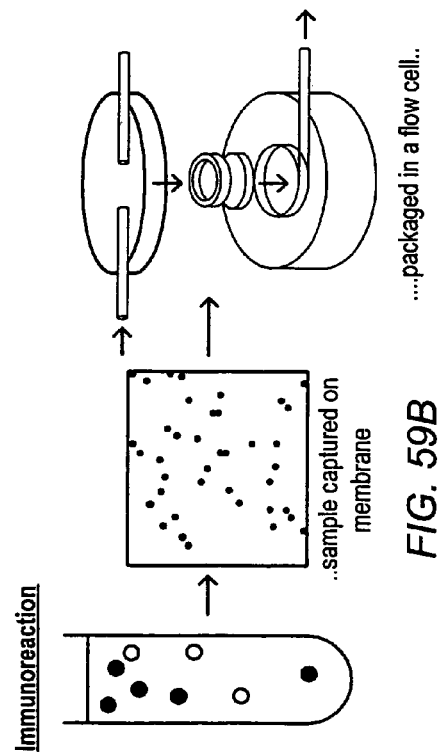
FIG. 59A
FIG. 59B
FIG. 59C

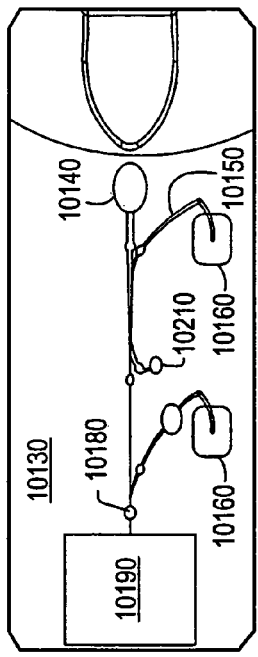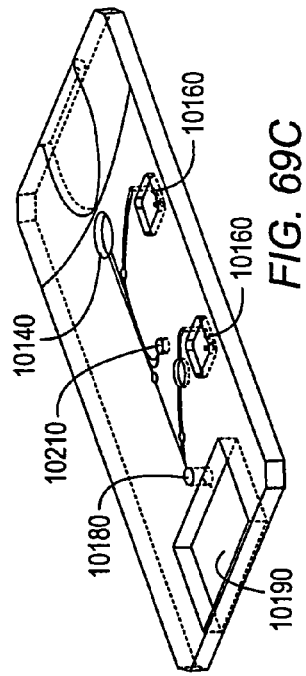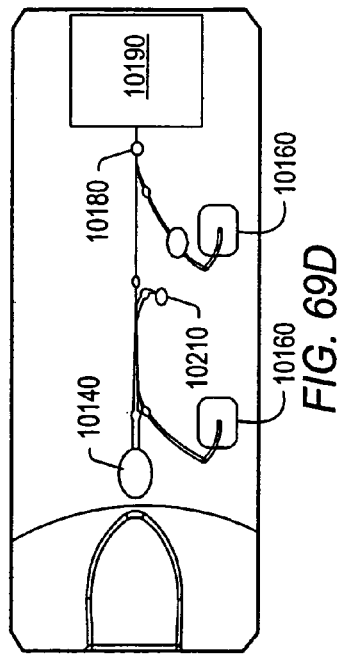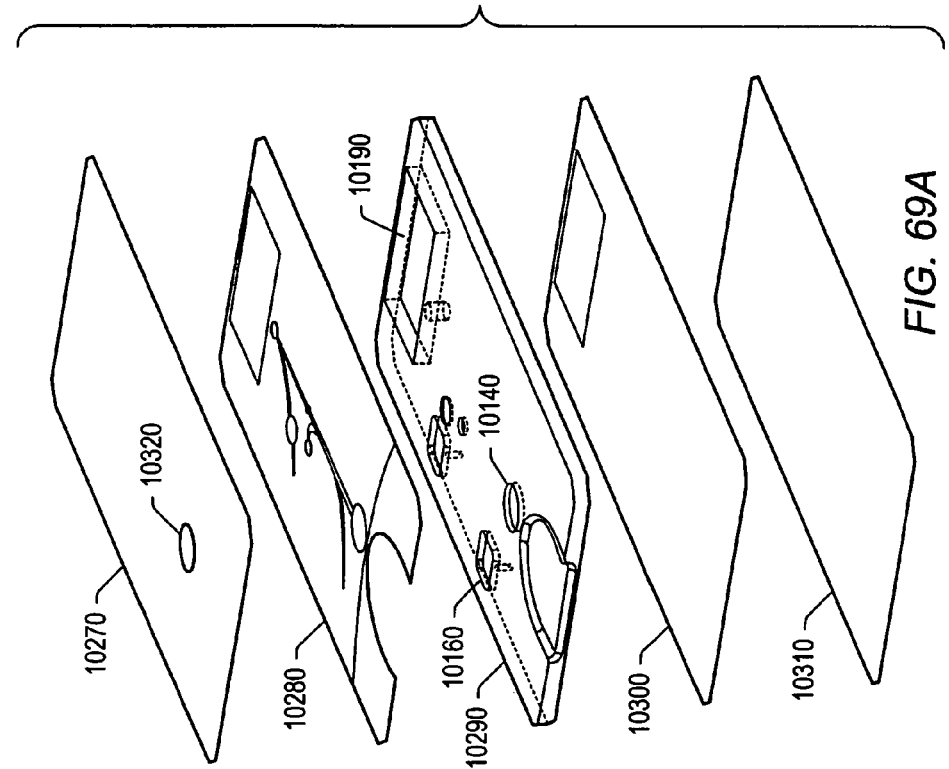

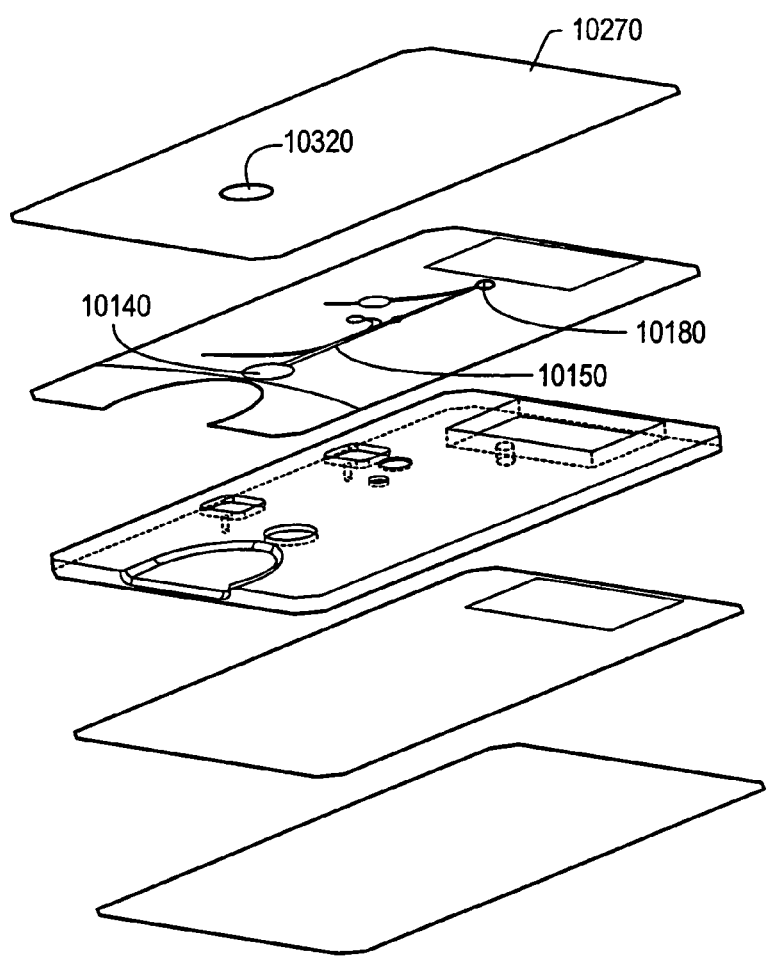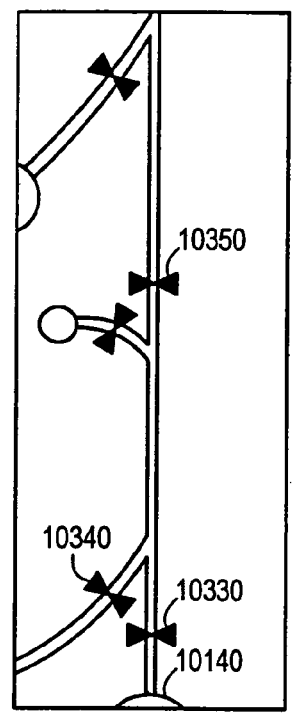
FIG. 72A
FIG. 72B

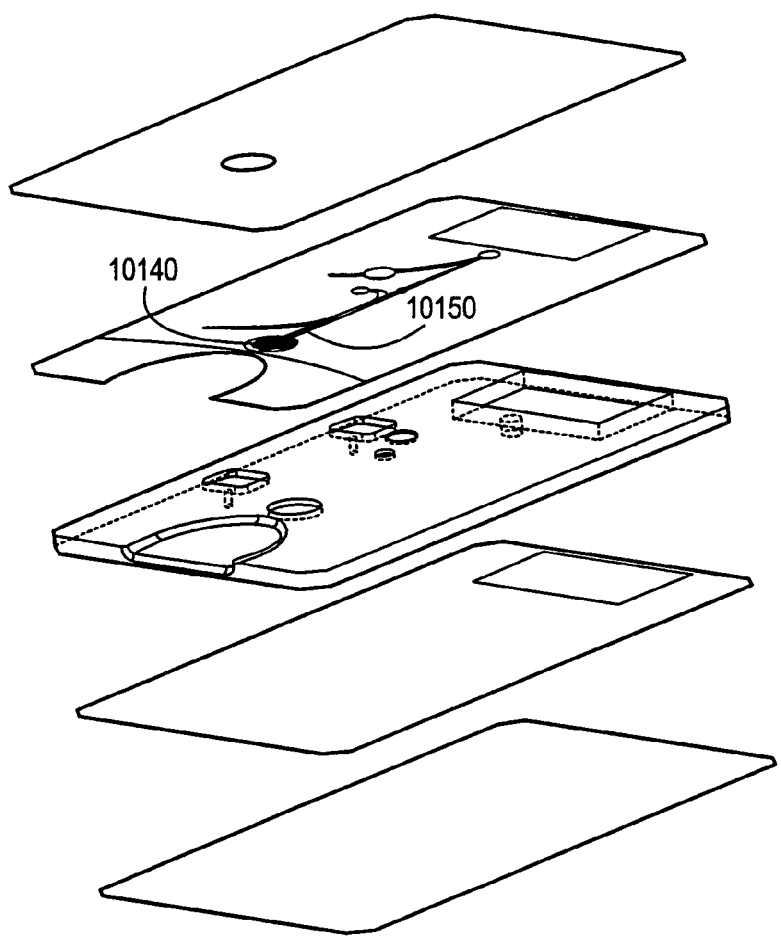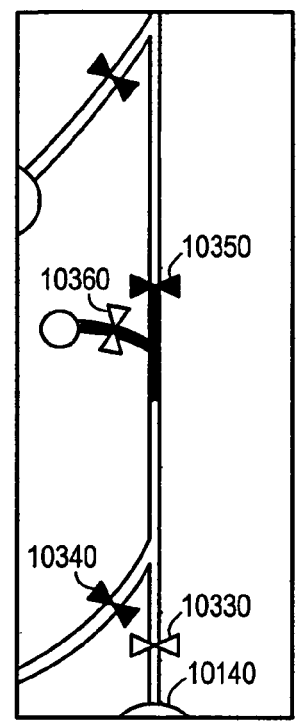
FIG. 73A
FIG. 73B

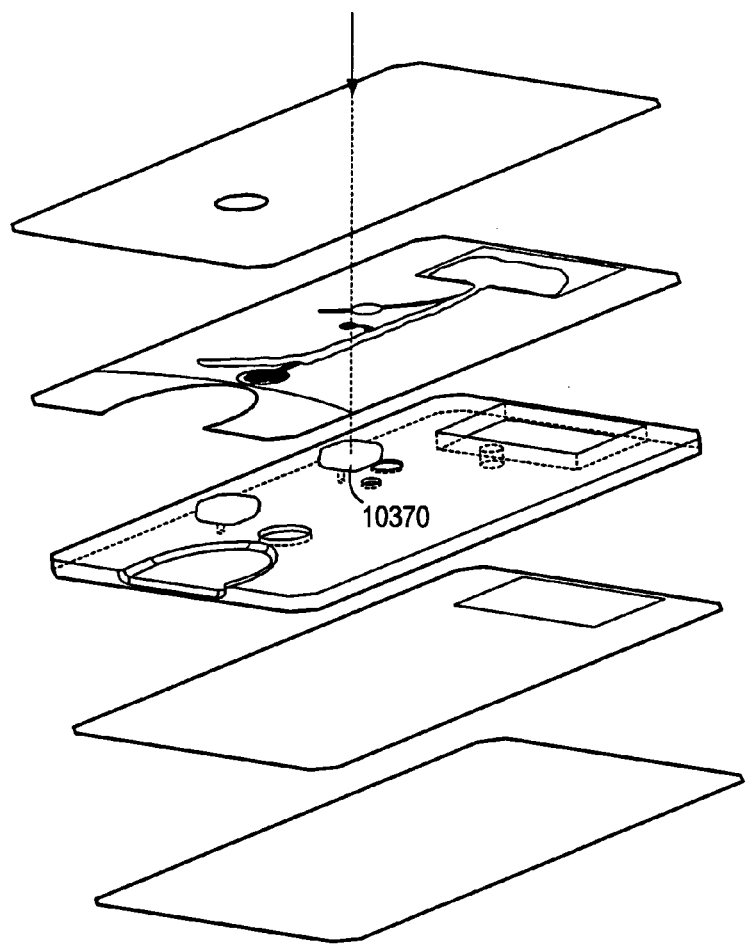
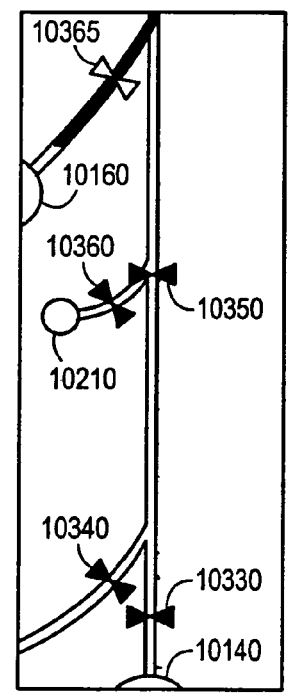
FIG. 78A
FIG. 78B

PARTICLE ON MEMBRANE ASSAY SYSTEM

PRIORITY CLAIM

This application claims priority to U.S. Provisional Application No. 60/548,613 entitled "PORTABLE INSTRUMENT FOR MICROARRAY ANALYSIS" filed on Feb. 27, 2004; U.S. Provisional Application No. 60/548,601 entitled "ON-CHIP COMBINATION OF CHEMICAL AND CELLULAR PANELS FOR ANALYSIS OF FLUID SAMPLES" filed on Feb. 27, 2004; and U.S. Provisional Application No. 60/548,190 entitled "CUSTOMIZED TESTING ENSEMBLES FOR COMPLEX FLUID ANALYSIS USING PORTABLE INTEGRATED MICROFLUIDICS/DETECTING UNITS" filed on Feb. 27, 2004.

BACKGROUND

1. Field of the Invention

The present invention generally relates to a method and device for the detection of analytes in a fluid. More particularly, the invention relates to a portable apparatus for obtaining analytical information using both membrane- and particle-based detectors.

2. Description of Related Art

Current methodology used to complete medical diagnostics, environmental monitoring, and detection of bioterrorism-related agents often require large and expensive instruments and highly specialized personnel found only in certain hospitals, laboratories or government agencies. Furthermore, these instruments are often restricted to a limited number of applications. For example, in the area of medical diagnostics, each instrument is very specialized and designed either to measure protein levels or to analyze cellular matter but, typically, may never do both. Additionally, each system is capable of analyzing only a few of the relevant markers of a disease, therefore adding another component to an already tedious and time consuming process that can vary from hours to days. Long delays can be generated between the time of the initial visit, diagnosis, and administration of treatment, potentially having detrimental effects on the prognosis of the disease. Similarly, timely identification of an unknown environmental or deliberately introduced contaminant is crucial. For example, two of the envelopes from the 2001 anthrax attacks were processed at a facility that remained open for 9 days after the initial contamination, exposing more than 60 million mail items and more than 2000 employees to *Bacillus anthracis* spores.

It is therefore desirable that new methods and systems capable of discriminating analytes and/or microbes be developed for health and safety, environmental, homeland defense, military, medical/clinical diagnostic, food/beverage, and chemical processing applications. It is further desired that the methods and systems facilitate rapid screening of analytes and/or microbes to be used as a trigger for more specific and confirmatory testing. It is further desired that sensor arrays be developed that are tailored specifically to serve as efficient microbe collection media.

SUMMARY

In an embodiment, an analyte detection system for both membrane and/or sensor array particle-based measurements may be used to determine the presence of analytes. In one embodiment, the system may include a sample collection device, an off-line sample processing unit, a fluid delivery system, a disposable cartridge, a cartridge self-positioning system, an optical platform, electronics, power supplies, computer processor(s), and/or software and firmware. In operation, a sample may be collected using the sample collection device. Sample collection devices may include needles, capillary tubes, pipettes, and/or vacutainers. A sample collection device may be configured to consume a portion of the sample collection device that contacts a sample. A sample collection device may include a sample pick-up pad configured to receive a sample and deliver the sample to the cartridge.

In an embodiment, a sample may be transported to a cartridge with the fluid delivery system. A sample may flow from the sample collection device to a sample reservoir in a cartridge. Reagents and/or buffers may be delivered to the sample reservoir. Reagents may be delivered by a reagent delivery system and/or contained in reagent reservoirs, reagent packs, and/or reagent pads. A sample reservoir may include a mixing chamber where a sample may react with reagents. An actuator coupled to the cartridge may drive fluid through the cartridge.

A cartridge may include one or more particle-based or particle-based platform detection regions and/or membrane based detection regions. Light from an optical platform may pass onto a detection region and a detector in the optical platform may acquire images (e.g., visual or fluorescent) of the sample, and/or of sample-modulated particles. The images may be processed and analyzed using software, algorithms, and/or neural networks.

In one embodiment, the system includes the use of defined populations of assay particles that are chemically sensitized to detect the presence of a specific analyte in a fluid by binding to the analyte. Chemically sensitizing a population of particles to detect an analyte may include coupling a receptor for the analyte to the population of particles. In an embodiment, receptors for analytes may include antibodies that bind to the analyte. In an embodiment, populations of particles may be defined by color and/or size. Defining populations of particles by color may include coupling a fluorescent dye to the population of particles. In an embodiment, analytes may be detected by including a second chemical that binds to the analyte. In an embodiment, the second chemical may be a receptor and/or antibody to the analyte. In an embodiment, the second chemical may be defined by a color that is different from the color that defines the population of particles. In an embodiment, the second chemical may be defined by fluorescent dye that is different from the fluorescent dye that defines the population of particles. In an embodiment, detecting an analyte in a fluid may include detecting two different signals.

In one embodiment, populations of particles may be mechanically captured on the surface of a filter or membrane-equipped flow cell system. The membrane-equipped flow cell system may be configured to allow fluid flow through the flow cell system and the filter or membrane. In one embodiment, the membrane-equipped flow cell system may be coupled to an optical/digital acquisition system that may be configured to allow the visualization of particles captured thereon. In an embodiment, the membrane-equipped flow cell system coupled to an optical/digital acquisition system may comprise a device that may facilitate the digital/optical acquisition of fluorescent signals resulting from immunological reactions that take place on the surface of the membrane-captured particles.

In an embodiment, a detecting an analyte in a fluid may include forming a mixture of size- and color-coded particles with the fluid. The particles may be coupled to a receptor that interacts with the analyte. In an embodiment, the particle/ fluid mixture may be passed across a porous membrane equipped in an analyte detection device. In an embodiment, an analyte detection device may include a flow cell system. In an embodiment, the analyte detection device may be configured to capture the particles on the porous membrane. In an embodiment, the analyte detection device may be configured to visualize the particles captured on the membrane. In an embodiment, detecting the analyte may include detecting spectroscopic signals from the particles captured on the membrane.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIGS. 36A-B depict an embodiment of a fluid delivery system that includes a three-way fluidics interface;

FIG. 43 depicts a schematic diagram of an optical platform that includes multiple optical fiber microlenses;

FIGS. 55A-D depict different embodiments of channels for delivering fluids within a cartridge;

FIGS. 56A-B depicts different embodiments of cartridges that include a trap;

FIGS. 57A-C depict different embodiments of cartridges that include a fluidics interface;

FIGS. 59A-C depicts an embodiment of the particle on membrane assay system;

FIG. 69A depicts an exploded view of an embodiment of a cartridge that includes a sensor array;

FIG. 69B depicts a top view of the cartridge of FIG. 69A;

FIG. 69C depicts a perspective view of an embodiment of the cartridge of FIG. 69A;

FIG. 69D depicts a bottom view of an embodiment of the cartridge of FIG. 69A;

FIG. 72A depicts an exploded view of an alternate embodiment of a cartridge that includes a sensor array;

FIG. 72B depicts an embodiment of an arrangement of valves in the cartridge of FIG. 72A;

FIG. 73A depicts an exploded view of an embodiment of the cartridge depicted in FIG. 72A as sample is introduced in the cartridge;

FIG. 73B depicts an embodiment of an arrangement of valves in a cartridge as sample is introduced in the cartridge;

FIG. 78A depicts an exploded view of an embodiment of a cartridge; and

FIG. 78B depicts an embodiment of an arrangement of valves in a cartridge.

DETAILED DESCRIPTION

Figure 1A:
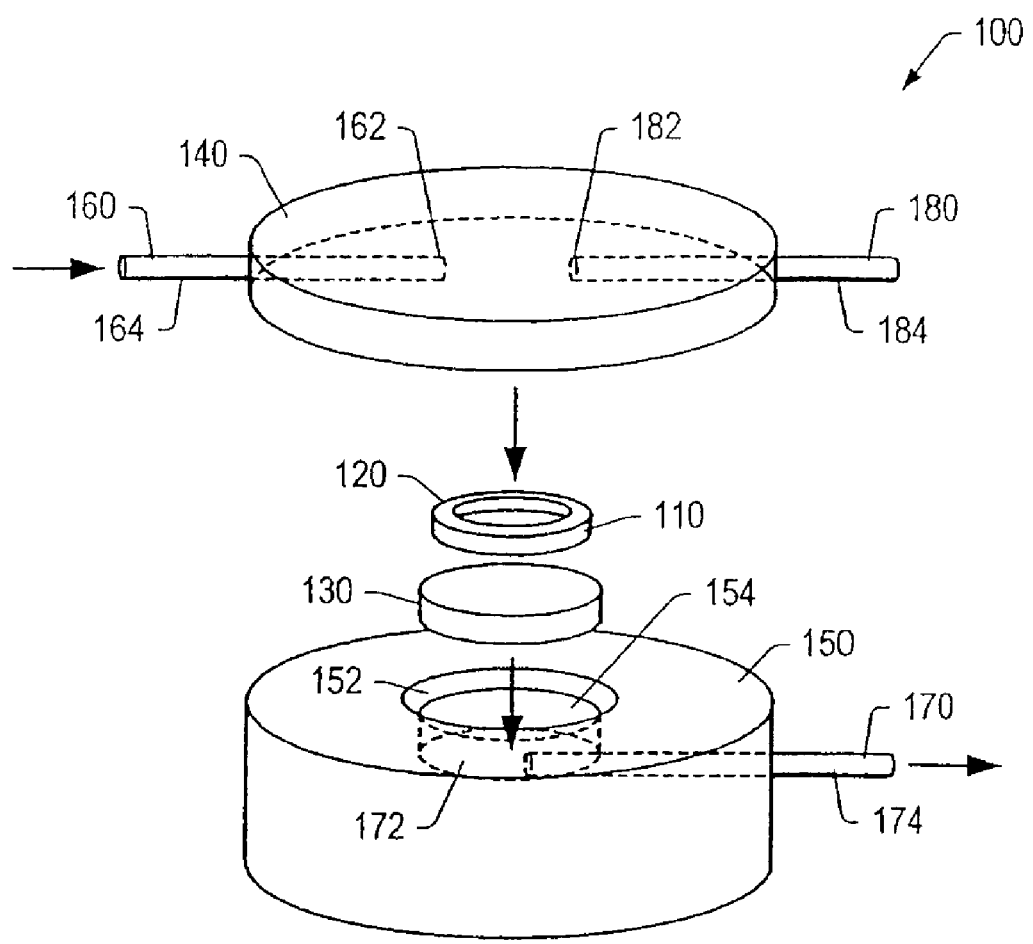
FIG. 1A depicts an exploded view of a membrane based flow sensor.

Herein we describe a system and method for the simultaneous analysis of a fluid containing multiple analytes. The system may generate patterns that are diagnostic for both individual analytes and mixtures of the analytes. The system, in some embodiments, is made of a combination of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

Details regarding analyte detection systems can be found in the following U.S. patents and patent applications, all of which are incorporated herein by reference: U.S. patent application Ser. No. 09/287,248 entitled "Fluid Based Analysis of Multiple Analytes by a Sensor Array"; U.S. Pat. No. 6,680,206 entitled "Sensor Arrays for the Measurement and Identification of Multiple Analytes in Solutions"; U.S. Pat. No. 6,602,702 entitled "Detection System Based on an Analyte Reactive Particle"; U.S. Pat. No. 6,589,779 entitled "General Signaling Protocols for Chemical Receptors in Immobilized Matrices"; U.S. patent application Ser. No. 09/616,731 entitled "Method and Apparatus for the Delivery of Samples to a Chemical Sensor Array"; U.S. patent application Ser. No. 09/775,342 entitled "Magnetic-Based Placement and Retention of Sensor Elements in a Sensor Array" (Published as U.S. Publication No.: 2002-0160363-A1); U.S. patent application Ser. No. 09/775,340 entitled "Method and System for Collecting and Transmitting Chemical Information" (Published as U.S. Publication No.: 2002-0064422-A1); U.S. patent application Ser. No. 09/775,344 entitled "System and Method for the Analysis of Bodily Fluids" (Published as U.S. Publication No.: 2004-0053322); U.S. Pat. No. 6,649,403 entitled "Method of Preparing a Sensor Array"; U.S. patent application Ser. No. 09/775,048 entitled "System for Transferring Fluid Samples Through A Sensor Array" (Published as U.S. Publication No.: 2002-0045272-A1); U.S. patent application Ser. No. 09/775,343 entitled "Portable Sensor Array System"

(Published as U.S. Publication No.: 2003-0186228-A1); U.S. patent application Ser. No. 10/072,800 entitled "Method and Apparatus for the Confinement of Materials in a Micromachined Chemical Sensor Array" (Published as U.S. Publication No.: 2002-0197622-A1); and U.S. patent application Ser. No. 10/427,744 entitled "Method and System for the Detection of Cardiac Risk Factors" (Published as U.S. Publication No.: 2004-0029259-A1).

In another embodiment, a sensor array system may be a membrane based flow sensor. A membrane based flow sensor may be configured to accommodate the capture of microbes and/or cells with a filter that is placed within a fluidics device. Microbes and/or cells, whose size is larger than the pores of the filter, are captured in the flow cell assembly. The captured microbes and/or cells may be analyzed directly or may be treated with visualization compounds.

A variety of microbes may be captured and analyzed using a membrane based flow sensor as described herein. As used herein, "microbe" refers to any microorganism, including but not limited to, a bacteria, spore, protozoan, yeast, virus, and algae. Some microbes that are of particular interested for detection include a variety of toxic bacteria. Examples of bacteria that may be detected using a membrane based flow sensor include, but are not limited to *Escherichia coli* O157: H7, *Cryptosporidium*, *Vibrio cholerae*, *Shigella*, *Legionnella*, *Lysteria*, *Bacillus globigii*, and *Bacillus anthracis* (anthrax). Viruses may also be detected using a membrane, including the HIV virus.

Shown in FIG. 1A is an exploded view of a membrane based flow sensor 100. Flow sensor 100 includes a membrane 110 that is sandwiched between at least two members 140 and 150. Members 140 and 150 are configured to allow fluid to flow to and through membrane 110. Members 140 and 150 are also configured to allow detection of analytes, after the analytes have been captured on membrane 110. A variety of different materials may be used for membrane 110, including, but not limited to, NUCLEPORE® (Whatman, Inc.; Clifton, N.J.) track-etched membranes, nitrocellulose, nylon, and cellulose acetate. Generally, the material used for membrane 110 should have resistance to non-specific binding of antibodies and stains used during the visualization and detection processes. Additionally, membrane 110 is composed of a material that is inert to a variety of reagents, buffers, and solvents. Membrane 110 may include a plurality of sub-micron pores that are fairly evenly distributed. The use of membranes having an even distribution of pores allows better control of fluid flow and control of the isolation of analytes.

Members 140 and 150 are composed of a material that is substantially transparent to wavelengths of light that are used to perform the analyte detection. For example, if the analyte detection method requires the use of ultraviolet light, member 140 should be composed of a material that is substantially transparent to ultraviolet light. Member 140 may be composed of any suitable material meeting the criteria of the detection method. A transparent material that may be used to form member 140 includes, but is not limited to, glass, quartz glass, and polymers such as acrylate polymers (e.g., polymethylmethacrylate). In some embodiments, both top member 140 and bottom member 150 are composed of transparent materials. The use of transparent materials for the top member and the bottom member allow detection to be performed through the membrane based flow sensor.

As shown in FIG. 1A, membrane 110 is sandwiched between top member 140 and bottom member 150. Bottom member 150 and/or top member 140 may include indentations configured to hold a membrane. For example, in FIG. 1A, bottom member 150 includes an indentation 152 that is configured to receive membrane 110, along with any other accompanying pieces that are used to support or seal membrane 110. Indentations or cavities may be etched into top member 140 and/or bottom member 150 using standard etching techniques.

Referring to FIG. 1A, bottom member 150 includes a first indentation 152, which is configured to receive a membrane support 130. Bottom member also includes a second indentation 154. Second indentation is configured such that membrane support 130 is inhibited from entering the second indentation. Second indentation may include a ridge disposed near the membrane support 130 such that membrane support 130 rests upon the ridge. Alternatively, as depicted in FIG. 1A, second indentation may be to may have a size that is smaller than the size of membrane support 130. In either case, when assembled, membrane support 130 is inhibited from entering second indentation 154, thus creating a cavity under membrane support 130. Cavity 154 may be used to collect fluids that pass through the membrane support 130 prior to exiting the system.

Membrane support 130 is configured to provide support to membrane 110 during use. Membrane support 130 may be formed from a porous material that allows fluid to pass through the membrane support. The pores of membrane support 130 should have a size that allows fluid to pass through membrane support 130 at a speed that is equal to or greater than the speed that fluid passes through membrane 110. In one embodiment, pores of membrane support 130 are larger than pores in membrane 110. The pores, however, cannot be too large. One function of membrane support 130 is to provide support to membrane 110. Therefore, pores in membrane support 130 should be sufficiently small enough to inhibit sagging of membrane 110 during use. Membrane support 130 may be formed of a variety of materials including, but not limited to, polymeric materials, metals, and glass. In one embodiment, a polymeric material (e.g., celcon acrylic) may serve as a material for membrane support 130. Additionally, membrane support 130 helps to keep the membrane planar during use. Keeping the membrane planar simplifies detection of the analytes by allowing the capture and detection of the analytes on a single focal plane. Membrane 110, as described above, may rest upon membrane support 130 when the membrane based flow sensor 100 is assembled. In some embodiments, a gasket 120, may be positioned on top of membrane 110. A gasket may be used to provide a fluid resistant seal between members 130 and 140 and membrane 110. Gasket may inhibit the leakage of fluid from the system during use.

Top member 140 may include a fluid inlet 160. Fluids for analysis may be introduced into device 100 via fluid inlet 160. Fluid inlet 160 may pass through a portion of top member 140. In some embodiments, a channel 162 may be formed in top member 140 such that tubing 164 may be inserted into channel 162. Channel 162 may turn near the center of the top member to deliver the fluids to an upper surface of membrane 110.

Bottom member 150 may include a fluid outlet 170. Fluids that are introduced into the device 100 via fluid inlet 160 pass through top member 140 and through membrane 110. The fluids are then collected in cavity 154. A fluid outlet 170 may pass through a portion of bottom member 150. In some embodiments, a channel 172 may be formed in bottom member 150 such that tubing 174 may be inserted into channel 172. Channel 172 may be positioned to receive fluids that are collected in cavity 154 during use.

Optionally, a washing fluid outlet 180 may be formed in top member 140. Washing fluid outlet 180 is configured to receive fluids that pass through or over membrane 110 during a washing operation. Washing fluid outlet 180 may pass through a portion of top member 140. In some embodiments, a channel 182 may be formed in top member 140 such that tubing 184 may be inserted into channel 182. Channel 182 may be positioned to receive fluids that are used to wash membrane 110 during use.

Membrane 110 is selected from a material capable of filtering the analytes of interest from a fluid stream. For examples, if microbes represent the analyte of interest, the filter should be capable of removing microbes from a fluid stream. A suitable membrane may include a plurality of pores that have a size significantly less than the size of the analyte of interest. For airborne toxic microbes (e.g., anthrax), the membrane may be configured to capture microbes that have a diameter of greater than about 1 μm. It is believed that microbes that have a diameter of less than about 1 μm are very difficult to generate in large quantities, and if the organisms are viable, environmental stresses tend to interfere with the action of the microbes due to the high surface area/mass ratio. Membranes may be formed from a variety of materials known in the art. In one embodiment, membrane 110 may be a track-etched-NUCLEPORE® polycarbonate membrane. A NUCLEPORE® membrane is available from Whatman plc. Membrane 110 may be about 5-10 microns in thickness. Membrane 110 includes a plurality of pores. Pores may range from -about 0.2 μm in diameter up to about 12 μm in diameter to capture potentially dangerous microbes.

In some embodiments, a membrane may include a plastic and/or metallic material with a high density of pores. A membrane may be made of a material which is substantially non-reflective and/or substantially inhibits emission in the UV-vis range. For example, materials that a membrane may be formed from include, but are not limited to, polymethylmethacrylate (PMMA); polycarbonate (PC); Delrin® (commercially available from DuPont); titanium; silicon; silicon nitride; and/or combinations thereof. A membrane support may be formed from various materials including, but not limited to, polymethylmethacrylate (PMMA); polycarbonate (PC); Delrin®; titanium; silicon; silicon nitride; and/or combinations thereof.

In some embodiments, a membrane and a membrane support may be combined to create a monolithic microchip. A monolithic microchip may be made through various techniques such as LIGA fabrication, which may allow design and fabrication of high aspect ratio features; injection molding; through bundled optical fibers assemblies; and/or LASER etching. A microchip may be substantially circular, substantially rectangular, substantially square, substantially triangular, and/or have an irregular shape.

Figure 1B:
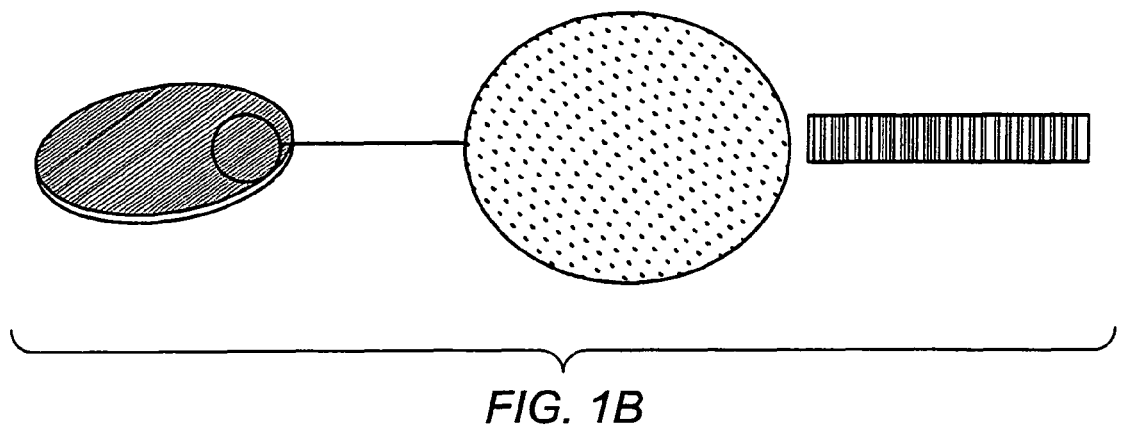
FIG. 1B depicts a schematic of an embodiment of a microchip.

FIG. 1B depicts a schematic of an embodiment of a membrane. In FIG. 1B, holes in the membrane are drawn larger than their actual size for clarity. A membrane may be configured to have pore dimensions to accommodate a variety of applications including, but not limited to, capturing microorganisms and/or particles in the range of about 100 nm to about 1 mm in size. A membrane may have a thickness, t; a diameter, D; holes with a diameter, d; and/or a density of holes on the microchip, ρ. In an embodiment, a specific set of parameters for t, D, d, and ρ may be used for a specific application. Various applications may include various definitions of specific sets of parameters for ρ, D, d, and t. In an embodiment, a membrane may have pores ranging from about 100 nm to about 1 mm and/or a thickness ranging from about 1 to about 5000 microns. A membrane may have a thickness of from about 1 μm to about 2000 μm.

Figure 1C:
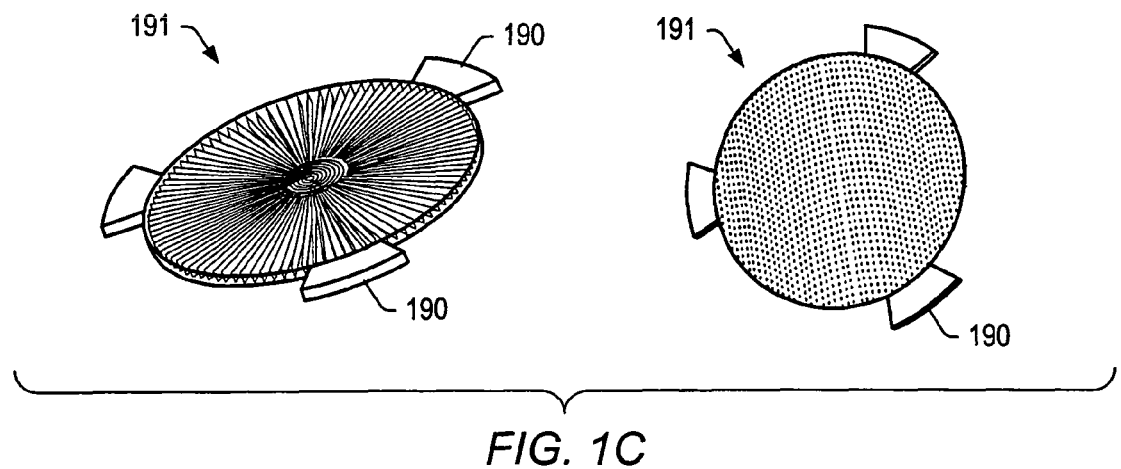
FIG. 1C depicts a schematic of an embodiment of a microchip with a locking mechanism.

As depicted in FIG. 1C, a membrane may include a locking mechanism. A locking mechanism 190 for a microchip 191 may be substantially circular, substantially rectangular, substantially square, substantially triangular, and/or have an irregular shape. A locking mechanism may inhibit insertion of an incorrect microchip in a system. For example, an analyte detection system may be capable of receiving a membrane that has the correct corresponding locking mechanism. If the locking mechanism is not of the proper shape and/or orientation, the membrane will not fit into the system. In this way only the proper membrane may be inserted into the system. A locking mechanism may also facilitate secure placement of a membrane in a desired location. Using a locking mechanism may facilitate consistent placement of a membrane in the same location in the system. A locking mechanism 190 may be positioned on a side and/or bottom of a membrane 191. It should be understood that particle based sensor arrays, as described herein, may also include a similar locking mechanism for ensure insertion of the correct sensor array in the correct position.

Figure 1D:
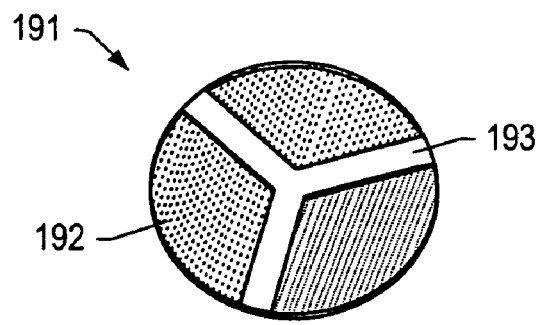
FIG. 1D depicts a schematic of an embodiment of positions of cavities in a microchip.
Figure 1E:
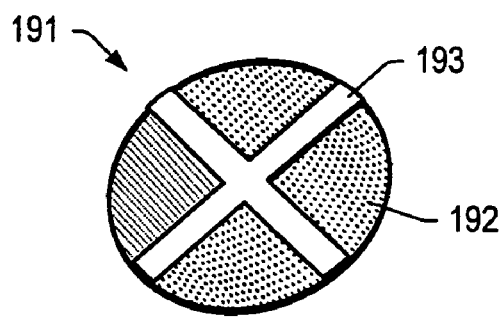
FIG. 1E depicts a schematic of an embodiment of a pattern of cavities in a microchip.

FIGS. 1D-E depict patterns of cavities or holes in a membrane. Holes, openings, or cavities in a membrane may be positioned in a pattern, randomly positioned, and/or orderly positioned. Patterns created by holes in a membrane may cover the whole membrane or may be restricted to given areas of the membrane. In some embodiments, a membrane 191 may have independent compartments 192 separated by walls 193 or ridges. Walls in a membrane may be configured to have various geometries and height. A wall may define multiple compartments. In certain embodiments, compartments of a membrane may be connected to either the same drain and/or separate independent drains. Using compartments may allow delivery of fractions of a given sample to different compartments. Using compartments may also allow one sample to be delivered sequentially to various independent areas of a membrane. In another embodiment, different samples may be delivered to different compartments allowing analysis of multiple samples using a single membrane.

In some embodiments, the independent areas or compartments of a membrane may be characterized as having pores of different sizes. Pore sizes in a compartment may be configured to accommodate applications such as, but not limited to, sequential sieving, cell sorting, bead sorting, and multiplexing based on size. In an embodiment, a membrane or various compartments of a membrane may be configured to include one or more cavities. Cavities may include particles that interact with an analyte to produce a detectable signal. The cavities may be square-based pyramidal or conical and/or may have a shape to accommodate beads of different sizes.

Figure 1F:
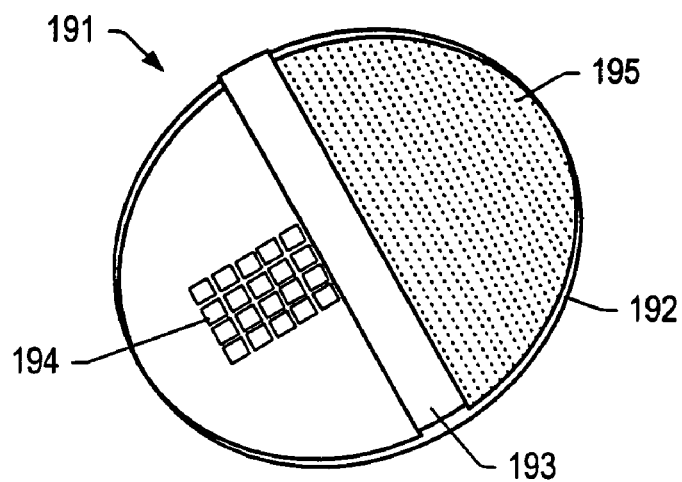
FIG. 1F depicts a schematic of an embodiment of an alternate pattern of cavities in a microchip.

FIG. 1F depicts a schematic of an embodiment of a membrane that includes a particle-based sensor array. A membrane 191 may include a combination of cavities 194 capable of receiving one or more particles and holes 195 that may be used to capture analytes by filtration. Cavities 194, capable of receiving particles or beads, may be in a different compartment 192 from holes 195 in a membrane. Walls 193 on a membrane 191 may separate compartments including cavities 194 with particles from compartments that include holes 195. In some embodiments, a combination of particle wells and holes in different compartments may allow simultaneous on-chip capture and detection of cells and protein analysis of complex fluids (i.e., blood, urine, CSF, etc.). In certain embodiments, a microchip may include one or more calibration aids such as, but not limited to, beads, fluorescent elements, size reference, and/or topographical points of reference.

Figure 2:
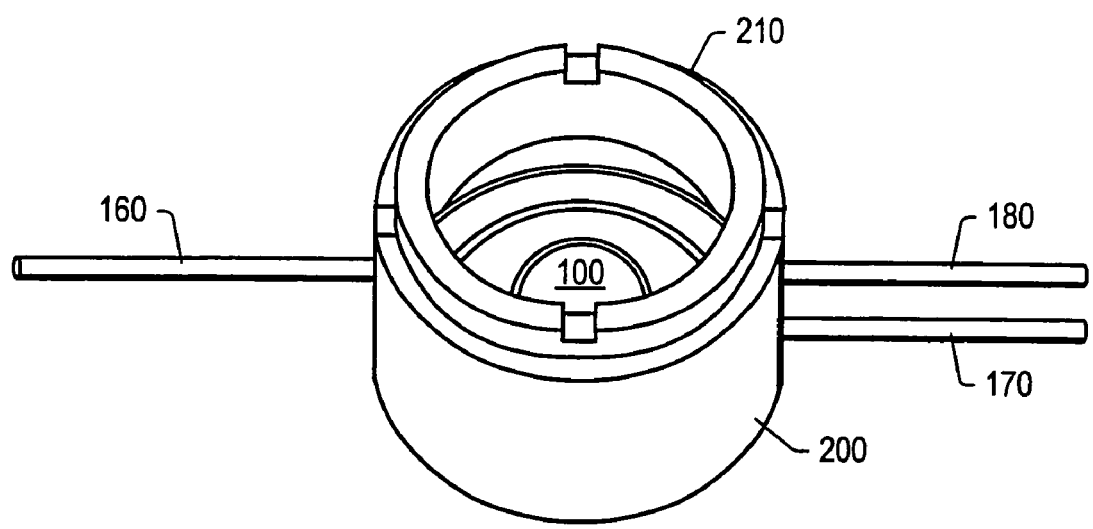
FIG. 2 depicts an embodiment of a membrane based flow sensor disposed in a housing.

FIG. 2 depicts an embodiment of a membrane based flow sensor disposed in housing 200. Top member 140, gasket 120, membrane 110, membrane support 130, and bottom member 150 may be assembled and placed inside housing 200. Housing 200 may encompass membrane based fluid sensor. A cap 210 may be used to retain membrane based fluid sensor within housing 200. Cap 210 may include a window to allow viewing of membrane 110. When positioned within housing 200, fluid inlet 160, fluid outlet 170 and washing fluid outlet 180 extend from housing 200 to allow easy access to the membrane based fluid sensor 100.

Figure 3:
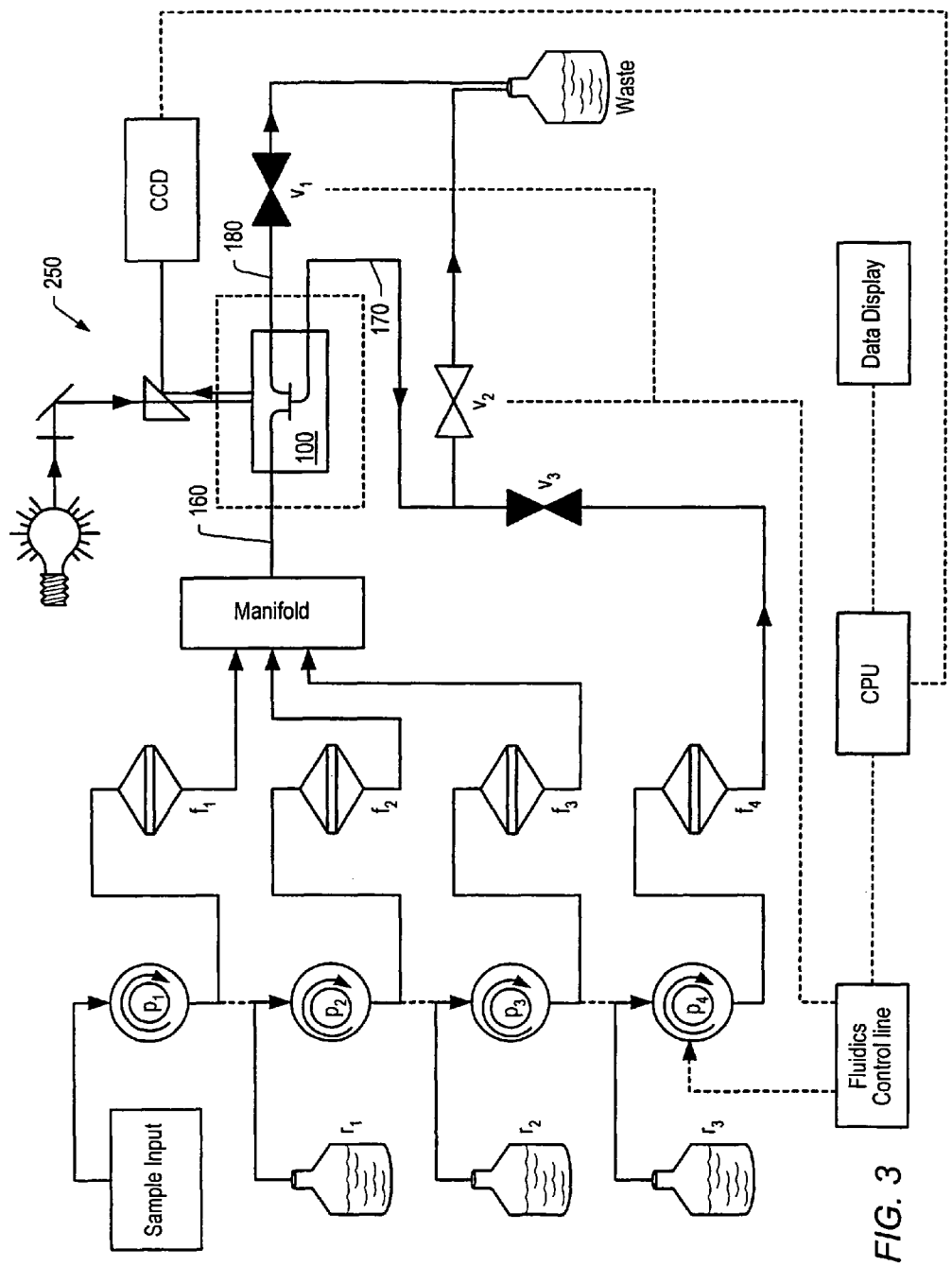
FIG. 3 depicts a schematic diagram of an analyte detection system in flow-through mode.

A schematic of a complete membrane based analysis system is shown in FIG. 3. Analysis system includes a plurality of pumps ($p_1$, $p_2$, $p_3$ and $p_4$). Pumps are configured to deliver samples ($p_1$), visualization reagents ($p_2$ and $p_3$) and membrane washing fluids ($p_4$) to the membrane based fluid sensor 100 during use. Reagents, washing fluids, and visualization agents are passed through pre-filters ($f_1$, $f_2$, $f_3$, and $f_4$) before the fluids are sent to membrane based fluid sensor 100. Pre-filters are used to screen out large particulate matter that may clog membrane 110. The nature and pore size of each pre-filter may be optimized in order to satisfy efficient capture of large dust particles or particulate matter aggregates while resisting clogging. Pre-filter f1 is configured to filter samples before the samples reach the membrane based fluid sensor 100. Pre-filter f1 is configured to allow the analyte of interest to pass through while inhibiting some of the particles that are not related to the analyte of interest. For example, spores, whose size is smaller than the pores of the pre-filter $f_1$, are passed through the pre-filter and captured in the membrane based fluid sensor 100. After passing through pre-filters $f_1$-$f_4$, fluids are passed through a manifold. In some embodiments, membrane based fluid sensor 100 includes a single input line. The manifold couples the different fluid lines to the single input line of the membrane based fluid sensor 100.

After passing through the manifold, fluids are introduced into fluid inlet of the membrane based fluid sensor 100. At appropriate times, a detector 250 is used to determine if any analytes have been captured by the membrane based fluid sensor 100. As depicted in FIG. 3, a detector may be placed over a portion of membrane based fluid sensor 100 such that the detector may capture an image of the membrane. For example, detector may be placed such that images of the membrane may be taken through a window in the membrane based fluid sensor 100. Detector 250 may be used to acquire an image of the particulate matter captured on membrane 110. Image acquisition may include generating a "digital map" of the image. In an embodiment, detector 250 may include a high sensitivity CCD array. The CCD arrays may be interfaced with filters, light sources, fluid delivery, so as to create a functional sensor array. Data acquisition and handling may be performed with existing CCD technology. In some embodiments, the light is broken down into three-color components, red, green and blue. Evaluation of the optical changes may be completed by visual inspection (e.g., with a microscope) or by use of a microprocessor ("CPU") coupled to the detector. For fluorescence measurements, a filter may be placed between detector 250 and membrane 110 to remove the excitation wavelength. The microprocessor may also be used to control pumps and valves as depicted in FIG. 3.

The analyte detection system may be operated in different modes based on which valves are opened and closed. A configuration of a system in a "flow through" mode is depicted in FIG. 3. In this mode, fluid is passed from the manifold to the membrane based fluid sensor 100 to allow capture of analytes or the addition of development agents. Fluids for analysis may be introduced into membrane based fluid sensor 100 via fluid inlet 160. During a "flow through" operation, valve $V_1$ is placed in a closed position to inhibit the flow of fluid through wash fluid outlet 180. The fluids may, therefore, be forced to pass through membrane based fluid sensor 100 exit the sensor via fluid outlet 170. Valve $V_2$ is placed in an open position to allow the flow of fluid to the waste receptacle. Valve $V_3$ is placed in a closed position to inhibit the flow of fluid into the wash fluid supply line.

Figure 4:
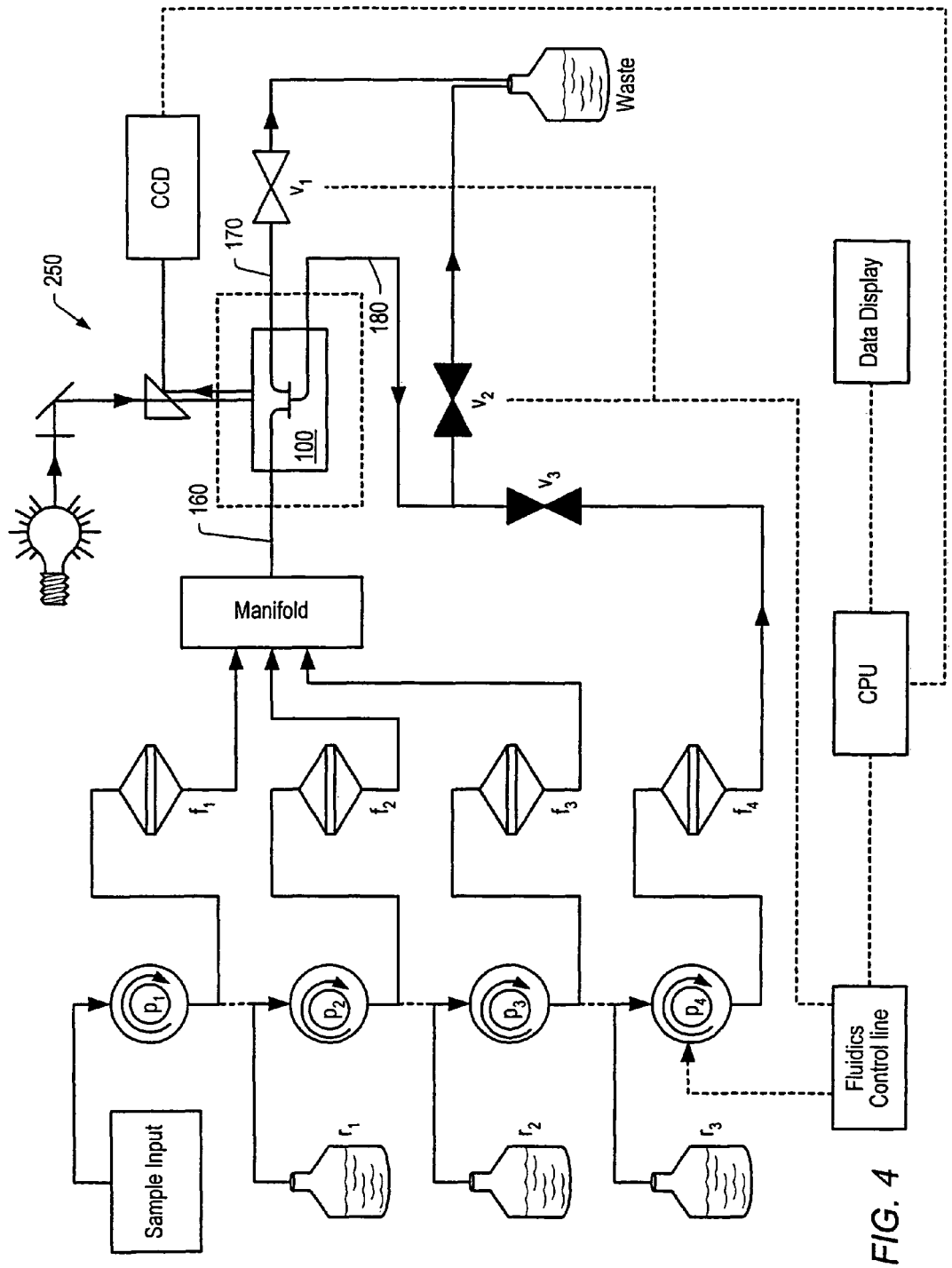
FIG. 4 depicts a schematic diagram of an analyte detection system in lateral flow mode.

The analyte detection system may also be operated in a "lateral membrane wash" mode, as depicted in FIG. 4. In this mode, the membrane is cleared by the passage of a fluid across the collection surface of the membrane. This allows the membrane to be reused for subsequent testing. Fluids for washing the membrane may be introduced into sensor 100 via fluid inlet 160. During a "lateral membrane wash" operation, outlet valves $V_2$ and $V_3$ are placed in a closed position to inhibit the flow of fluid through fluid outlet 170. The closure of outlet valves $V_2$ and $V_3$ also inhibits the flow of fluid through the membrane of sensor 100. The fluids entering sensor 100 may, therefore, be forced to exit sensor 100 through washing fluid outlet 180. Valve $V_2$ is placed in an open position to allow the flow of fluid through washing fluid outlet 180 and into the waster receptacle. Since fluid is inhibited from flowing through the membrane, any analytes and other particles collected by the membrane may be "washed" from the membrane to allow further use.

Figure 5:
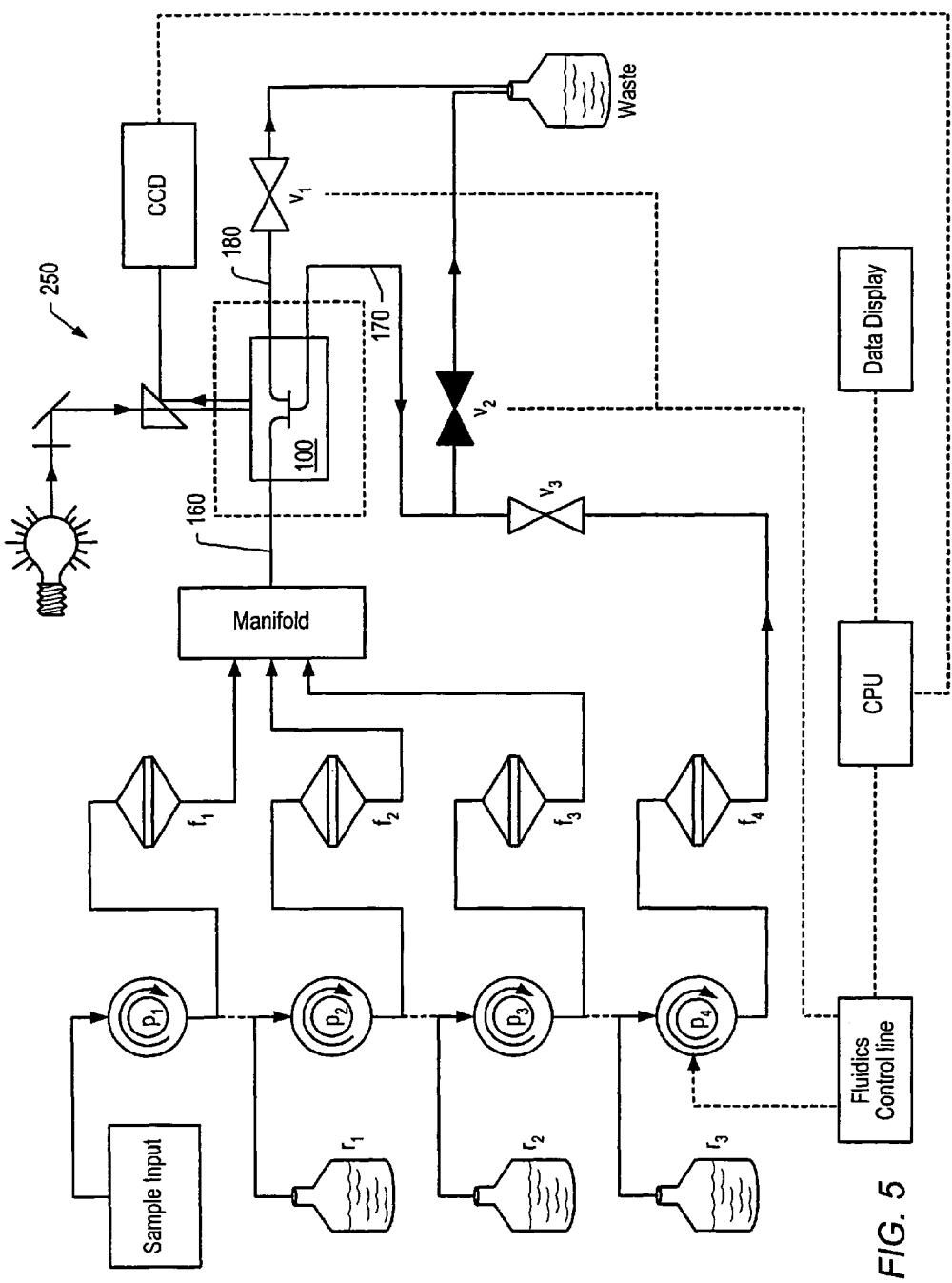
FIG. 5 depicts a schematic diagram of an analyte detection system in back-flush mode.

The analyte detection system may also be operated in a "backwash" mode, as depicted in FIG. 5. During a backwash operation, fluid outlet 170 is used to introduce a fluid into the analyte detection system, while wash fluid outlet 180 is used to allow the fluid to exit the device. This "reverse" flow of fluid through the cell allows the membrane to be cleared. In an embodiment, valves may be configured as depicted FIG. 5, with the washing fluid being introduced through fluid outlet 170. Specifically, valves V1 and V3 are open, while valve V2 is closed.

Either a lateral membrane wash or a back flush treatment may be used to clear analytes and other particles from a membrane. Both methods of clearing the membrane surface may be enhanced by the use of ultrasound or mechanical agitation. During use, analytes in the fluid sample are trapped by the membrane since the analytes are bigger than the openings in the membrane. The analytes tend to be randomly distributed across the membrane after use. Analytes that occupy positions on the membrane that are between the positions of pores may be harder to remove them analytes that are position on or proximate to a pore in the membrane. Analytes that occupy positions on the membrane that is between the positions of pores may be more difficult to remove, since the force of the backwash fluid may not contact the analytes. During backwash and lateral wash operations, removal of trapped analytes may be enhanced by the use of ultrasound of mechanical agitation. Both methods cause the analytes to move across the membrane surface, increasing the chances that the analyte will encounter a column of washing fluid passing through one of the pores.

Figure 6:
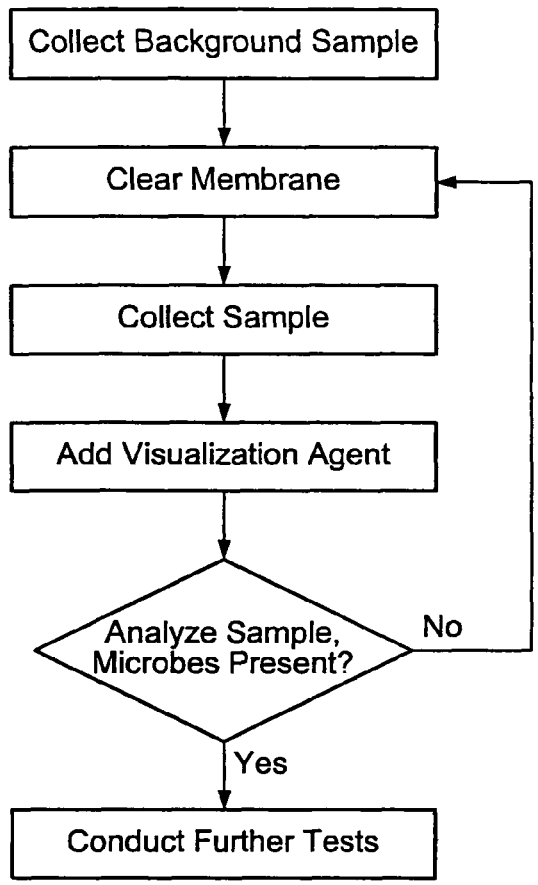
FIG. 6 depicts a flow chart of a method of collecting samples.

An analyte detection system may be used to determine the presence of analytes in a fluid system. One embodiment of a process for determining analytes in a fluid sample is depicted in the flow chart of FIG. 6. Prior to the analysis of any samples, a background sample may be collected and analyzed. Solid analytes are typically collected and stored in a liquid fluid. The liquid fluid that is used to prepare the samples may be analyzed to determine if any analytes are present in the fluid. In one embodiment, a sample of the liquid fluid used to collect the solid analytes is introduced into an analyte detection device to determine the background "noise" contributed by the fluid. Any particles collected by the membrane during the background collection are viewed to determine the level of particulate matter in the liquid fluid. In some embodiments, particles collected by the membrane during the collection stage may be treated with a visualization agent to determine if any analytes are present in the liquid fluid. The information collected from the background check may be used during the analysis of collected samples to reduce false positive indications.

After collection of the background sample, the membrane may be cleared using either a back flush wash or a lateral wash, as described herein. After clearing the membrane, the system may be used to analyze samples for solid analytes (e.g., microbes). As used herein the term "microbes" refers to a variety of living organisms including bacteria, spores, viruses, and protozoa. As the collected sample is passed through the porous membrane, the porous membrane traps any particles that have a size that is greater than the size of the pores in the porous membrane. Collection of particles may be continued for a predetermined time, or until all of the collected sample has been passed through the membrane.

After collection, the particles collected by the membrane may be analyzed using a detector. In some embodiments, the detector may be a camera that will capture an image of the membrane. For example, a detector may be a CCD camera. Analysis of the particles captured by the membrane may be performed by analyzing the size and/or shape of the particles. By comparing the size and/or shape of the particles captured by the membrane to the size and shape of known particles the presence of a predetermined analyte may be indicated. Alternatively, microbe analytes will react to a variety of visualization agents (e.g., colored and fluorescent dyes). In one embodiment, the detection of microbe analytes may be aided by the staining of the microbe with a visualization agent. The visualization agent will induce a known color change or impart fluorescence to a microbe. In an embodiment, particles captured by the membrane are stained and the particles analyzed using an appropriate detector. The presence of particles that have the appropriate color and/or fluorescence may indicate the presence of the analyte being tested. Typically, non-microbe particles (e.g., dust) will not undergo the same color and/or fluorescent changes that microbes will when treated with the visualization agent. The visualization agent may include a "cocktail" mixture of semi-specific dyes, which may be designed to mark microbes of interest. Selection of the mixture may be based on the capacity of the dye chromophore to create an optical fingerprint that can be recognized by a detector and associated imaging software as being associated with specific pathogenic bacteria or spores, while at the same time distinguishing from the signal exhibited by dust and other background particulate matter.

The analysis of the particles may indicate that an analyte of interest is present in the sample. In this case, the particles may be flushed from the membrane and sent out of the system for further testing. Further testing may include techniques such as cultures or ELISA techniques that may allow more accurate determination of the specific analytes present. Alternatively, the particles may be sent to a sensor array, as described herein, for further testing. If no significant amounts of analytes are found on the membrane, the membrane may be washed and other samples analyzed.

In an embodiment, user-defined threshold criteria may be established to indicate a probability that one or more specific microbes are present on the membrane. The criteria may be based on one or more of a variety of characteristics of the image. In some embodiments, the criteria may be based on pixel or color fingerprints established in advance for specific microbes. The characteristics that may be used include, but are not limited to, the size, shape, or color of portions of matter on the image, the aggregate area represented by the matter, or the total fluorescent intensity of the matter. In an embodiment, the system may implement an automated counting procedure developed for one or more pathogenic and non-pathogenic bacteria.

In an embodiment, the membrane system may include a computer system (not shown). Computer system may include one or more software applications executable to process a digital map of the image generated using detector. For example, a software application available on the computer system may be used to compare the test image to a pre-defined optical fingerprint. Alternatively, a software application available on computer system may be used to determine if a count exceeds a pre-defined threshold limit.

A detector may be used to acquire an image of the analytes and other particulate matter captured on a membrane. Microbes may collect on a membrane along with dust and other particulate matter and be captured in an image produced from a detector. The image acquired by the detector may be analyzed based on a pre-established criteria. A positive result may indicate the presence of a microbe. The test criteria may be based on a variety of characteristics of the image, including, but not limited to, the size, shape, aspect ratio, or color of a portion or portions of the image. Applying test criteria may allow microbes to be distinguished from dust and other particulate matter. During analysis, the flow of sample through from a fluid delivery system may be continued.

In some embodiments, a positive result may create a presumption that the fluid contains a particular analyte. If the image yields a positive result with respect to the test criteria, a sample of the fluid may be subjected to a confirmatory or specific testing. On the other hand, if the image yields a negative result with respect to the test criteria, membrane may be rinsed and the preceding method may be carried out for fluid from another sample.

During analyte testing a sample may be introduced into the analyte detection device. A trigger parameter may be measured to determine when to introduce the visualization agent into the analyte detection device. Measurement of the trigger parameter may be continuous or may be initiated by a user. Alternatively, the stain may be introduced into the analyte detection device immediately after the sample is introduced.

In one embodiment, the trigger parameter may be the time elapsed since initiation of introducing the fluid into an analyte detection device at a controlled flow rate. For example, the stain may be introduced 20 seconds after initiation of introducing the fluid sample into an analyte detection device at a flow rate of 1 milliliter per minute. In another embodiment, the trigger parameter may be the pressure drop across the membrane. The pressure drop across the membrane may be determined using a pressure transducer located on either side of the membrane.

In another embodiment, the trigger parameter may be the autofluorescence of analytes captured by the membrane. A detector may be switched on until a pre-defined level of signal from the autofluorescence of the analytes has been reached. In still another embodiment, filtering software may be used to create a data map of the autofluorescence of the matter on the membrane that excludes any pixels that contain color in a blue or red spectral range. The data map may be used to compute a value for particles that are autofluorescent only in the "pure green" portion of the visible spectrum.

In some embodiments, a presumptive positive result may be inferred if the trigger parameter exceeds a certain value without applying a stain. For example, a presumptive positive result may be inferred where the autofluorescence value is more than twice the value that would indicate application of a stain. In such a case, the application of a stain may be dispensed with and a confirmatory test may be conducted for the sample.

If the value of the trigger parameter is less than would indicate proceeding directly to the confirmatory test, but exceeds the value established to trigger the application of a stain, then a stain may be introduced into an analyte detection device.

Collecting a sample of a fluid may include gathering a sample from a solid, liquid, or gas. In some embodiments, the sample may be derived from collecting air from a target environment in an aerosol form, then converting aerosol into a hydrosol. For example, particles from 500 liters of an air sample may be collected deposited into about 0.5 milliliters of liquid. U.S. Pat. No. 6,217,636 to McFarland, entitled "TRANSPIRATED WALL AEROSOL COLLECTION SYSTEM AND METHOD," which is incorporated herein by reference as if fully set forth herein, describes a system for collecting particulate matter from a gas flow into a liquid using a porous wall.

In one embodiment, a system as described above, may be used to determine the presence of anthrax spores or bacteria. Collection of air samples in a potentially contaminated area may be concentrated in a fluid sample using an aerosol collector. The fluid sample may be passed through a membrane based detector system as described herein. The membrane based detection system may collect any particle collected by the aerosol collector. The particles collected may be treated with a visualization agent that includes stains that are specific for anthrax bacteria. Such visualization agents are know to one of ordinary skill in the art. The presence of particles that exhibit the appropriate color/fluorescence may indicate that anthrax is presence. The indication of anthrax may be further determined by additional confirmation testing.

Experimental

Flow Cell

The flow cell assembly was created from a 3-piece stainless steel cell holder consisting of a base, a support and a screw-on cap. Two circular polymethylmethacrylate (PMMA) inserts house the NUCLEPORE® membrane. These two PMMA inserts have been drilled along their edge and side to allow for passage of the fluid to and from the chip through stainless steel tubing (#304-H-19.5, Microgroup, Medway, Mass.). The tubes, which were fixed with epoxy glue in the drilled PMMA inserts had an outer diameter of 0.039" (19.5 gauge), and a 0.0255-0.0285" inner-diameter. The basic components of the flow cell are two disc-shaped PMMA "inserts". The bottom PMMA insert is modified in order to feature a drain and to contain a plastic screen disc (Celcon acrylic) that acts as a support for the filter. Each insert features a length of stainless steel tubing, which enters a hole in the side of the PMMA disk. The top insert also features an additional outlet which is used when regeneration of the filter is needed. Silicone tubing is snapped on the stainless steel tubing, and as such is readily compatible with a wide range of fluidic accessories (i.e., pumps, valves, etc.) and solvents. The flow cell was shown to be resistant to leaks and pressures generated by flow rates as high as 20 mL/min.

Fluid Delivery, Optical Instrumentation and Software

The complete analysis system shown in FIGS. 3, 4, and 5 includes a fluidics system composed of four peristaltic pumps ($p_1$, $P_2$, $P_3$, and $P_4$), dedicated to the delivery of the analyte collected from the air, antibody, wash buffer to the flow cell, and clean-up off the flow cell in the regeneration mode. Its integrated software was used to assure fluid delivery to the chip, and accommodate wash cycles through the proper use of valves. The sample, antibody, PBS, and regeneration lines are also filtered (pre-filters $f_1$, $f_2$, $f_3$, and $f_4$) to screen out large particulate matter. Pre-filter $f_1$ is a NUCLEPORE® membrane with a pore size of 5 μm. Pre-filters $f_2$, $f_3$, $f_4$ are 0.4 μm NUCLEPORE® membranes. Spores which size is smaller than the pores of pre-filter $f_1$ are passed through the filter and captured in the analysis flow cell, positioned on the motorized stage of a modified compound BX2 Olympus microscope. The microscope is equipped with various objectives, optical filters, and a charged-coupled device (CCD) camera which operation can be automated.

A Mercury lamp was used as the light source. Fluorescence images shown in this report were obtained with a FITC filter cube (fluoroisothiocyanate, 480 nm excitation, 505 long pass beam splitter dichroic mirror, and 535±25 nm emission), and captured by a DVC 1312C (Digital Video Company, Austin, Tex.) charge-coupled device (CCD) mounted on the microscope and interfaced to Image Pro Plus 4.0 software (Media Cybernetics). Areas of interest of the images of the array for were selected in an automated fashion and used to extract numerical values of the red, green, and blue (RGB) pixel intensities.

Reagents

Phosphate buffer saline (PBS), pH 7.4, was purchased from Pierce_(# 28374, 0.008M $Na_3PO_4$, 0.14M NaCl, 0.01M KC1). The content of the pre-weighted pack was dissolved in 500 mL dI water. After complete dissolution, the buffer solution was filtered using a 60 mL disposable syringe (Becton Dickinson #309654) and a 0.2 mm pore size syringe filter (Whatman 25 mm, 0.2 mm Polyethersulfone (PES) filters #6896-2502). Polyoxyethylene-Sorbitan Monolaurate (Tween-20) and Bovine Serum Albumine (BSA) were purchased from Sigma (# P-1379, and # A-0281). The anti-bg antibody was generously given to us by Tetracore, and tagged with a fluorophore. The naked Antibody was labeled according to the protocol described in the ALEXA FLUOR® 488 Protein labeling kit from Molecular Probes (now Invitrogen; Eugene, OR) (# A-10235), and stored at 4° C. The final concentration of the labeled anti-bg was 0.5 mg/mL. When prepared for the assay the antibody was diluted 50 times in a filtered (3 mL Disposable Syringes from Becton Dickinson # 309574; Syringe Filters from Pall Gelman 13 mm, 0.2 μm Acrodisc CR Polytetrafluoroethylene PTFE # 4423) solution of 1% BSA/PBS (0.01 g of BSA per mL of PBS). The spore preparations were given to us by Edgewood/Dugway Proving Grounds. For their evaluation, the spores were membered onto Petri dishes and grown with Luria Bertani plating medium. The medium is composed of Bacto Tryptone, Bacto Yeast Extract, Agar Technical purchased from Difco (# 211705, # 212750, # 281230 respectively), and NaCl purchased from EM (# SX0420-1). Distilled Water, de-ionized with a Barnstead Nanopure Column was autoclaved for 30 min. at 121° C. to sterilize it.

Polymer Microsphere Solutions

The fluorescent polymer green microspheres were purchased from Duke Scientific Corporation (Palo Alto, Calif.). A bead stock solution was prepared by diluting several drops of the original bead solution in 500 mL of DI water. A bright line counting chamber, or hemacytometer (Hausser Scientific, Horsham, Pa.) was used to determine the exact concentration of this solution. The concentration of a solution is typically obtained from the average of several measurements following a well established protocol. The concentration of our stock solution was found to be 1,883,750 beads/mL±8539 or a relative standard deviation of 0.45%. For the solutions used in FIG. 3 and FIG. 4, we used a 1 to 50 dilution of the stock solution, and added 50 μL, 100 μL, 150 μL, 200 μL, and 250 μL of that solution to the same flow cell, and captured images at different magnifications.

Bg Spore Solutions Preparation

A 1 mg/mL spore stock solution (A) was prepared in sterile water by suspending x mg of spores in x mL of sterile water. Solutions B, C, D, E, F, G, H and I with respective concentrations of 10e-1, 10e-2, 10e-3, 10e-4, 10e-5, 10e-6, 10e-7, and 10e-8 mg/mL were obtained by serial dilution of the stock solution A.

Bg Spore Solutions Characterization

Figure 7:
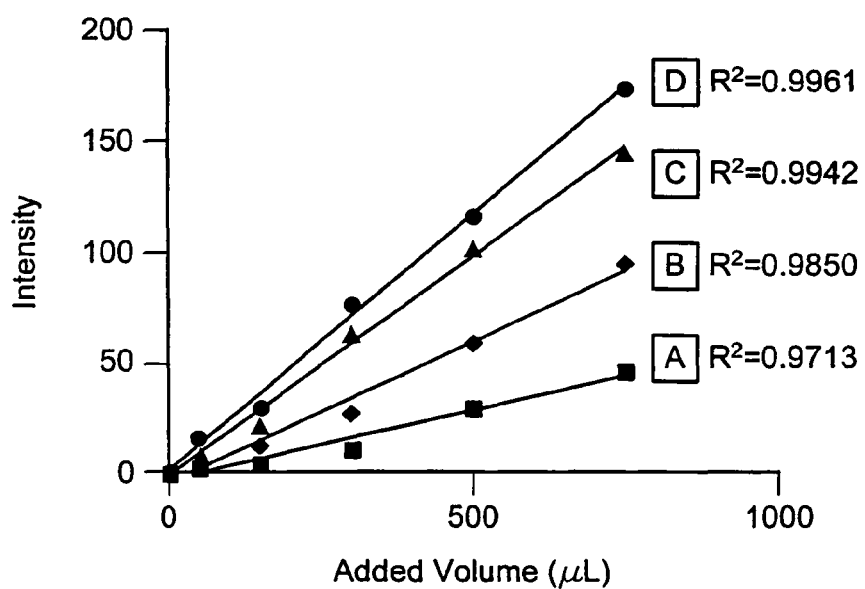
FIG. 7 depicts a graph of calibration bead intensity vs. amount of sample added.

The concentration of spores per mg of preparation was evaluated by growing colonies in a Luria Bertani culture media and expressed in Colonies Formation Unit (CFU) per mg of spore. 15 g of Bacto Tryptone, 7.5 g of Bacto Yeast Extract and 15 g of NaCl were dissolved in 1.5 L of s Bead Tests In order to determine the functionality as well as the analytical validity of our system, we tested our integrated system with 2.3 μm and 1 μm fluorescent polymer microspheres (purchased from Duke Scientific Corporation). The size of these particles was chosen to best simulate populations of spores and bacteria. The calibration curves displaying the average density per pixel as a function of added volume are shown in FIG. 7. Examination of these graphs reveals that the linearity of the detected response is not affected by the magnification. However, as expected, the slope of the regression lines increases with increasing magnification as the signal from the beads is brighter at high magnification. Many factors, such as the size and brightness of the bacteria or spores, the total area of the membrane exposed to the analyte, the field of view, dictate the experimental parameters to be used. Because they are very homogeneous in size and intensity, polymeric beads represent an ideal calibrator and simulant for spores. However, the actual size of spores is slightly smaller than that of the beads that were used, and the signal produced from a single spore-antibody-fluorophore complex is much less intense than that of the microspheres. Additionally, fluidics concerns prevent us from using too small a filter area, because the internal pressure is greatly raised as the fluid is forced through a dramatically reduced number of pores. Because the magnification does not change the linearity of the calibration curves as shown in FIG. 7, and in order to accommodate a sustained flow through the flow cell, an objective of 5×, for a total magnification of 100× was chosen for the assay.

Spores and Bacteria

To illustrate the capabilities of our detection system, we targeted *Bacillus globigii* (*Bg*), a commonly used non-pathogenic simulant for *Bacillus anthracis* (*Ba*). An immuno-assay was created, based on the capture of Bg spores and their interaction with a Bg-specific antibody resulting in the formation of an immuno-complex. The effect of possible interferences in the assay was also tested with a variety of species such as yeast, talc powder, and other species of Bacillus as will be discussed later in this report. In FIG. 5 is shown a fluorescent micrograph of Bg spores stained with an ALEXA FLUOR® 488-labeled anti-*Bacillus globigii* antibody. The schematic of the immuno-complex is shown in the inset. In order to demonstrate the specificity of the interaction of the anti-Bg antibody with the Bg spores, we conducted some correlation studies between the fluorescence micrographs and the images obtained from transmission electron microscopy (TEM) and scanning electron microscopy (SEM). An aliquot of immuno-labeled Bg was placed on a Formvar-coated TEM finder grid, and epifluorescence micrographs were obtained at various magnifications. The grids were then imaged with transmission electron microscopy (TEM), after which they were coated with gold palladium and imaged with scanning electron microscopy (SEM). As illustrated by the correspondence of the fluorescence signal with the position of the spores, the finder grid made it possible to unequivocally locate the same area in each instrument, clearly indicating that the fluorescence signal arises from the ALEXA FLUOR® 488-tagged antibody that is specifically binding to the Bg spores. Fluorescence micrographs obtained at a total magnification of ≈400× are shown in order to better represent this correlation. However, the correlation of the fluorescence signal from spores with TEM or SEM micrographs is also established with magnification as low as ≈100×.

To determine the limit of detection of our system, we conducted a dose-dependence study. Solutions of spores were prepared by serial dilution of a stock spore solution, presuming that 1 mg of dry spores per mL yields $10^8$ spores per mL. Following the flow cell experiments, aliquots of the spore solutions were analyzed to determine the exact spore concentration in terms of colony forming units per mL (CFU). The background was determined as the signal obtained after passage of the antibody through a blank filter and subsequent rinsing with PBS. In order to assess the limit of detection, the standard deviation was calculated from the average of 5 such measurements of the background. The limit of detection was established to be 900 spores.

As the internal volume of the flow cell is very small, it is necessary to flush out all contaminants in order to avoid clogging of the membrane filter. Of particular importance for these studies is the control of dust, commonly and abundantly found in the postal environment. SEM studies (not shown) have demonstrated that the dust produced through transport, manipulation, and processing of postal mail, contains fibers, debris, and various kinds of bacteria. Most significantly, dust contains a large number of particles with a wide size distribution encompassing the size range of the biological agents of interest. Furthermore, many of the dust components exhibit autofluorescence, due to the use of fluorescent brighteners and inks in the paper and document industries. Many of the trigger systems currently used in military type detectors repose on size selection principles such as Aerodynamic Particle Sizing (APS) or Flow Cytometry (FC), and for the reasons exposed previously, do not appear as the ideal trigger systems. Our system was tested in a blind study against triggering by yeast, talc, and powdered detergents. The rate of success was 100% as no false positive was generated. Another major potential problem arising from accumulation of dust in our system is clogging of the NUCLEPORE® membrane. We have conducted studies which showed that failure of the flow cell operation occurs only after 60 mg of dust are passed through, building a pressure greater than 60 psi, corresponding to 400 hours of postal operation, assuming that the concentration of dust reaching the flow cell is an average 6.2 μg/L. However, this result is widely dependent on the efficiency of the aerosol system and it is based on the assumption that the aerosol collection system has a built-in capability of discarding at least 95% of dust particles of 10 μm or higher. In these conditions, even though the accumulation of dust in the flow cell is inevitable in the long run, the device still exhibits a lifetime well above that desired for military applications. Additionally, we have shown that it is possible to regenerate the flow cell and extend its lifetime by flushing out up to 99% of the dust, spores, or debris accumulated on the filter. This function can easily be implemented through the use of an additional outlet within the top insert of the flow cell, and implementation of an automated flush protocol. A combined method of sonication, backflow, and lateral flow is used to eliminate unwanted material from the membrane. This allows for extended operation of the detection system without the attention of a technician. The removal of spore-sized (0.93 μm) fluorescent polymer microspheres from the membrane surface during five consecutive trials was performed. Surface plots in column i represents the initial loading of the membrane in the flow cell. Efficiencies of 95%, 98%, 99%, 99%, 99% is reached, respectively, for the five trials.

Pixel Analysis Methods for Detection of Microbes

In some embodiments, pixel analysis methods may be used in the analysis of an image of a fluid or captured matter. For example, pixel analysis may be used to discriminate microbes from dust and other particulate matter captured on a membrane. Pixel analysis may include analyzing characteristics of an image to determine whether a microbe is present in the imaged fluid.

Pixel analysis may be based on characteristics including, but not limited to, the size, shape, color, and intensity ratios of an image or portions of an image. As an example, the total area that emits light in an image may be used to conduct analysis. As another example, the green fluorescent intensity of an image may be used to conduct analysis. In an embodiment, an "optical fingerprint" for a specific microbe or set of microbes may be established for use in pixel analysis. In some embodiments, pixel analysis may be based on ratios between values, such as an aspect ratio of an element of matter captured on an image. In other embodiments, pixel analysis may be based on threshold values.

During use, a visualization agent may cause different particles to emit different wavelengths of light depending on the nature of the particle. When the particles are analyzed with a camera, a user may be able to determine if a particular analyte is present based on the color of the particle. For example, a green particle may indicate the presence of an analyte of interest. Any other colored particles may not be of interest to a user. While a person may be able to discern between colors, it is desirable for a computer system to also be able to discern different colors from a membrane sample. Many detectors can only discern specific colors when analyzing an image. For example, many CCD detectors can only discern red, blue and green colors. Thus, a CCD detector may not be able to discern the difference between a particle that emits both blue and green light and a particle that just emits green light, although the color difference may be apparent to a person using the system. To overcome this problem a method of subtracting out particles having the "wrong" color may be used.

In some embodiments, pixels of an image that do not fall within a color range specified by a user may be discarded from the image. In one embodiment, a fluid may be stained to cause a microbe of interest to emit light in only the green portion of the visible spectrum. By contrast, dust and other particles contained in the fluid may emit light in combinations of green, blue, and red portions of the visible spectrum in the presence of the stain. To isolate the portion of the image that represents only the microbe of interest, binary masks may be created to eliminate light emissions caused by non-microbial matter from the image.

Figure 8A:
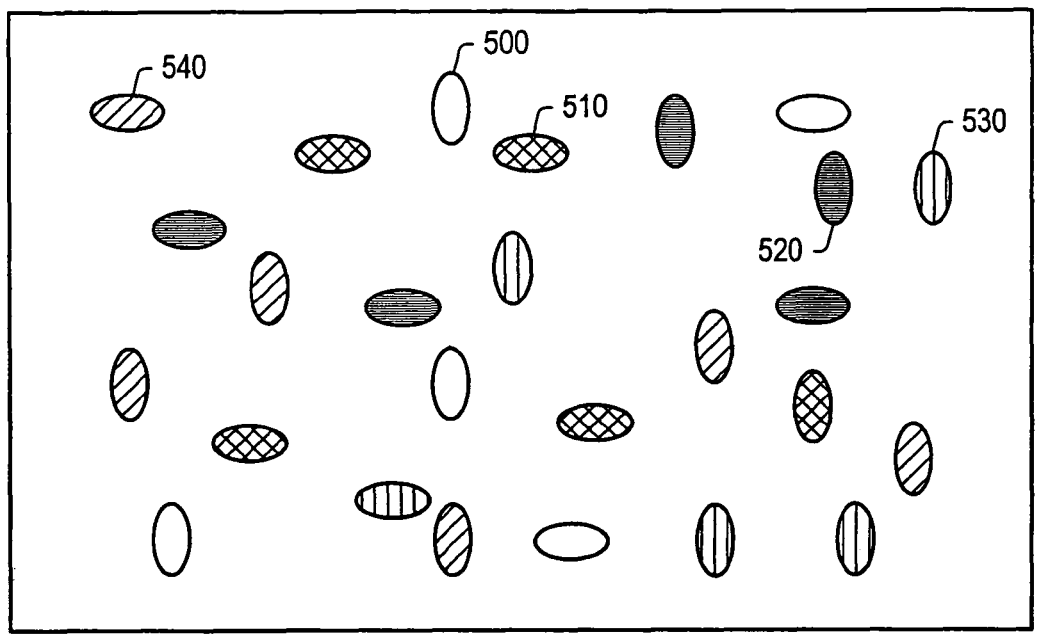
FIGS. 8A-8F depict a method of analysis of particles captured by a membrane.

Such a method is depicted in FIGS. 8A-F. FIG. 8A shows an image of all particles captured by a membrane. For purposes of this example, particles 500, having the no fill pattern, exhibit a green color; particles having a fill pattern identical to the fill pattern of particle 510 have a red color; particles having the a fill pattern identical to the fill pattern of particle 520 have both green and blue light absorption; particles having a fill pattern identical to the fill pattern of particle 530 have both red and blue light absorption; and particles having a fill pattern identical to the fill pattern of particle 540 have a blue color. It should be understood that these color assignments are for illustrative purposes only. In the current example, the goal of the analysis is to find all of the green particles.

Figure 8B:
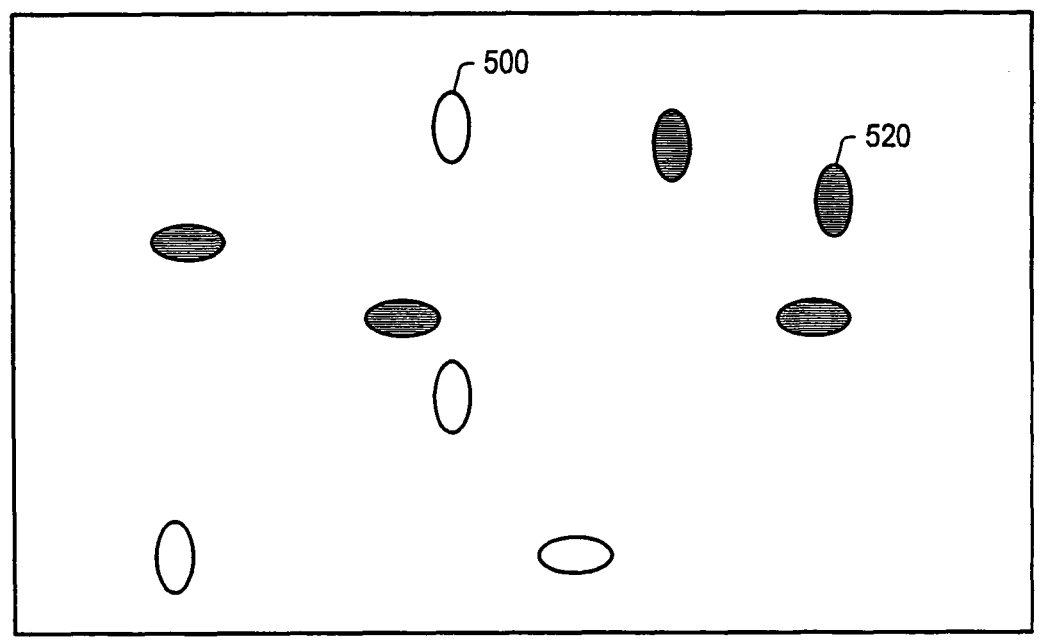
Figure 8C:
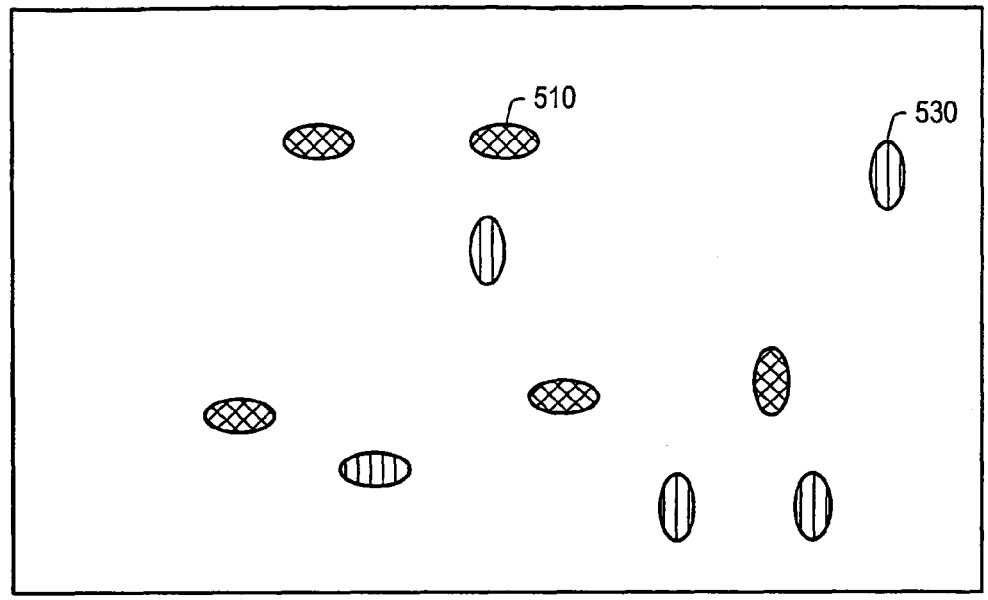

One method of finding the green particles is to use a filter that will allow only particles that are green are shown. FIG. 8B depict the particles that would remain if such a filter is used. All of the particles shown in FIG. 8B have a green light absorption, however, not all of the particles that are depicted in FIG. 8B would exhibit a green color only. Particles 520 absorb both green and blue light. Since the detector can't differentiate between the two types of particles, a false positive may result.

Figure 8D:
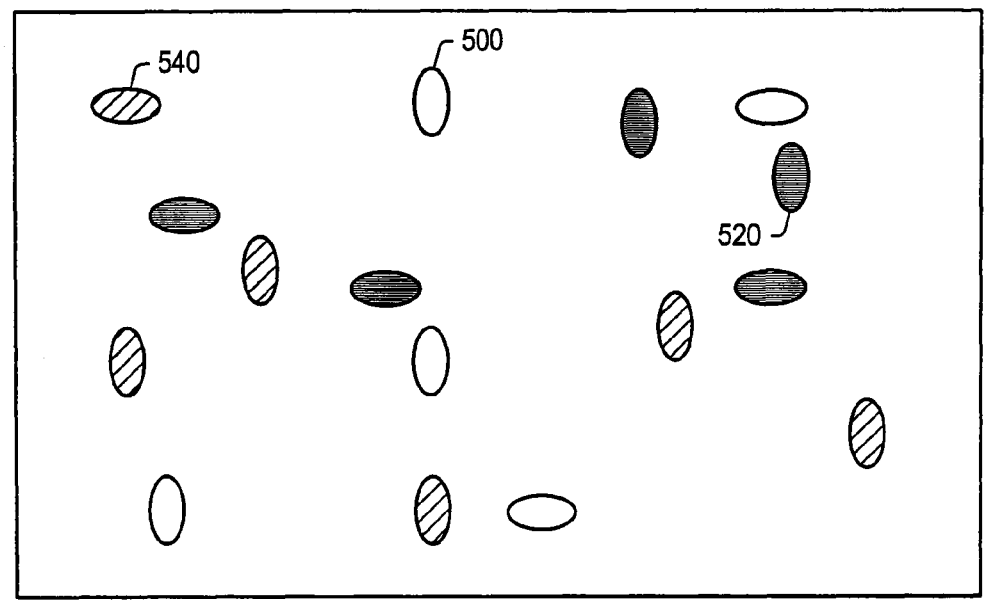

To compensate for this phenomena, images of particles that absorb blue and red are also analyzed using appropriate filters. By creating masks of which particles exhibit blue and red absorption, a process of elimination may be used to determine how many green particles are present. In an embodiment, an image is then captured of only the particles that exhibit color in the red portion of the spectrum (See FIG. 8C). The image of "red" particles is used to create a mask that may be compared to the full spectrum view of the particles. Since the analytes of interest only exhibit color in the green portion of the spectrum, any particle with color in the red portion of the spectrum may be removed from the original image. FIG. 8D shows the original image but with the particles that appear in the red portion of the spectrum subtracted from the image. The remaining particles are potential particles that may be the analyte of interest.

Figure 8E:
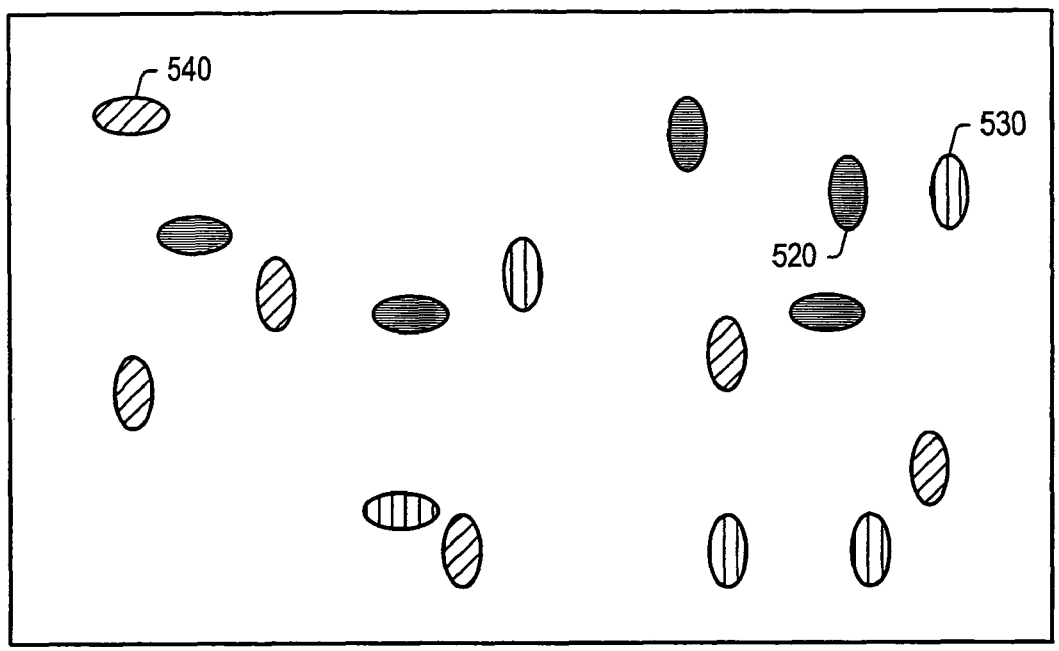
Figure 8F:
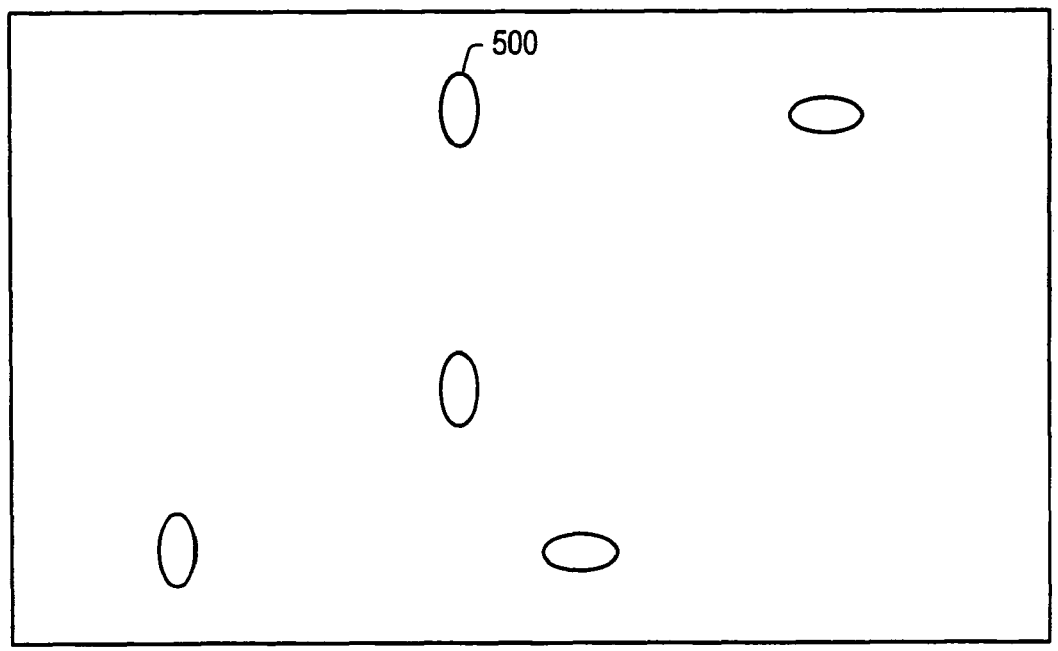

In a second iteration, FIG. 8E shows a binary mask that may be used to mask any pixels that include a blue component. An image is captured of only the particles that exhibit color in the blue portion of the spectrum (See FIG. 8E). The image of "blue" particles is used to create a mask that may be compared to the full spectrum view of the particles. Since the analytes of interest only exhibit color in the green portion of the spectrum, any particle with color in the blue portion of the spectrum may be removed from the original image. FIG. 8F shows the original image but with the red binary mask and blue binary mask applied so that pixels including a red or blue component are excluded. The particles that remain in the image are thus particles that only exhibit a green color. Thus, the method may be used to produce an image that includes only "pure green" pixels. Such an image may be analyzed to detect the presence of a microbe by eliminating particles that are not relevant. It should be understood that while the above recited example is directed to determining the presence of green particles it should be understood that the process can be modified to determine blue particles only, red particles only, or particles that exhibit combinations of colors (e.g., red and blue, red and green, blue and green, or red, blue and green).

In some embodiments, pixel analysis may be used in combination with the membrane method for detecting a microbe described herein. Pixel analysis may be conducted either before or after the application of a stain. In an embodiment, pixel analysis may be used to determine when to apply a stain.

After an analyte of interest is detected using a membrane based detection device further testing may be performed to identify the analyte. In one example, the particles captured by the membrane may be transferred to a sensor array as described in any of the patents and patent applications previously listed.

Figure 9:
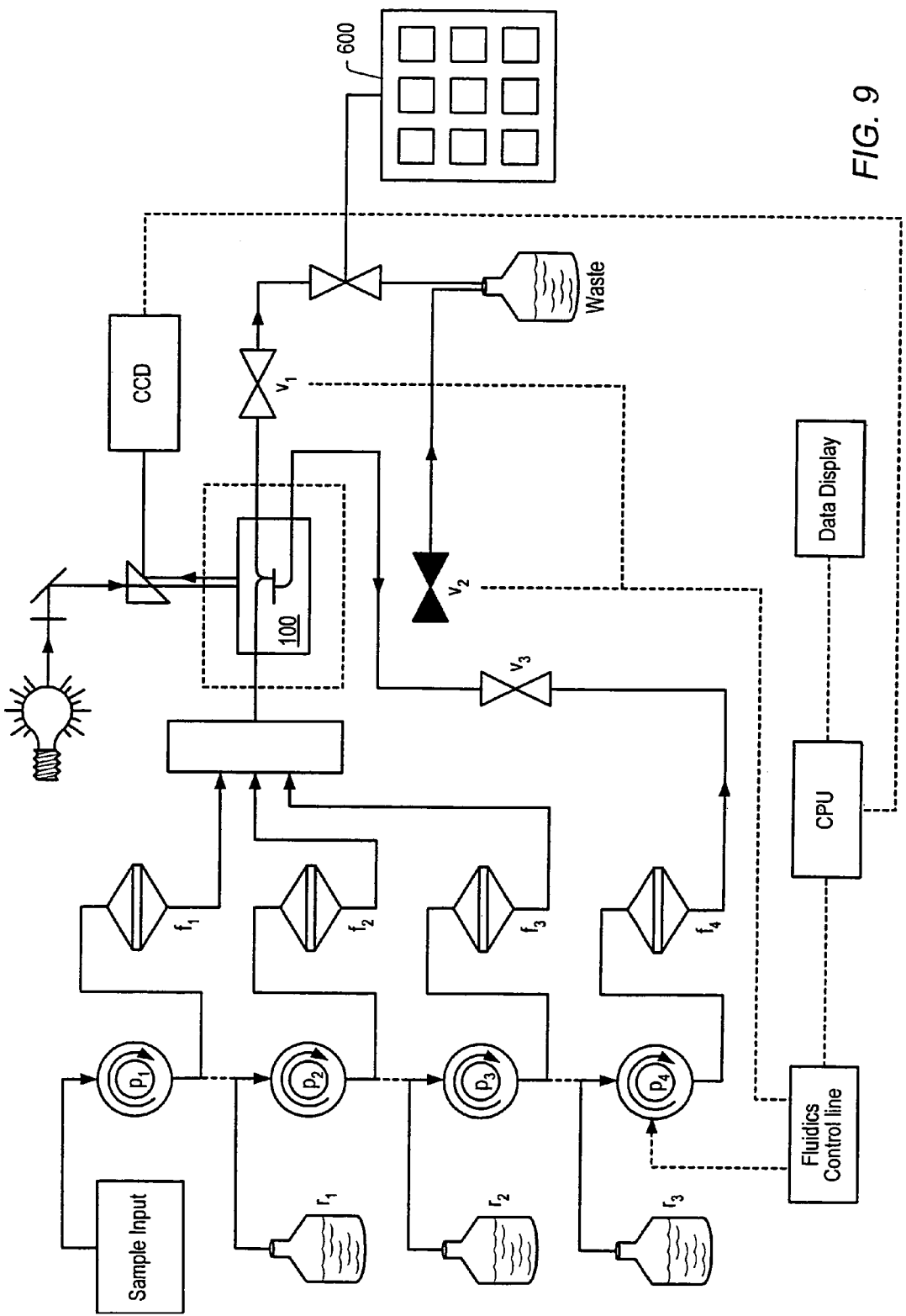
FIG. 9 depicts a schematic diagram of a membrane based analyte detection system that includes a sensor array detection device.

FIG. 9 depicts a system in which a particle sensor array detector 600 is coupled to a membrane analyte detection device 100. Membrane based analyte detection device may be part of an analyte detection system as previously described. After a sample is passed through a membrane, the particles collected by the membrane may be subjected to an additional test to further identify the analytes. In one embodiment, the analytes may be washed from the surface o the membrane and transferred to a sensor based analyte detection system, as described in any of the previously referenced patent applications. The analytes extracted from the sample may react with beads that are placed in a sensor array. The reaction of the analytes with the sensor array beads may allow confirmation (or further identification) of the analytes. Methods of detecting microbes using a sensor array system are described in further detail in the above-referenced patent applications.

Many microbes may not react with a bead of a sensor array. Large microbes may be unable to make proper contact with the bead and therefore are not detected by the bead. In one embodiment, the microbes are subjected to a treatment that allows better detection by a bead based detection system In one embodiment, the particles may be subjected to lysis conditions. Lysis of microbes will cause the disintegration or dissolution of the microbe. For bacteria, lysis may be induced by treatment with an alkali base or by use of enzymes. Lysis of the bacteria allows portions of the material contained by the bacteria to be released and analyzed. Typically, either proteins or nucleic acids released from the bacteria may be analyzed.

Microbes such as bacteria, spores, and protozoa in a fluid may be captured in the macropores of the beads. In some embodiments, receptors, including, but not limited to, selective antibodies or semi-selective ligands such as lectins, may be coupled to a particle in an internal pore region of the particle to create a selective bead. Suitable receptors may be selected using the methods described herein. In some embodiments, a visualization antibody may be introduced that may couple with the captured analyte. The visual antibody may yield a colorimetric or fluorescence signature that can be recorded by the CCD detector. In some embodiments, a series of selective and semi-selective beads may be used in conjunction with the sensor array system described herein.

In an embodiment, an agent that is known to bind or interact with a microbe may be introduced into a fluid prior to the time that the microbes are placed in proximity with a sensor array. Such agents may have characteristics that facilitate capture of a microbe by a particle in the sensor array.

Macroporous Particles

Figure 10:
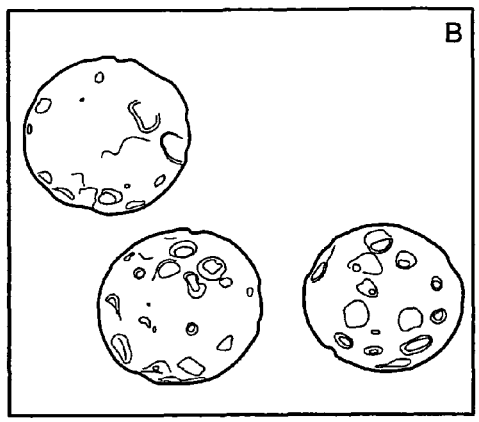
FIG. 10 depicts porous particles.

In an embodiment, a particle having macropores may be formed of agarose. A depiction of such a particle is shown in FIG. 10. A particle may be in the form of a spherical bead. The particle may include a plurality of macropores on its surface and interior.

In an embodiment, agarose may be used as a starting material for a macroporous particle because it is biocompatible and may be capable of interacting with biomolecules and living organisms. Activated agarose may demonstrate an affinity interaction with bacteria and microorganisms. To facilitate this interaction, specific properties on particles may be used to target specific microorganisms or cells. Processed agarose, in which sulfate groups have been eliminated from the agarose chain, may consist of an uncharged hydrophilic matrix with primary and secondary alcohols that can be used for activation and attachment. For example, the chemical surface of particles may be modified by oxidizing adjacent diols into aldehyde groups. Using sodium meta-periodate ($NaIO_4$) aliphatic aldehydes may be obtained that can be used in reductive amination coupling procedures.

In an embodiment, macroporous particles may be formed by suspension polymerization using a gel. Size, shape, and uniformity of the particle may depend on the hydrophilic or hydrophobic additives used to stabilize the emulsion. Pore size may be determined by agarose concentration of the gel. Mechanical properties, such as gel strength, may be affected by the molecular weight of the agarose. In one embodiment, suspension polymerization may be accomplished using a biphasic system containing the agarose monomer and emulsion stabilizers. A dispersion of a hydrophilic emulsifier (such as TWEEN 85) in cyclohexane may be added to a stirring aqueous solution of agarose at 60° C. for 5 min to produce an oil-in-water emulsion. Fine particles of agarose stabilized by the emulsifier may be formed in this step. Next, a solution of a hydrophobic emulsifier (such as SPAN 85) may be added to the first emulsion forming a water-in-oil emulsion. Afterwards, the water-in-emulsion may be cooled to room temperature. Polymeric particles may appear at about 40° C. The aggregation of droplets, which may be referred to as flocculation, may form a matrix with oil droplets that will form pores or conduits in the beads. The particles may be washed with distilled water and alcohol, sized with industrial sieves, and preserved in water.

Emulsifiers added to the hydrophilic and/or hydrophilic phases and the concentration of the agarose solution may influence the quality of the beads. Additionally, mixing speed, nature of the agitation, and temperature during the preparation process may be important. The stability of the solutions may depend on the selected emulsifiers and the solvents used.

A particle may be of a substantially spherical shape. Particles with spherical geometry may enhance the available area for surface interaction with the analytes. Creating pores within the particles may also increase surface area. Particles may have large connecting flow pores in addition to normal diffusion pores. A macroporous particle may have improved mass transfer properties compared to a non-macroporous particle.

A particle may have a diameter of between about 250-300 microns. Macropores in a particle may be less than about 1 micron. Different pore sizes and shapes may allow for the entrapment and detection of a variety of analytes, including, but not limited to, cells, bacteria, DNA oligomers, proteins/antibodies, and small molecules.

An alternative process to suspension polymerization may be the use of a foaming agent to vary the porosity of the particles. For example, the decomposition of azides or carbonates during polymerization may allow incorporation of nitrogen or carbon dioxide "bubbles" into the particles. Because the gelling point for agarose is 40° C., the decomposition reaction should be performed at low temperatures.

Another alternative to suspension polymerization may be the use of molecular imprinting. The imprinting of particles may occur by non-covalent and covalent methods. Non-covalent imprinting may be based on non-covalent interactions such hydrogen bonds, ionic bonds, and Van der Waals forces between functional monomer and a temmember. The stability of the monomer-temmember complex prior to polymerization may depend on the affinity constants between the temmember and the functional monomers. In the covalent method, the bonds formed between the functional monomer and the temmember may be cleaved once the polymerized matrix is obtained.

Within the covalent and non-covalent based approaches, there may be different methods for making molecular imprinted polymers. One approach may involve grinding the imprinted polymer to reduce their size to approximately 25 µm and expose the imprinted surfaces. Another technique, which may be referred to as 'surface temmember polymerization,' uses water and oil. In this technique, the water-soluble temmember may interact with the functional monomer at the water-oil interface. The complex monomer-temmember in the organic phase may be polymerized yielding a polymer-imprinted surface. This technique may allow the imprinting of water-soluble substances like zinc ions.

Other methodologies for imprinting polymers may be suitable. Molecular imprinting on microgel spheres may be a convenient procedure for imprinting agarose because the imprinted gel does not need to be reduced in size by grinding as in conventional molecular imprinting. Discrete imprinted microgels and imprinted microspheres may be synthesized by cross-linking polymerization of the monomer in the presence of the temmember, a process known as "precipitation polymerization."

Surface temmember polymerization and precipitation polymerization may be suitable alternative techniques to chemical surface modification of regular particles. Both techniques may be suitable for imprinting agarose with such temmembers as bacterial spores. A chromatography column mounted with imprinted beads may be a fast method for evaluating the efficacy of the imprinted beads. For example, bacteria may be re-bound, exposed to the fluorescent calcium-sensitive indicator known as calcein, and detected by fluorescence spectroscopy.

Molecular imprinting may allow the exploitation of organisms as reactors. The pores in the particle may facilitate feeding of entrapped microorganism reactants and cause them to produce a desired product. Molecular imprinting may be used for encapsulating bacteria such as the *Rhizobium* organisms into agarose. These bacteria may convert nitrogen from the atmosphere into ammonia. By "feeding" these bacteria nitrogen, ammonia may be produced. The pores encapsulating the bacteria may retain an imprint of the organism for morphologic studies of the bacteria's surface.

High-performance liquid chromatography and fluorescent assays may be a valuable tool for studying the molecularly imprinted polymers. The fluorescent dye acridine orange may stain agarose beads so they may be morphologically analyzed with confocal scanning laser microscopy. Other morphological studies include atomic force microscopy, scanning electron microscopy, and microtome techniques. Characterization of the surface area of the beads may be achieved by measuring the adsorption isotherm and using the Brunauer, Emmet, and Teller equation.

In some embodiments, the surface of a particle may be chemically modified. In other embodiments, chemical functionality, including, but not limited to non-specific (i.e., functional groups) and highly specific (i.e., bio-ligands such as antibodies) may be localized into the confines of the pore region. Chemical functionality may facilitate the entrapment of a variety of analytes.

In an embodiment, a particle may include a receptor that includes a particular metal. The metal may be capable of binding a material that is characteristic of a particular analyte. For example, a particle may be formed that includes terbium (III). Terbium (III) forms a luminescent complex with dipicolinic acid, a substance unique to spores.

EXAMPLE

Macroporous beads were prepared using the method for biphasic suspension polymerization method described herein. The beads so obtained were analyzed using light and fluorescence microscopy. The transparency of the agarose beads permitted the visualization of the fluorescent beads in different sections of the agarose beads. The presence of pores was confirmed by adding 1 μm fluorescent beads. Using light and fluorescence microscopy, the presence of conduits could not be conclusively determined. The beads accumulated into voids present in the bead, probably the ends of conduits.

Experiments were initially performed using Merck's Omnipure agarose powder. Low yields of non-spherical particles ranging between 250 and 300 μm were obtained. Experiments performed with an exaggerated amount of the hydrophilic emulsifier, 3.5 mL span 85 resulted in beads without pores but with a rough surface. By reducing the amount of the hydrophobic emulsifier, massive gellation due to the poor stabilization of the agarose particles in the oil in water emulsion occurred.

TABLE 1

Effect of the stirring speed on the fabrication of porous agarose beads
Agarose aqueous solution concentration 4% (w/v),
o/w emulsion: 0.7 mL tween 80/10 mL cyclohexane
w/o emulsion: 7 mL span 85/75 mL cyclohexane

| Stirring speed with a magnetic stirrer | Fluorescence and light microscopy | Apparent porosity | Efficiency Size 250-300 μm |
|---|---|---|---|
| 10 | With oil inclusions, regular integrity | A few | Less than 10% |
| 9 | Medium integrity | None | About 10% |
| 8 | Better integrity | A few but more than stir at 10 | About 10% |

The effect of stirring speed has been briefly evaluated. With higher stirring speeds the integrity of the beads was poor. Smaller particles are expected to be the result of faster stirring speeds, but exposure to higher physical stress only results in the disintegration of the beads. Trials performed under the same conditions using Sigma agarose gave similar results to Merck agarose, but with slightly higher yields around 20%. The integrity of the beads improved slightly suggesting better mechanical properties such as gel strength.

Experiments for producing homogeneous particles were performed using agarose obtained from Merck at a constant concentration of agarose solution and stirring. The results are shown in Table 2.

TABLE 2

Effect of the emulsifier on the fabrication of homogeneous agarose beads
Agarose aqueous solution concentration 4% (w/v),
o/w emulsion: 0.7 mL tween 80/10 mL cyclohexane
w/o emulsion: 7 mL span 85/75 mL cyclohexane

| Stirring speed with a magnetic stirrer | Fluorescence and light microscopy | Efficiency Size 250-300 μm |
|---|---|---|
| 10 | Opaque beads | About 10% |
| 10 | Regular integrity | About 10% |
| 10 | Bad integrity | Less than 10% |

Excessive stabilization of the water in oil emulsion causes reduced flocculation and increases the formation of fines resulting in a lower yield. Performing the same experiment with a fixed stirrer speed of 8 (Corning stirrer/hot member, model # PC420) slightly increased the yield. Magnetic stirring may not be appropriate for viscous solutions or the foam obtained during emulsification (creaming).

Bead Selection Techniques

Sensor arrays that use beads (either non-porous or porous) can be used to determine the presence of a variety of analytes. Typically, the beads include a receptor that binds to an analyte. The receptor may also bind to an indicator. The indicator typically produces a signal in the presence of an analyte that is different from a signal produced in the absence of an analyte. The selection of beads for use with a particular analyte may be important to the success of the sensor array. In general, a bead should have a high affinity for the analyte and produce an easily detectable signal. A method is described herein which may be used to determine an optimal receptor for a given analyte and indicator.

One method used to determine the presence of an analyte is a displacement assay. In a displacement assay a bead that includes a receptor is preloaded with an indicator. The indicator interacts (e.g., is bound to) the receptor such that the bead appears to have a specific color or fluorescence due to the indicator. When a solution that includes an analyte is brought into contact with the bead, the analyte may displace the indicator from the receptor. This displacement may cause a loss of color or fluorescence of the bead since the indicator is no longer associated with the bead. By measuring the loss of color or fluorescence of the bead, the presence of an analyte may be determined. The success of such an assay for determining the presence of an analyte is dependent, in part, on the interaction of the receptor with the analyte and the indicator. Generally, the bead should show a maximum color and fluorescence when an indicator is bound to the receptor, however, the indicator should be easily displaced by the analyte.

In one embodiment, a plurality of beads having a variety of receptors may be produced. In one embodiment, the receptors may be formed from a variety of different receptor types. Alternatively, the beads may have similar receptors. For example, techniques are well known to create libraries of peptide, peptide mimics, or nucleotides upon polymeric beads. For peptide libraries up to $20^n$ different beads may be produced in a library, where n is the number of amino acids in the peptide chain. Nucleic acid libraries may have up to $4^n$ different beads where n is the number of nucleic acid bases. Because of the large number of different beads in these libraries, the testing of each individual bead is very difficult.

Figure 11:
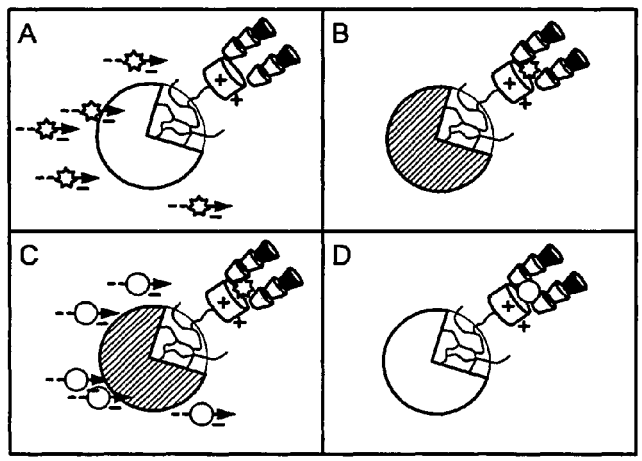
FIGS. 11A-D depicts a schematic diagram of a bead optimization method.

FIG. 11 depicts a schematic drawing of a method for optimizing a receptor on a bead. In FIG. 11A, a bead is depicted that includes a receptor X. Receptor X is composed of 6 subparts that extend from a base. The base is coupled to the bead. The bead is first contacted with an indicator, denoted as the stars in FIG. 11A. The indicator interacts with each of the beads in the library, binding to the receptors. FIG. 11B shows the indicator coupled to the receptor of the bead. As depicted in FIG. 11$b$, the color or fluorescence of the bead is altered due to the interaction of the indicator with the receptor. The change in color or fluorescence of the bead indicates that the bead is capable of interacting with the indicator.

Figure 12:
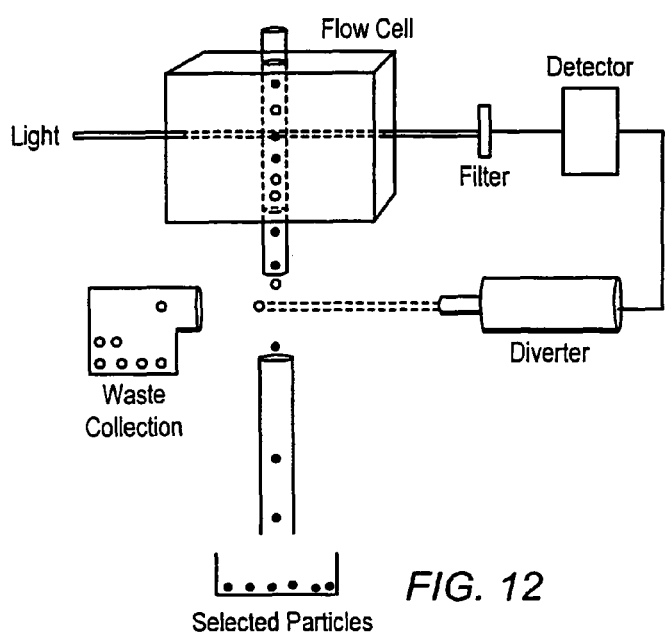
FIG. 12 depicts a schematic diagram of a flow cytometer.

When a plurality of beads is used, the indicator will bind to the beads at various strengths. The strength of binding is typically associated with the degree of color or fluorescence produced by the bead. A bead that exhibits a strong color or fluorescence in the presence of the indicator has a receptor that binds with the indicator. A bead that exhibits a weak or no color or fluorescence has a receptor that only weakly binds the indicator. Ideally, the beads that have the best binding with the indicator should be selected for use over beads that have weak or no binding with the indicator. FIG. 12 depicts a schematic of a flow cytometer that may be used to separate beads based on the intensity of color or fluorescence of the bead. Generally, a flow cytometer allows analysis of each individual bead. The beads may be passed through a flow cell that allows the intensity of color or fluorescence of the bead to be measured. Depending on the measured intensity, the bead may be collected or sent to a waste collection vessel, as indicated in FIG. 12. For the determination of an optimal bead for interaction with an indicator, the flow cytometer may be set up to accept only beads having an color or fluorescence above a certain threshold. Beads that do not meet the selected threshold, (i.e., beads that have weak or no binding with the indicator) are not collected and removed from the screening process. Flow cytometers are commercially available from a number of sources.

After the bead library has been optimized for the indicator, the beads that have been collected represent a reduced population of the originally produced beads. If the population of beads is too large, additional screening may be done by raising the intensity threshold. Now that the beads that exhibit optimal interaction with a receptor have been identified, the remaining beads are optimized for displacement of the indicator by the analyte of interest. Thus, the remaining beads are treated with a fluid that includes the analyte of interested, as depicted in FIG. 11C. The analyte is represented by the circle. For some beads, the analyte will cause displacement of the indicator, causing the color or fluorescence of the bead to be reduced, as depicted in FIG. 11D. The intensity of the color or fluorescence of the bead after it interacts with an analyte will be based on how the competitive displacement of the indicator. A bead that exhibits weak or no color or fluorescence when treated with an analyte is the most desirable. Such beads show that the analyte is readily bound by the receptor and can readily displace the indicator from the receptor.

Once again a flow cytometer may be used to determine the optimal beads for use in an assay. A library of beads that have been optimized for interaction with an indicator are treated with a fluid that includes an analyte. The treated beads are passed through a flow cytometer and the beads are separated based on intensity of color or fluorescence. The beads that exhibit a color or fluorescence below a predetermined intensity are collected, while beads that show a color or fluorescence above the predetermined intensity are sent to a waste collection. The collected beads represent the optimal beads for use with the selected analyte and indicator. The identity of the receptor coupled to the bead may be determined using known techniques. After the receptor is identified, the bead may be reproduced and used for analysis of samples.

The previously described sensor array systems and membrane-based systems may be used in diagnostic testing. Examples of diagnostic testing are described in U.S. application Ser. No. 10/072,800, entitled "METHOD AND APPARATUS FOR THE CONFINEMENT OF MATERIALS IN A MICROMACHINED CHEMICAL SENSOR ARRAY" filed Jan. 31, 2002 and published as U.S. Publication No. 2002-0197622-A1.

In many common diagnostic tests, antibodies may be used to generate an antigen specific response. Generally, the antibodies may be produced by injecting an antigen into an animal (e.g., a mouse, chicken, rabbit, or goat) and allowing the animal to have an immune response to the antigen. Once an animal has begun producing antibodies to the antigen, the antibodies may be removed from the animal's bodily fluids, typically an animal's blood (the serum or plasma) or from the animal's milk. Techniques for producing an immune response to antigens in animals are well known.

Once removed from the animal, the antibody may be coupled to a polymeric particle. The antibody may then act as a receptor for the antigen that was introduced into the animal. In this way, a variety of chemically specific receptors may be produced and used for the formation of a chemically sensitive particle. Once coupled to a particle, a number of well-known techniques may be used for the determination of the presence of the antigen in a fluid sample. These techniques include radioimmunoassay (RIA), microparticle capture enzyme immunoassay (MEIA), fluorescence polarization immunoassay (FPIA), and enzyme immunoassays such as enzyme-linked immunosorbent assay (ELISA). Immunoassay tests, as used herein, are tests that involve the coupling of an antibody to a polymeric particle for the detection of an analyte.

ELISA, FPIA and MEIA tests may typically involve the adsorption of an antibody onto a solid support. The antigen may be introduced and allowed to interact with the antibody. After the interaction is completed, a chromogenic signal generating process may be performed which creates an optically detectable signal if the antigen is present. Alternatively, the antigen may be bound to a solid support and a signal is generated if the antibody is present. Immunoassay techniques have been previously described, and are also described in the following U.S. Pat. Nos: 3,843,696; 3,876,504; 3,709,868; 3,856,469; 4,902,630; 4,567,149 and 5,681,754.

In ELISA testing, an antibody may be adsorbed onto a polymeric particle. The antigen may be introduced to the assay and allowed to interact with an antibody for a period of hours or days. After the interaction is complete, the assay may be treated with a dye or stain, which reacts with the antibody. The excess dye may be removed through washing and transferring of material. The detection limit and range for this assay may be dependent on the technique of the operator.

Microparticle capture enzyme immunoassay (MEIA) may be used for the detection of high molecular mass and low concentration analytes. The MEIA system is based on increased reaction rate brought about with the use of very small particles (e.g., 0.47 μm in diameter) as the solid phase. Efficient separation of bound from unbound material may be captured by microparticles in a glass-fiber matrix. Detection limits using this type of assay are typically 50 ng/mL.

Fluorescence polarization immunoassay (FPIA) may be used for the detection of low-molecular mass analytes, such as therapeutic drugs and hormones. In FPIA, the drug molecules from a patient serum and drug tracer molecules, labeled with fluorescein, compete for the limited binding sites of antibody molecules. With low patient drug concentration, the greater number of binding sites may be occupied by the tracer molecules. The reverse situation may apply for high patient drug concentration. The extent of this binding may be measured by fluorescence polarization, governed by the dipolarity and fluorescent capacity.

Cardiovascular risk factors may be predicted through the identification of many different plasma-based factors using immunoassay. In one embodiment, a sensor array may include one or more particles that produce a detectable signal in the presence of a cardiac risk factor. In some embodiments, all of the particles in a sensor array may produce detectable signals in the presence of one or more cardiac risk factors. Particles disposed in a sensor array may use an immunoassay test to determine the presence of cardiovascular risk factors. Further details regarding the use pf particle based sensor arrays for the detection of cardiac risk factors may be found in U.S. patent application Ser. No. 10/427,744 entitled "Method and System for the Detection of Cardiac Risk Factors" (Published as U.S. Publication No.: 2004-0029259-A1) and U.S. patent application entitled "Method and System for the Analysis of Saliva Using a Sensor Array" to McDevitt et al., filed on Dec. 13, 2004.

The sensor array may be adapted for use with blood. Other body fluids such as, saliva, sweat, mucus, semen, urine and milk may also be analyzed using a sensor array. The analysis of most bodily fluids, typically, will require filtration of the material prior to analysis. For example, cellular material and proteins may need to be removed from the bodily fluids. As previously described, the incorporation of filters onto the sensor array platform, may allow the use of a sensor array with blood samples. These filters may also work in a similar manner with other bodily fluids, especially urine. Alternatively, a filter may be attached to a sample input port of the sensor array system, allowing the filtration to take place as the sample is introduced into the sensor array.

In an embodiment of a sensor array, particles may be selectively arranged in micromachined cavities localized on silicon wafers. The cavities may be created with an anisotropic etching process as described in U.S. application Ser. No. 10/072,800, entitled "METHOD AND APPARATUS FOR THE CONFINEMENT OF MATERIALS IN A MICROMACHINED CHEMICAL SENSOR ARRAY" filed Jan. 31, 2002 and published as U.S. Publication No. 2002-0197622-A1.

In some embodiments, to observe the sensor array, a flow cell is mounted upon the stage of an optical imaging system To accommodate various detection schemes, the imaging system is outfitted for both brightfield and epifluorescence imaging. Appended to the imaging system is a computer controlled CCD camera, which yields digital photomicrographs of the array in real time. Use of a CCD may allow multiple optical signals at spatially separated locations to be observed simultaneously. Digitization also permits quantification of optical changes, which is performed with imaging software. As mentioned earlier, the flow cell is readily compatible with a variety of fluidic accessories. Typically, solutions are delivered to the flow cell with the assistance of a pump, often accompanied by one or more valves for stream selection, sample injection, etc.

As fluid samples are delivered to the flow cell, optical responses of the sensor array are observed and reported by the CCD camera. As such, the raw data produced by this platform are digital optical photomicrographs. Once an image has been captured, quantification of the particles' responses begins. Multiple areas of interest (AOIs) are defined within each image, typically corresponding to the individual particles. Average red, green, and blue (R, G, and B, respectively) pixel intensities are determined for each AOI, and exported as the raw numerical data. Software modules have been composed allowing many of these tasks to be performed in an automated fashion. Automated tasks include periodic acquisition of images, determination of AOIs (recognition of particles), extraction and exportation of numerical data to spreadsheet, and some data manipulation.

Several manipulations of the RGB intensities may be quantified for each particle in the array. In addition to the indicator particles, blank particles (ones containing no receptors or indicators) were also included in the array to serve as references for absorbance measurements. The $R_n$, $G_n$, and $B_n$ values were used to refer to the average intensities, in each color channel, for particle n. Similarly, $R_0$, $G_0$, $B_0$ values represented the average intensities, in each color channel, for a blank reference particle. "Effective absorbance" values for each color channel, $A_{Rn}$, $A_{Gn}$, and $A_{Bn}$, were then calculated using equations 3.1-3.3.

$$A_{Rn} = -\log(R_n/R_0) \qquad \text{Eq. 3.1}$$

$$A_{Gn} = -\log(G_n/G_0) \qquad \text{Eq. 3.2}$$

$$A_{Bn} = -\log(B_n/B_0) \qquad \text{Eq. 3.3}$$

These effective absorbance values were also normalized to their maximum value for a given experiment and were referred to as $A'_{Rn}$, $A'_{Gn}$, $A'_{Bn}$. The ratios of a given particle's different color intensities may also be calculated. For a given particle, n, the ratio of the red intensity over the green intensity was expressed as $(R:G)_n$, that of red over blue as $(R:B)_n$, and that of green over blue as $(G:B)_n$.

Figure 13A:
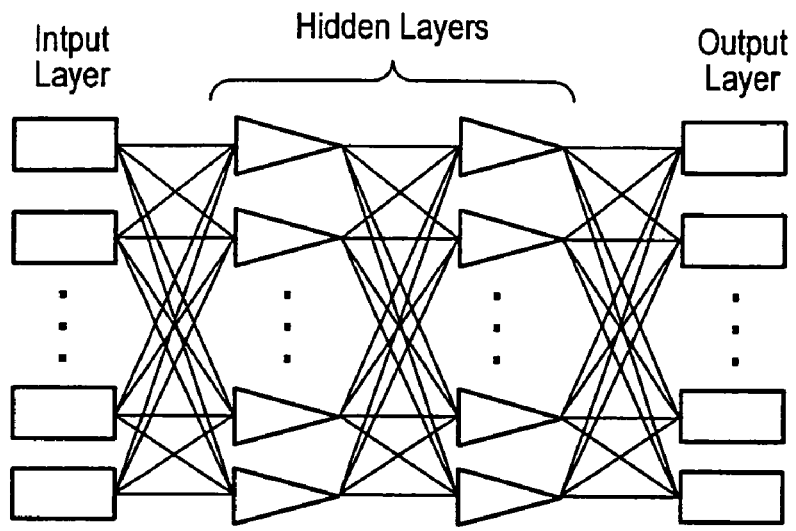
FIGS. 13A-B depict a schematic diagram of a multi-layer artificial neural network.

In order to create an array with broad analyte response properties and accurate measurement capabilities, it is necessary to develop procedures for translating optical changes into analyte quantification values. Here, the collective response of numerous particles and selective color channels must be considered. For this purpose, artificial neural network (ANN) methods were utilized due to their capacity to process multiple inputs. Multilayer Feedforward ANNs are the most popular ANNs and are characterized by a layered architecture, each layer comprising a number of processing units or neurons. An explanation of how a multi-layer ANN functions is facilitated by the schematic diagram provided in FIGS. 13A and B. In FIG. 13A is shown a generic representation of a multi-layer ANN. There is both an input layer and an output layer. The number of neurons in the input layer is typically equal to the number of data points to be submitted to the network. On the other hand, the number of neurons in the output layer may vary with the nature of the application (e.g. either one or multiple values may be appropriate as the network's output). Layers between the input and output are termed "intermediate" or "hidden" layers. Inclusion of hidden layers greatly increases a network's capabilities. However, there is a concomitant increase in complexity, which rapidly becomes computationally cumbersome, even with modern computers. Likewise, it is desirable to identify ANN methods that are both simple, yet effective, for the given application goals.

Figure 13B:
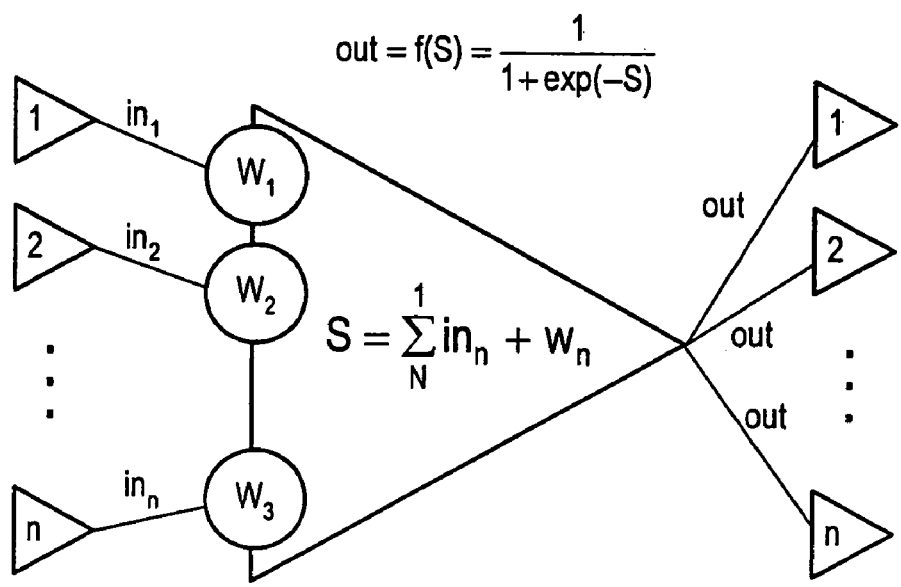

When data are submitted to the input layer of such an ANN, corresponding results are yielded in the output layer. The transformation of the data into the results occurs as the data or "signal" progresses through the layers of the network. To reveal how these transformations are made, FIG. 13B focuses on the interactions between three layers in a multi-layer ANN. From each neuron (1, 2, . . . , n) in the preceding layer, the centrally featured neuron receives an individual input ($in_1$, $in_2$, . . . , $in_n$). The neuron has a number of weight values ($w_1$, $w_2$, . . . , $w_n$) which correspond to the received inputs. The neuron assigns a weight to each of these inputs and subsequently calculates their weighted sum, S:

$$S = \sum_n^1 in_n * w_n \qquad \text{Eq. 3.4}$$

An output (out) is then generated by passing this weighted sum of inputs through a sigmoidal function, $$out = f(S) = 1/(1+\exp{-S}) \qquad \text{Eq. 3.5}$$

effectively narrowing the potential output range. This output value is then sent to every neuron in the subsequent layer of the network. Connecting lines between the neurons (such as those in FIG. 13A) are typically used to demonstrate that each neuron has such interactions with every neuron in the layers immediately preceding and following its own.

The accuracy (and consequent utility) of an ANN may be dependent upon its training. The training methods that may be utilized may be either the Levenberg-Marquardt (LM) algorithm or the Back Propagation algorithm (BP). The BP algorithm Typically, training involves gathering a large, representative data set (e.g., a simple calibration curve) and designating it as a training data set, including both inputs and corresponding desired outputs. Both the inputs and the desired outputs are supplied to the network, which then refines itself in an iterative manner. The network (whose architecture has been chosen by the user) processes the supplied inputs, yielding a set of outputs. These outputs are generated in the manner described above, initially using random values for the neurons' weights. The use of random weights produces nonsensical results, but provides the network with a necessary starting point. The network then refines itself by comparing its produced outputs with the desired outputs, and then altering its neurons' weights for the subsequent iteration in order to decrease the difference between the two. Each cycle comprising input submission, output generation, and weight adjustments, is referred to as an epoch. Training proceeds for a user-defined number of epochs, often on the order of 1000, even for relatively simple networks.

Once an ANN has been trained, the difference between the desired outputs of the training data set and the outputs actually generated by the network is quantified as the training error. Obviously, minimal training errors are desired. High training errors may be due to any number of factors, but can often be attributed to network architecture or insufficient training. More complex architecture (i.e., more layers and/or more neurons per layer) may improve the training error, but may also greatly increase the time and computational power required for training and use.

To assess the predictive ability of an ANN during the training process, a second iterative process may be employed. In a given iteration of this process, a single data point from the training data set is omitted, the ANN is trained on the remaining data, and then tested on the omitted point. This "leave-one-out" strategy is useful for evaluating the network's ability to extrapolate. It should be kept in mind, though, that this is a pseudo-extrapolation (in that the omitted test point originated in the training data). As such, the average error associated with this pseudo-external data is typically lower than that of truly external data (data gathered outside of the original training data set). The error measured when the ANN is used on truly external data is the most meaningful measure of the network's utility. However, many reports of chemical sensor arrays employing ANNs fail to distinguish between error values associated with truly external data and pseudo-external data. The extraction of intuitively useful trends is often difficult from many ANN studies described in the literature, making the targeted improvement of array members difficult.

Values of $R_n$, $G_n$, $B_n$; $A_{Rn}$, $A_{Gn}$, $A_{Bn}$, and $(R:G)_n$, $(R:B)_n$, $(G:B)_n$, are all considered for participation in the training network as input data. Raw intensity inputs such as $R_n$, $G_n$, $B_n$ are discarded early on in this study because they are found to be highly dependent on the light calibration setting and the size of the particle. However, using a "blank" particle to convert raw intensities to "effective absorbance" results in measurements that take into account possible fluctuations of the light source during the course of an experiment. As mentioned above, ANNs may be sensitive to the format of the inputs and sometimes necessitate the completion of data transformation or pre-processing of the inputs. Normalization of the absorbance readings homogenizes the data by transforming every measurement into a value between 0 and 1. Therefore, "effective absorbance" readings are also discarded as inputs in the network and replaced by $A'_{Rn}$, $A'_{Gn}$, $A'_{Bn}$. This switch presumably reduces the influence of error caused by variations in particle diameter. The use of color ratios provides a second method to reduce the noise contribution introduced by the selection of particles with a slight distribution in their sizes.

For network training, evaluation, and method selection, every recorded data set may contain replicates (or cases) for each data point through the acquisition of a sequence of images. Preliminary experiments tested the influence of the number of cases on the accuracy of the network. The main advantage of using multiple cases is to provide complex networks with a much greater number of data points than the number of connections between neurons. Further, the procedure allows for some of the data to be used in cross-validation.

It is generally recommended that the number of training cases be at least twice that of adjustable parameters in the network. The number of epochs necessary to train a given network may be assessed carefully by first introducing cross-validation cases in the training set. The inclusion of cross-validation data does not enhance the performance of the network to any great extent, but rather serves to limit the number of over-fitting occurrences. All data collection events are completed with at least one duplicate of each particle, and the same for the blank particle. The use of redundant inputs is intended to not only provide a back-up for each data type, but also to serve to increase the dimensionality of the network in order to optimize pattern recognition. However, despite the good particle-to-particle reproducibility observed in prior experiments, the performance of the network is found consistently to be greater with a single replicate for each particle rather than taking average values recorded from multiple similar type particles.

The preparation of functional shells within the polymer microspheres was accomplished via methods based on those outlined by Fourkas and coworkers (Farrer, R. A. et al. "Production, analysis, and application of spatially resolved shells in solid-phase polymer spheres", *Journal of the American Chemical Society* 124, 1994-2003 (2002)). Synthetic modification of a given microsphere entails immobilization of a species to the reactive sites of the particle. Intuitively, this begins at the particle's surface and proceeds inward in a radial manner. In the event that the coupling reaction between the solution borne species and the particle's reactive sites occurs more rapidly than the species' diffusion into the particle, the advancing reaction front will remain abrupt. At any point during the reaction, then, there are two distinct regions: a growing exterior region in which the reactive sites have been modified and a shrinking, unmodified core region. Thus, if the reaction is aborted prior to completion (i.e., before the advancing reaction front reaches the center of the particle) it will yield a microsphere with two distinct concentric regions. In theory, multiple such controlled-penetration reactions can be performed sequentially to yield additional shells.

As mentioned above, the utility of this technique is limited to scenarios in which diffusion of the species to be immobilized is the rate limiting step. If this is not the case, definition of the regions may be very poor or even nonexistent. Recently, however, Farrer et al reported an indirect method for the creation of discrete regions within polymer microspheres which circumvents the issue of diffusion vs. reaction rates, vastly broadening the range of species which may be immobilized in distinctly defined shells. Instead of directly immobilizing the desired species, temporary shells were created by capping peripheral reactive sites with a removable protecting group. With an exterior protected shell in place, the internal core region of the particle may be modified with a subsequent coupling reaction. Removal of the protecting group from the external region then yields a particle in which the core has been modified, but the exterior has not. In this manner, multishell particles are prepared from the core outward. Again, repeated protection/modification/deprotection cycles may be performed sequentially to increase the number of shells.

The key advantage to this indirect modification technique is that the sharpness of the interface between two shells is established by the protecting group. Variations on this technique, including the generation of five or more layers within individual particles, the simultaneous use of multiple orthogonal protecting groups, and the spatially resolved immobilization of three different species within particles. In all of these variations, though, the controlled penetration of the protecting group is used to define the shells. Thus, the spatial resolution of the shells is independent of the diffusion and reaction rates of the species to be immobilized within them.

Figure 14:
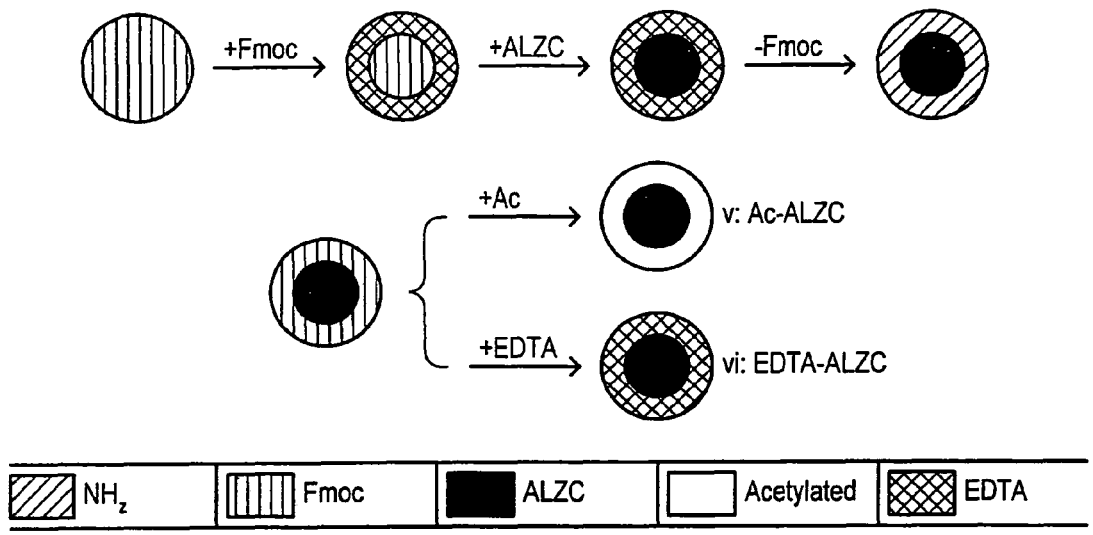
FIG. 14 depicts a schematic diagram of the preparation of multi-shell particles.

FIG. 14 displays schematically the synthesis of functional multi-shell particles. Initially, distinctly heterogeneous regions are created within the amine terminated polystyrene-polyethylene glycol particles (i) via the controlled penetration of the resin in a radial manner with 9-fluorenylmethoxy-carbonyl chloroformate (Fmoc), yielding resin with an exterior region of protected amines (ii). Subsequent coupling of ALZC to ii results in particles with the complexone immobilized only within their cores (iii). Removal of the Fmoc protecting group then yields resin with an ALZC core and an exterior region of free amines (iv). Two aliquots of iv are individually treated with acetic anhydride and EDTA dianhydride, respectively, yielding two batches with identical cores, but different exterior regions. While batch vi is functionalized with a strongly chelating EDTA shell, the amines in the exterior of batch v are capped, rendering the shell relatively inert with respect to metal cations. Multishell particle types will be named by combining their functionalities, listing them from the exterior inwards. For example, particles from batch vi in FIG. 14 will be referred to as "EDTA-ALZC" particles.

Particles from batches v (Ac-ALZC) and vi (EDTA-ALZC) were arranged in a sensor array with each truncated pyramidal well hosting an individual particle, directing solution flow to the particle while allowing optical measurements to be made. The red, green, and blue absorbance values (calculated using a blank particle as a reference intensity, as previously described) of each particle were monitored vs. time as various metal cation solutions were delivered to the flow cell. In one experiment, RGB absorbance was measured vs. time for a particle from batch v and a particle from batch vi, during a representative experiment (specifically the introduction of 10 mM $Ni^{2+}$). Both particles exhibit an overall increase in absorbance, as was expected from the ALZC "detector" core. In the particle with the "inert" acetylated shell, (A,C) the absorbance increase begins roughly 8 s after the $Ni^{2+}$ flow begins. This value was constant from particle to particle (within Batch v) and also from trial to trial. In contrast, the absorbance increase was not observed in the EDTA-coated particles (Batch vi) until ~40 s later. This delay is consistent with the idea that the ligand shell hinders the diffusion of metal cations through the polymer matrix.

It is also interesting to note that the two different particles have very different absorbance values prior to arrival of the metal cation solution. Here, it is speculated that ligand groups in the outer shells may function to buffer the microenvironments of the particles, thereby playing a role in dictating the color of the detection scheme. With higher concentration acidic and basic rinses, the color of the ALZC in the two batches of particles was readily equalized. However, with the 50 mM acetate buffer used here, the different particle batches consistently exhibited different (but stable) absorbance values, as consistent with the above explanation. Further, it should be noted that for the EDTA particle (batch vi, panels B and D) a decrease in absorbance was observed prior to the overall increase in absorbance. This behavior is consistent with a temporary lowering of the pH of the particle microenvironment, which may be attributed to deprotonation of the ligands upon metal complexation, and has been observed in related systems. Recent data indicate that this feature of the multishell particles' responses may be useful in identifying metals and determining their concentrations.

Figure 15:
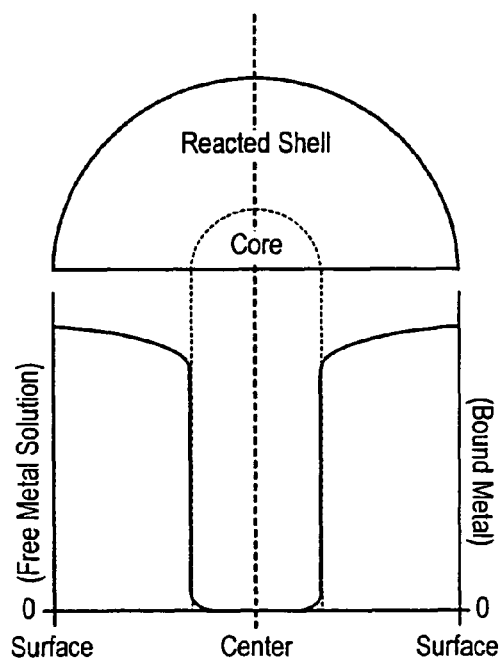
FIG. 15 depicts a diagram of the shrinking core model for multi-shell particles in a monoanalyte system.
Figure 16A:
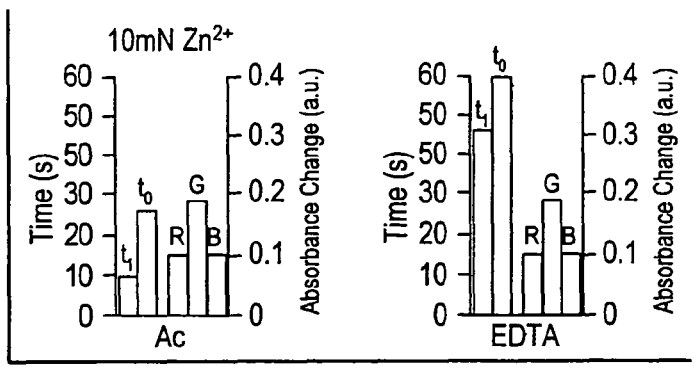
FIGS. 16A-D depict graphical representations of multi-component fingerprint responses yielded by functional multi-shell particles upon the introduction of an analyte.
Figure 16B:
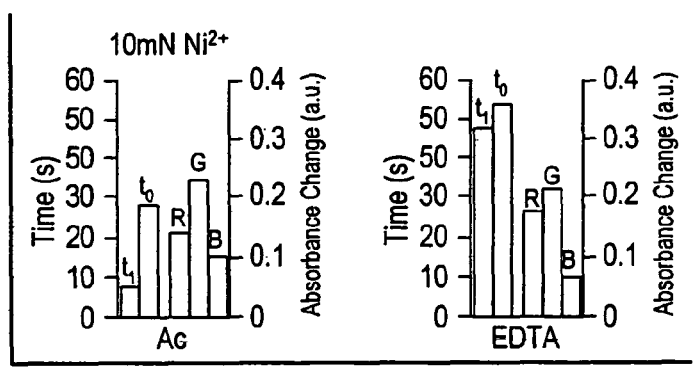
Figure 16C:
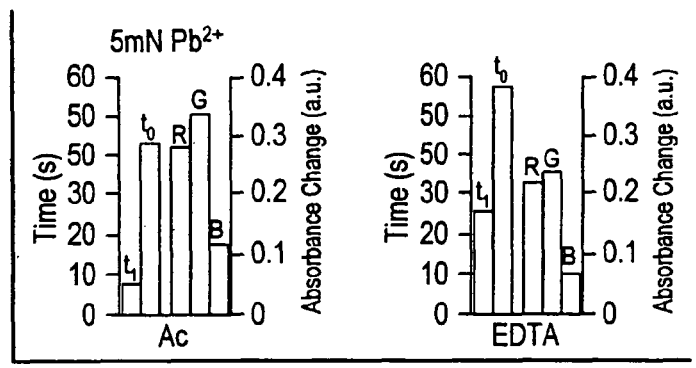
Figure 16D:
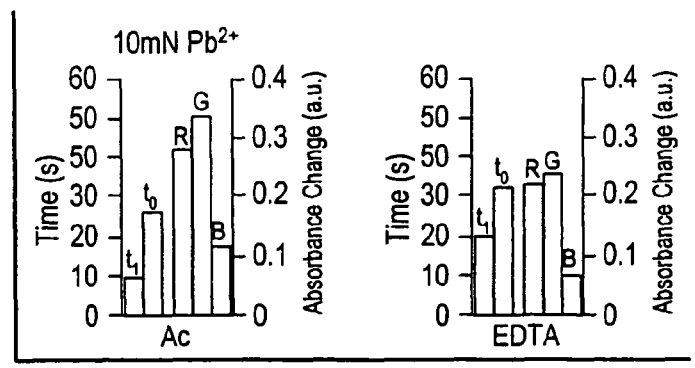

The delayed response of the EDTA coated particle can be rationalized in terms of a "moving boundary" or "shrinking core" effect. The diagram in FIG. 15 illustrates the shrinking-core model as it pertains to a microsphere functionalized homogeneously with a chelating moiety (i.e., iminodiacetate resin). The lower portion of the figure contains a pair of graphs, one depicting the concentration of metal in solution as a function of radial position within the particle, the other displaying the concentration of metal bound by the solid resin, also as a function of radial position. The two graphs are oriented in opposing directions (separated by a dashed line) such that the radial positions on the x-axis of each correspond to the semicircular diagram of a microsphere, included above them.

Upon exposure to solution containing an analyte (e.g., metal cations), the concentration gradient between the interior of the particle and the surrounding solution prompts diffusion of the analytes into the particle. However, given a large formation constant between the ligand and the analyte, the analytes achieving contact with the polymer may be associated (e.g. through binding or complexation) with the polymer, removing solution dissolved analytes from the liquid. This effective consumption of the analytes as they progress through the polymer results in the preservation of a large concentration gradient across a well-defined, moving boundary. Consequently, at a given point in time prior to complete equilibration, there are two distinct regions in the microsphere: a reacted shell and an unreacted core, as shown in FIG. 15. The shell is defined by local equilibrium between the solution and the polymer matrix. Accordingly, the two concentration profiles shown in the schematic suggest the presence of both free and bound analytes in this region. If equilibration is achieved rapidly, the concentrations of each would be expected to remain approximately constant throughout the shell. The core, on the other hand, is defined by an absence of any analytes, neither free nor bound forms are here located at this time interval. As such, there exists a concentration gradient across the boundary (indicated with dotted lines) between the two regions. This concentration gradient naturally promotes mass transport of the analytes across the boundary. However, since the interaction of the analytes with the polymer occurs more rapidly than their diffusion, the net result is an inward shift of the boundary with the concentration gradient preserved. It should be noted that the existence of the two regions is transient, and that, with prolonged time intervals, the entire particle will attain equilibrium with the analyte resulting in a homogeneous system.

In the EDTA-ALZC particle described above here, arrival of the boundary at the dye-containing core is signaled by the increase in absorbance. Following the initial arrival at the core, there continues to be a slower rate of signal development compared to the reference Ac-ALZC particle. This behavior may be indicative of the fact that the concentration gradient is not perfectly maintained, or rather, that the boundary region broadens as it progresses through the matrix. Also, it should be kept in mind that the EDTA-ALZC particle used here differs somewhat from the homogeneous particle discussed in the model. In particular, we must consider that the ALZC core is also an immobilized chelator, and as such that the rate of signal development will also be dependent upon interactions between the metal and the dye. Furthermore, if complexation of metal ions by the ligand shell does indeed affect the pH of the particle microenvironment, as proposed above, it may also significantly affect the binding characteristics of the complexometric dye. Nevertheless, the model provides a qualitative explanation of the key processes that may occur within the particle as metal cations are incorporated therein.

In order to facilitate an examination of the benefits of this multishell approach, three key intuitive components of a particle's response are defined as follows: 1) the color change of a particle is calculated by subtracting its initial effective absorbance value from its final effective absorbance value; 2) $t_D$ is the time measured from the beginning of a particle's color change until the particle has completed half of its color change; 3) $t_L$ is the time required to penetrate the ligand shell as defined by the length of time prior to the observation of the color change. These components of the particles' responses can be combined to yield a multi-component "fingerprint" summarizing the array's response to a given metal cation solution.

Examples of such multi-component responses are graphically summarized in FIGS. 16A-D for the particles prepared according to the scheme of FIG. 14. Each of the four panels here included corresponds to the indicated metal solution and features two separate data sets associated with EDTA and acetylated outer shells. Interestingly, the fingerprints yielded by the two multishell particles exhibit unique characteristics for each of the solutions studied. These data are well-suited for use with pattern recognition algorithms. A comparison of FIG. 16C (5 mM $Pb^{2+}$) and FIG. 16D (10 mM $Pb^{2+}$) emphasizes the benefits of the increased dimensionality of the fingerprint response. While the color changes exhibited by the two particle types show little, if any, meaningful difference between the two concentrations, the $t_D$ values of both particles, and the $t_L$ values of the EDTA particle, differ significantly between the two concentrations. It is evident from these data that the final static colorimetric response (the color change) of the ALZC alone is insufficient for discriminating between the two concentrations of $Pb^{2+}$, and that the functional EDTA shells and the time domain have added to the array's capabilities. Conversely, in the cases displayed in FIG. 16A (10 mM $Zn^{2+}$) and FIG. 16B (10 mM $Ni^{2+}$) the $t_D$ and $t_L$ values of the particles differ only slightly between the two metals, while their color changes are distinctly different. For these cases, the calorimetric responses of the ALZC contribute more to the discrimination than do the temporal components of the response. Likewise, a comparison of panel D (10 mM $Pb^{2+}$) with either panel A (10 mM $Zn^{2+}$) or B (10 mM $Ni^{2+}$) demonstrates a situation in which both the temporal and calorimetric components differ between metals. That the $t_L$ values of the acetylated (v) particle do not fluctuate significantly between these four cases agrees well with the idea of an "inert" shell, and highlights the chromatographic role provided by the EDTA functionality.

It is important to appreciate that with the multishell approach used here, the polymer microsphere itself is the sensor element, rather than merely a substrate for immobilization of a detection scheme. While optical detection of the analytes still arises from the immobilized indicator, modification of the polymer matrix surrounding the indicator may be used to augment the analytical characteristics of the detection scheme. Consequently, preparing particles with different ligand shells, but having a common indicator core generates a collection of complementary sensing elements with overlapping selectivity and varied analytical characteristics. Such elements are the building blocks of cross-reactive sensor arrays. It should be emphasized here that this is accomplished without any direct synthetic modification of the indicator itself.

Figure 17:
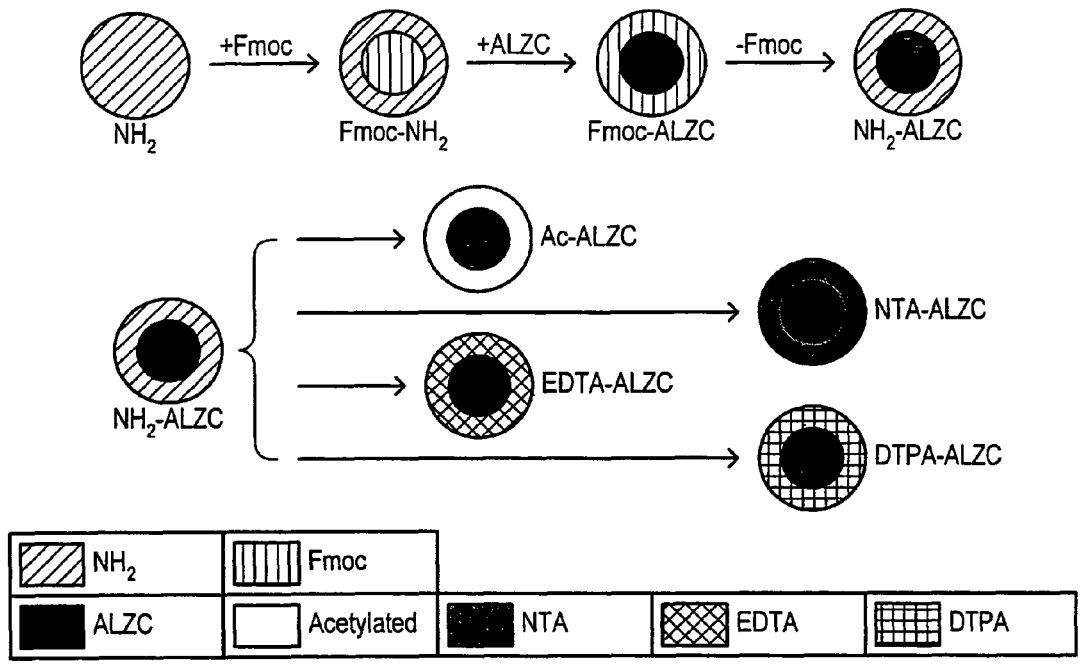
FIG. 17 depicts a schematic diagram of the preparation of multi-shell particles having a common core with different outer layer ligands.

In order to investigate the advantages of varying the nature of the ligand shell, a new batch of multishell particles was prepared. Preparation followed the strategy outlined previously and is depicted schematically in FIG. 17. As before, the controlled penetration of Fmoc was employed to generate a batch of $NH_2$-ALZC resin. Four aliquots of this resin were removed and the exterior regions of each aliquot was modified independently. In addition to capping the amines in one aliquot via acetylation, and immobilizing EDTA in the shell of a second, two other polyaminocarboxylate ligands, nitrilotriacetic acid (NTA) and diethylenetriaminepentaacetic acid (DTPA), were immobilized in the shells of the remaining two aliquots. The DTPA ligand system was immobilized in a similar fashion as EDTA, via DTPA dianhydride, where as NTA was immobilized similarly to the complexometric dye, via a DCC coupling reaction.

Samples of the four particle types prepared here were assembled in a sensor array in order to probe the effects of the different ligands on the particles' responses. The "split-pool" preparation of these particles (described above) ensures that the shell depth and dye core are identical (within the tolerances described in later) from batch to batch. Accordingly, any observed significant differences in $t_L$ values between batches may be attributed to their respective ligands, rather than differences in shell depth. Different concentration solutions of $Ca(NO_3)_2$ and $Mg(NO_3)_2$ were introduced to the array and plots of absorbance vs. time were generated for each particle in the array. Solutions contained only a single metal (i.e., either $Ca^{2+}$ or $Mg^{2+}$) and their concentrations ranged from 5 μM to 10 mM. All solutions were buffered at pH 9.8 with 50 mM alanine. The duration of each trial varied with the anticipated $t_L$ values. One image was captured every 2 s.

Figure 18:
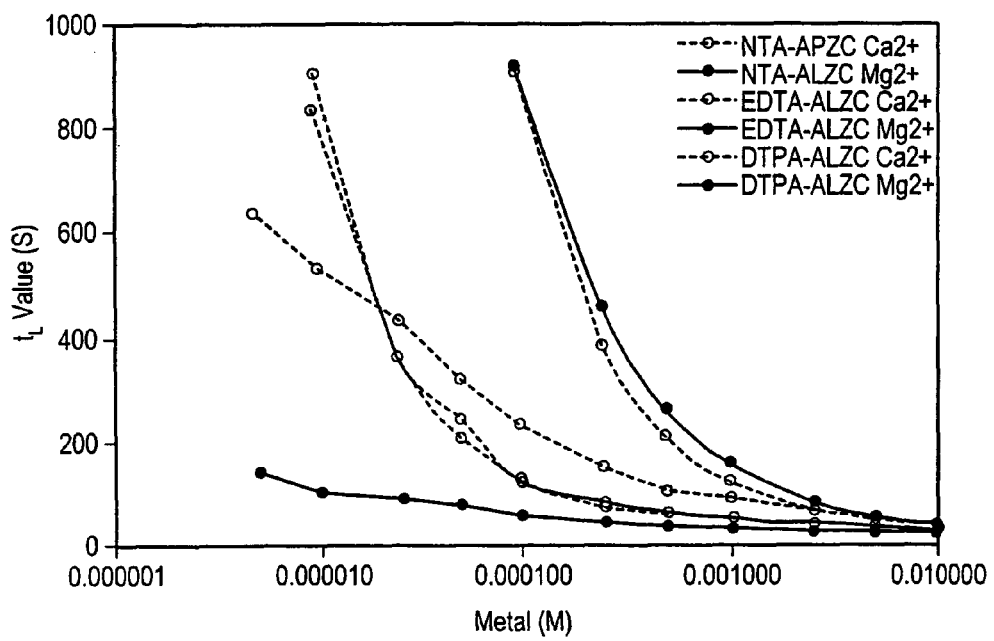
FIG. 18 depicts plots of $t_L$ values for three different multi-shell particle types vs. metal concentration.

FIG. 18 features plots of the $t_L$ values of three different particle types (NTA-ALZC, EDTA-ALZC, and DTPA-ALZC) vs. metal concentration for both $Mg^{2+}$ and $Ca^{2+}$. An examination of these data reveals several advantages of the multi-shell approach. It is evident from the data that all three ligand shells employed here exhibit dose dependent responses for both $Ca^{2+}$ (empty circles, dashed lines) and $Mg^{2+}$ (filled circles, solid lines). This concentration dependence of the $t_L$ values indicates that the ligand shells should be directly applicable to concentration determination. Furthermore, it should be noted that for a given metal the dose dependence of each ligand shell shown here is significantly different. This agrees well with the intuitive notion that the $t_L$ value should be heavily dependent upon the identity of the ligand in the exterior region. This then implies that the $t_L$ value of each ligand shell should be useful over a different range of metal cation concentration. If this is indeed the case, then by combining particles with various ligand shells, it should be possible to extend the effective dynamic range of an array towards a given metal cation. Additionally, although the EDTA and DTPA shells appear to treat $Ca^{2+}$ and $Mg^{2+}$ very similarly, the NTA shells clearly discriminate between the two metals. As such, the NTA ligand shell can be considered to impart a degree of selectivity to a particle.

In an experiment, multiple samples of a 10 mM $Pb^{2+}$ solution (buffered at pH 4.8 with 50 mM alanine) were delivered to an array of multishell particles, and their responses were recorded. The 5×7 array used in this work contained 7 of each of the 5 following particle types: blank ($NH_2$), Ac-ALZC, NTA-ALZC, EDTA-ALZC, and DTPA-ALZC. Between each trial, an acidic rinse (10 mM HCl at 3 mL/min for ~15 min) was used in an attempt to remove bound $Pb^{2+}$ from the particle. The acidic rinse was followed by a buffer rinse (2 mL/min for ~5-7 min) to ensure a uniform starting point for each trial. Images of the array were captured every two seconds and an absorbance vs. time plot was recorded for each particle in the array. From these responses, a $t_L$ value was extracted for each particle, for each trial. For a given particle, the $t_L$ value was quantified by taking the slope of the slope of the particle's green absorbance vs. time and observing the peak which corresponded to the most rapid rate of increase in absorbance. In each case, this method yielded values which agreed well with visual inspections of the raw data.

Mean $t_L$ values were calculated for individual particles by averaging $t_L$ values from the five redundant trials.

Several observations were made concerning the particles' temporal reproducibility. First, different ligand shells exhibited different $t_L$ values for the 10 mM $Pb^{2+}$ solution. This suggests that the inclusion of multiple ligand types should contribute to the generation of fingerprint style responses. Additionally, the average standard deviations for the different particle types are as follows: 1.3 s for Ac-ALZC; 2.6 s for NTA-ALZC; 1.6 s for EDTA-ALZC; 3.5 s for DTPA-ALZC. Considering that the temporal resolution of the measurements was only 2 s, and that the reproducibility was also dependent upon manual synchronization of two independent software packages (one controlling fluid delivery, one controlling image capture), these data are very encouraging with respect to trial-to-trial reproducibility. Furthermore, since the time of these studies, it has been observed that the acidic rinse used here is inadequate for the DTPA ligand shell. This may well have contributed to the modest reproducibility exhibited here by the DTPA coated particles.

Concerning particle-to-particle reproducibility, the absolute and percent relative standard deviations (% RSD) of the average $t_L$ values for each particle type are as follows: 1.1 s, 9.3% for Ac-ALZC; 13.8 s, 13.9% for NTA-ALZC; 1.6 s, 4.9% for EDTA-ALZC; 3.4 s, 7.8% for DTPA-ALZC. It is encouraging that, in this initial study, only the NTA-ALZC particles' responses exhibited % RSDs greater than that of the shell depth (9.9%). It is possible that uneven solution flow through the wells of the array results in unequal delivery of analyte and therefore hampers particle-to-particle reproducibility. If this is indeed the case, it would not be surprising if it was most evident in the particles with the highest $t_L$ values.

The ligand shell of a multishell particle can be thought of as a chromatographic layer, while the indicator at the core functions as a detector. Indeed, data presented thus far have indicated that the progression of analytes through the particles' exterior regions is hindered by the presence of an immobilized ligand and that the rate of progression is dependent upon the nature of the ligand and the identity and concentration of the analyte. Certainly, in their interactions with individually delivered analytes, the multishell particles have demonstrated a potential utility for metal cation speciation and concentration determination. It should be kept in mind though that the primary goal of cross-reactive sensor arrays is the ability to detect multiple species simultaneously.

Figure 19:
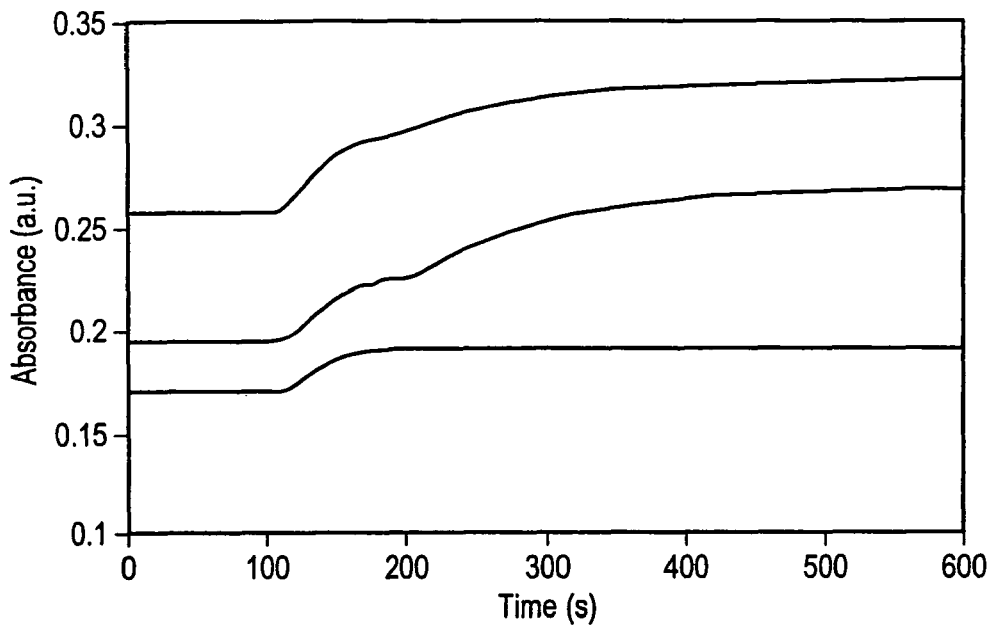
FIG. 19 depicts plots of red, blue and green absorbance of a multi-shell particle vs. time for multiple analytes.

The plot displayed in FIG. 19 chronicles the development of an EDTA-ALZC particle's response to a solution containing both $Mg^{2+}$ and $Ca^{2+}$. The top line represents the green absorbance, the middle line represents the red absorbance, and the top line represents the blue absorbance. Each metal was present at a concentration of 1 mM, the solution was buffered at pH 9.8 with 50 mM alanine, and the flow rate during the experiment was 2 mL/min. As was seen with the introduction of single cations, there is a significant delay prior to observation of the dye's response. However, the evolution of the dye's response is clearly different here than with any of the individually delivered analytes. Specifically, the observed color change appears to occur in two distinct steps, the first commencing roughly 115 s after the beginning of sample introduction, the second beginning almost 100 s later. This is most readily evident in the response recorded by the red channel (middle line) of the CCD. The presence of these two steps, and the plateau between them, is indicative of two samples arriving at the dye core of the particle at different times, suggesting that the EDTA shell may have actually separated the two species during their progression through the exterior region. It should also be noted that the two steps in the signal development differ spectrally. The first step is defined by an absorbance increase which spans all three channels of the CCD, whereas the second step is observed primarily in the red channel, slightly in the green channel, and not at all in the blue. This bathochromic shift in the dye's absorbance agrees with the idea of two cation waves of different composition arriving at the dye core at different times.

Figure 20:
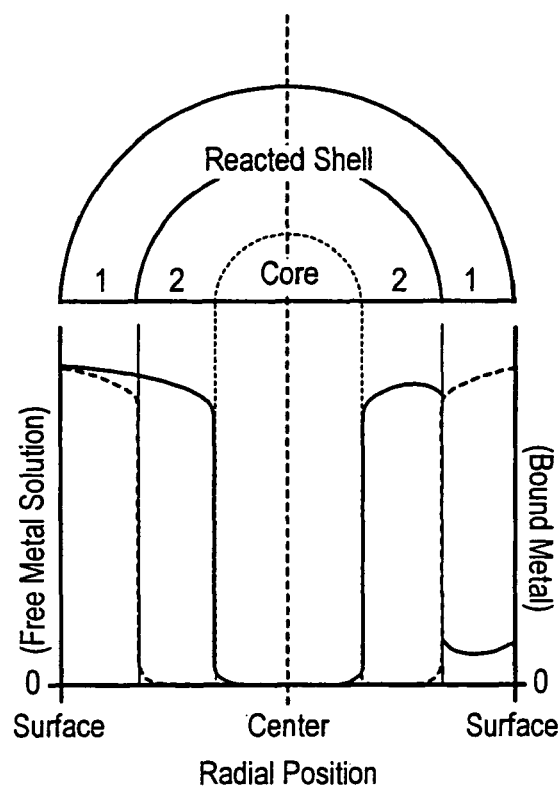
FIG. 20 depicts a diagram of the shrinking core model for multi-shell particles in a bianalyte system.

Interpretation of the microsphere's response is again facilitated by a consideration of a moving boundary scenario. In FIG. 20 a diagram is used to illustrate the model developed by Mijangos and Diaz for a moving boundary system involving two species of metal cations. The arrangement and format of the diagram match that of FIG. 15. For this example, the same concentration of each species has been introduced to the microsphere, and the ligating polymer matrix is assumed to bind each species with a different affinity. Additionally, the diffusivities of the two species are taken to be identical. On each graph the concentrations (free or bound as indicated on the y-axes) of the two cations are shown. The dashed plots (- - -) correspond to the analyte with the higher affinity for the matrix, the solid plots correspond to the less preferred analyte.

Upon sample introduction, both analytes are subject to a concentration gradient between the external solution and the particle. Consequently, both diffuse into an outer shell of the particle in equal concentrations where they are bound differentially by the immobilized chelator. This preferential binding establishes a different concentration gradient for each species. The solution in the shell has been depleted of the higher affinity species, and so its gradient effectively remains at the surface of the particle. On the other hand, the less preferred analyte is still present in solution in relatively high concentrations and so it experiences a gradient between the outer shell and the inner region. Diffusion of the two species in accordance with the described gradients results (temporarily) in a situation similar to that depicted in FIG. 20.

The two concentration gradients in solution (depicted in the left hand graph) explain both the encroachment of region 2 on the unreacted core, and that of region 1 on region 2. Region 2 contains only the less preferred analyte and progresses into the core as in the monoanalyte system described previously. In contrast, the outer region (1) contains both species, and its progression (also driven by a concentration gradient in solution) entails the displacement of the less preferred analyte from the chelating matrix.

Figure 21A:
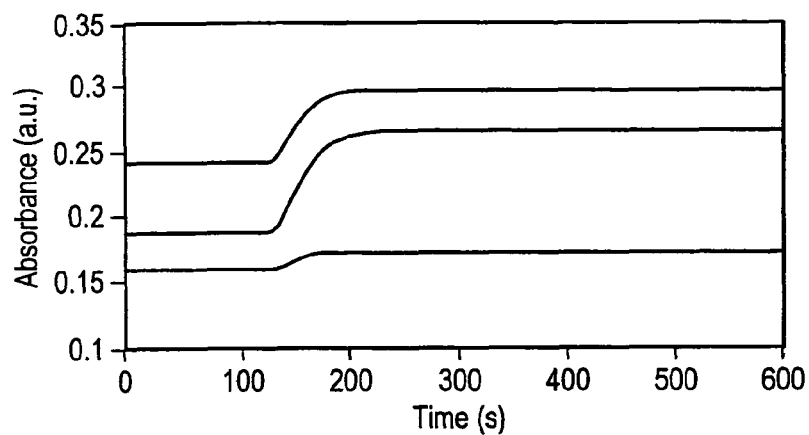
FIG. 21A-C depicts plots of red, blue and green Absorbance vs. time plots for an EDTA-ALZC particle.
Figure 21B:
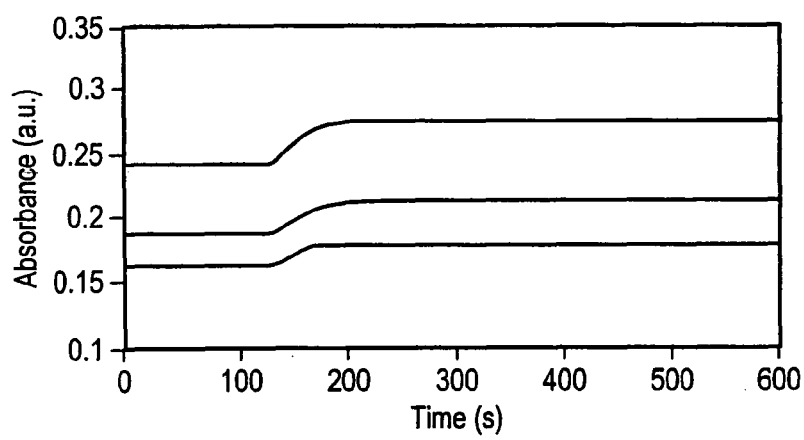
Figure 21C:
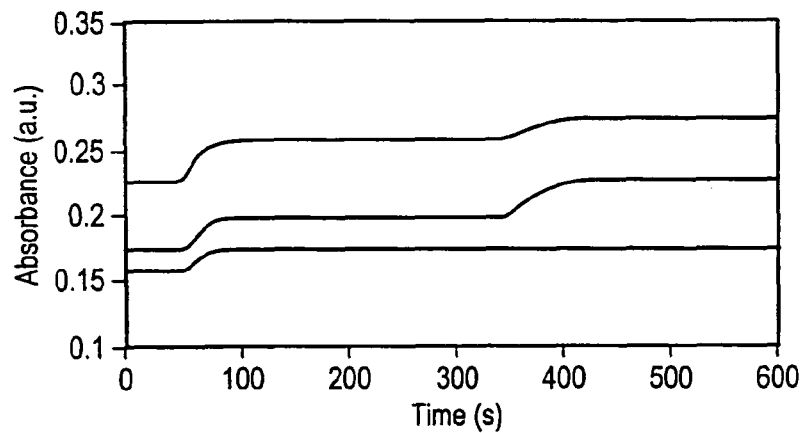
Figure 22A:
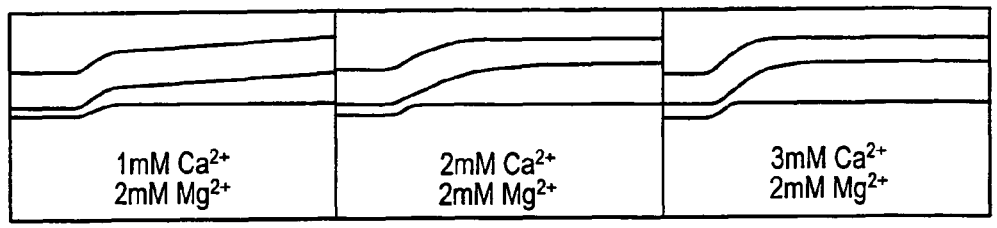
FIG. 22A-D depicts an array of graphs showing the responses of an EDTA-ALZC particle to binary mixtures of $Ca(NO_3)_2$ and $MgCl_2$.
Figure 22B:
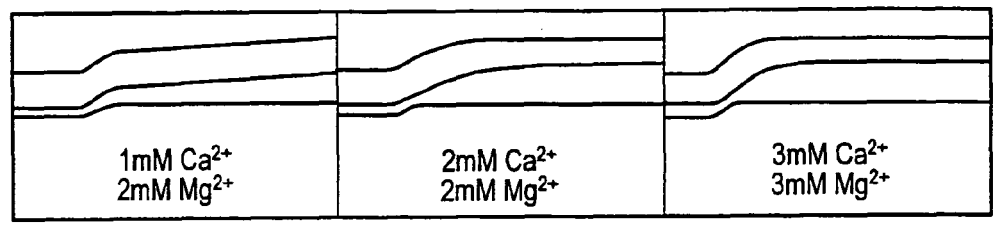
Figure 22C:
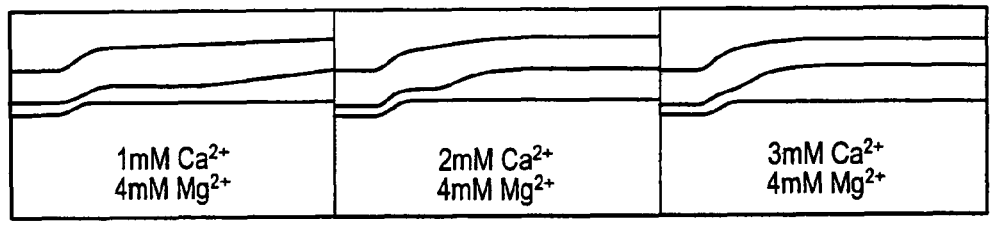
Figure 22D:
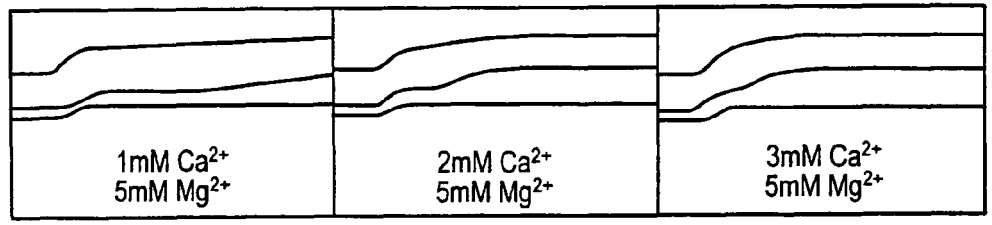

According to the model described above, the two steps within the EDTA-ALZC particle's response should correspond to the arrival of a single analyte at the dye core followed by the arrival of a mixture of the two analytes. The time dependent 3-color absorbance curves provided in FIGS. 21A-C allow us to begin rationalizing the features seen within the bianalyte response. In FIG. 21A-C, the top line represents the green absorbance, the middle line represents the red absorbance, and the top line represents the blue absorbance. These plots show three different responses from an EDTA-ALZC particle. FIGS. 21A and 21B show the particle's response to 2 mM $Ca(NO_3)_2$ and 2 mM $Mg(NO_3)_2$, respectively. Each response exhibits a delay, as expected, and each response is spectrally different also. While the dye's response to $Mg^{2+}$ appears simply to be an increase in absorbance, the $Ca^{2+}$ solution elicits not only an increase in absorbance, but also a significant spectral shift into the red channel of the CCD. These two monometallic responses aid in interpretation of the bimetallic response shown in FIG. 19, implying the presence of $Ca^{2+}$ in the second step of the signal development, and its absence from the first.

FIG. 21C shows an EDTA-ALZC particle's response to the sequential delivery of two different samples, the first consisting of 5 mM $Mg^{2+}$, the second containing 5 mM concentrations of both $Mg^{2+}$ and $Ca^{2+}$. The sequential delivery was employed here to simulate the separation predicted by Mijangos and Diaz. The response elicited by the bimetallic sample (shown in FIG. 19) is mimicked closely by the response generated via the sequential delivery of two samples (FIG. 21C). It is interesting here to note that in the instances of the monometallic samples (FIGS. 21A, B) the equilibrium absorbance values of the dye core provide far more information regarding the nature of the sample than do the temporal components of the responses. In particular, the final absorbance values in the red channel relative to those in the green and blue channels, are useful here for speciation. However, the utility of the ligand shell, and of the associated temporal consideration, are confirmed by the bimetallic response shown in FIG. 21C.

The moving boundary models (both mono- and bimetallic) outlined above predict that the progress of a metal cation through a ligand shell will be dependent upon two factors: the diffusion coefficient of the species and its conditional formation constant with the immobilized ligand. This is confirmed by the data featured in FIG. 19 and FIGS. 21A-C, which, interestingly, present an apparent dichotomy. The plots shown in FIG. 21A and FIG. 21B reveal that the EDTA shell yields almost identical $t_L$ values for $Ca(NO_3)_2$ and $Mg(NO_3)_2$. Intuitively, this suggests that the immobilized ligand does not appreciably discriminate between the two species. However, the "separation" of the bimetallic sample in FIG. 19, indicates that the EDTA shell does in fact discriminate between $Ca^{2+}$ and $Mg^{2+}$. Given the similar diffusion coefficients of the two species, ($Ca^{2+}$: $0.792 \times 10^{-5}$ $cm^2 s^{-1}$; $Mg^{2+}$: $0.706 \times 10^{-5}$ $cm^2 s^{-1}$; measured in aqueous solutions at 25° C.) these data suggest that when delivered individually the cations' progress through the matrix is governed by their diffusion coefficients. On the other hand, the discrimination observed in the bimetallic sample may then be attributed to the ligand's preferential binding of $Ca^{2+}$ over $Mg^{2+}$. In solution, the formation constants of EDTA-$Ca^{2+}$ complexes are typically two orders of magnitude greater than those of EDTA-$Mg^{2+}$ complexes. While the consideration of both diffusion and formation constants may greatly hamper facile rationalization of complex responses, the added degree of molecular level information contained within the response is welcome.

The application of pattern recognition is useful for the analyses of complex mixtures with cross-reactive sensor arrays. It is often desirable to demonstrate trends within simple multi-analyte systems. This is useful not only as proof-of-concept data, but, more importantly, it often provides insight into the workings of the array, allowing the user to make intelligent decisions regarding the choices of pattern recognition techniques and their application to the data. To this end, an array of ligand shell particles was assembled and its responses to binary mixtures of $MgCl_2$ and $Ca(NO_3)_2$ were examined. Interest in simultaneous analyses of $Mg^{2+}$ and $Ca^{2+}$ derives from a unique combination of their biological relevance, and their inherent similarity. Indeed, as one species often interferes with detection of the other, their coexistence within biological samples has historically challenged analysts. The concentrations of each metal salt varied from 1 to 5 mM in 1 mM increments, for a total of 25 combinations. FIG. 22 features the absorbance vs. time responses of an EDTA- ALZC particle to a subset of these solutions. In each of the plots depicted in FIG. 22, the top line represents the green absorbance, the middle line represents the red absorbance, and the top line represents the blue absorbance. In the responses presented here, a number of trends are evident. At a glance, it can be seen that there is a significant delay prior to each response, and that many of the responses appear to occur in two steps. It can also be seen that the temporal development of these steps varies considerably with the concentrations of the individual components. Furthermore, based on the spectral characteristics of the individual steps, it again appears that $Mg^{2+}$ reaches the dye core before $Ca^{2+}$. It is also interesting to note that the net color changes in these responses have little if any variation.

Figure 23A:
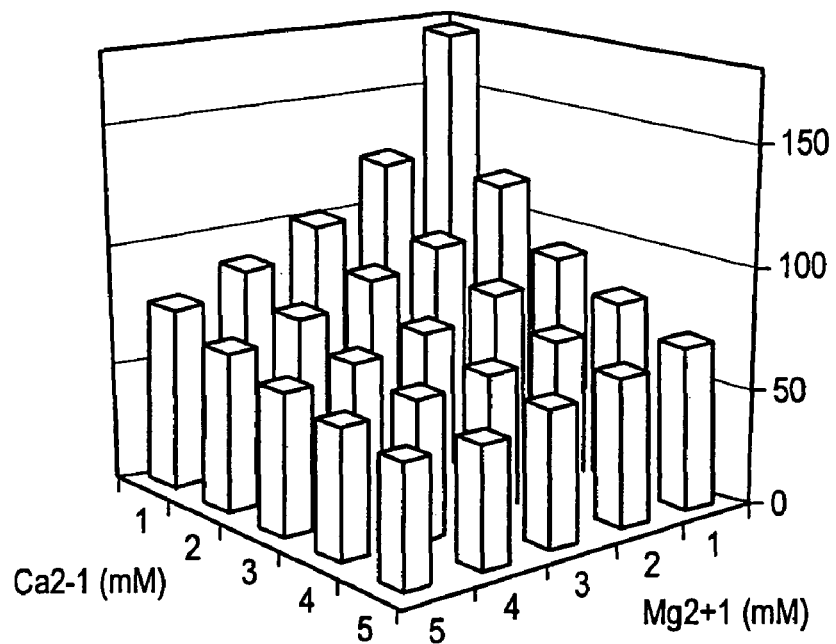
FIG. 23A-B depict plots of a particles primary (23A) and secondary (23B) delays vs. $Mg^{2+}$ and $Ca^{2+}$ concentration.
Figure 23B:
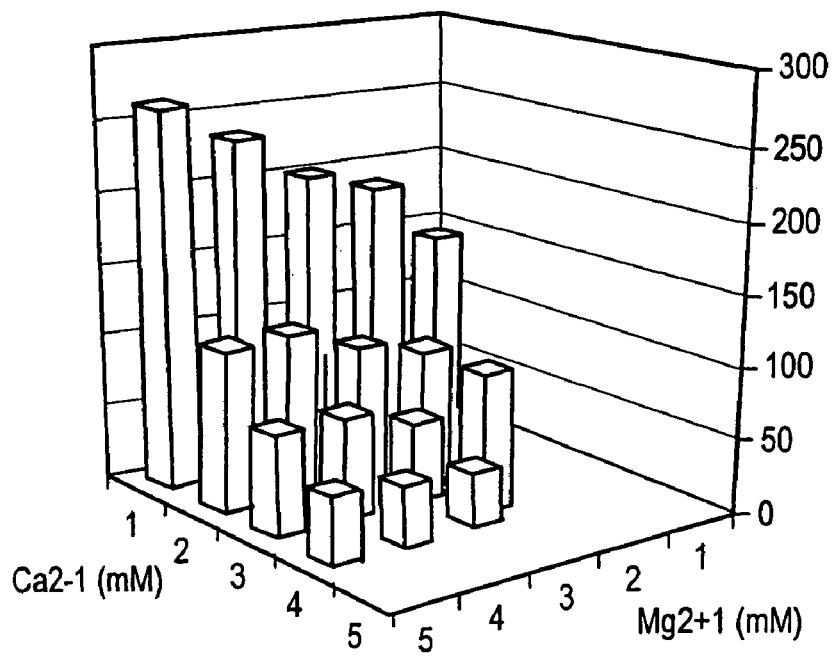

For each of the 25 binary mixtures introduced to the array, two temporal components of the EDTA-ALZC particle's response were quantified manually: the initial delay prior to the dye's observed response (termed "primary delay") and the duration between initial observation of the dye's response and the observation of a second step in the dye's response (termed "secondary delay"). FIGS. 23A-B features plots of the particle's primary (FIG. 23A) and secondary (FIG. 23B) delays vs. $Mg^{2+}$ and $Ca^{2+}$ concentration. No secondary delay was recorded for solutions that did not elicit discernable steps. Interestingly, two different concentration dependent trends are evident in these plots. Increasing the concentration of either metal decreases the primary delay, whereas the secondary delay increases with increasing $Mg^{2+}$ concentrations but decreases with increasing $Ca^{2+}$ concentrations. In this case, these trends are directly applicable to determining the concentrations of the two species, even without further data processing.

In another embodiment, particles were prepared having an indicator in an inner core of the particle, and having an amino acid, peptide, or other nitrogen containing ligands, coupled to the exterior region of the particle. The amino acid was selected based on the ability of the amino acid to complex with various metal cations. Each particle was exposed to a variety of metal salts to determine the amount of time it takes for the metal cation to reach the core and induce a colorimetric change in the indicator. The time required to induce a change in the indicator is referred herein as the "breakthrough" time. Table 1 shows the breakthrough times for various metals with various particles. The "conjugate" column indicates the molecule bound to the exterior region. Two runs were performed for Hg, Pb, Cu, and Ni, only one runs was performed for Cd.

Table 2 shows the breakthrough times for Hg with various particles. The "conjugate" column indicates the molecule bound to the exterior region. The times shown are an average of four runs for each conjugate.

TABLE 2

| CONJUGATE | AVERAGE BREAKTHROUGH TIME |
|---|---|
| 1-Cysteine | 831 ± 4 |
| Cysteine dipeptide | 989 ± 5 |
| Cysteine tripeptide | 1317 ± 6 |
| 1-Histidine | 604 ± 3 |
| EDTA | 577 ± 6 |

Figure 24:
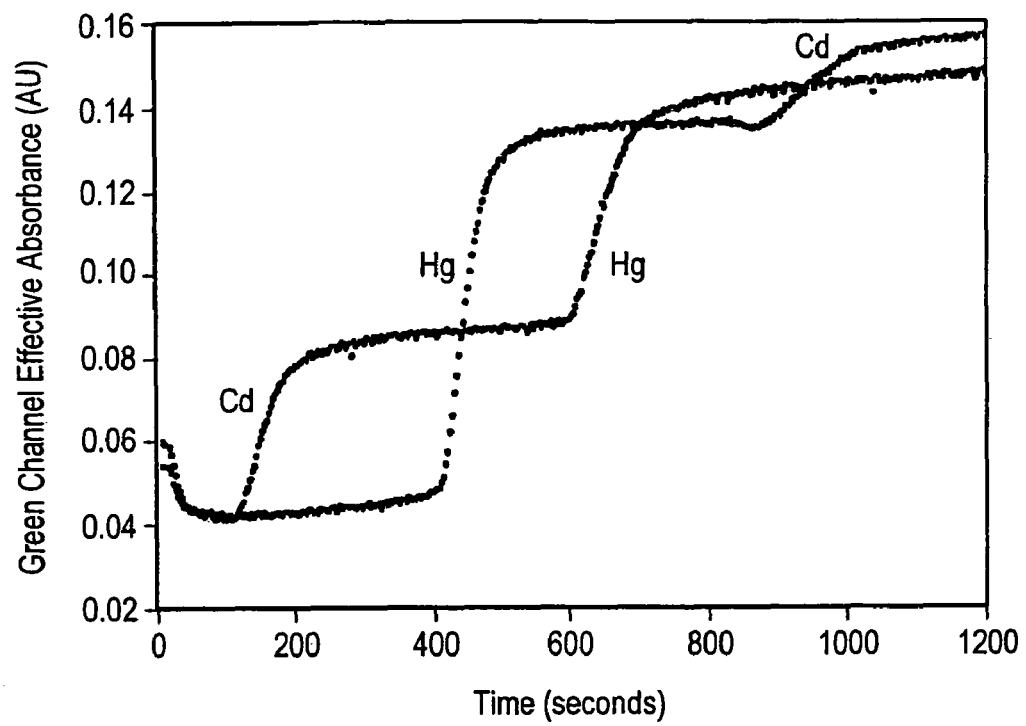
FIG. 24 depicts breakthrough curves for a Cd and Hg mixture on cysteine and histidine conjugated particles.

FIG. 24 shows a breakthrough curve characteristic of two metals passing through a single particle. Here we show two separate particles (histidine conjugated and cysteine conjugated) with a solution of 5 mM Cd and 5 mM Hg. Utilizing HSAB theory, we expect that Cd will bind more tightly to the histidine conjugated particles than to a cysteine conjugated particle. We would expect the opposite phenomenon for Hg. This data and subsequent control studies demonstrates these basic principles as well as the separation of two metals on a single 200 um particle.

The selection of the appropriate ligands for coupling to the exterior region of a multi-shell particle may be performed using combinatorial methodologies. One method used to determine the presence of an analyte is a displacement assay. In one embodiment, particles that are conjugated with a receptor on the exterior region are reacted with the analyte of interest. Those particles with an exterior region with a strongly chelating peptide will remain fluorescent since the metal will not reach the core in a specified time period; whereas, the metal will quickly pass into the core of particles with shells that are weakly chelating and quench the fluorescence. By stopping the influx of the analyte and then analyzing the library, the particles with a strongly chelating shell can be separated. In embodiments where the exterior region is coupled with peptides, the peptides may be removed from the particle and separated using Edmond sequencing techniques.

In one embodiment, a plurality of particles having a variety of peptides coupled to their outer shell may be produced. The inner core of all of the particles may have the same indicator (e.g., Fluorexon). For peptide libraries up to $20^n$ different particles may be produced in a library, where n is the number of amino acids in the peptide chain. Because of the large number of different particles in these libraries, the testing of each individual particle is very difficult.

When a plurality of particles is used, the analyte will bind to the particles at various strengths, depending on the receptor coupled to the particle. The strength of binding is typically

TABLE 1

| CONJUGATE | $Cd^{2+}$ | $Hg^{2+}$ | $Pb^{2+}$ | $Cu^{2+}$ | $Ni^{2+}$ |
|---|---|---|---|---|---|
| 1-Cysteine | 1562 s | 945 s, 952 s | 799 s, 803 s | n/a | 1182 s, 1195 s |
| 1-Histidine | 284 s | 589 s, 589 s | 80 s, 98 s | 1173 s, 1176 s | 1158 s, 1687 s |
| EDTA | 492 s | 360 s, 403 s | 267 s, 275 s | 315 s, 411 s | 211 s, 438 s | associated with the degree of color or fluorescence produced by the particle. A particle that exhibits a strong color or fluorescence in the presence of the indicator has a receptor that strongly binds with the indicator. A particle that exhibits a weak or no color or fluorescence has a receptor that only weakly binds the indicator. Ideally, the particles which have the best binding with the indicator should be selected for use over particles that have weak or no binding with the indicator. In one embodiment, a flow cytometer may be used to separate particles based on the intensity of color or fluorescence of the particle. Generally, a flow cytometer allows analysis of each individual particle. The particles may be passed through a flow cell that allows the intensity of color or fluorescence of the particle to be measured. Depending on the measured intensity, the particle may be collected or sent to a waste collection vessel. For the determination of an optimal particle for interaction with an indicator, the flow cytometer may be set up to accept only particles having an color or fluorescence above a certain threshold. Particles that do not meet the selected threshold, (i.e., particles that have weak or no binding with the indicator) are not collected and removed from the screening process. Flow cytometers are commercially available from a number of sources.

After the particle library has been optimized for the indicator, the particles that have been collected represent a reduced population of the originally produced particles. If the population of particles is too large, additional screening may be done by raising the intensity threshold.

The collected particles represent the optimal particles for use with the selected analyte and indicator. The identity of the receptor coupled to the particle may be determined using known techniques. After the receptor is identified, the particle may be reproduced and used for analysis of samples.

EXAMPLES

Materials

Polystyrene-polyethylene glycol (PS-PEG) graft copolymer microspheres (≈130 μm in diameter when dry and 230 μm when hydrated) were purchased from Novabiochem. Normal amine activation substitution levels for these particles were between 0.2 and 0.4 mmol/g. Commercial-grade reagents were purchased from Aldrich and used without further purification except as indicated below. Fluorescein isothiocyanate was purchased from Molecular Probes. All solvents were purchased from EM Science and those used for solid-phase synthesis were dried over molecular sieves. Methanol was distilled from magnesium turnings.

Immunoassays were performed using carbonyl diimidazole (CDI) activated Trisacryl® GF-2000 available from Pierce Chemical (Rockford, Ill.). The particle size for this support ranged between 40 and 80 μm. The reported CDI activation level was >50 μmoles/mL gel. Viral antigen and monoclonal antibody reagents were purchased from Biodesign International (Kennebunk, Me.). Rhodamine and Cy2-conjugated goat anti-mouse antibody was purchased from Jackson ImmunoResearch Laboratories, Inc. (West Grove, Pa.). Antigen and antibody reagents were aliquoted and stored at 2-8° C. for short term and at −20° C. for long term. Goat anti-mouse antibody was diluted with glycerol (50%)/water (50%) and stored at −20° C.

Agarose particles (6% crosslinked) used for the enzyme-based studies were purchased from XC Particle Corp. (Lowell, Mass.). The particles were glyoxal activated (20 μmoles of activation sites per milliliter) and were stored in sodium azide solution. Agarose particle sizes ranged from 250 μm to 350 μm.

Alizarin complexone (ALZC), N,N-diisopropylethylamine (DIEA), 1,3-dicyclohexylcarbodiimide (DCC, 1.0 M in dichloromethane), N,N-dimethylformamide (DMF), 9-fluorenylmethoxycarbonyl chloroformate (Fmoc), ethylenediaminetetraacetic acid dianhydride (EDTAan), diethylenetriaminepentaacetic acid dianhydride (DTPAan), nitrilotriacetic acid (NTA), acetic anhydride ($AC_2O$), triethylamine (TEA), and piperidine were all purchased from Aldrich and used without any further purification. NovaSyn TG amino resin LL ($TG-NH_2$) was purchased from NovaBiochem (San Diego, Calif.). The amine concentration was listed by the manufacturer as 0.29 mmol/g. The average diameter was listed as 130 μm when dry and was measured as ~170 μm in aqueous solutions buffered at pH 9.8 with 50 mM alanine. The following metal salts were used in making the metal cation solutions: $Ni(NO_3)_2.6H_2O$, $Zn(NO_3)_2.6H_2O$, and $Pb(NO_3)_2$ $Ca(NO_3)_2.4H_2O$, $Mg(NO_3)_2.6H_2O$, and $MgCl_2.6H_2O$. $Ca^{2+}$ and $Mg^{2+}$ solutions were buffered at pH 9.8 with 50 mM alanine. Solutions of heavier metals were buffered at pH 4.8 with 50 mM acetate.

Particle Preparations

All final functionalized PS-PEG copolymer microsphere batches (resin) were dried under high vacuum for at least twelve hours. The resin was washed thoroughly before and after each coupling reaction on the solid phase using a rotary evaporator motor to tumble the reaction vessel in an oblong fashion (shaking), for a specified period of time (i.e., the "1×1" notation refers to one wash for one minute before the solvent was drained).

Indicator Immobilization via Amide Linkages

Amino-terminated polystyrene-polyethylene glycol graft copolymer resin (0.20 g, 0.29 mmol/g, 0.058 mmol) was placed in a solid phase reaction vessel and washed with 1×1 minute dichloromethane, 2×5 minutes N,N-dimethyl formamide (DMF), and 2×2 minutes dichloromethane. While the resin was being washed, an oven-dried round-bottom flask was charged with dicyclohexylcarbodiimide (DCC) (0.059 g, 0.29 mmol, 5 eq.) and hydroxybenzotriazole (HOBt) (0.039 g, 0.29 mmol, 5 eq.) in 8 mL DMF and cooled in an ice-bath. To this mixture, alizarin complexone (0.20 g, 0.29 mmol, 5 eq.) was added and the solution stirred at 0° C. for 30 minutes. After completing the washes of the resin, this solution was filtered and added to the resin. The heterogeneous system was allowed to shake for 2-15 hours at 25° C. At the end of this time, the coupling solution was removed and the resin was washed with 2×2 minute DMF, 1×2 minute dichloromethane, 1×2 minute methanol, 1×5 minute DMF and 1×1 minute dichloromethane. A small portion of this resin was then subjected to a quantitative ninhydrin (Kaiser) test to assay for the presence of primary amines, using Merrifield's quantitative procedures. Various indicator substitution levels were used as required for the desired assays.

Other dyes such as xylenol orange (Sigma), calconcarboxylic acid (Aldrich) and thymolphthalexon (Aldrich) were conjugated to the resin particles using similar protocols as described above.

Indicator Immobilization via Thiourea Linkage

Once the resin (0.075 g, 0.30 mmol/g, 0.0218 mmol) had been completely washed, fluorescein isothiocyanate (0.034 g, 0.087 mmol, 4 eq.) in 5 mL dichloromethane and 5 mL DMF was added to it. Two different levels of dye loading were created so as to service the specific needs of the colorimetric and fluorescence-based measurements. If the resin was to be used for colorimetric studies, it was allowed to shake in an oven at 55° C. for 1-5 days. The subsequent work-up of washes was followed as previously mentioned. If a positive ninhydrin test was obtained, the resin was resubmitted to the reaction conditions until ninhydrin gave a negative result. Resin designated for fluorescence studies was shaken at 25° C. only for 1-3 days as lower dye loading was needed. A quantitative ninhydrin test was then performed to assess the level of substitution. A low loading volume was required to minimize fluorescence self-quenching.

Acetylated Resin

Prewashed resin (0.10 g, 0.29 mmol/g, 0.029 mmol) was treated with acetic anhydride (1.5 mL, 15.9 mmol, 548 eq.) and triethylamine (0.034 g, 7.2 mmol, 248 eq.) in 5 mL dichloromethane. After 30 minutes of shaking at 25° C., the reaction mixture was removed and the resin was washed (as described above). A ninhydrin test produced a negative result.

Antigen Immobilization for Viral Immunoassays

Hepatitis B surface antigen (HbsAg) was coupled to the CDI-activated Trisacryl support in the following manner: 20 μL of a 50% (by volume) particle slurry was pipetted into a 0.6 mL microcentrifuge tube. The number of moles activated CDI sites per mL particle slurry was determined and reacted with HBsAg in a 1:3000 ratio (1 mole protein: 3000 moles CDI sites). To the microcentrifuge tube was added 500 μL of a solution of phosphate buffered saline at pH 8. The resulting reaction mixture was allowed to react overnight at RT with shaking. Similar procedures were performed with HIV gp 41/120 and influenza A antigens.

Enzyme Immobilization

Diaphorase was immobilized onto porous cross-linked agarose particles (XC Particle Corp., Lowell, Mass.). The particles were purchased pre-activated with glyoxal groups. A standard procedure for enzyme immobilization follows. About 2 mg lyophilized diaphorase was dissolved into 1.00 ml solution of 200 mM phosphate buffer at pH 7.00. To 1.5 ml Eppendorf tube, 100 μl of fresh particles were added and the supernatant was removed with a pipette. To the particles was added 500 μL of 200 mM phosphate buffer (pH 7.00). A 50 μl aliquot of the diaphorase suspension was combined to the particle slurry and finally 20 μl of a 0.75 mM solution of sodium cyanoborohydride was added to the mixture. The resulting sample was then shaken at the lowest speed on a Vortex Genie overnight. The supernatant was removed the next day and the particles were washed with 200 mM phosphate buffer (pH 7.00) twice before use.

Array Preparation

Individual microspheres were placed into chemically etched microcavities patterned in a square array on 4-inch single crystal (100) double polished silicon wafers (~220 μm thick) using a micromanipulator on an x-y-z translator. The cavities were prepared using bulk KOH anisotropic etching of the silicon substrate. To mask the substrate during the KOH etch, a silicon nitride layer was prepared using a low pressure chemical vapor deposition (LPCVD) technique. Removal of the mask layer from one side of the silicon substrate was carried out by protecting the other side with photoresist and plasma etching ($CF_4$ and $O_2$ at 100 watts) the $Si_3N_4$ layer. The silicon substrate was etched anisotropically using a 40% KOH solution (Transene silicon etchant PSE-200) at 100° C. The etch rate of the (100) silicon was about 1 μm/min at 100° C. Successful patterning requires that a highly stable temperature be maintained throughout the etch process. After completion of the KOH etch, the nitride masking layer was completely removed from both sides of the silicon substrate using plasma etching. To improve surface wetting characteristics, the completed device was soaked in 30% $H_2O_2$ for 15 to 20 min. to form a thin $SiO_2$ layer on the surface of the silicon.

Flow Cell Construction

Construction of the flow cell began with the machining of two Teflon frames. Drilling a hole through the Teflon allowed for the penetration of the interior of the frame with segments of the fluid delivery tubing. A siloxane polymer casing was then poured around each frame-tubing ensemble. Two different molds were used when pouring the siloxane resin. The mold for the upper layer coated the Teflon with a thin layer of resin and filled in the center of the frame, but left a shallow indentation in the center (at the end of the PEEK tubing) which served as a reservoir. The lower mold yielded an almost identical piece, except that it had two concentric indentations: one to hold the chip in place and a second to serve as a reservoir below the array of particles. The chip was then placed between the two siloxane/Teflon layers and the multi-layered structure was held together by an aluminum casing. The resulting assembly was a cell with optical windows above and below the chip and a small exchange volume (~50 μL) capable of handling flow rates as high as 10 mL/min.

Fluid Delivery

Solutions were typically introduced into the flow cell using an Amersham Pharmacia Biotech ÄKTA Fast Protein Liquid Chromatograph (FPLC). This instrumentation was used without placement of in-line chromatographic columns and served as a precise, versatile and programmable pump. The FPLC instrumentation included a number of on-board diagnostic elements that aided in the characterization of the system. The siloxane layers mentioned above were used to hold the chip in place and also provided fluid coupling to the delivery tubing.

Particles within the sensor array were exposed to analytes as solution was pumped into the upper reservoir of the cell, forced down through the wells to the lower reservoir and out through the drain. The cell was designed specifically to force all introduced solution to pass through the wells of the array. The FPLC unit utilized here was able to draw from as many as 16 different solutions and was also equipped with an injection valve and sample loop, allowing for a wide range of fluid samples to be analyzed.

Microscope and CCD Camera

The flow cell sat on the stage of an Olympus SZX12 stereo microscope. The microscope was outfitted for both top and bottom white illumination. The scope also had a mercury lamp for fluorescence excitation. Removable filter cubes were inserted to control the excitation and emission wavelengths. The array was observed through the microscope optics and images were captured using an Optronics DEI-750 3-chip charge coupled device (CCD) (mounted on the microscope) in conjunction with an Integral Technology Flashbus capture card.

Software

Image Pro Plus 4.0 software from Media Cybernetics was used on a Dell Precision 420 workstation to capture and analyze images. Solution introduction, image capture and data extraction were completed in an automated fashion. The FPLC was controlled by Unicorn 3.0 software (Amersham Pharmacia Biotech).

Total Analysis System

Automated data acquisition and analysis was completed typically as a multi-step process. Initially, methods were composed within the FPLC's software. The method was laid out as a timeline and controls the fluid delivery (i.e. flow rate, solution concentration, timing of sample injections, etc.). Similarly, macros within the imaging software were used to control the timing and frequency of data capture. Typically, raw data was in the form of a movie, or a sequence of images. After a sequence had been captured, there was a pause in the automation, during which time the user would define specific areas of interest to be analyzed (i.e., the central regions of the particles) and also specify what information was to be extracted (i.e., average red, green, and blue intensities). A macro would then proceed through the sequence of images applying the same areas of interest to each frame and exporting the appropriate information to a pre-formatted spreadsheet.

Other Instrumentation

The $^1$H and $^{13}$C NMR spectra were obtained in $CDCl_3$ solvent solution that was used as purchased. Spectra were recorded on a Varian Unity 300 (300 MHz) Instrument. Low- and high-resolution mass spectra were measured with Finnigan TSQ70 and VG analytical ZAB2-E mass spectrometers, respectively. Immunoassay reagent quality control tests were performed on a Molecular Devices SpectraMax Plus UV/VIS microplate reader and a Molecular Devices SpectraMax Gemini XS Spectrofluorometer microplate reader.

Coupling of Antibodies to Particles Using a Sensor Array System

In an embodiment, different particles were manufactured by coupling a different antibody to an agarose particle. The agarose particle particles were obtained from XC Corporation, Lowell Mass. The particles had an average diameter of about 280 μm The receptor ligands of the antibodies were attached to agarose particle particles using a reductive amination process between a terminal resin bound glyoxal and an antibody to form a reversible Schiff Base complex which can be selectively reduced and stabilized as covalent linkages by using a reducing agent such as sodium cyanoborohydride. (See Borch et al. *J. Am. Chem. Soc.* 1971, 93, 2897-2904, which is incorporated fully herein.).

Detection Methods Using a Sensor Array System

Spectrophotometric assays to probe for the presence of the particle-analyte-visualization reagent complex were performed calorimetrically using a CCD device, as previously described. For identification and quantification of the analyte species, changes in the light absorption and light emission properties of the immobilized particle-analyte-visualization reagent complex were exploited. Identification based upon absorption properties are described herein. Upon exposure to the chromogenic signal generating process, color changes for the particles were about 90% complete within about one hour of exposure. Data streams composed of red, green, and blue (RGB) light intensities were acquired and processed for each of the individual particle elements.

Figure 25A:
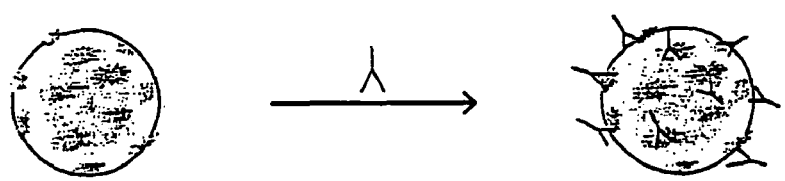
FIGS. 25A-B depict the detection of Hepatitis B HbsAg in the presence of HIV gp41/120 and Influenza A in an embodiment of a sensor array system.
Figure 25B:
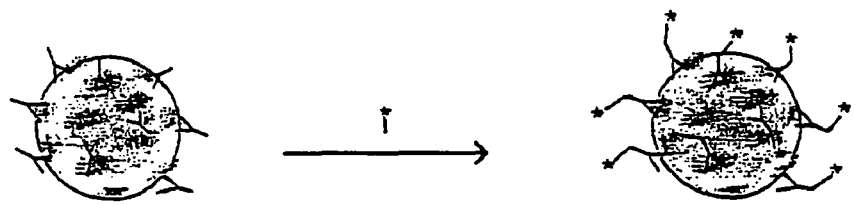

Detection of Hepatitis B HBsAg in the Presence of HIV gp41/120, Influenza a Using a Sensor Array System In an embodiment, three different particles were manufactured by coupling a HIV gp41/120, Influenza A and Hepatitis B (HBsAg) antigens to a particle (FIG. 25A). A series of HIV gp41/120 particles were placed within micromachined wells in a column of a sensor array. Similarly, Influenza A and Hepatitis B HBsAg particles are placed within micromachined wells of the sensor array. Introduction of a fluid containing HBsAg specific IgG was accomplished through the top of the sensor array with passage through the openings at the bottom of each cavity. Unbound HBsAg-IgG was washed away using a pH 7.6 TRIS buffer solution. The particle-analyte complex was then exposed to a fluorophore visualization reagent (e.g., CY2, FIG. 25B). A wash fluid was passed over the sensor array to remove the unreacted visualization agent. Spectrophotometric assays to probe for the presence of the particle-analyte-visualization reagent complex was performed calorimetrically using a CCD device. Particles that have form complexes with HBsAg specific IgG exhibit a higher fluorescent value than the noncomplexed Influenza A and HIV gp41/120 particles.

Detection of CRP Using a Sensor Array System

In an embodiment, a series of 10 particles were manufactured by coupling a CRP antibody to the particles at a high concentration (6 mg/mL). A second series of 10 particles were manufactured by coupling the CRP antibody to the particles at medium concentration (3 mg/mL). A third series of 10 particles were manufactured by coupling the CRP antibody to particles at a low concentration (0.5 mg/mL). A fourth series of 5 particles were manufactured by coupling an immunoglobulin to the particles. The fourth series of particles were a control for the assay. The particles were positioned in columns within micromachined wells formed in silicon/silicon nitride wafers, thus confining the particles to individually addressable positions on a multi-component chip.

Figure 26:
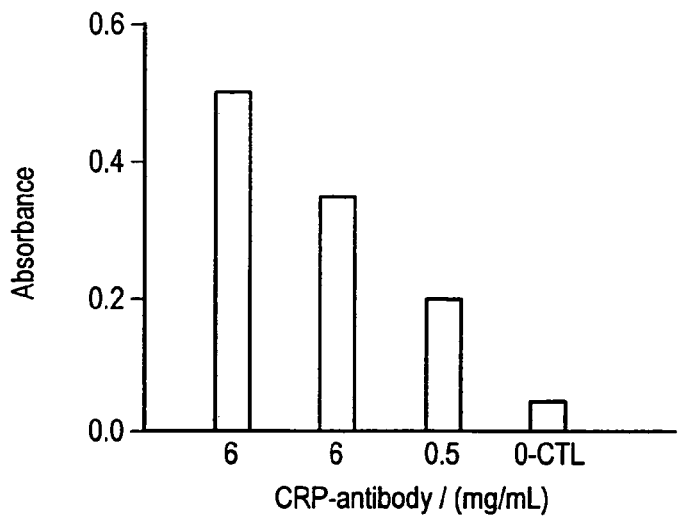
FIG. 26 depict the detection of CRP in an embodiment of a sensor array system.

The sensor array was blocked with 3% bovine serum albumin in phosphate buffered solution (PBS) was passed through the sensor array system Introduction of the analyte fluid (1,000 ng/mL of CRP) was accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed colorimetrically using a CCD device. The average blue responses of the particles to CRP are depicted in FIG. 26. The particles with the highest concentration of CRP-specific antibody (6 mg/mL) exhibited a darker blue color. The control particles (0 mg/mL) exhibited little color.

Dosage Response for CRP Using a Sensor Array System

In an embodiment, a series of 10 particles were manufactured by coupling a CRP antibody to the particles at a high concentration (6 mg/mL). A second series of 10 particles were manufactured by coupling the CRP antibody to the particles at a medium concentration (3 mg/mL). A third series of 10 particles were manufactured by coupling the CRP antibody to the particles at a low concentration (0.5 mg/mL). A fourth series of 5 particles were manufactured by coupling an immunoglobulin to the particles. The fourth series of particles were a control for the assay. The particles were positioned in columns within micromachined wells formed in silicon/silicon nitride wafers, thus confining the particles to individually addressable positions on a multi-component chip.

Figure 27:
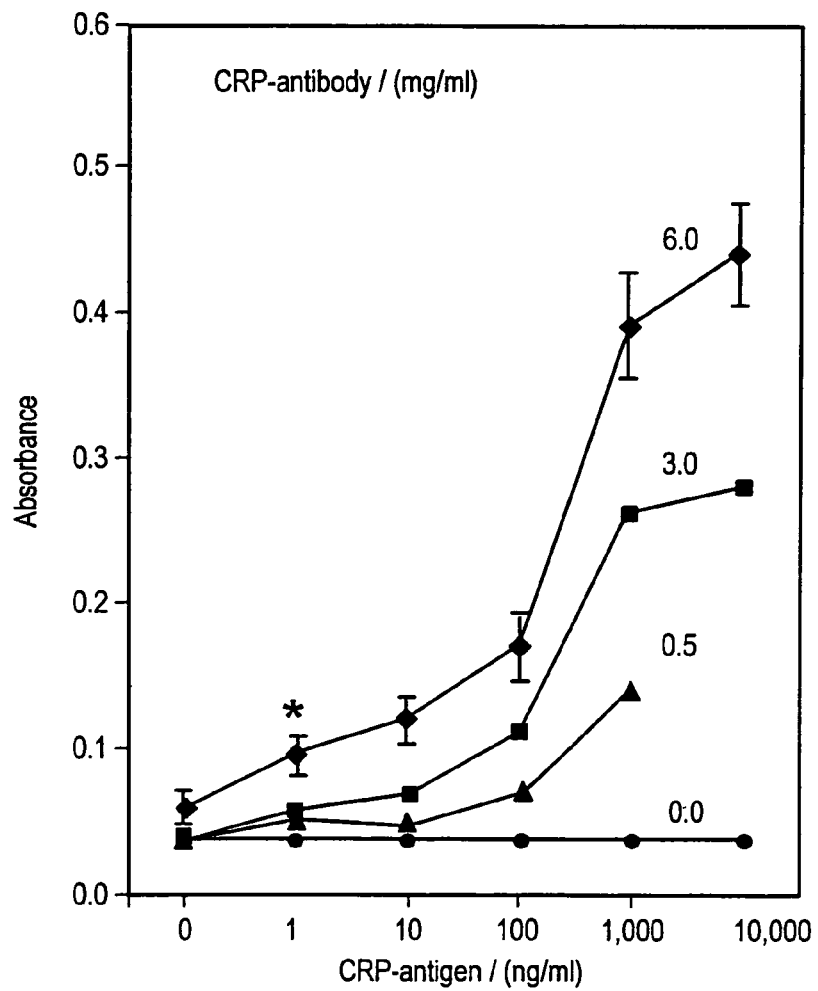
FIG. 27 depicts the dosage response of CRP levels in an embodiment of a sensor array system.

The sensor array was blocked with 3% bovine serum albumin in phosphate buffered solution (PBS) was passed through the sensor array system. Introduction of multiple streams of analyte fluids at varying concentrations (0 to 10,000 ng/mL) were accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed calorimetrically using a CCD device. The dose dependent signals are graphically depicted in FIG. 27.

Simultaneous Detection of CRP and IL-6 Using a Sensor Array System

Figure 28A:
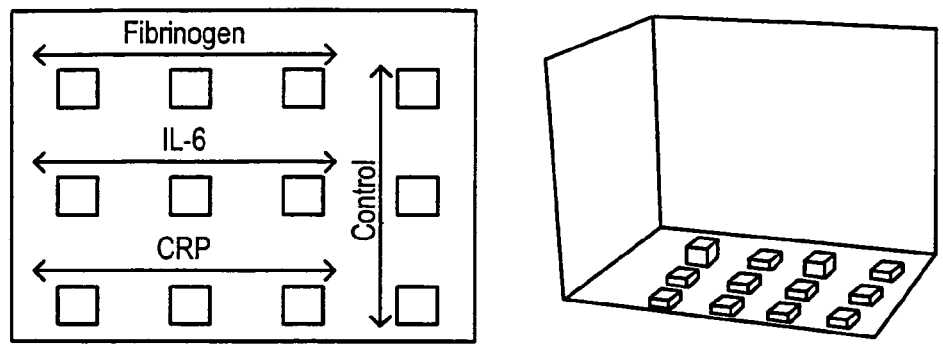
FIGS. 28A-D depict the multi-analyte detection of CRP and IL-6 in an embodiment of a sensor array system.
Figure 28B:
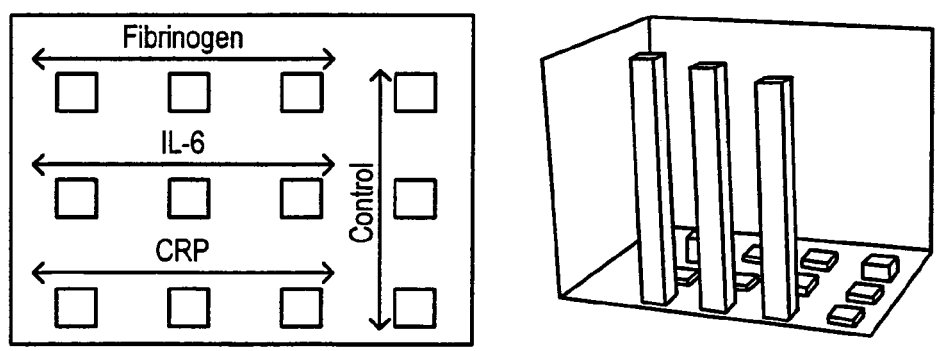
Figure 28C:
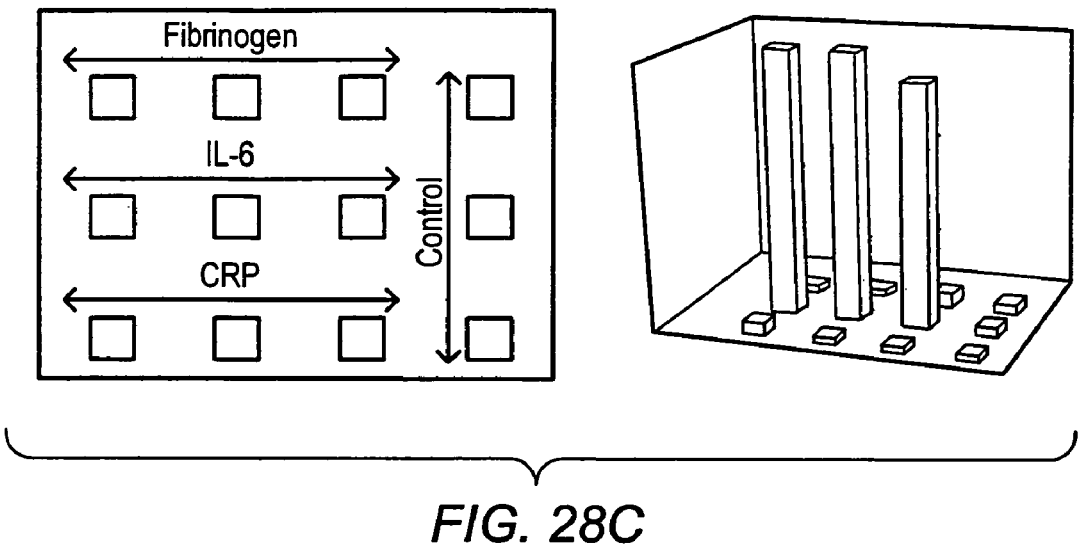
Figure 28D:
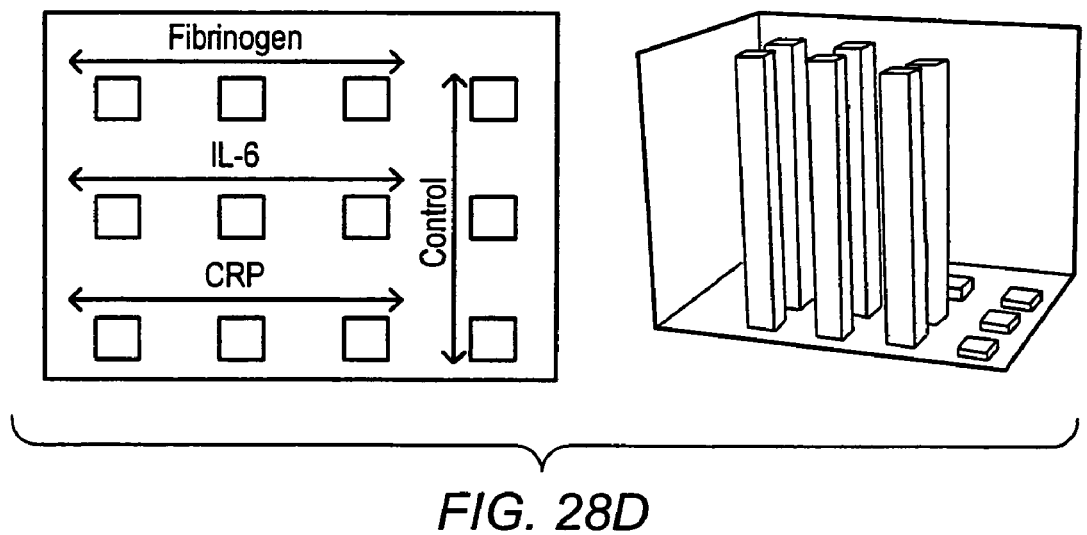

In an embodiment, three different particles were manufactured by coupling Fibrinogen. CRP and IL-6 antibodies to an agarose particle. A series of CRP and IL-6 antibodies receptor particles, were positioned within micromachined wells formed in silicon/silicon nitride wafers, thus confining the particles to individually addressable positions on a multi-component chip. A series of control particles were also placed in the sensor array. The sensor array was blocked by passing 3% bovine serum albumin in phosphate buffered solution (PBS) through the sensor array system. Introduction of the analyte fluids was accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed colorimetrically using a CCD device. The average blue responses of the particles to a fluid that includes buffer only (FIG. 28A), CRP (FIG. 28B), interluekin-6 (FIG. 28C) and a combination of CRP and interleukin-6 (FIG. 28D) are graphically depicted in FIG. 28.

This example demonstrated a number of important factors related to the design, testing, and functionality of micromachined array sensors for cardiac risk factor analyses. First, derivatization of agarose particles with both antibodies was completed. These structures were shown to be responsive to plasma and a visualization process. Second, response times well under one hour was found for colorimetric analysis. Third, micromachined arrays suitable both for confinement of particles, as well as optical characterization of the particles, have been prepared. Fourth, each particle is a fill assay, which allows for simultaneous execution of multiple trials. More trials provide results that are more accurate. Finally, simultaneous detection of several analytes in a mixture was made possible by analysis of the blue color patterns created by the sensor array.

In an embodiment, 35 particles were manufactured by coupling a CRP antibody to the particles. The particles were positioned in columns within micromachined wells formed in silicon/silicon nitride wafers, thus confining the particles to individually addressable positions on a multi-component chip.

Regeneration of Sensor Array for Performing Multiple Tests

Figure 29:
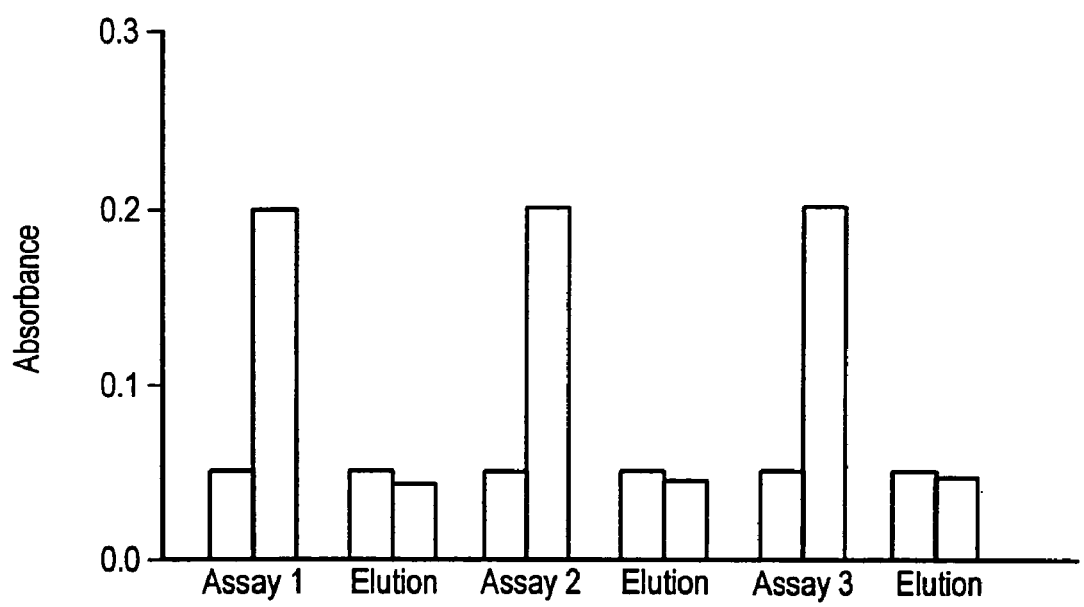
FIG. 29 depicts the regeneration of receptor particles in an embodiment of a sensor array system.

Particles coupled to 3 mg of antibody/ml of particles of either rabbit CRP-specific capture antibody (CRP) or an irrelevant rabbit anti-*H. pylori*-specific antibody (CTL) are tested for their capacity to detect 1,000 ng/ml of CRP in human serum in continuous repetitive runs. FIG. 29 depicts data collected using a colorimetric method. Here each cycle involves: i) injection of 1,000 ng/ml CRP, ii) addition of HRP-conjugated anti-CRP detecting antibody, iii) addition of AEC, iv) elution of signal with 80% methanol, v) wash with PBS, vi) regeneration with glycine-HCl buffer and vii) equilibration with PBS. Results shown in FIG. 29 are for the mean blue absorbance values. The results show that regeneration of the system can be achieved over to allow multiple testing cycles to be performed with a single sensor array.

Particle Preparation—Multi-layer Particles

Preparations were performed in a custom-made fritted solid-phase reaction vessel. The body of the reaction vessel was roughly cylindrical with a radius of ~12 mm, a height of ~82 mm, and a measured volume of 24 mL. The top of the body had a polytetrafluoroethylene (PTFE) lined screw cap, the removal of which permitted the addition of resin and/or solutions. The other end of the body terminated in a porous glass frit (diameter: 20 mm; porosity: coarse). Appended to the frit end of the vessel was a double oblique bore stopcock with a PTFE plug. One of the stopcock's three stems was mated to the frit, such that either of the two opposing sterns could be used to drain solution from the vessel. An example of a commercially available vessel of similar design is LABGLASS item# LG-5000 (www.lab-glass.com). The vessel was mounted on modified GlasCol® mini-rotator, allowing end-over-end tumbling of the vessel.

Provided in tabular form here is the procedure used to prepare batches iv, v and vi (see FIG. 14 and accompanying discussion). This description is applicable to numerous types of multishell particle preparations. Within a given table, each row represents a single step of that specific preparation. Each step may be characterized as either an incubation or a rinse procedure. Incubations include the removal (via aspiration) of any solution from the reaction vessel, the addition of the indicated solution to the reaction vessel, and the subsequent tumbling of the vessel at ~40 rpm for the listed time interval (hours:minutes). Rinses include the removal (via aspiration) of any solution from the reaction vessel followed by the addition of the indicated solution. Multiple rinses of a single solvent are condensed into a single step in the table, with the number of rinses indicated. Additionally, entries in the third column in each table comment on the purpose of the key synthetic steps. The total solution volume was held consistently at 18 mL, unless otherwise noted. It should be mentioned that incubations in excess of 3 hrs represent the resin being left overnight, and that their times were based on convenience rather than necessity. Initially, 200 mg of TG-NH$_2$ was modified as shown below in Table 3.

TABLE 3

Preparation of Multishell Particle Batch iv

| Incubation Time (hrs:min) | Number of Rinses | Solution Composition | Purpose |
|---|---|---|---|
| | 1× | DMF | |
| 0:10 | | DMF | |
| 1:04 | | DMF | |
| 2:10 | | 100 uL DIEA in 18 mL DMF | |
| 0:18 | | 8 mM Fmoc, 50 uL DIEA in 15 mL DMF | protect exterior region |
| 0:20 | | 3 mM ALZC, 3 mM DCC in 18 mL DMF | dye core |
| | 2× | DMF | |
| | 2× | HCl (10 mM) | |
| 0:03 | | HCl (10 mM) | |
| 0:09 | | HCl (10 mM) | |
| 0:03 | | NaOH (10 mM) | |
| | 1× | HCl (10 mM) | |
| 0:30 | | NaOH (10 mM) | |
| | 1× | HCl (10 mM) | |
| 2:30 | | NaOH (10 mM) | |
| | 1× | HCl (10 mM) | |
| | 1× | NaOH (10 mM) | |
| | 2× | H2O | |
| | 3× | DMF | |
| 1:12 | | DMF | |
| 0:15 | | 25% piperidine in DMF | cleave Fmoc |
| 0:35 | | 25% piperidine in DMF | cleave Fmoc |
| | 1× | DMF | |
| 13:42 | | DMF | |
| 1:53 | | 25% piperidine in DMF | cleave Fmoc |
| | 1× | DMF | |
| 30:00 | | DMF | |

TABLE 4

Preparation of Multishell Particle Batch v

| Incubation Time (hrs:min) | Number of Rinses | Solution Composition | Purpose |
|---|---|---|---|
| 0:25 | | DMF | |
| 0:35 | | 1:1:3 Ac2O:TEA:DMF | acetylate exterior |
| | 1× | DMF | |
| 0:05 | | DMF | |
| 0:12 | | DMF | |
| 15:15 | | DMF | |
| 0:09 | | DMF | |
| | 2× | H2O | |
| 0:15 | | H2O | |
| 1:15 | | H2O | |
| 1:12 | | H2O | |

The resulting resin, with acetylated exterior amines and ALZC cores, was collected and labeled as Batch v. A second aliquot of Batch iv was treated with EDTA anhydride and then washed, as shown below in Table 5.

TABLE 5

Preparation of Multishell Particle Batch vi

| Incubation Time (hrs:min) | Number of Rinses | Solution Composition | Purpose |
|---|---|---|---|
| 0:25 | | DMF | |
| 0:40 | | 10 mM EDTAan in 20% TEA/DMF | EDTA in exterior |
| | 1× | DMF | |
| 0:05 | | DMF | |
| 0:12 | | DMF | |
| 15:15 | | DMF | |
| 0:09 | | DMF | |
| | 2× | H2O | |
| 0:15 | | H2O | |
| 1:15 | | H2O | |
| 1:12 | | H2O | |

The resulting resin, with immobilized EDTA in the exterior regions and ALZC in the cores, was collected and labeled as Batch vi. Samples from Batches v and vi were subjected to a further attempted dye-immobilization reaction in order to reveal any free amines in the exterior regions. Visual inspection indicated that no dye was successfully immobilized in the outer shells of either batch.

Data Acquisition and Analysis

Arrays of multishell particles are arranged on silicon chips and subsequently sealed in custom-built flow cells. The flow cell is readily interfaced with a variety of fluidic devices (i.e., pumps, valves), the precise configuration of which is dictated by individual experiments. In the flow cell, the array is illuminated from below while being viewed with a DVC 1312C CCD camera (DVC Co., Austin, Tex.) through the optics of an Olympus SZX12 stereo microscope. For this work, image acquisition was controlled via LabVIEW software (National Instruments, Austin, Tex.), ensuring high temporal fidelity. Macros written and executed within Image Pro Plus 4.0 (Mediacybernetics) were used to generate RGB absorbance vs. time plots for individual microspheres. The RGB effective absorbance values were calculated as described earlier.

Further Improvements

Figure 30:
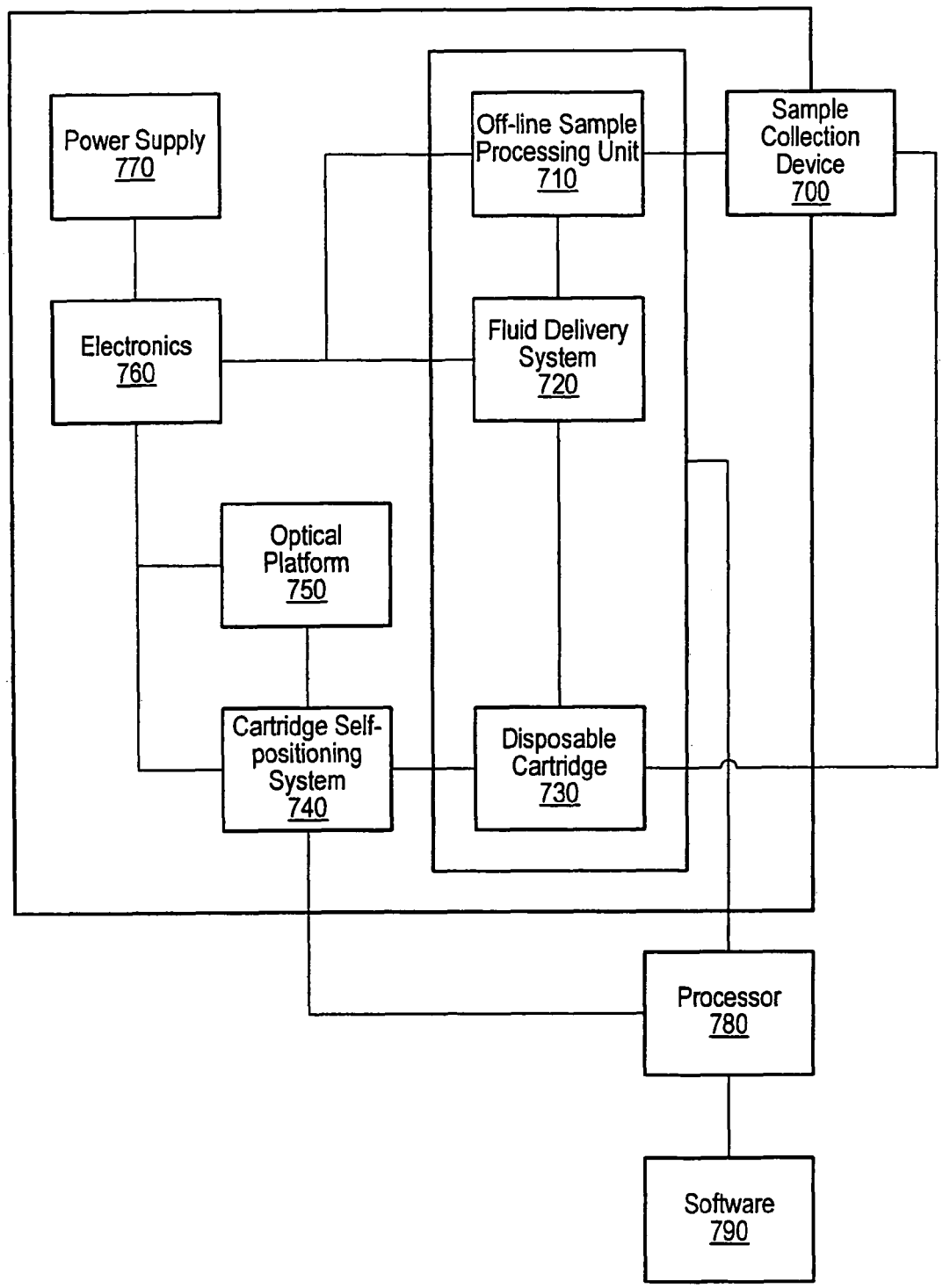
FIG. 30 depicts a schematic diagram of a device for membrane and/or particle-based analyte detection.

In some embodiments, an optical analysis instrument for both membrane and/or sensor array particle-based measurements may be used to determine the presence of analytes. A schematic diagram of an embodiment of an instrument is depicted in FIG. 30. In one embodiment, an instrument may include a sample collection device 700, an off-line sample processing unit 710, a fluid delivery system 720, a disposable cartridge 730, a cartridge self-positioning system 740, an optical platform 750, electronics 760, power supplies 770, one or more computer processors 780, and/or software 790 and/or firmware.

In some embodiments, the instrument may include one or more disposable cartridges. A disposable sample cartridge may be the chemical and biochemical-sensing component of the analysis instrument. A cartridge may include index-matching, molded or machined plastics, metals, glass or a combination thereof. A cartridge may also include one or more reservoirs for holding reagents, samples, and/or waste. Reservoirs may be coupled to a cartridge via one or more microfluidic channels.

A cartridge may include one or more detection systems. As used herein the term "detection system" refers to a system having an analyte detection platform. Detection systems include both particle-based analyte detection platforms and membrane-based analyte detection platforms. A particle-based analyte detection platform may include a particle-based platform includes particles configured to produce a signal in the presence of one or more analytes. The analysis and/or separation surfaces (e.g., membrane or the like) and/or sensing particles housed on a support member, may be used to determine the presence of analytes. The membrane surface traps and/or separates particulate matter of interest (e.g., cells, microbes, small pieces of tissue, polymer, glass or metal particles, or conjugates thereof). The support member includes sensing particles functionalized to react with analytes of interest (e.g., proteins, DNA and RNA oligonucleotides, metals or other solution-phase analytes). As such, the cartridge may have the capability to detect both particulate matter and/or solution-phase analytes concurrently.

In certain embodiments, the particle-based analyte detection platform may include a supporting member that supports one or more particles. Particles may be optically encoded with one or more fluorophores, chromophores, etc. and used to identify the particle, regardless of the location of the particle and/or analyte. Such an encoding scheme may be used in a combination membrane/particle-based cartridge and may make manufacture of the cartridge easier.

In an embodiment, (micron-sized) encoded particles may be placed in the fluid sample for the purpose of sample and/or reagent identification (e.g., a sample identification bar code). In operation, the membrane may be used to trap the particles and identify the patient (perhaps in addition to membrane-based analysis), followed by sensor-array analysis. Such particles may also be used to calibrate the instrument and/or monitor the flow rate.

In some embodiments, a cartridge may be designed such that the cartridge is removably positionable in an instrument. Cartridge alignment may be performed manually or automatically using the cartridge positioning system. A cartridge positioning system may automatically or manually position the disposable cartridge in the instrument. In certain embodiments, the disposable cartridge may be placed in the cartridge self-positioning system prior to sample introduction. In one embodiment, a fluid delivery system may deliver reagents to a disposable cartridge. Once the disposable cartridge is placed inside the instrument, the cartridge positioning system may be used to align the one or more areas of the cartridge containing the sample to be analyzed with the instrument's optical platform. The optical platform may acquire images (e.g., visual or fluorescent) of the sample, and/or of sample-modulated particle-based platforms. The images may be processed and analyzed using software, algorithms, and/or neural networks.

An instrument may be used to analyze one or more samples. A sample may include one or more analytes, cells, and/or bacteria. A sample may be collected for analysis with a sample collection device. The sample collection device may be external or internal to the instrument and may be interfaced with the analysis instrument. In some embodiments, a sample collection device obtains and delivers one or more samples directly to an instrument. Depending on the type of measurement to be performed, a sample may be transported through one of two pathways by the sample collection device. In one application, a sample may be transported to an off-line sample-processing unit where the sample may be manipulated. The sample may then be transported to a disposable cartridge via a fluid delivery system. In another embodiment, a sample may be transported directly to a disposable cartridge by a sample collection device. The disposable cartridge, including the sample, may then be inserted into the instrument.

Figure 31A:
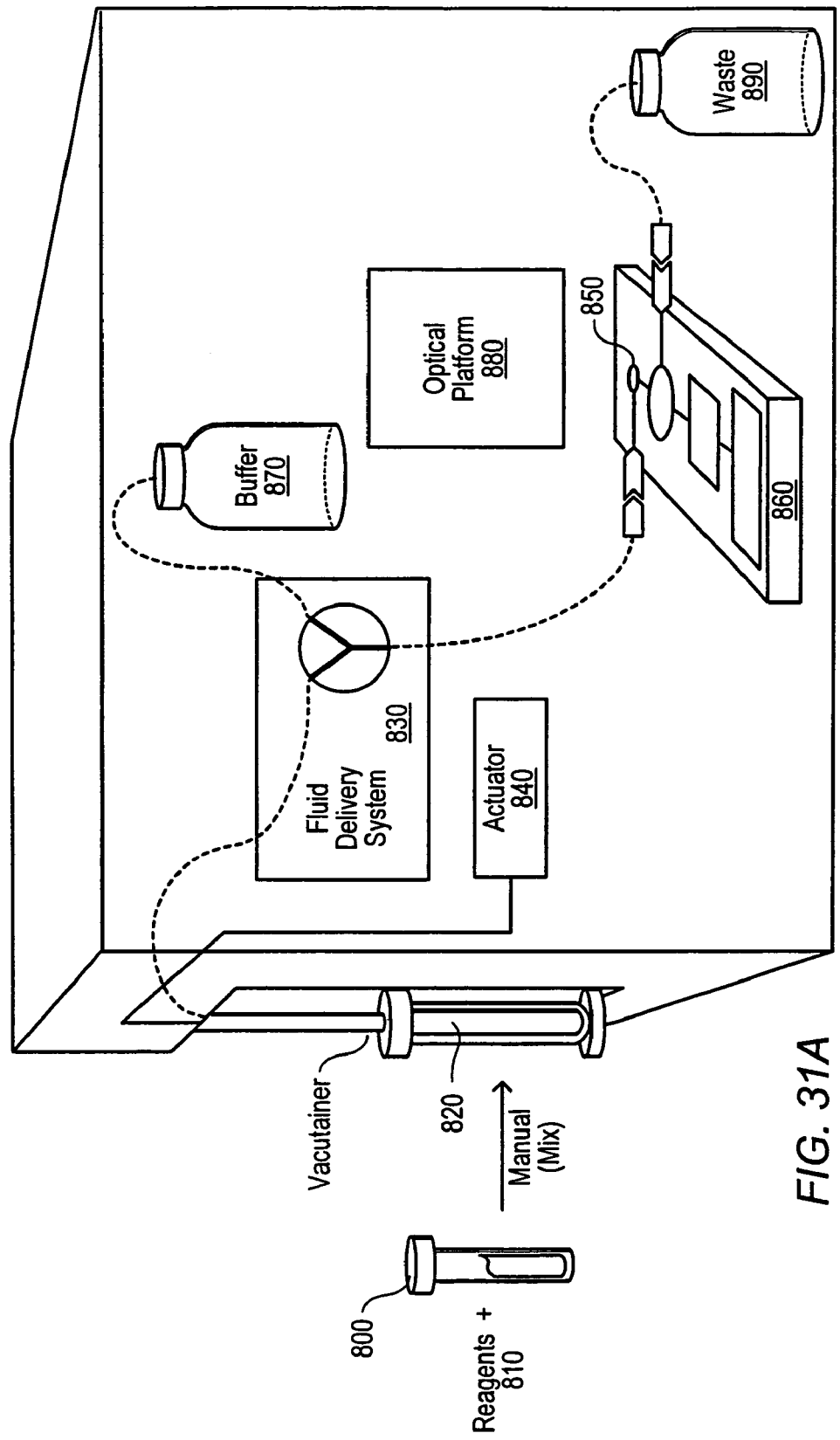
FIGS. 31A-D depict schematic diagrams of sample collection systems.

FIG. 31A depicts an embodiment of an optical analysis instrument. A sample collection device may be used to obtain a sample 800. A sample 800 may be mixed with reagents 810 in an analysis instrument's off-line sample processing unit. The modified sample 820 may be coupled to the instrument via a fluid delivery system 830. The instrument may include an actuator 840 that may force fluid, such as samples, reagents, and/or waste, through the instrument. The fluid delivery system 830 may allow a modified sample 820 to pass over a reagent pad 850 positioned on a cartridge 860. A buffer 870 may also flow over the reagent pad 850. Passing the modified sample 820 and/or buffer 870 may reconstitute one or more reagents on the reagent pad 850. The modified sample may then pass through a trap configured to remove air from the fluid. The modified sample may then flow to a particle-based platform and/or a membrane-based platform for analysis. The cartridge 860 may be automatically or manually aligned with the optical platform 880 for analysis. Residual reagents, buffer, and/or sample may flow to a waste reservoir 890 for storage. A waste reservoir may be positioned in the instrument or external to the instrument. A waste reservoir may reduce hazards to operators by reducing an operator's contact with samples and/or reagents.

Figure 31B:
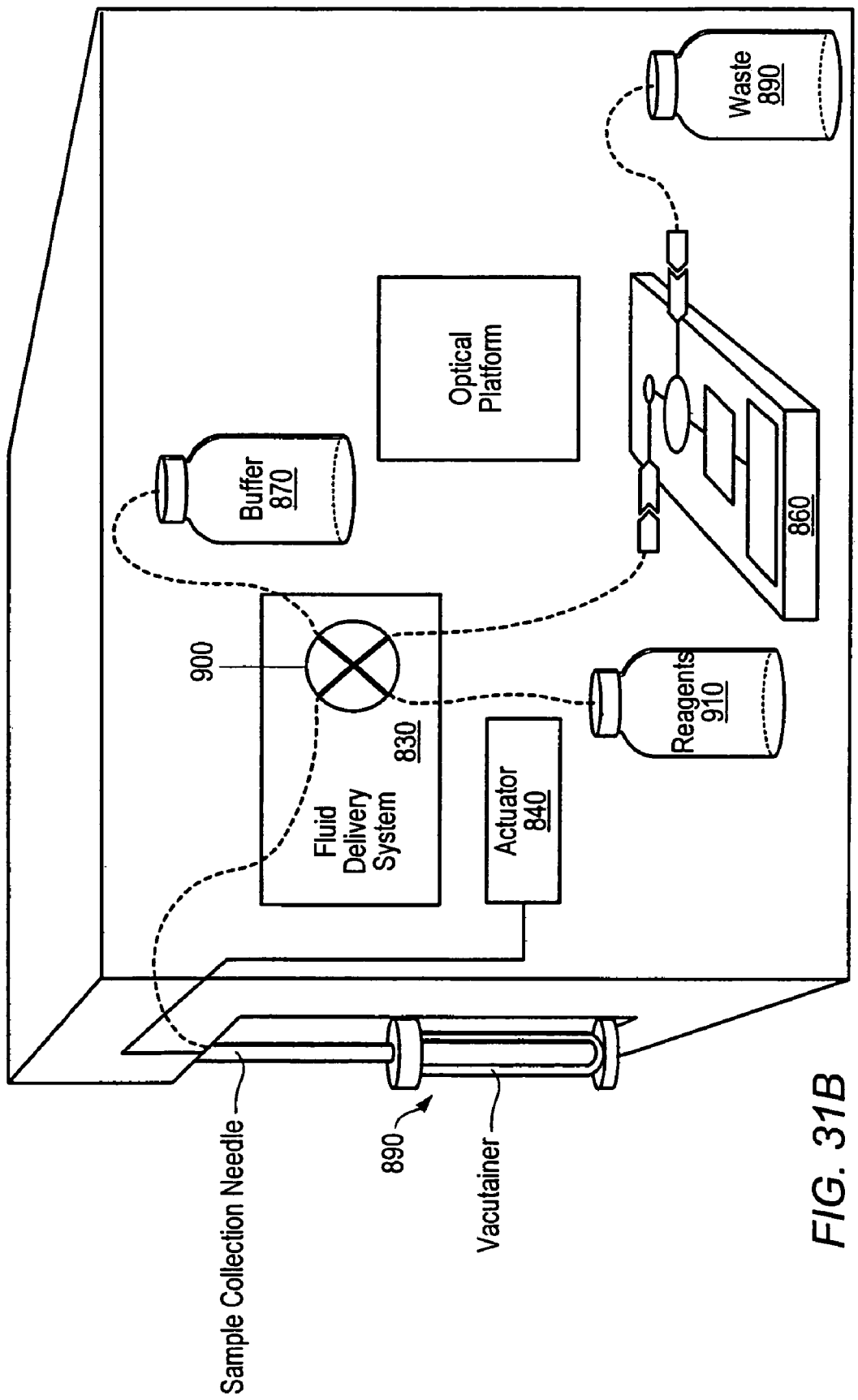

The use of a sample collection device may help to limit the operator's exposure to pathogens that may be present in the sample. Ideally, the sample collection device will have the ability to consume the portion of the device (e.g., a needle) that has contacted the sample. One embodiment of a sample collection device is a pressurized unit that operates analogous to a vacutainer used to collect blood samples, as depicted in FIG. 31B. Using such a device, samples may be directly transported from the source to the instrument without further handling by the operator.

In some embodiments, a sample may be obtained intravenously using sample collection device 890 including a needle and vacutainer. In operation, a filled vacutainer may be coupled or secured to the portable reader instrument. A sharp sample collection needle, that is part of the portable reader instrument, may be actuated to pierce the vacutainer's rubber septum. The sample may then flow through the instrument for analysis via a fluid delivery system 830 driven by an actuator 840. A sample may flow from a sample collection device to a sample reservoir 900. Reagents 910 and/or buffer 870 may mix with the sample in the sample reservoir 900. The modified sample may then flow from the sample reservoir 900 to the cartridge 860 for analysis. Samples, reagents, buffers, and/or other fluids may flow from the cartridge 860 to a waste reservoir 890 after analysis.

Figure 31C:
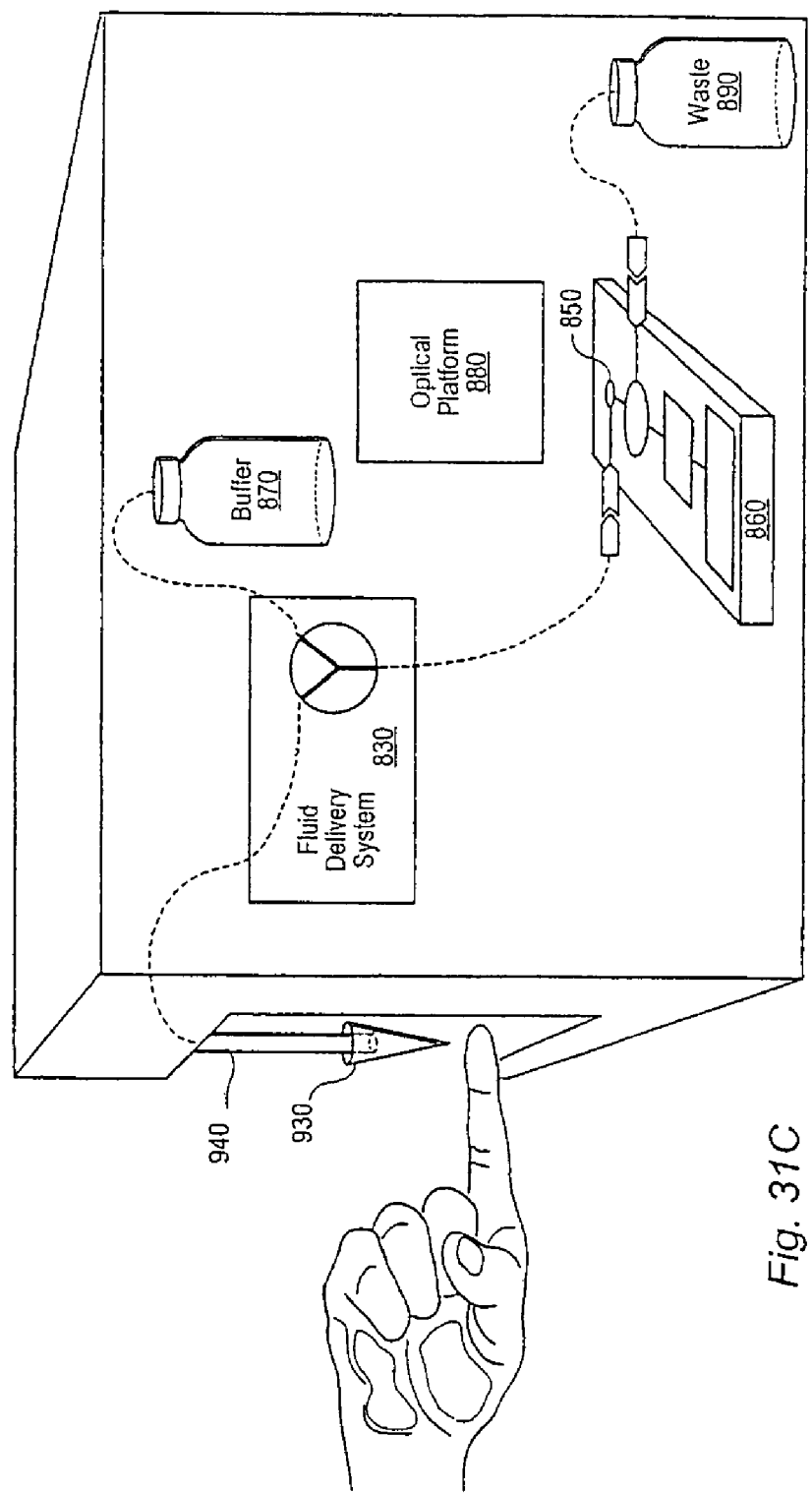

In another embodiment, the sample may be obtained from a fingerstick or small incision and may be collected using a disposable pipette, as shown in FIG. 31C. A portion of a body may be brought proximate the instrument where a sample collection device is positioned. A sample collection needle may be part of the portable reader instrument. A sample collection device may include a disposable tip 930 and/or a filter 940. Using a disposable tip on a sample collection needle may inhibit sample-to sample cross-contamination. In some embodiments, a disposable tip may be at least partially coated with appropriate reagents. A sample may be incubated in a disposable tip before being drawn into an instrument. In an embodiment, a sample collection needle may include a filter and/or screen on a distal end. A filter and/or screen may inhibit the entry of debris into an instrument, inhibit clogging or obstruction of an instrument, and/or inhibit clogging or obstruction of sample cartridge microfluidic channels.

Sample may flow from the sample collection device to the cartridge 860 via a fluid delivery system 830. A sample may pass over a reagent pad 850 positioned on the cartridge 860. Sample and/or buffer 870 may reconstitute reagents on the reagent pad 850. After reacting with one or more reagents, a sample may flow to a particle-based platform or a membrane-based platform for analysis. A cartridge 860 and/or optical platform 880 may be adjusted such that the optical platform is in alignment with the particle or membrane platform being analyzed. After analysis, the sample may flow to a waste reservoir 890. A cartridge 860 may be washed prior to analysis of the next sample. A fluid and/or buffer 870 may flow through the cartridge 860 and into the waste reservoir 890.

In an embodiment, a sample collection device may include a disposable pipette or capillary tube. A disposable pipette may contain, or may be coated with, one or more appropriate reagents to aid in visualization. For example, a stain may aid in visualization of particles and/or cells in a sample. A disposable pipette may also collect a precise sample volume. It may be desirable to incubate a sample prior to analysis. A sample may be incubated in a disposable tip before being drawn into an instrument. In one embodiment, after incubation, the sample may be delivered to the cartridge manually using the disposable pipette. In another embodiment, a sample cartridge may include one or more appropriate reagents for incubation in the sample or reagent reservoir. In some embodiments, incubation may be performed within the sample cartridge using reagents from a sample or reagent reservoir. After the sample is incubated with one or more reagents, the fluid delivery system may deliver a buffer solution to the sample/reagent reservoir. Delivering a buffer solution to the sample/reagent reservoir may push the labeled sample to a membrane in the cartridge for subsequent rinsing and sample analysis. After analysis of the sample is completed, the sample may be delivered to a waste reservoir. A waste reservoir may be positioned in the sample cartridge, internal or external to the instrument.

Figure 31D:
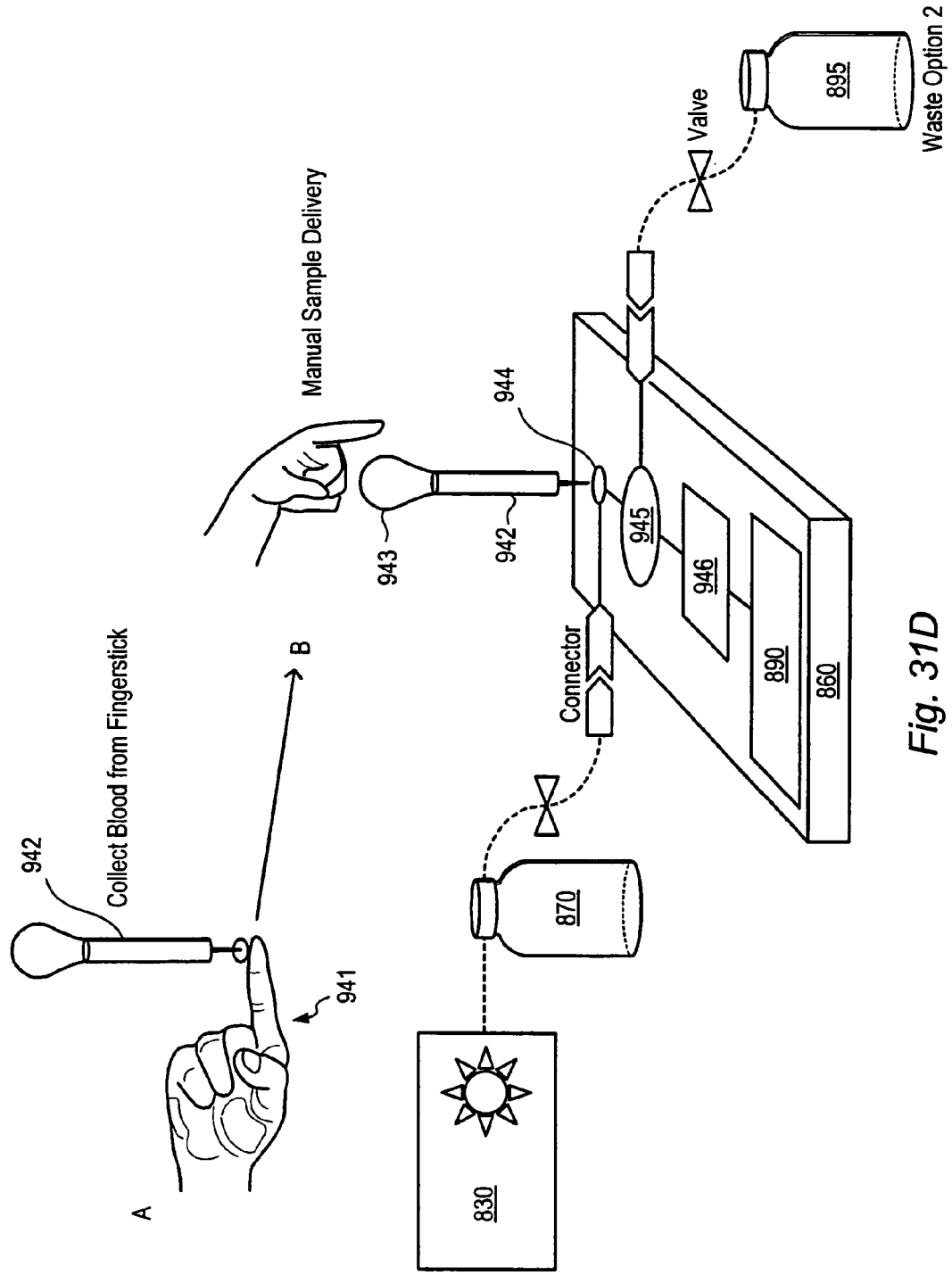

In some embodiments, a sample may be obtained from a fingerstick or small incision in a portion of a human body 941, as depicted in FIG. 31D. In an embodiment, sample collection device 942 may include a sample reservoir. A sample collection device 942 and/or sample reservoir may be configured to collect a predetermined volume of a sample. A sample collector device 942 may include a pipette. A sample collection device 942 may be coupled to a cartridge 860 to deliver a sample to the cartridge. In one embodiment, a bulb 943 on a pipette may force a sample from a sample collection device 942 into the cartridge 860. A fluid delivery system 830 coupled to the cartridge 860 may deliver buffer 870 to a cartridge 860 and/or reagents. In an embodiment, sample, buffer, and/or reagents mix in a mixing chamber 944 of a sample reservoir in the cartridge 860. After the sample has been reacted with one or more reagents, the sample may flow into a membrane 945 and/or particle-based platform 946 of the cartridge 860 for analysis. Waste reservoirs 890, 895 positioned in the cartridge or externally, respectively, may collect waste from cartridge 860.

In an embodiment, a portion of a human body, such as a finger, may be positioned proximate a sample reservoir of a cartridge. A portion of a human body may contact a portion of the sample reservoir. A sample reservoir may have a size that allows a predetermined volume of sample to be collected. A cartridge sample reservoir may include a sample pick-up pad. A sample pick-up pad may be a pad that absorbs and/or collects samples deposited on a surface of the sample pick-up pad. A sample pick-up pad may be made of an absorbent material. A sample pick-up pad may draw a sample from a portion of a human body in contact with the sample pick-up pad to a sample reservoir. For example, a sample collection device may make a small incision in a portion of a human body. The portion of the human body may be brought proximate a sample pick-up pad. Blood from the small incision may flow onto the sample pick-up pad. Blood from the sample pick-up pad may then be delivered to the cartridge via a fluid delivery system. In an embodiment, a sample pick-up pad may include one or more anti-coagulants and/or reagents for sample labeling. A sample reservoir may include one or more anti-coagulants and/or reagents for sample labeling.

In some embodiments, the instrument may include an off-line sample-processing unit. An off-line sample-processing unit may process samples prior to delivery to a cartridge. An off-line processing unit may allow sample processing including, but not limited to, incubation with reagents, cell lyses and/or sample amplification techniques such as Polymerase Chain Reaction (PCR). Depending on the type of diagnostic assay or measurement being performed, an off-line sample-processing unit may be bypassed and a sample may be directly delivered to a disposable cartridge.

In certain embodiments, a fluid delivery system may include metered pumps (e.g., syringe, rotary, and/or peristaltic), valves, connectors, and/or pressure-driven actuation (e.g., roller with motorized translation). A fluid delivery system may be vacuum-driven (e.g., a cartridge may be under vacuum). A fluid delivery system may draw one or more samples into an instrument, deliver one or more samples to a sample cartridge, and/or move fluids such as sample, reagents and/or buffers through the cartridge and other channels or fluid lines. A fluid delivery system may deliver samples and/or other fluids to a waste reservoir after analysis. In one embodiment, a fluid delivery system may be used to wash a cartridge after sample analysis. Fluid may be driven through a cartridge after a sample is analyzed by the fluid delivery system. The fluid may then flow from the cartridge to a waste reservoir.

Figure 32A:
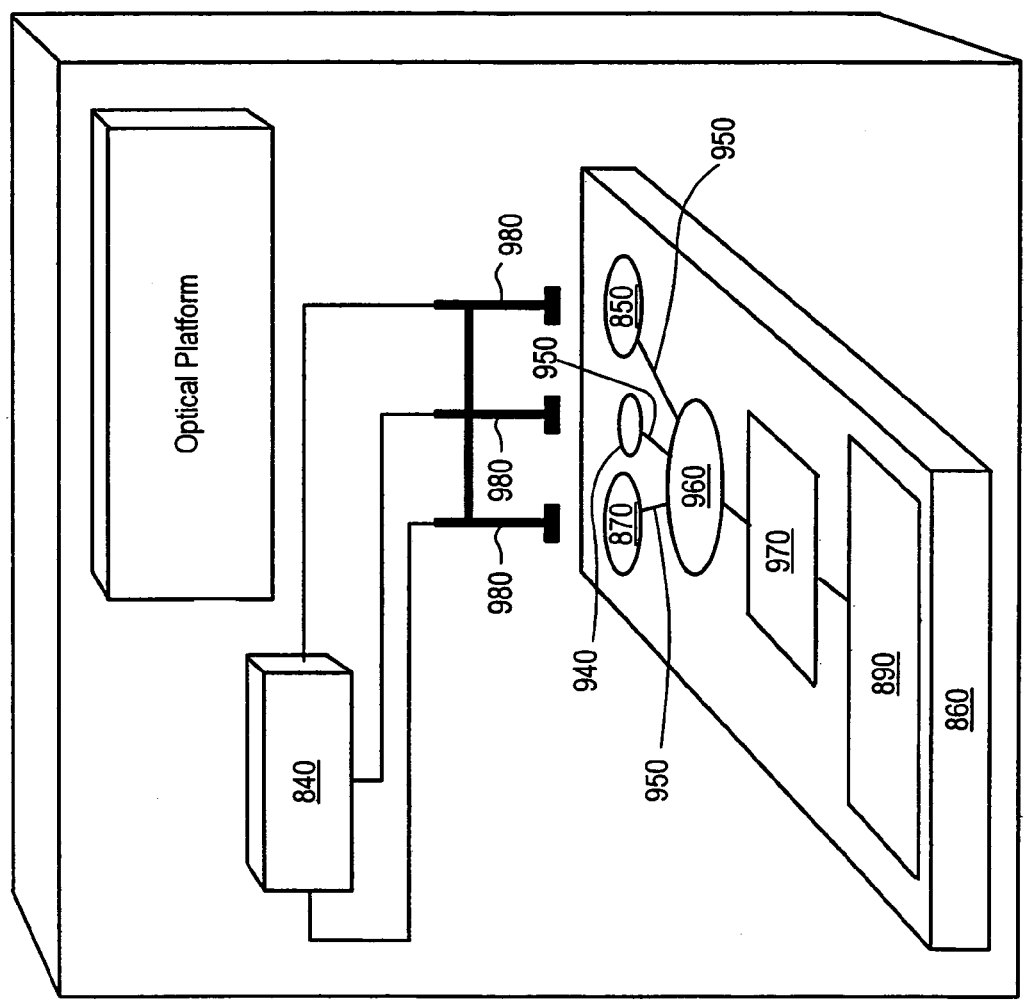
FIG. 32A depicts a schematic diagram of a detection system with actuators.
Figure 32B:
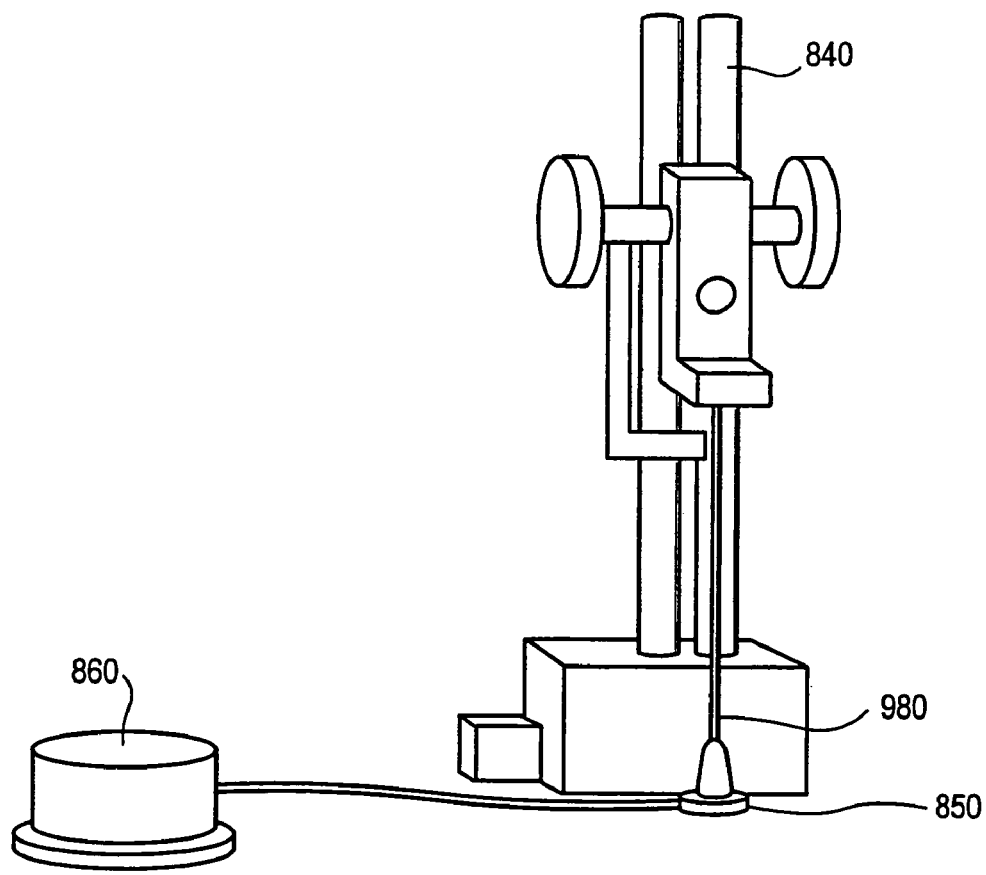
FIG. 32B depicts an embodiment of an actuator.
Figure 32C:
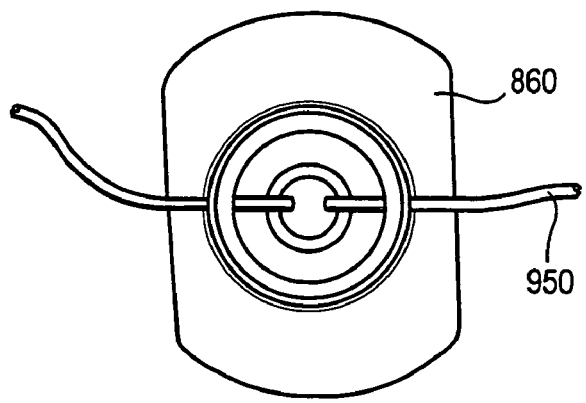
FIG. 32C depicts an embodiment of a channel coupled to a sample cartridge.

FIG. 32A depicts one embodiment of a sample cartridge and its interface with an actuated fluid delivery system. In this example, the buffer 870, reagents 850, and/or sample 940 are contained in reservoirs. Reservoirs may be substantially sealed reservoirs positioned in a cartridge. In an embodiment, applying pressure to a reservoir may release the contents of the reservoir into channels 950. Actuators 840 may press down on the fluid containing reservoirs, delivering the contents to the membrane 960 and/or particle-based platform 970. FIG. 32B depicts an embodiment of an actuator 840. Actuator 840 may include a mechanism for applying pressure to one or more reagent packs 850, either individually or simultaneously. In one embodiment, actuator 840 includes an elongated member 980 that is moved by the actuator 840 to apply pressure on one or more reagent packs 850, causing the reagent packs to release one or more reagents to a cartridge 860. During use, an actuator 840 may apply pressure to a reagent pack 850, forcing one or more reagents in the reagent pack through a channel 950, as depicted in FIG. 32A. Channels 950 may couple a reagent pack 850 to a membrane 960 and/or a particle-based platform 970 in a sample cartridge 860. As pressure on a reagent pack 850 increases, more reagent may be released from the reagent pack and into a channel 950. As depicted in FIG. 32C, reagents may flow through a channel 950 and into a sample cartridge 860. Sample and reagent may flow out the sample cartridge 860 via a channel due to actuation. Increased pressure from actuators on buffer 870, sample 940, and/or reagent packs 850 may drive fluid from the membrane 960 and/or particle-based platforms 970 and into a waste reservoir 890, see FIG. 32A. A waste reservoir 890 may be positioned in the cartridge 860.

Figure 33A:
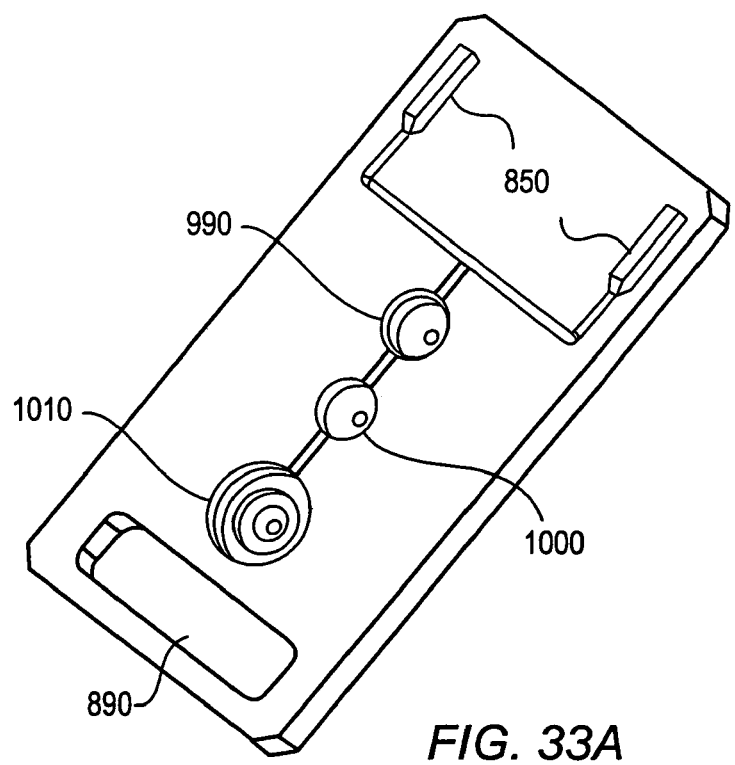
FIGS. 33A-C depict schematic diagrams of disposable sample cartridges.

FIG. 33A depicts an embodiment of a disposable cartridge including reagent packs. During use, a sample (e.g., blood obtained from a fingerstick) may be delivered to a sample reservoir 990. A reagent pack 850 may deliver one or more reagents to a sample reservoir 990 by actuation. In an embodiment, an actuator may apply pressure on a reagent pack 850 and force reagent from a reagent pack through channels 950 and into a sample reservoir 990. Reagents and a sample may react in the sample reservoir 990. In certain embodiments, further actuation may cause the modified sample, or sample reacted with reagents, into a trap 1000. Trap 1000 may be a bubble trap. Trap 1000 may be designed to release air from a fluid passing through it. Trap 1000 may substantially remove air from a sample flowing through a trap. Further actuation may then push a substantially air free sample from a trap 1000 into a membrane and/or particle-based platform 1010. In a membrane and/or particle-based platform 1010, a sample may be washed with a solution and/or analyzed. Residual reagents and/or discarded samples may be collected and/or contained in a waste reservoir 890 positioned in the cartridge 860. Collecting reagents and/or samples in a waste reservoir may facilitate hazard-free disposal of the cartridge.

Figure 33B:
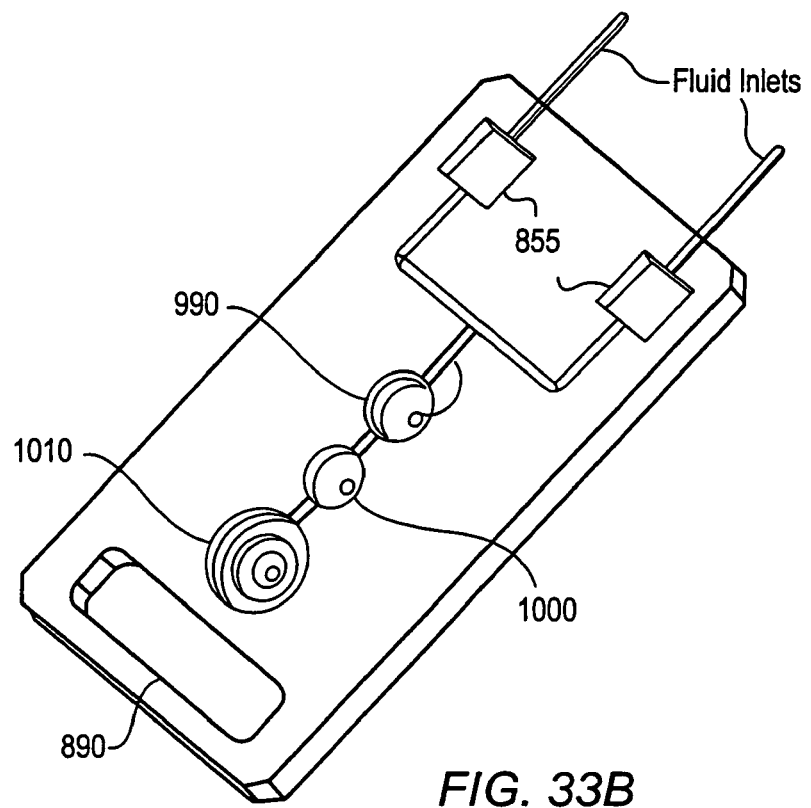

FIG. 33B depicts an embodiment of a cartridge including reagent packs. A reagent pack may be a pad 855 including one or more reagents that have been dried on a surface of the reagent pad. A reagent pack may include a pad with one or more reagents within the pad. In certain embodiments, reagents and/or a reagent pad may include one or more stabilizers. Stabilizers may increase reagent stability. During use, a sample may be deposited in a sample reservoir 990. Buffer may be delivered through fluid inlets and flow over reagent pads 855. When a buffer passes over reagent pads 855, one or more reagents may be reconstituted and delivered to a sample reservoir 990. In one embodiment, a buffer may reconstitute a desired reagent on a reagent pad 855. A buffer solution containing the reconstituted reagents may pass into a sample reservoir 990 and react with a sample. A fluid delivery system may then push the chemically modified sample (e.g., the sample reacted with one or more reagents) into a trap 1000. In the trap 1000, air may be released from the chemically modified sample. Further pressure or actuation may push the air free sample into a membrane and/or particle-based platform 1010 of a cartridge 860. In a membrane and/or particle-based platform 1010, a chemically modified sample may be washed and/or analyzed. Residual reagents and/or discarded samples may flow to a waste reservoir 890 to reduce hazards during disposal.

Figure 33C:
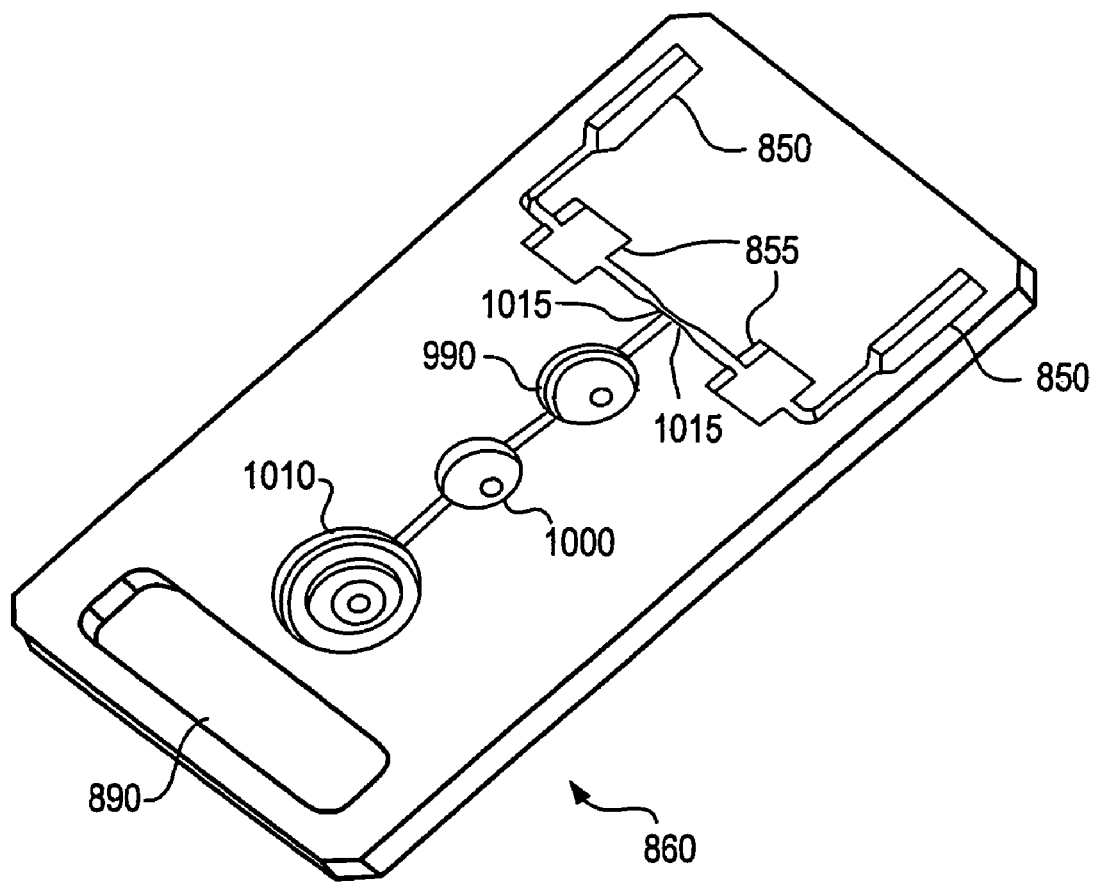

In some embodiments, a combination of reagent reservoirs, reagent packs, and/or reagent pads may be positioned in a cartridge, as depicted in FIG. 33C. Reagent packs and/or reservoirs 850 may be coupled to reagent pads 855 such that pressure on the reagent packs 850 may deliver one or more reagents to one or more reagent pads 855. Reagents from the reagent packs 850 may reconstitute one or more reagents on the reagent pads 855. Further actuation may force the reagents from the reagent pad to the sample reservoir 990. For example, an actuated lever may apply pressure to reagent packs and force reagent through one or more channels connecting one or more reagent packs and a sample reservoir. A channel may direct reagent from a reagent pack to flow over a reagent pad. In some embodiments, a cartridge 860 may include passive valves 1015, as depicted in FIG. 33C. Passive valves provide a path of least resistance to flow. Passive valves 1015 may be used to facilitate fluid flow towards a sample reservoir 990 and/or other areas of the cartridge 860. A fluid delivery system may then push the chemically modified sample (e.g., the sample reacted with one or more reagents) into a trap 1000. In the trap 1000, air may be released from the chemically modified sample. Further pressure or actuation may push the air free sample into a membrane and/or particle-based platform 1010 of a cartridge 860. In a membrane and/or particle-based platform 1010, a chemically modified sample may be washed and/or analyzed. Residual reagents and/or discarded samples may flow to a waste reservoir 890 to reduce hazards during disposal.

In some embodiments, disposable cartridges may include reagent pads. Reagent pads may store reagents in a self-contained manner that may provide increased stability, reduce and/or eliminate reagent aggregation and/or precipitation (e.g., clumping) and increase effective reagent concentrations. Increasing effective reagent concentrations may reduce response times for sample analysis. Disposable, self-contained cartridges may have important implications for point-of-care diagnostics, such as, not requiring refrigerated storage nor reagent preparation and/or not requiring handling of waste material. Cartridges may allow fast and inexpensive diagnostics to be transported to and performed in situations where time is critical.

Figure 33D:
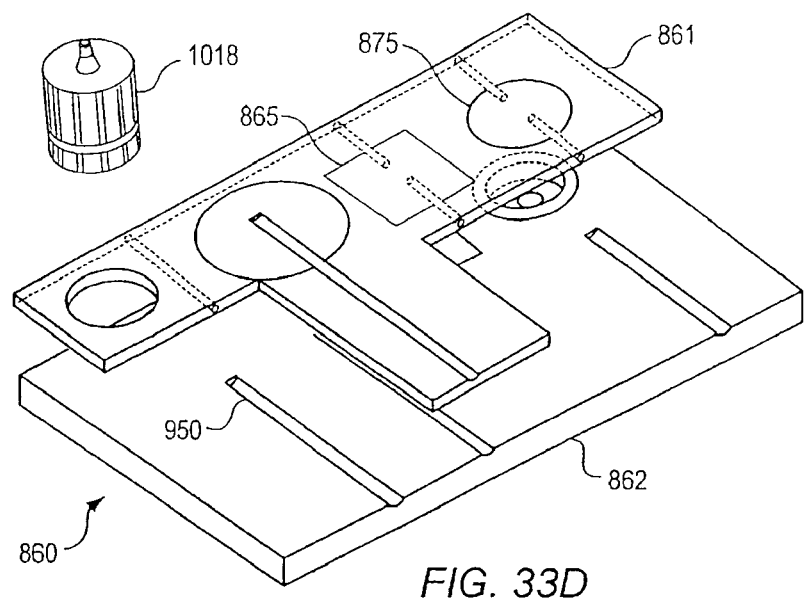
FIG. 33D depicts an exploded view of a cartridge with a reagent capsule.
Figure 33E:
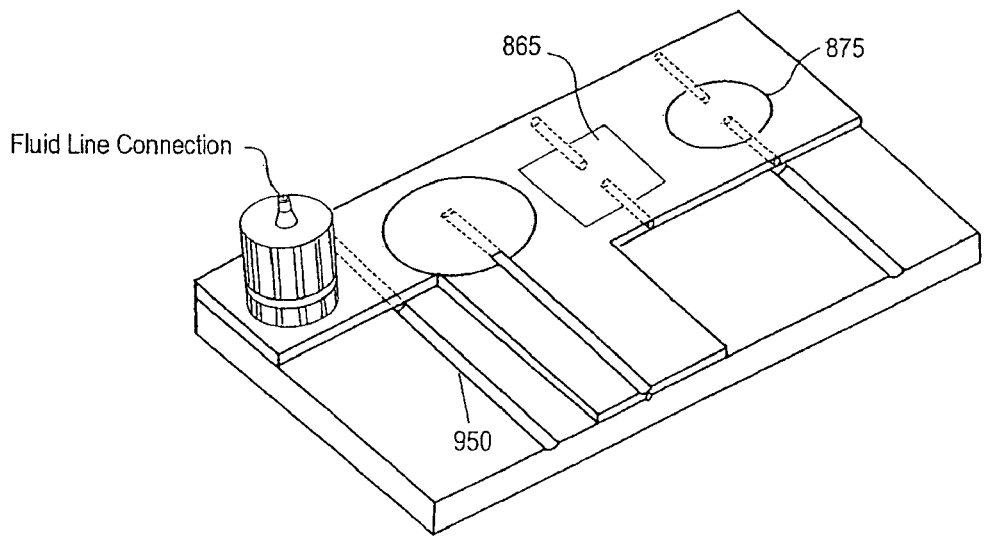
FIG. 33E depicts schematic diagram of a cartridge with a reagent capsule.

In some embodiments, a reagent capsule including one or more reagents may be coupled to a cartridge. Reagent capsule may include liquid and/or dried (e.g., reagents in solid or powder form) reagents. In one embodiment, a reagent pad with dried reagent on the pad may be positioned in the reagent capsule. FIG. 33D depicts an exploded view of an embodiment of a reagent capsule 1018 coupled to a cartridge 860 including membrane-based- and particle-based platform analysis regions (portions). A cartridge 860 may include a top portion 861 and a bottom portion 862. A reagent capsule 1018 may be coupled to the cartridge 860 such that channels 950 coupled the reagent capsule to a trap, particle-based platform portion 865, and/or membrane-based platform portion 875 of the cartridge. FIG. 33E depicts an embodiment of a reagent capsule 1018 coupled to a cartridge 860 including membrane-based platform portion 875 and particle-based platform portion 865. A sample may enter a reagent capsule 1018 via a fluid connection line and flow via channels 950 in the cartridge 860 to the particle-based platform portion 865 and/or membrane-based platform portion 875.

In some embodiments, a cartridge may include reagent delivery systems, such as a reagent pack, a reservoir containing reagent, and/or a regent pad. In some embodiments, a cartridge includes a reagent delivery system that includes a reagent pack and reagent pad. During use, a sample may be deposited in a sample reservoir and reagents may be delivered to the sample reservoir by actuation. In one embodiment, an actuator may apply pressure to a reagent pack and force reagent through a channel, over a reagent pad and into the sample reservoir where the reconstituted reagents react with the sample. Further actuation may cause the chemically modified sample into a trap where substantially all of the air in a sample may be released. The chemically modified, air free sample may be forced by actuation onto a membrane and/or a particle-based platform of a cartridge. In a membrane and/or a particle-based platform of a cartridge, a sample may be washed and/or analyzed. Residual reagents and/or sample may flow into a waste reservoir after analysis to reduce the risk of hazard during disposal.

Figure 34:
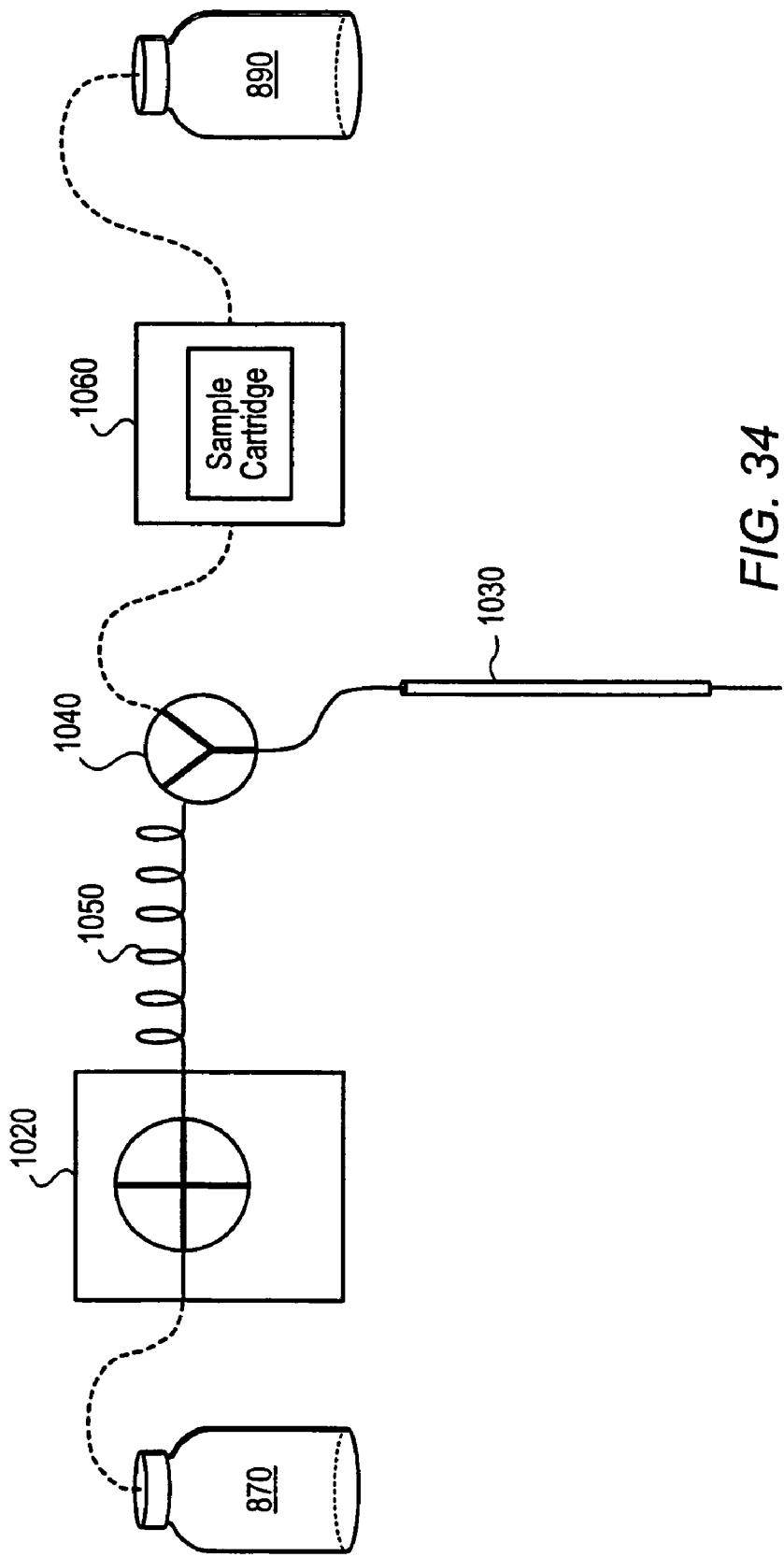
FIG. 34 depicts an embodiment of a fluid delivery system that includes a sample probe.

FIG. 34 depicts another embodiment of a fluid delivery system. In this example, the system may be primed and filled with buffer 870. Pump 1020 may draw sample (which may or may not contain reagents) into the sample needle 1030, through the three-way valve 1040 and into the sample loop 1050. The valve 1040 is then switched and the pump 1020 pushes the sample through the valve and into the sample cartridge 1060, followed by a buffer wash. After sample analysis, the sample is pushed to a waste reservoir 890 and the system is washed with buffer 870.

Figure 35:
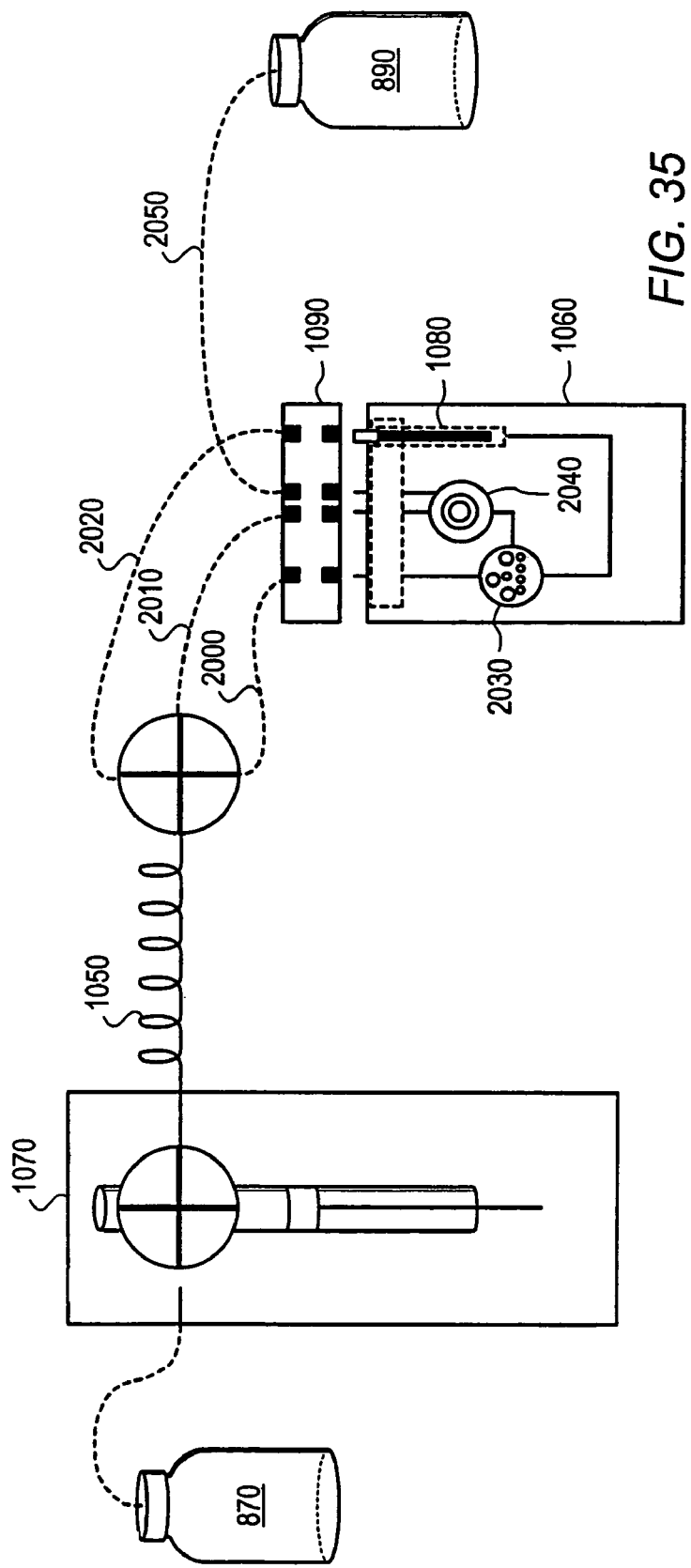
FIG. 35 depicts an embodiment of a fluid delivery system that includes a four-way fluidics interface.

FIG. 35 depicts another embodiment of a fluid delivery system. In this example, a metered (e.g., controlled volume) syringe pump 1070 may push and pull fluids through the system. In operation, a capillary 1080 filled with sample may be inserted into the sample cartridge 1060. The cartridge 1060 may be "quick" connected to a fluidics bus 1090, which may at least partially seal the system. Quick connecting the cartridge 1060 to the fluidics bus 1090 may seal the system. The system may be primed and filled with buffer 870 through lines 2000 and 2010. Using line 2020, the sample may be pushed into a trap 2030. In the trap 2030, the sample may be diluted with buffer 870 and air bubbles may be released. Line 2010 may be used to draw a known volume of the diluted sample into the detection region 2040. Alternatively, Line 2000 may draw sample into the sample loop 1050 and the sample is pushed into the detection region 2040 via line 2010. A four-way valve may couple fluid lines and the sample loop. After sample analysis, the system may be washed with buffer 870 and waste may be delivered to a waste reservoir 890 using line 2050.

FIGS. 36A-B depicts another embodiment of a fluid delivery system. FIG. 36A depicts a schematic drawing of the fluid delivery system. In this embodiment, a metered (e.g., controlled volume) syringe pump 1070 may push and pull fluids through the system. In operation, a capillary 1080 filled with sample may be inserted into the sample cartridge 1060. The cartridge 1060 is "quick" connected to a fluidics bus 1090, which seals the system. The system may be primed and filled with buffer 870 through lines 2060 and 2070. Using line 2060, the entire sample may be drawn into the sample loop 1050 (see magnified view of sample loop, FIG. 36B). The first one-third of the sample (a) may then be pushed back into line 2060 as waste to remove air bubbles from the sample. The second one-third of the sample (b) may be pushed into the detection region 2040 of the cartridge 1060 using line 2070. The last one-third of the sample may be pushed into line 2060 as waste to remove air bubbles from the sample. Since the pump 1070 may be metered, this method provides volume control for sample delivery, without the need for a trap. After sample analysis, the system is washed with buffer 870 and waste is discarded through line 2080 into a waste reservoir 890.

In some embodiments, a cartridge self-positioning system may perform two functions. First, the system may be used to align (manually or automatically) the area(s) of the cartridge containing the sample to be analyzed with the instrument's optical platform Second, the self-positioning system may reposition the cartridge such that multiple areas of the sample may be analyzed in sequence.

Figure 37:
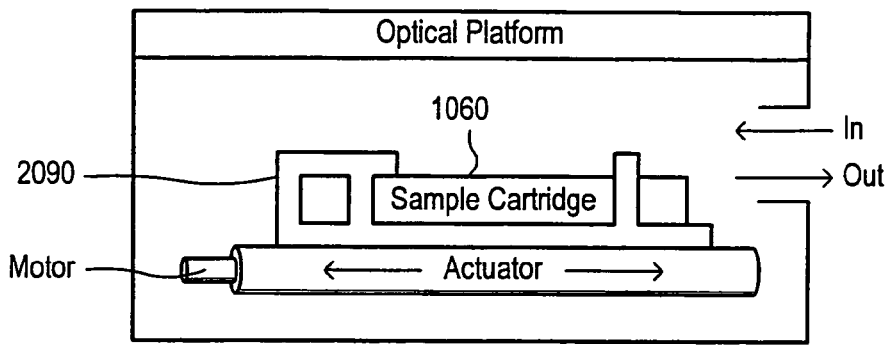
FIG. 37 depicts a schematic diagram of a cartridge self-positioning system.

A cartridge self-positioning system may include at least two components, as shown in the embodiment of a cartridge self position system depicted in FIG. 37. One component is an apparatus 2090 that may hold or secure the cartridge 1060 in place. An example of such is an apparatus that functions analogous to a computer disk mount. In operation, such a device would accept and/or eject a disposable cartridge into/out of the analysis instrument.

A second component of the cartridge self-positioning system may be hardware, software, and/or firmware capable of registering and verifying the position of the disposable cartridge in relation to the optical components of the analysis instrument. For example, position registration hardware may be comprised of an x- and/or y-motor-driven translation stage in which position is tracked by counting the motor's steps to or from a home position. Alternative embodiments of position registration hardware include, but are not limited to: a motorized micrometer or actuator, a piezo-electric actuator coupled to an optical positioning device, an encoder wheel gear monitored by a sensor, and/or a manual translation stage or micrometer.

An instrument may include one or more optical platforms. An instrument's optical platform may acquire images of a sample, and/or of sample-modulated detection regions. An optical platform may translate the acquired images into meaningful values. Images, in some embodiments, may include captured spectroscopic changes within the optical platform. In one embodiment, components of an optical platform may include one or more light sources, one or more lenses, one or more dichroic mirrors, one or more photodetectors, one or more emission filters, and/or one or more excitation filters.

The one or more light sources may include: a collimated, monochromatic light source, such as a diode laser; a white light source, such as a tungsten-halogen lamp; and/or light emitting diodes (LEDs). Optionally, one or more light sources may be modulated using a transistor-transistor logic (TTL) pulse, an electronic shutter and/or an on/off switch. The one or more light sources may emit light suitable for the excitation of one or more reporter or encoding labels present in the sample and/or on particles contained within the device (e.g., fluorophores; chromophores; luminophores such as single dyes, tandem or conjugate dyes; particles; and/or a combination or multiplex thereof). The excitation of each species may cause one or more spectroscopic changes, such as intensity, lifetime, spectral characteristics, and/or polarization. An optical detector may include one or more detectors. Detectors (e.g., an array detector such as a charge-couple device camera) may measure the resulting properties of the excitation of each species. One or more processors equipped with software may translate each measured property to a meaningful value.

Figure 38A:
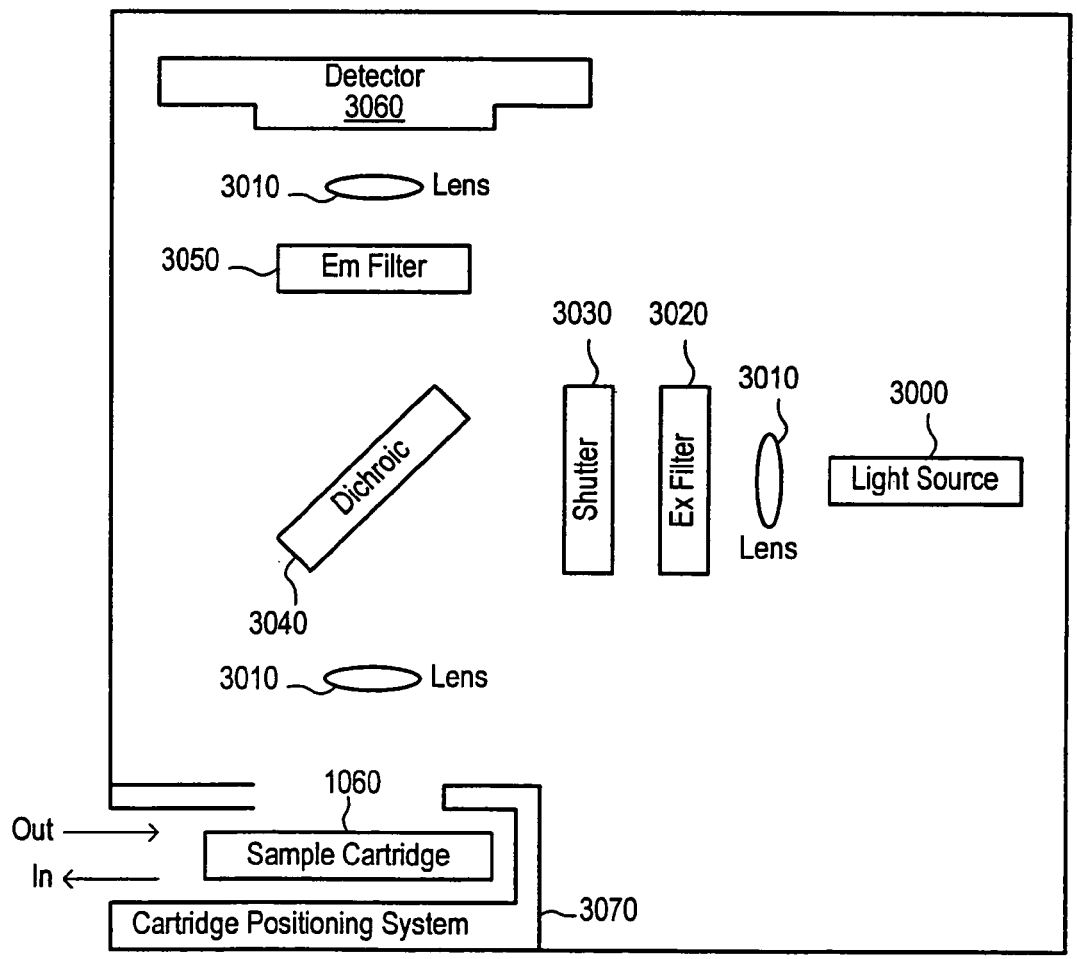
FIG. 38A depicts a schematic diagram of an optical platform.

In one embodiment, shown in FIG. 38A, an optical platform may include a light source 3000, focusing lenses 3010, at least one excitation filter 3020, an electronic shutter 3030, a dichroic mirror 3040, at least one emission filter 3050, and/or an array detector 3060. In one operation, the sample cartridge 1060 containing sample reacted with one or more fluorescent reporter labels, may be placed in a cartridge positioning system 3070. The positioning system 3070 aligns the sample area with the optical path. Light from the excitation source 3000 may be collimated with a lens 3010, filtered to the appropriate wavelength, passed through an open shutter 3030, reflected 90° by a (long pass or multi-bandpass) dichroic mirror 3040 and focused onto the sample using a lens 3010. The excitation light 3000 may excite one or more fluorophores present in the sample. The fluorescence emission from excited fluorophores may be collected by a 3010 lens and transmitted through the dichroic mirror 3040, filtered 3050 to the appropriate wavelength(s) and imaged with a detector 3060, such as a CCD camera. Fluorescence images may be processed and a meaningful value may be reported to an operator. While the above description is specific for fluorescent changes, it should be understood that the system may be modified to capture any kind of spectroscopic change.

Figure 38B:
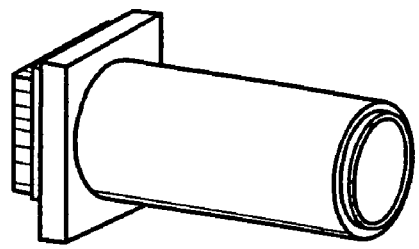
FIG. 38B depicts an embodiment of a light emitting diode assembly.
Figure 38C:
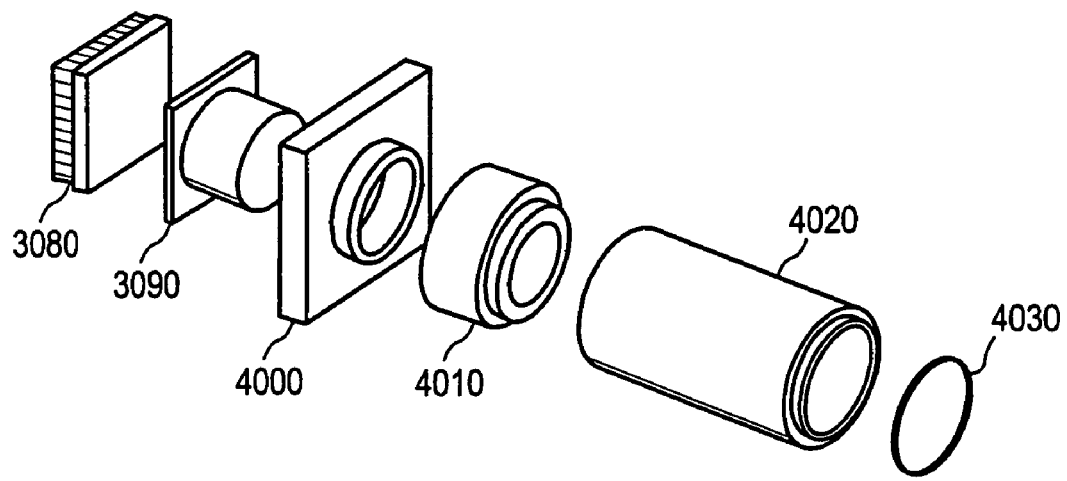
FIG. 38C depicts an exploded view of an embodiment of light emitting diode assembly.

In some embodiments, a light emitting diode (LED) assembly may be used in place of a light source in an optical system. An embodiment of an LED assembly is depicted in FIG. 38B. An exploded view of the LED assembly depicted in FIG. 38B is depicted in FIG. 38C. The LED assembly 3000 may include a heat sink 3080, a LED 3090, a mount 4000, a filter 4010, a lens tube 4020, and a focusing lens 4030.

Figure 39:
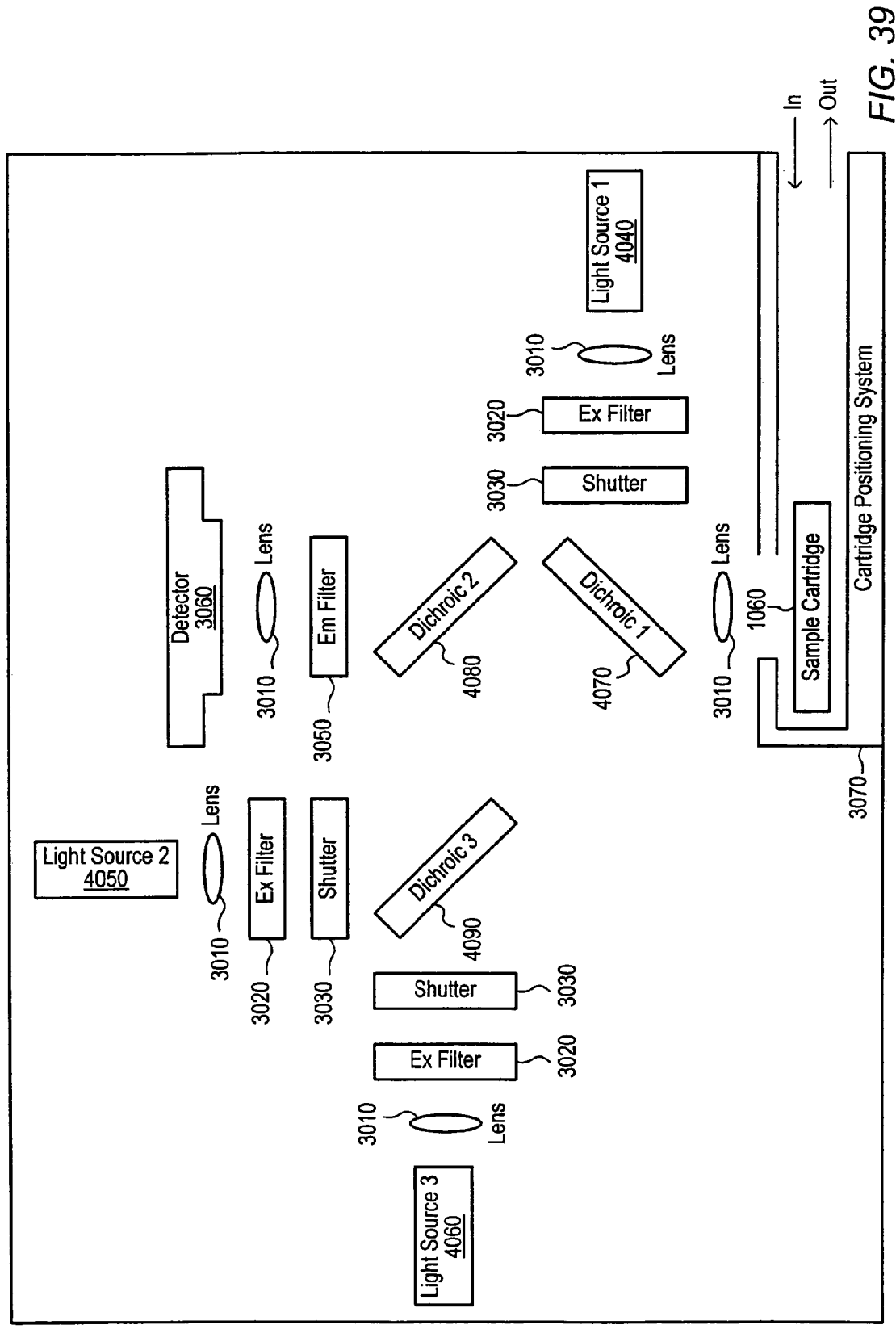
FIG. 39 depicts a schematic diagram of an optical platform that includes three light sources.

In a second embodiment, depicted in FIG. 39, the optical platform includes three LED light sources 4040, 4050, 4060 (e.g., blue, green and red); focusing lenses 3010 for each of the LED lights; three excitation filters 3020; three light source modulation units (e.g., electronic shutters) 3030; three dichroic mirrors 4070, 4080, 4090; at least one emission filter 3050; and an array detector 3060. In one embodiment, a sample cartridge 1060 containing sample reacted with one or more fluorescent reporter labels may be placed in a cartridge positioning system 3070. The cartridge positioning system 3070 aligns the sample area with the optical path. Blue light from excitation source 4040 may be collimated with a lens 3010, filtered to the appropriate wavelength, passed through an open shutter 3030, reflected 90° by a (long pass) dichroic mirror 4070 and focused onto the sample using a lens 3010. The blue excitation light may excite blue-excited fluorophores present in the sample. The fluorescence emission from the blue-excited fluorophores may be collected by a lens 3010, transmitted through dichroic mirrors 4070 and 4080 (multi-bandpass dichroic), filtered 3050 to the appropriate wavelength(s), and imaged with a detector 3060, such as a CCD camera. Next, green light from excitation source 4050 may be collimated with a lens 3010, filtered 3020 to the appropriate wavelength, passed through an open shutter 3030, reflected 90° by dichroic mirror 4090 (long pass), reflected 90° by dichroic mirror 4080 (multi-bandpass dichroic), transmitted through dichroic mirror 4070 (long pass) and focused onto the sample using a lens 3010. The green excitation light may excite green-excited fluorophores present in the sample. The fluorescence emission from the green-excited fluorophores may be collected by a lens 3010, transmitted through dichroic mirrors 4070 and 4080 (multi-bandpass dichroic), filtered to the appropriate wavelength(s), and imaged with detector 3060. Next, red light from excitation source 4060 may be collimated with a lens 3010, filtered to the appropriate wavelength, passed through an open shutter 3030, transmitted through dichroic mirror 4090 (long pass), reflected 90° by dichroic mirror 4080 (multi-bandpass dichroic), transmitted through dichroic mirror 4070 (long pass), and focused onto the sample using a lens 3010. The red excitation light may excite red-excited fluorophores present in the sample. The fluorescence emission from the red excited fluorophore may be collected by a lens 3010; transmitted through dichroic mirrors 4070 and 4080 (multi-bandpass dichroic); filtered 3050 to the appropriate wavelength(s); and imaged with a detector 3060. The three-color fluorescence images may then be processed and a meaningful value may be reported to the operator. While the above description is specific for fluorescent changes, it should be understood that the system may be modified to capture any kind of spectroscopic change.

Figure 40:
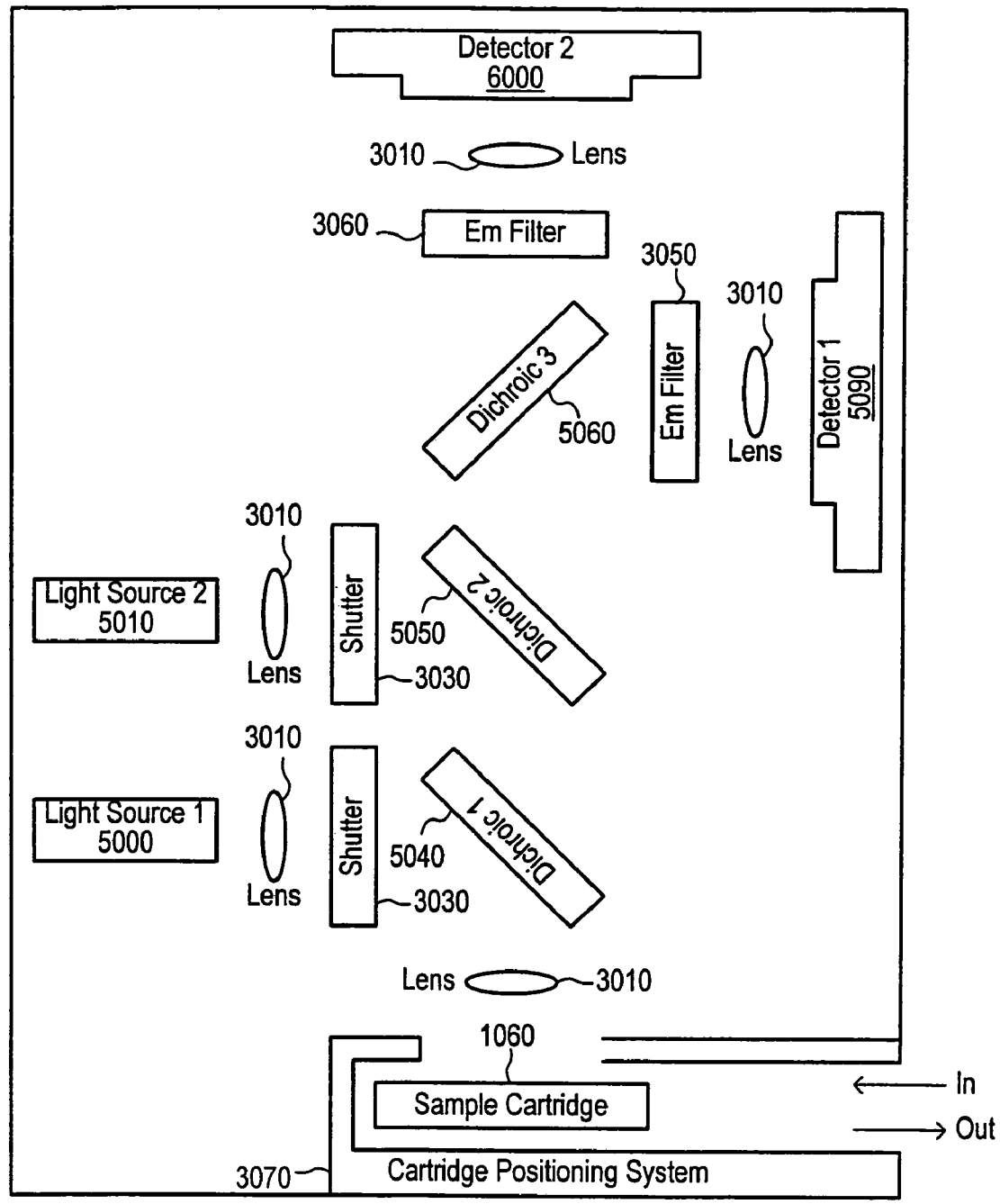
FIG. 40 depicts a schematic diagram of an optical platform that includes two light sources.

In an embodiment, shown in FIG. 40, images of multiple colors may be acquired simultaneously. In this embodiment, the optical platform includes two diode laser light sources (e.g., green and red) 5000, 5010; focusing lenses 3010; two light source modulation units (e.g., electronic shutters) 5020, 5030; three dichroic mirrors 5040, 5050, 5060; two emission filters 5070, 5080 and two array detectors 5090, 6000. A sample cartridge 1060 containing sample reacted with one or more fluorescent reporter labels may be placed into the cartridge positioning system 3070. The cartridge positioning system 3070 may align the sample area with the optical path. Green light from excitation source 5000 may be focused with a lens 3010, passed through an open shutter 3030, reflected 90° by (long pass) dichroic mirror 5040, and focused onto the sample using a lens 3010. The green excitation light may excite green-excited fluorophores present in the sample. The fluorescence emission from the green-excited fluorophores may be collected by a lens 3010, transmitted through dichroic mirrors 5040 (long pass), 5050 (dual-bandpass dichroic), reflected 90° by dichroic mirror 5060 (long pass), filtered 3050 to the appropriate wavelength and imaged with detector 5090. Simultaneously, red light from excitation source 5010 may be focused with a lens 3010, passed through an open shutter 3030, reflected 90° by dichroic mirror 5050 (dual-bandpass dichroic), transmitted through dichroic mirror 5040 (long pass), and focused onto the sample using a lens 3010. The red excitation light may excite red-excited fluorophores present in the sample. The fluorescence emission from the red-excited fluorophores may be collected by a lens 3010; transmitted through dichroic mirrors 5040 (long pass); 5050 (dual-bandpass dichroic) and 5060 (long pass); filtered 3060 to the appropriate wavelength; and imaged with detector 6000. The two-color fluorescence images may be processed simultaneously and a meaningful value may be reported to the operator. While the above description is specific for fluorescent changes, it should be understood that the system may be modified to capture any kind of spectroscopic change.

Figure 41:
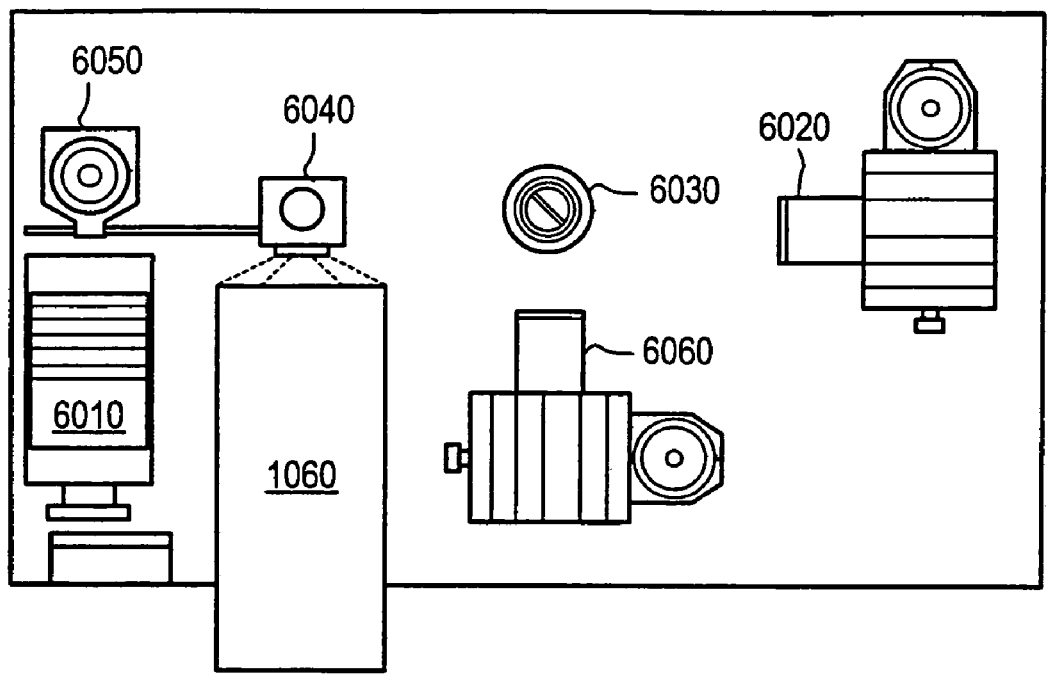
FIG. 41 depicts an optical platform that includes two laser light sources.

FIG. 41 is a schematic drawing of an embodiment of an optical system in which the light sources are laser diodes. A sample may be delivered to the sample cartridge 1060 using a syringe pump-based fluid delivery system 6010. Light from laser diode 6020 may be transmitted through dichroic mirror 6030, optionally filtered, reflected off dichroic mirror 6040, and focused onto the sample. Fluorescence from the sample is collected by the lens; reflected off dichroic mirror 6040; filtered to the appropriate wavelength; and imaged onto a detector 6050. Simultaneously, or in sequence, light from laser diode 6060 may be reflected off dichroic mirror 6030, optionally filtered, reflected off dichroic mirror 6040, and focused onto the sample. Fluorescence from the sample may be collected by a lens, reflected off dichroic 6040, filtered to the appropriate wavelength, and imaged onto a detector 6050. While the above description is specific for fluorescent changes, it should be understood that the system may be modified to capture any kind of spectroscopic change.

Optionally, an optical platform may include one or more optical fibers (e.g., single-core optical fibers, imaging fibers, bifurcated fibers, or a group thereof). Optical fibers may carry excitation light to the one or more labels present in the sample and may carry the emitted fluorescence properties to one or more detectors. Additionally, multiple fibers may be employed to image multiple regions of the sample area simultaneously, thus eliminating the need for sample cartridge actuation.

Figure 42:
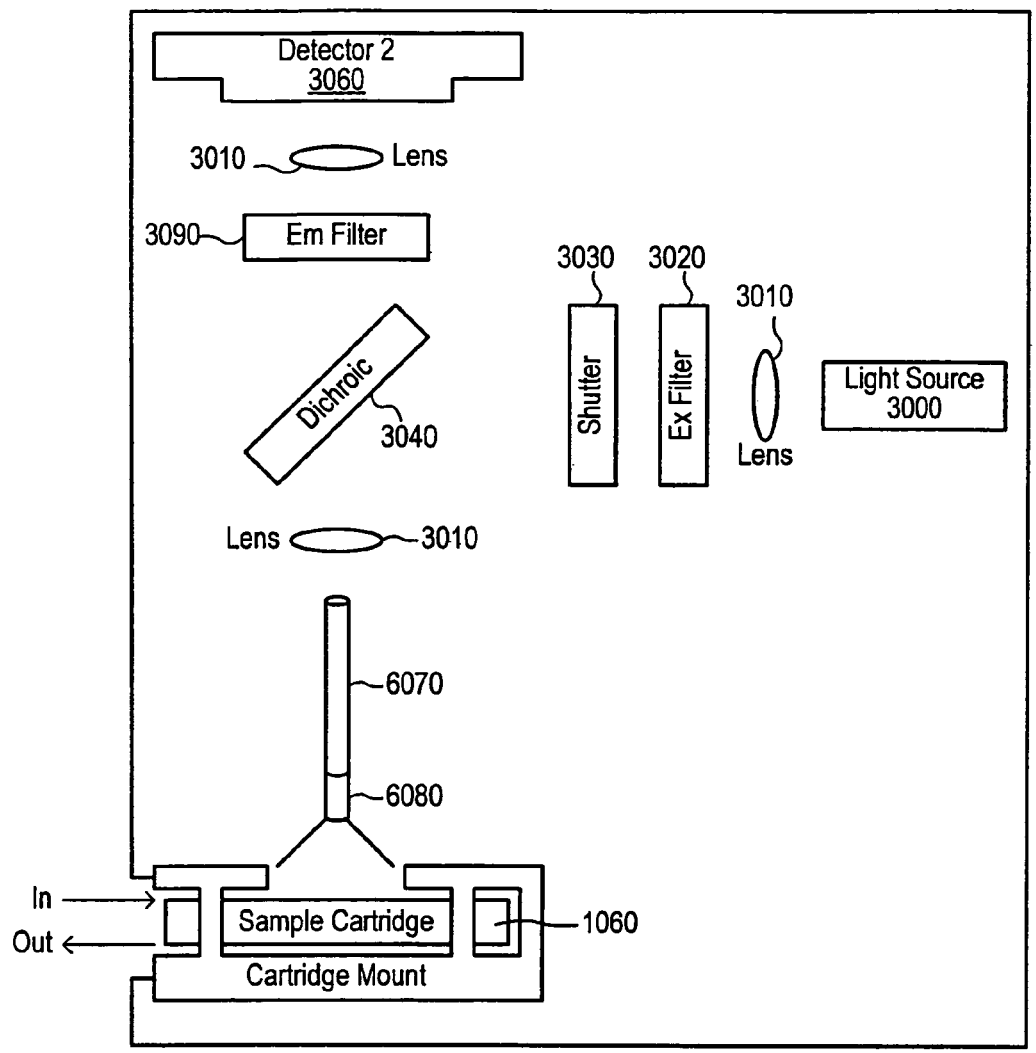
FIG. 42 depicts a schematic diagram of an optical platform that includes a single optical fiber microlens.

In one embodiment, shown in FIG. 42, an imaging fiber 6070 with a microlens 6080 (e.g., a GRIN lens) may be positioned in the optical pathway. Light from an excitation source 3000 may be collimated with a lens 3010, filtered 3020 to the appropriate wavelength, passed through an open shutter 3030, reflected 90° by a (long pass) dichroic mirror 3040, and focused onto the distal end of the fiber 6070 with a lens 3010. The excitation light may travel through the fiber 6070 and excite fluorophores present in the sample. The fluorescence emission from the excited fluorophores may be collected by the fiber's microlens 6080, transmitted through the fiber 6070, collected with a lens 3010, passed through a long pass dichroic mirror 3040, filtered 3050 to the appropriate wavelength(s), and imaged with a detector 3060. The fluorescence images may then be processed and a meaningful value may be reported to an operator. This optical platform may provide more uniform illumination and an increased field of view. While the above description is specific for fluorescent changes, it should be understood that the system may be modified to capture any kind of spectroscopic change.

In another embodiment, shown in FIG. 43, multiple optical (imaging) fibers 6070 containing microlenses 6080, may be used to image simultaneously multiple regions of interest in the sample, eliminating the need to actuate the sample cartridge 1060. At the proximal end, the fibers may be separated at fixed positions, relative to the sample. At the distal end, the fibers may be bundled together. In operation, the light path is similar to previous examples, except that multiple areas of the sample are excited. The fluorescence emission from the multiple excited sample areas is collected by the fibers 6070 and imaged 6090 simultaneously with a CCD camera. The fluorescence image may be processed and a meaningful value may be reported to an operator. An advantage to using multiple optical fibers is that multiple areas can be imaged simultaneously with one image and without moving the sample and/or cartridge. While the above description is specific for fluorescent changes, it should be understood that the system may be modified to capture any kind of spectroscopic change.

Figure 44B:
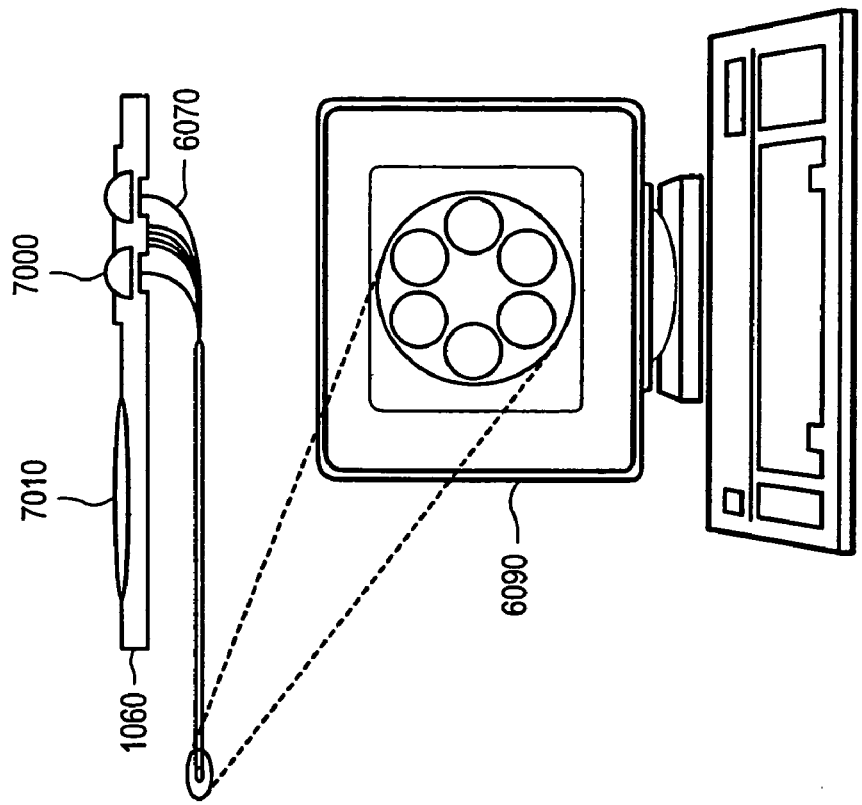
FIG. 44A-B depicts a schematic diagram of an optical platform that includes a multiple optical fibers to conduct signals to an analysis device.
Figure 44A:
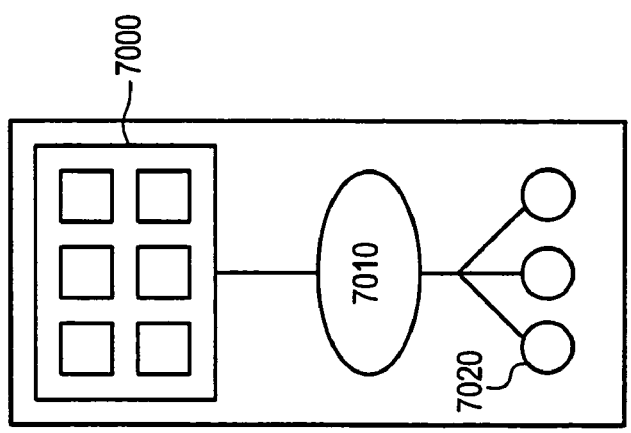

FIG. 44A depicts a top view of a sample cartridge 1060 including a particle-based platform 7000, a membrane platform 7010, and reagents 7020 positioned on the cartridge. FIG. 44B depicts a side view of a sample cartridge 1060 including a particle-based platform 7000, and a membrane platform 7010. In an embodiment, single core optical fibers 6070 may be used in the optical platform to provide more uniform fluorescent signals from particle-based platforms 7000 containing fluorescent particles. At the proximal end, the fibers 6070 may be separated at fixed positions, relative to the particle-based platform 7000 (e.g., one fiber per particle, above or below). The fibers 6070 may automatically line up when the sample cartridge 1060 is snapped into position. At the distal end, the fibers 6070 may be bundled together. In operation, the light path may be similar to previous examples. The fluorescence emission from the multiple excited particles may be collected by the fibers and imaged 6090 simultaneously with a CCD camera. The fluorescence intensities may be processed and a meaningful value may be reported to the operator. An advantage is that multiple particles may be imaged simultaneously in one image, with improved signal uniformity and with moving the sample or cartridge. While the above description is specific for fluorescent changes, it should be understood that the system may be modified to capture any kind of spectroscopic change.

An optical platform may display images detected by a detector on a computer. A computer coupled to the instrument may be a desktop, laptop, handheld or other computer equipped with commercial or custom software. The software may contain algorithms and/or neural networks for image analysis. Images may be analyzed by the computer for fluorescence properties, such as intensity, lifetime, spectral characteristics, polarization, absorption properties, luminescence properties, number of particles or some function thereof, size, shape or combination of any of these.

In another embodiment, an analyte detection device may include a cartridge that holds a particle-based detector and/or a membrane-based detector. The cartridge may be a disposable cartridge and may act as the chemical and biochemical-sensing component of the analyte detection device. The cartridge, which shape may be adapted to various needs, may be composed of index-matching, molded or machined plastics, metals, glass or a combination thereof. In one embodiment, a cartridge may include one or more reservoirs for holding reagents, sample, buffer, fluids for analysis of samples, and waste, that are connected via one or more microfluidic channels and/or valves. The cartridge may include one or more analysis and/or separation surfaces (e.g., membrane or the like) and/or sensing particles housed in a supporting array. A membrane surface may trap and/or separate particulate matter of interest (e.g., cells, microbes, small pieces of tissue, polymer, glass or metal particles, or conjugates thereof). The particle-based platform component may include sensing particles. Sensing particles may react with analytes of interest (e.g., proteins, DNA and RNA oligonucleotides, metals or other solution-phase analytes). In certain embodiments, a cartridge may be able to detect particulate matter and/or solution-phase analytes concurrently.

In some embodiments, particles in a sensor array may be optically encoded with one or more fluorophores, chromophores, etc. which may be used to identify the location of the particle in the array and/or the identity of the analyte. Such an encoding scheme may be used in a combination membrane-particle-based cartridge and may facilitate manufacture of the cartridge. Encoded particles may be placed in the sample for the purpose of sample or reagent identification (e.g., a sample identification bar code). In one embodiment, the membrane may be used to trap the particles. Particles may identify a patient. In an embodiment, in addition to membrane-based analysis, particle-based analysis is performed by the instrument. Such particles may also be used to calibrate the instrument and/or monitor flow rates.

A system for analysis of analytes is configured, in one embodiment, to substantially simultaneously combine the analysis of cellular and protein material in fluids. In one embodiment, a dual function analyte detection device may include both particle- and membrane-based platforms, suitable for the measurement of a variety of analytes simultaneously. In one embodiment, the dual function analyte detection device may be used to measure both blood proteins and count blood cells. The device may provide quick and accurate diagnosis of specific diseases, which may save lives and lift the financial strain on both the healthcare system and the patient.

Figure 45:
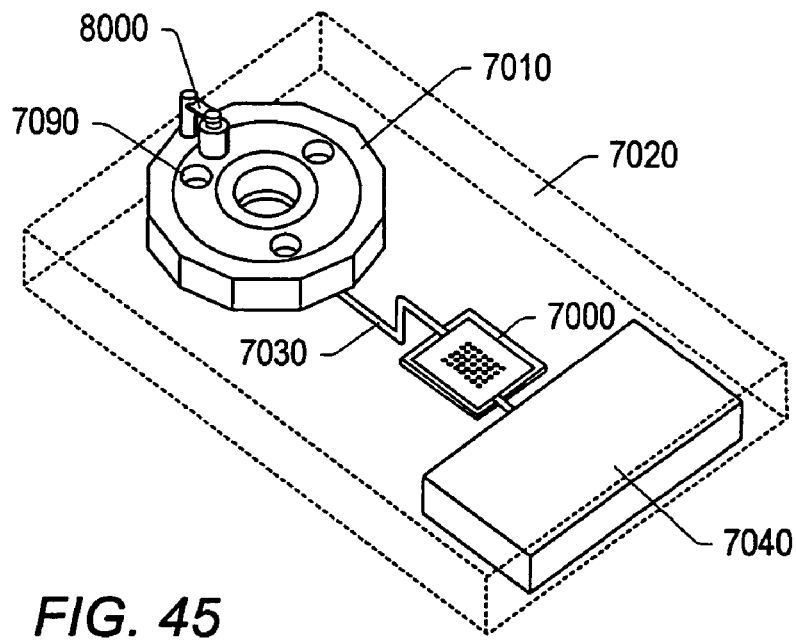
FIG. 45 depicts an analyte detection device that includes both a particle-based detection system and a membrane-based detection system.

FIG. 45 depicts one embodiment of an analyte detection device that includes both a particle-based detection system 7000 and a membrane-based detection system 7010. Both the particle-based detection system 7000 and the membrane-based detection system 7010 are formed within a body 7020. Body 7020 may be formed from a thermoplastic material (e.g., polydimethylsiloxane). In one embodiment, the device may be casted in a thermoplastic material from a micromachined mold that has been modified to accommodate both the particle-based and membrane-based detection systems. A channel 7030 may be formed between membrane-based detection system 7010 and the particle-based detection system 7000 and connect the two analysis devices. A waste reservoir 7040 may also be incorporated into the body 7020 to collect liquid samples after analysis.

Figure 46:
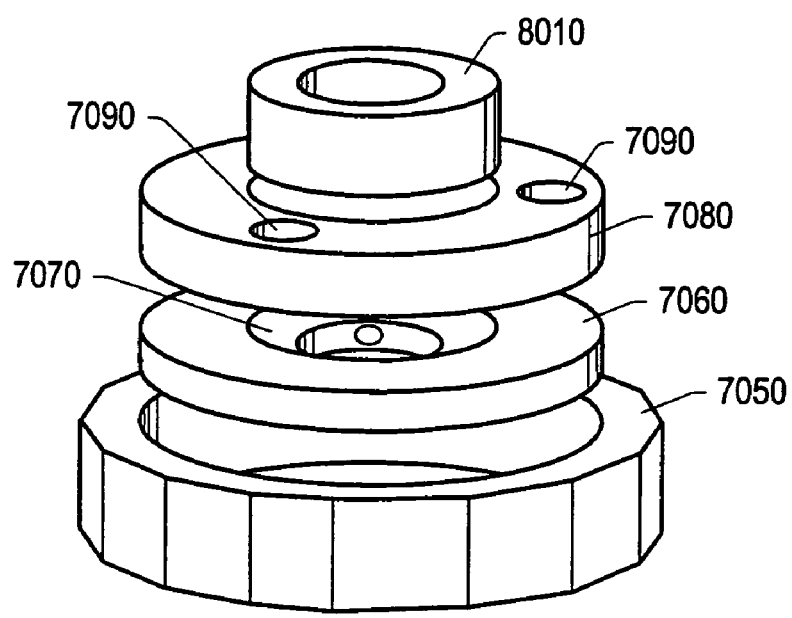
FIG. 46 depicts an exploded view of a portion of a detection system support system.

FIG. 46 depicts an exploded view of a portion of a detection system support system. The device depicted in FIG. 46 may be used to support a particle-based detection system or a membrane-based detection system. Detection system support system may be composed of multiple concentric rings. In one embodiment, the detection system support system may be composed of four concentric rings. A structure ring 7050 may hold the whole assembly. A compression ring 7060 may hold the membrane or a particle based sensor array in place as it screws down into structure ring 7050. The compression ring 7060 may also include a sample delivery opening 7070 through which fluids are delivered on to the membrane or the particle based sensor array. A reagent ring 7080 may be positioned adjacent to compression ring 7050. Reagent ring 7080 may be actuated such that sample delivery may occur through reservoir holes 7090. During use, reagent ring 7080 may be rotated such that reservoir holes 7090 may be aligned with sample delivery opening 7070 of the compression ring 7050. An opening (not depicted) is formed on the top surface of compression ring 7050 to allow fluid to flow from a reservoir hole 7090 through compression ring 7060 and out of the sample delivery opening, onto the membrane or particle based sensor array, see FIGS. 45 and 46. This allows the reagents to be delivered sequentially through the operation of an actuator system. An actuator system 8000 is depicted in FIG. 45. A window ring 8010 may hold an optical window in a place that allows optical observation of the sample on the membrane or the particles in the particle-based sensor array. A system of actuators may be used to push liquid down through the system. Alternate actuating systems may be used that include an additional ring to push down onto reservoirs formed in reagent ring 7080. In an embodiment, a pressure of the ring on the reservoir may pressurize a liquid sending the liquid to the detection system.

In the embodiment depicted in FIG. 45, an actuator system 8000 may be used to send samples and/or regents through the membrane based detection system and the particle-based detection system. During use, a sample or a reagent may be introduced into any of the reservoir holes 7090. At the appropriate times, reagent ring 7080 may be rotated to a position with one of the reservoir holes 7090 oriented over an opening in compression ring 7060. Operation of actuator 8000 may deliver fluid from reservoir hole 7090 through compression ring 7060 to the membrane-based detection system 7010. After flowing through membrane-based detection system 7010, fluid that is not trapped by the membrane-based detection system may flow into channel 7030 and to particle-based detection system 7000. In one embodiment, a reagent ring 7080 may be customized to include various numbers and volumes of reagents. Reagent ring 7080 may also be prepackaged and easily mass produced. The size and shape of reagent ring 7080 may be adjusted to accommodate the different needs dictated by various applications.

Figure 47:
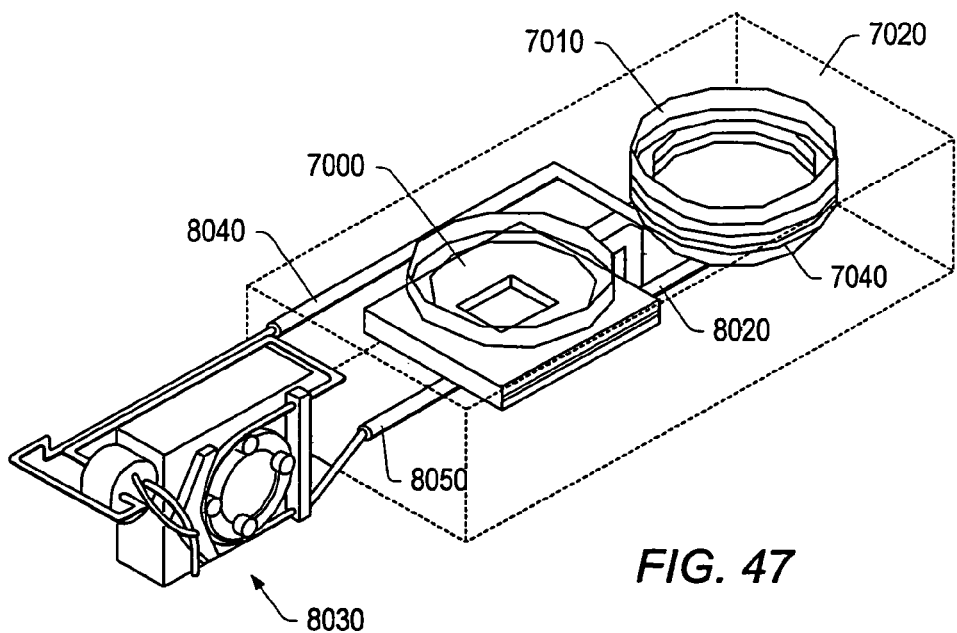
FIG. 47 depicts an analyte detection device that includes both a particle-based detection system and a membrane-based detection system having an external pump.

In some embodiments, an external pumping system may be used to deliver fluids to an analyte detection device, as depicted in FIG. 47. An analyte detection device may include both a particle-based detection system 7000 and a membrane-based detection system 7010. Both the particle-based detection system 7000 and the membrane-based detection system 7010 are formed within a body 7020. Body 7020 may be formed from a thermoplastic material (e.g., polydimethylsiloxane). In one embodiment, the device may be casted in a thermoplastic material from a micromachined mold that has been modified to accommodate both the particle-based and membrane-based detection systems. A first channel 8020 may couple pump 8030 to particle-based detection system 7000. A second channel 8040 may couple pump 8030 to membrane based detection system 7010. Pump 8030 may allow delivery of different samples or the same sample to each of the detection systems. A third channel 8050 may be formed between particle-based detection system 7000 and waste reservoir 7040. Waste reservoir 7040 may also be coupled to membrane-based detection system 7010 to receive waste fluids.

Figure 48:
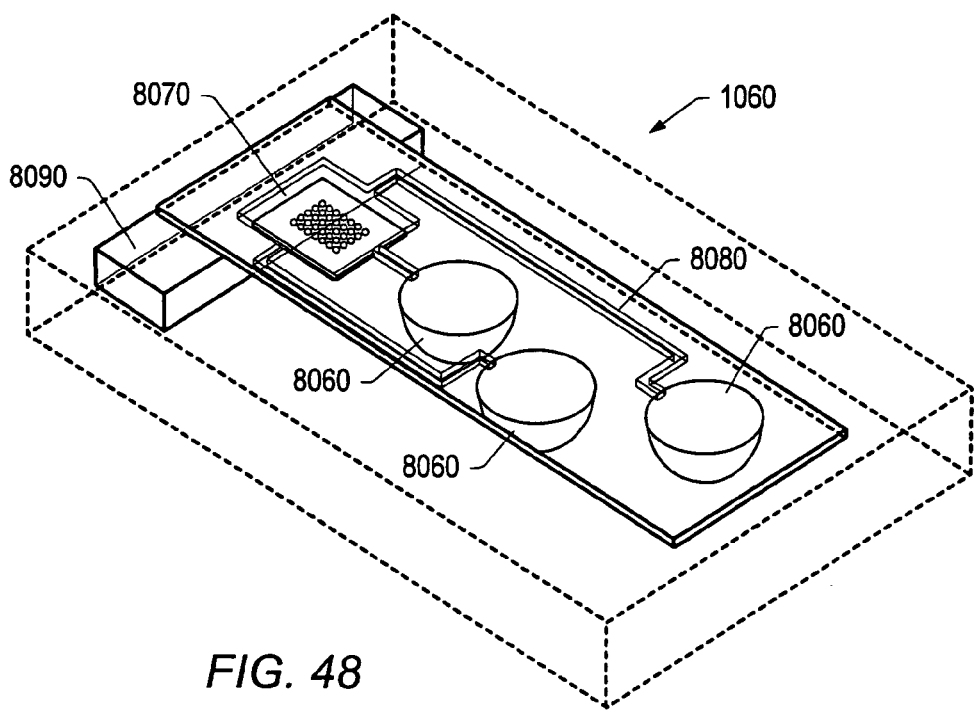
FIG. 48 depicts an embodiment of a disposable cartridge for use in the detection of analytes.

FIG. 48 depicts an embodiment of a single-use cartridge for use in the detection of analytes. Cartridge 1060 may be formed from a variety of materials, such as polymers, glasses, or metals. In one embodiment, a polydimethylsiloxane (PDMS) casting may be used. The cartridge 1060 may be designed to interface with a variety of peripheral fluidics systems. Alternatively, a pumpless design may be used by incorporating a customizable number of blister packs 8060, or substantially sealed reservoirs, into the cartridge 1060. Blister packs 8060 may include delivery fluids, reagents or other development fluids. Blister packs 8060 may be coupled to a detection system 8070 through microchannels 8080. Detection system 8070 may be a membrane-based detection system or a particle based detection system. Reservoir 8090 may be used to collect the fluids from detection system 8070.

Figure 49:
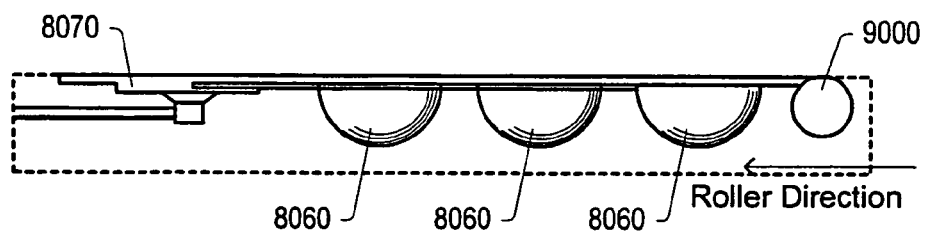
FIG. 49 depicts a roller system configured to force liquid from one or more blister packs disposed in a cartridge.

Blister packs 8060 may be used to deliver fluids to detection system 8070. Various activating systems may be used to force liquid from the blister through the microchannels 8080. Applying pressure to a blister pack may release delivery fluids, reagents, and/or other development fluids. Increasing pressure applied to blister pack may increase the amount of fluid delivered from the pack. In one embodiment, depicted in FIG. 49, liquid may be forced from blisters 8060 using a roller 9000. Contact of roller 9000 against blister 8060 may force liquid from blister toward detection system 8070.

Figure 50:
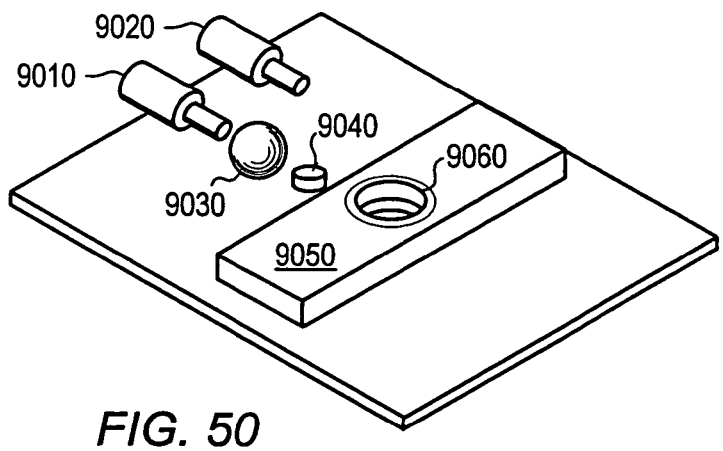
FIG. 50 depicts an embodiment of a disposable cartridge for use in the detection of analytes having input ports configured to connect to standard sampling equipment.

In some embodiments, a cartridge may be designed with connectors that may interface with standard human fluid collection devices. These connectors may be designed to be compatible with a wide variety of microfluidic fittings and tubings. An example of such cartridge is shown in FIG. 50. The cartridge includes two input connectors, a sample introduction port 9010 and a buffer port 9020. The sample introduction port 9010 may introduce samples into the cartridge. Samples introduced into the cartridge may be conducted through channels into a mixing chamber 9030. In the mixing chamber 9030, analytes in the sample may mix with reagents previously placed in the mixing chamber. The reagents may interact with the analytes in the sample to aid in visualization of the analytes. In one embodiment, cartridge may include a microfluidic valve 9040. Microfluidic valve 9040 may control a flow of the fluid through the cartridge. Flow of sample fluids may be directed through sample check window 9050 or to the membrane 9060 for detection of the analytes. Fluids passing through the membrane may be collected in waste reservoir. In an embodiment, fluids that pass through the sample check window may also be collected in the waste reservoir. It should be understood that while the above-description refers to a membrane-based detection system, the cartridge may be readily adapted to a particle-based detection system.

Figure 51A:
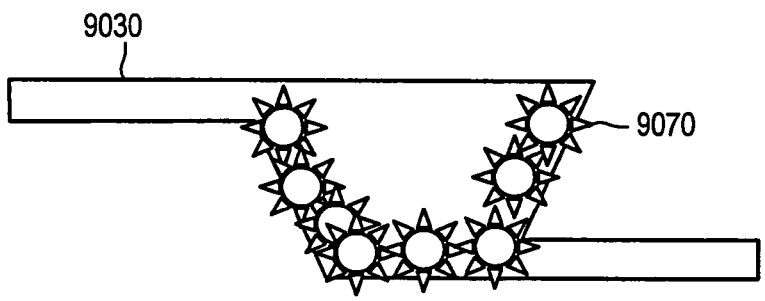
FIGS. 51A-C depict a sequence of steps for reacting a sample with a reagent in a mixing chamber.
Figure 51B:
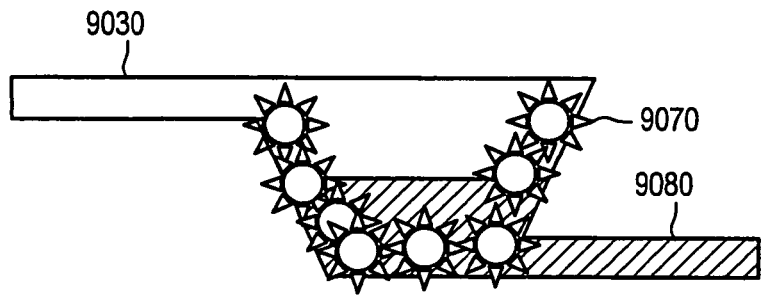
Figure 51C:
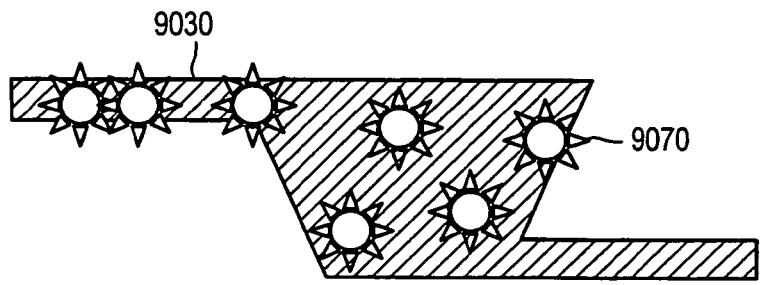

In one example, reagents may be stored in a lyophilized form. FIG. 51A depicts lyophilized reagents 9070 disposed in a mixing chamber 9030. Lyophilized reagents 9070 may be mixed with the sample 9080 upon introduction of the sample into mixing chamber 9030 of the cartridge, as depicted in FIG. 51B. Once the chamber 9030 is filled with the sample, the mixture of the sample and reagents 9070 will flow out of the chamber to other parts of the cartridge based on the positioning of microfluidic valves in the cartridge, as depicted in FIG. 51C.

Figure 52C:
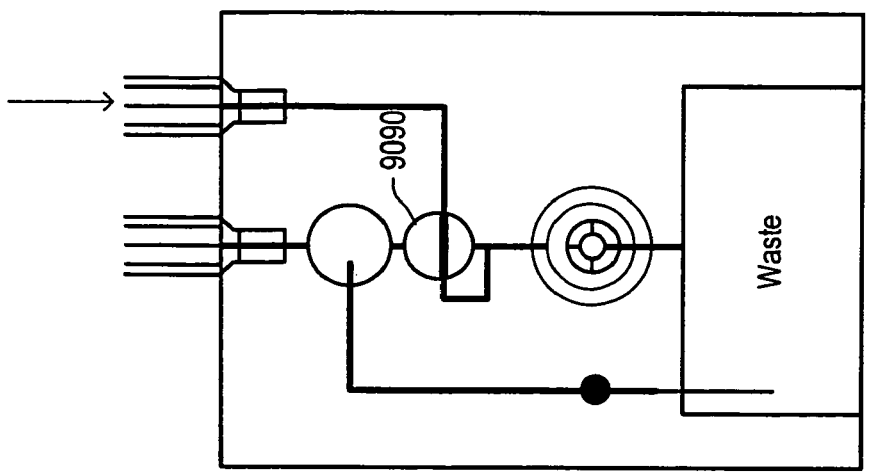
FIGS. 52A-C depict a series of schematic diagrams showing the operation of a cartridge.
Figure 52B:
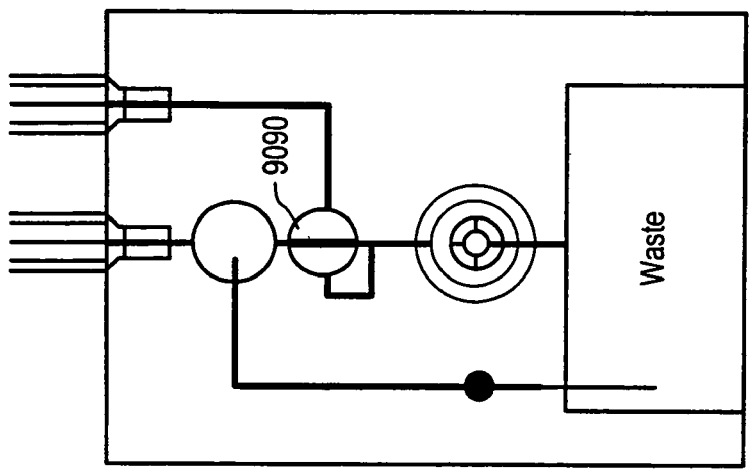
Figure 52A:
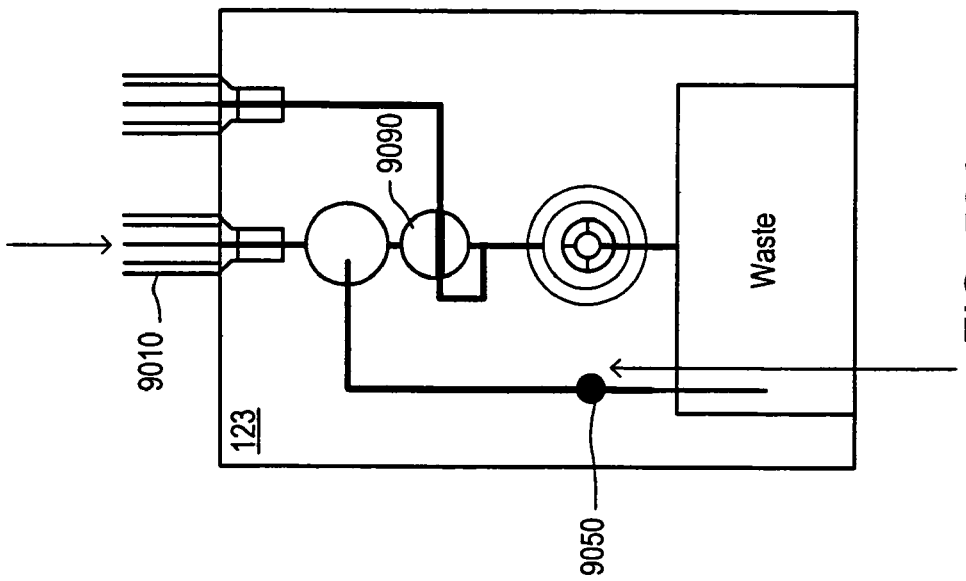

FIGS. 52A-52C depict a series of schematic diagrams showing an embodiment of the operation of the cartridge. Valves may be actuated electro-mechanically and/or manually through a keypad of a reader enclosing the cartridge. Various combinations of valves and actuators may be used to build various fluidics circuitries depending on the number and nature of the reagents needed for each application. For example, as depicted in FIG. 52A, the sample is introduced through the sample introduction port 9010. The microfluidic valve 9090 may be placed in an orientation that blocks flow of the sample to the detection system, as depicted in FIG. 52A. Thus, as the sample exceeds the customizable metered volume of the mixing chamber, the sample overflows and passes through a sample check 9050 channel and into a waste reservoir. The sample may be thus observed through an opening in the reader/cartridge assembly. After an incubation time typical of each application, delivery of the sample to the membrane is actuated, after switching of one or more microvalves 9090, as depicted in FIG. 52B. Once the desired sample volume has been delivered to the flow cell, the microvalve systems 9090 are actuated to allow passage of rinsing reagents through the membrane, as depicted in FIG. 52C.

Figure 53:
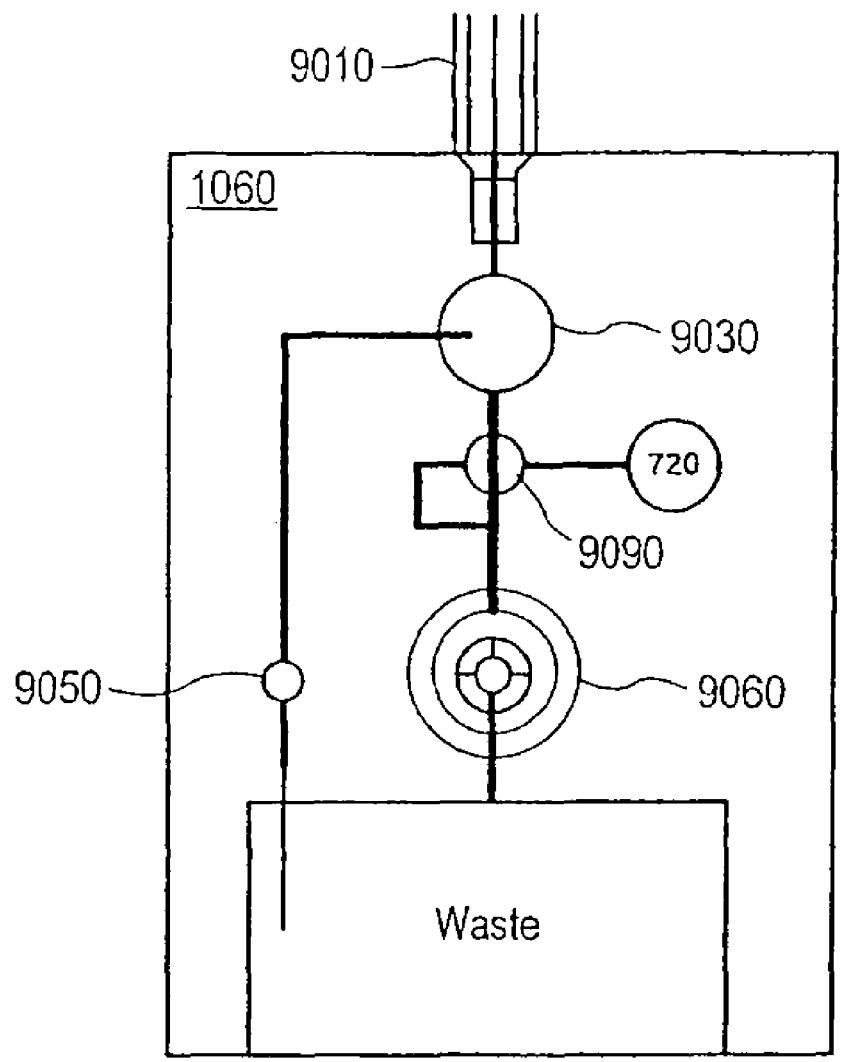
FIG. 53 depicts a schematic drawing of an alternate embodiment of a cartridge.

An alternate embodiment of a cartridge is depicted in FIG. 53. The cartridge 1060 includes a single input connector 9010 for sample introduction. The sample introduction port 9010 allows samples to be introduced into the cartridge 1060. Samples introduced into the cartridge 1060 may be conducted through channels into a mixing chamber 9030. In the mixing chamber, analytes in the sample may mix with reagents previously placed in the mixing chamber. The reagents may interact with the analytes in the sample to aid in visualization of the analytes. In one embodiment, cartridge 1060 may include a microfluidic valve 9090. Microfluidic valve 9090 may be used to control flow of the fluid through the cartridge 1060. Flow of the sample fluids may be directed through sample check window 9050 or to the membrane 9060 for detection of the analytes. Fluids passing through the membrane may be collected in waste reservoir. In one embodiment, fluids that pass through the sample check window 9050 may also be collected in the waste reservoir. In contrast to the device depicted in FIG. 50, the cartridge may include one or more blister packs 720. The blister packs 720 may be pressurized using either manual or automatic means to force liquid from the blister pack into the cartridge 1060. In an embodiment, the blister pack 720 may include a fluid for washing the membrane-based detection system (e.g., a PBS buffer solution). It should be understood that while the above-description refers to a membrane-based detection system, that the cartridge may be readily adapted to a particle-based detection system.

Figure 54A:
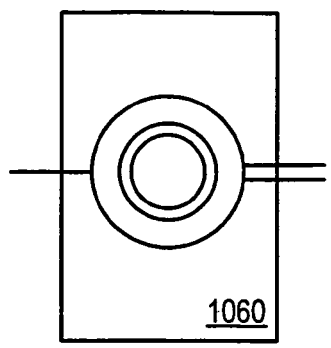
FIGS. 54A-C depict different embodiments of inlet and outlet channels in a cartridge.
Figure 54B:
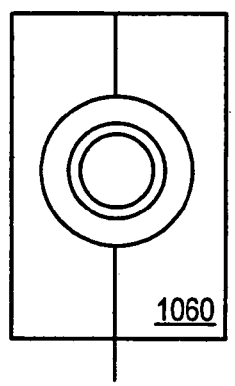
Figure 54C:
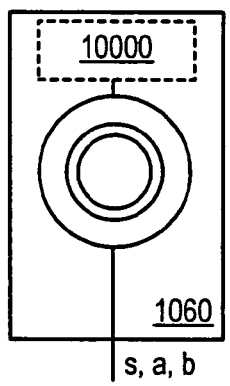

A cartridge may include a particle-based detection system, a membrane-based detection system, or both. A cartridge may be easily customized to accommodate various needs. A cartridge may include a combination of valves, channels, chambers, connectors to allow easy use and access. For example, cartridges 1060 shown in FIGS. 54A and 54B may be accommodated with an inlet, outlet, and lateral flow outlet that may be positioned in various configurations to accommodate various geometries of the fluid delivery. Additionally, a cartridge may be made with a built-in waste reservoir 10000 as depicted in FIG. 54C. The waste reservoir may be designed to handle bio-hazard materials. In an embodiment, a waste reservoir 10000 may be removable from a cartridge 1060 and safely replaceable.

Multiple channels may be created in a cartridge to allow the delivery to the detection system of a variety of reagents separately, as depicted in FIG. 55A. The reagents may be delivered to the membrane and/or particle-based platforms 10010 of a cartridge 1060 through standard or customized connectors 10020. These connectors may allow delivery of reagents to the membrane through syringes (e.g., using Luer fittings), or any standard or customized fittings to accommodate a variety of fluid delivery devices. Reagents may be pre-packaged within the cartridge and delivered to the detection system through capillary action or various actuation methods. FIG. 55B depicts an embodiment of a cartridge in which the sample may be deposited or introduced to a chamber 10030 where it is drawn to the membrane or particle-based platforms 10010 of a cartridge 1060 through capillary action, actuation, or pump action. FIG. 55C depicts an embodiment of a cartridge 1060 that may include a combination of standard or customized connectors 10020, and reagent chambers 10030 that may be actuated. This cartridge also may include a "bull's eye" window where the sample is delivered to a metered chamber. Observation of sample through the "bull's eye" indicates overfilling of the chamber to a waste reservoir, and readiness of the metered volume of sample to be delivered to the membrane. FIG. 55D depicts a diagram of an embodiment of a cartridge 1060 with one or more connectors and/or chambers 10030 modified to receive a capillary collection tube 10040 that includes an analyte. The capillary tube inner surface may be modified with a blood anti-coagulant. An inner surface of the capillary tube may be coated with an antibody mixture or other chemical or biological species used in the detection. The capillary 10040 is then introduced to the cartridge where the sample may be delivered to a membrane and/or a particle-based platform 10010 in the detection system through capillary action, actuation, or pumps.

In some embodiments cartridges 1060 may include a trap 10050, which is used to inhibit air from flowing to the detection system, as depicted in FIG. 56A. Using a trap 10050 may release air from a sample flowing from a capillary 10040 or sample collection device to a membrane or a particle-based platform 10010. A similar system including a built-in removable waste reservoir 10070 is shown in FIG. 56B. The cartridge depicted in FIG. 56B may also include a lateral flow outlet 10080 that may be directly coupled to the trap 10050 in order to get rid of accidental bubbles in the flow cell.

As is shown in FIGS. 57A-C, the cartridge flow cell may be connected to a pumping system through a variety of fluidics interfaces. The fluidics interface may include various types of fittings ranging from snug fit tubing, snap-on, standard or customized connectors that may be made re-usable or disposable. In these examples, the fluidics interfaces may be made complimentary to the cartridge connectors or tubes. A cartridge 1060 may be coupled to a fluid bus 1090 using snug fit tubing 10090, as depicted in FIG. 57A. A fluid bus 1090 may be coupled to a cartridge 1060 such that fluid in fluid delivery lines 10100 may not leak. During use, fluid may flow from fluid delivery lines 10100, through a fluid bus 1090, into a membrane or a particle-based platform 10010 in a cartridge 1060 and into a waste reservoir 10070. As depicted in FIG. 57B, a cartridge may be coupled to fluid lines 10100 via snap-on connectors 10110. A fluid bus 1090 may be sealed to a cartridge 1060 via snap-on connectors 10110. A sample may flow through a fluid delivery line 10100 into a capillary 10040 or sample reservoir and then into a bubble tap 10050. Air may escape a sample via a fluid delivery line 10100 coupled to the trap 10050 and sample may flow to a membrane and/or a particle-based platform 10010 of the cartridge 1060. Waste fluids may flow through fluid delivery lines 10100 to a waste reservoir 10070. A cartridge may also be coupled to fluid delivery lines 10100 and/or a fluid bus 1090 using customized connectors 10120, as depicted in FIG. 57C. A fluid bus may be reusable. Sample may flow into a capillary 10040 and into a trap 10050 and/or particle-based platform and/or membrane regions 10010 of a cartridge 1060 via fluid delivery lines 10100. Traps 10050 and/or particle-based or membrane platforms 10010 may be coupled to a waste reservoir 10070, such that waste fluid from traps, membranes platforms, and/or particle-based platforms may flow to a waste reservoir after analysis.

Dual functional analyte detection devices (e.g., analytes detection devices that use both membrane-based and particle-based detection systems) may be used in a number of applications. In one embodiment, a dual functional analyte detection device employs both particle- and membrane-based platforms suitable for the measurement of blood proteins and the counting of blood cells, respectively. Both platforms have been tested separately for each of their respective applications and were found to produce excellent assay characteristics. Here, a new design merging the two approaches/technologies is presented for the measurement of Troponin T and CRP and the counting of white blood cells from the blood of patients suffering from chest pain. On site measurement of Troponin T (particle-based) will identify those patients that indeed suffered a heart attack, while simultaneous measurements of CRP (particle-based) and counting of white blood cells (membrane-based) may identify those who have suffered a heart attack and are in need of immediate and aggressive therapy, such as coronary angioplasty. This portable Point-of-Care system may serve as the ideal instrument for the timely diagnosis of a heart attack and provide direction for the physician towards the appropriate treatment.

Another application for a dual functional analyte detection device is for detecting and identifying bacteria. Typical methods of detection, used for years by microbiologists, require the growth of single bacteria into bacterial colonies in different types of media, followed by a timely identification process involving morphological and biochemical tests. The classification of microorganisms through conventional microbiological counting and enumeration methods involves the use of nucleic acid stains or cocktails of stains, which are capable of differentiating between gram-positive and gram-negative bacteria, and between dead or living organisms. However, these procedures suffer from poor specificity and are not easily adapted to online rapid analysis. This series of steps, although often providing very accurate results repose on the expertise of highly trained personnel, and require lengthy and complicated analysis. Most commonly available assays for the detection of spores or bacteria involve the use of enzyme-linked immunosorbent assays (ELISA), polymerase chain reaction (PCR), electrochemical transduction, optical and microarray detection, flow-through immuno-filtration, acoustic sensors, and flow cytometry. While demonstrating high specificity, reproducibility, and some capabilities of multiplexing, these methods generally require lengthy analysis times, and are not compatible with real-time analysis. For example, PCR analysis presents the most promising technological response to an urgent need for a rapid detection method for *Bacillus anthracis*. However, despite the potential advantages of using PCR for this application, some of the drawbacks include long analysis time, reagent costs, and the difficulty of using PCR to detect many bacteria or spore species simultaneously.

In one embodiment, a dual functional analyte detection device employs both particle- and membrane-based platforms suitable for the measurement detection of specific bacteria. Using a dual functional analyte detection device, various types of spores and bacteria may first be captured on the membrane for a presumptive test. This analysis will include gram stain, live/dead distinction, shape and size recognition, and counting. The membrane test will also be utilized in conjunction with an antibody stain or stain cocktail for preliminary identification. A positive signal may then trigger a series of confirmation chip-based tests of the bacterial lysate for the detection of the protein/toxin/DNA content of the microbe, providing a final assessment of the nature of the microorganism.

Another application for a dual functional analyte detection device is for measuring complete blood count. The complete blood count (CBC) is the most common diagnostic test administered worldwide. It combines the analysis of platelets, red and white blood cells, with measurements of hemoglobin, and hematocrit. In addition to routinely providing a general health evaluation, CBC is widely used as the initial screening test for the diagnosis of a great number of diseases, as well as for monitoring disease progression and response to treatment. A complete and more definitive medical diagnosis however, very often requires the additional measurement of selected proteins, gases or chemicals in the blood stream. For example, an initial visit to the doctor's office may most likely include a CBC, in conjunction with other tests, such as a chemistry test ($Ca^{2+}$, phosphorus, glucose), electrolytes ($Na^+$, $K^+$, chlorides, bicarbonate, $CO_2$), kidney and liver functions (blood urea nitrogen, creatinine, alanine aminotransferase, aspartate aminotransferase, bilirubin, alkaline phosphatase, gamma glutamyl transpeptidase, and lactic dehydrogenase) and others (albumin, globulin, sedimentation rate). Outside the hospital, completion of these tests very often require multiple blood samples to be drawn and shipped for analysis in specialized laboratories, increasing the time form which results will be available form hours to days. In a great number of instances, the output of a CBC test determines the need for administering more specialized tests, which may require additional time, instruments and procedures. All of these delays are putting a toll on patients, doctor's overloaded schedule, and sometimes the outcome of a disease, when these tests are barely available.

The reporting interval for an emergency CBC test can vary from minutes to hours in a hospital setting to a number of hours for routine testing, but for most patients, samples are shipped to specialized locations for analysis, and are not available for at least a day. Hematology analyzers of FACS machines are routinely used for obtaining white blood cell differentials. However, the chemistry panel involves a battery of test that require various analytical tools and that are for the most part done separately.

In one embodiment, a dual functional analyte detection device employs both particle- and membrane-based platforms suitable for the measurement determination of CBC. The dual approach employs both the particle-based platform to measure levels of selected protein, enzymes, and chemicals in blood and a membrane-based platform that is dedicated to the cellular analysis of blood. The feasibility of the system with enzymes, metal cations, DNA, influenza, and hepatitis has already been shown. Analysis of blood cellular content has also been demonstrated with anti CD45 stains of leukocytes in whole blood.

In some embodiments, an analyte detection device may employ particle-based analysis using membrane-based platforms to detect one or more analytes in a fluid. This embodiment may be an alternative, or used in combination with, an array-based platform for detecting analytes. In an embodiment, defined populations of particles may be generated that detect a specific analyte. Defining populations of particles may include defining sets of size-and/or color-coded particles according to several measurable parameters.

Various types of schemes may be used to define different populations of particles. In an embodiment, the system may utilize, for example, pure populations of specific sizes of particles. Particles may range from about 1 µm to about 100 µm, with each population of particles having a particle size distribution within about 5 µm of the selected median particle size. In an embodiment, each population of size-coded particles may be further defined into coded subsets. Coding of particles may be accomplished by coupling an identification molecule to the particle. Examples of identification molecules include, but are not limited to colorimetric dyes and fluorescent dyes. Coding of particles may be accomplished by coupling different identification molecules to different sets of particles or by coupling varying concentrations of an identification molecule to different sets of particles. In such embodiments, individual populations of particles may be generated that are well defined and are distinguishable on the basis of size, light-absorbance, intensity of light absorbance or combinations thereof. For example, in an embodiment, two populations of particles may be generated by coupling particles of the same size to different amounts of a red fluorescent dye. The two populations of particles may be distinguished from each other in a mixed population of particles by collecting digital images of the mixed population of particles and comparing the pixel intensity of the particles in the mixed population.

In an embodiment, each defined population of particles may be chemically sensitized to detect one analyte of interest in a mixture of analytes. This may be achieved by coupling a receptor that binds the analyte to a defined population of particles. As used herein, a receptor that is capable of binding to the analyte may generally be referred to as a "capturing receptor." Binding of an analyte in a fluid to a capturing receptor may substantially remove at least a portion of the analyte from the fluid phase by capturing the analyte on the surface of the analyte-sensitized particles. Examples of capturing receptors include, but are not limited to DNA, RNA, proteins, enzymes, oligopeptides, oligonucleotides, antigens, and antibodies. In some embodiments, the defined set of particles may be dedicated to the capture and detection of one analyte of interest. By having multiple distinct populations of particles, each population of particles may be configured to capture and aid in the detection of a different analyte.

In an embodiment, different populations of particles may be chemically sensitized to detect different analytes in a mixture of analytes. The chemically sensitive particle, in one embodiment, may be capable of both binding the analyte(s) of interest and creating a detectable signal. In one embodiment, the particle creates an optical signal when bound to an analyte of interest. In one embodiment, a detectable signal may be caused by the altering of the physical properties of an indicator ligand bound to the receptor or the polymeric resin. In one embodiment, two different indicators may be attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme. This process, known as Forster energy transfer, is extremely sensitive to small changes in the distance between the indicator molecules. In another embodiment, an indicator ligand may be preloaded onto the receptor. An analyte may then displace the indicator ligand to produce a change in the spectroscopic properties of the particles. In this case, the initial background absorbance is relatively large and decreases when the analyte is present. The indicator ligand, in one embodiment, has a variety of spectroscopic properties that may be measured. These spectroscopic properties include, but are not limited to, ultraviolet absorption, visible absorption, infrared absorption, fluorescence, and magnetic resonance. The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the particles. Interaction of the receptors on the particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined. As previously described, the receptor itself may incorporate the indicator. The binding of the analyte to the receptor may directly lead to a modulation of the properties of the indicator. Such an approach may use a covalent attachment or strong non-covalent binding of the indicator onto or as part of the receptor, leading to additional covalent architecture. Each and every receptor may use a designed signaling protocol that is unique to that receptor. In an alternative embodiment, two or more indicators may be attached to the particle. Binding between the receptor and analyte causes a change in the communication between the indicators, again via either displacement of one or more indicators, or changes in the microenvironment around one or more indicators. The communication between the indicators may be, but is not limited to, fluorescence resonance energy transfer, quenching phenomenon, and/or direct binding. Further examples of methods of producing signals on particle that include a receptor specific for an analyte of interest are described in U.S. Pat. No. 6,589,779 entitled "General Signaling Protocol for Chemical Receptors in Immobilized Matrices," which is incorporated herein by reference.

In an embodiment, multiple analytes may be detected simultaneously using mixed populations of analyte-specific particles, where each population of analyte-specific particles is dedicated to the capture and detection of one analyte of interest. In one embodiment, adding a population of analyte-specific particles to a fluid containing that analyte may cause the analyte to bind to the particles. Because each population of particles is sensitized to detect only one analyte in a fluid, that analyte may have limited binding to any other population of particles.

In order to detect the presence of an analyte bound to the surface of a population of particles, a means of visualizing surface-bound analytes is required. This may include adding a visualization agent to the analyte-bound particles. As used herein, a "visualization agent" generally refers to an agent, such as a chemical agent, that interacts with analyte-bound particles, and allows the visualization of particles that have specifically bound the analyte for which they are chemically sensitized. In an embodiment, a visualization agent may include a second receptor that binds to the analyte. As used herein, a second receptor that binds to the analyte may generally be referred to as a "detecting receptor." Examples of detecting receptors may include, but are not limited to DNA, RNA, proteins, enzymes, oligopeptides, oligonucleotides, antigens, and antibodies. In an embodiment, the detecting receptor may be a polypeptide molecule that binds to the analyte. Alternatively, the detecting receptor may include a second antibody directed against the analyte. In one embodiment, a method of detecting multiple analytes in a fluid may rely on immunological reactions that take place on the surface of the particles. In an embodiment, the visualization agent may be optically distinguishable from the particles. For example, the visualization agent may be coupled to an indicator or dye that is spectroscopically distinct from the particles. In an embodiment, the visualization agent may be coupled to a fluorescent dye that is distinguishable from the fluorescent or colorimetric dye that defines the particles. In an embodiment, detecting an analyte in a fluid may include detecting a first signal from the particles, and a second signal from the visualization agent.

In an embodiment, populations of particles with captured analytes of interest may be passed through a flow cell equipped with a porous membrane, such as that which is described in detail above and depicted in FIG. 1. The analyte detection system may be configured to allow for the delivery of a test fluid and its flow through the system, as well as the visualization of the contents therein using an optical imaging apparatus. The use of a porous membrane may allow the particles to be captured on the surface of the membrane while allowing the passage of fluids and any compounds dissolved therein, including but not limited to uncaptured analytes, unbound receptors or antibodies, test fluids, diluents, solvents, wash buffers and the like. Suitable porous membranes for use in the embodiments presented herein would include those membranes with a pore size smaller than the diameter of the smallest population of size-coded particles used in the assay. In an embodiment, the membrane fitted to the flow cell system may be a polycarbonate track etched porous membrane such as, for example, a NUCLEPORE® membrane.

In an embodiment, detecting an analyte in a fluid may include mixing one or more populations of analyte-specific particles with the test fluid and a detecting receptor, and passing the mixture across a porous membrane disposed in an analyte detection device. In an embodiment, an analyte detection device may include a flow cell system, such as that which has been described in detail above. Passing the particle-containing fluid through the membrane equipped flow cell may cause the particles to be captured on the surface of the porous membrane. In an embodiment, the flow cell may be configured to allow for the microscopic examination of the contents captured on the membrane surface. This may include fabricating components of the flow cell, such as, for example, the top member 140 and bottom member 150, from a material that is substantially translucent to visible and/or ultraviolet light. This may facilitate the optical imaging of signals emitted from particles captured on the surface of the membrane using optical imaging techniques.

In an alternate embodiment, detecting an analyte in a fluid may include passing a test fluid through an analyte detection device equipped with a porous membrane and populations of analyte specific particles captured thereon. In an embodiment, the analyte detection device may include a flow cell system, such as that which has been described in detail above.

In this embodiment, passing the fluid through the porous membrane may cause the analyte to interact with the analyte-specific particles captured thereon. In an embodiment, the detecting receptor may be added to the test fluid prior to passing the test fluid though the analyte detection system. In another embodiment, the detecting receptor may be passed through the analyte detection system after the test fluid has been passed through the system.

In an embodiment, the analyte detection system may be coupled to an optical imaging station. The optical imaging station may include, for example, a microscope capable of visualizing the signals emitted from the particles and/or capable of determining the size of the particles. A detector may be used to capture images of the membrane-captured particles. A detector may include a detection device, such as a CCD digital imaging apparatus, and analytical software that is capable of analyzing digital images, such as, for example, Image Pro 4.0 or the like. Suitable optical instrumentation and imaging software platform for use in the embodiments presented herein have been described above. In some embodiments, the analyte detection system coupled to an optical imaging station may provide a means for efficient capture of populations of analyte-specific particles and the static imaging of the analytes captured thereon.

In an embodiment, digital images of particles captured on a field of the membrane may be acquired and the signals emitting from the particles may be analyzed. For example, in an embodiment where particle populations are defined by red fluorescence intensity, and the detecting receptor is defined by green fluorescence, optical imaging using a red dichroic filter would allow the identification of the particle type and its location on the membrane (which may be referred to as the "particle address"), and optical imaging using a green dichroic filter would identify particle populations that have bound to the analyte of interest. In an embodiment, acquired images may be processed digitally. In an embodiment, digital processing may be automated to facilitate the simultaneous detection and analysis of multiple populations of particles. Conversely, in alternate embodiments, a user may define areas of the membrane to be processed further. Automated digital processing of acquired images may allow: the rapid identification of the location of particles and the identification of the corresponding population to which they belong; the identification of particle populations that are specifically bound to an analyte; and the quantitation of the analyte in the fluid sample. Quantitation of the analyte in the fluid sample may be determined by measuring the intensity of the fluorescent signal emitted from the detecting receptor.

Figure 58A:
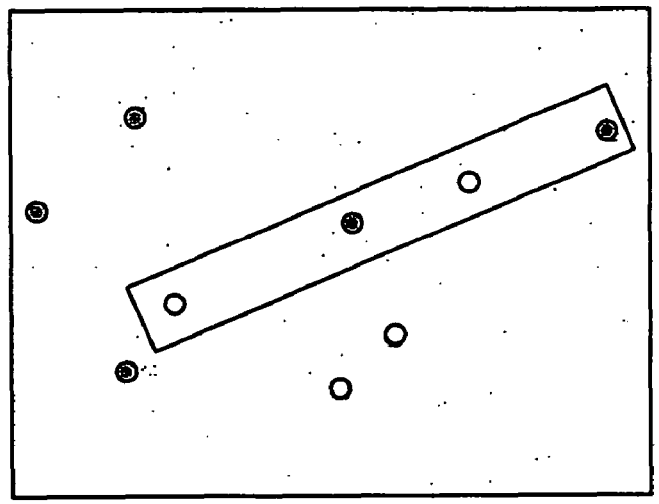
FIGS. 58A-B depict an embodiment of polystyrene particle types defined by size and by fluorescence signal intensity.
Figure 58B:
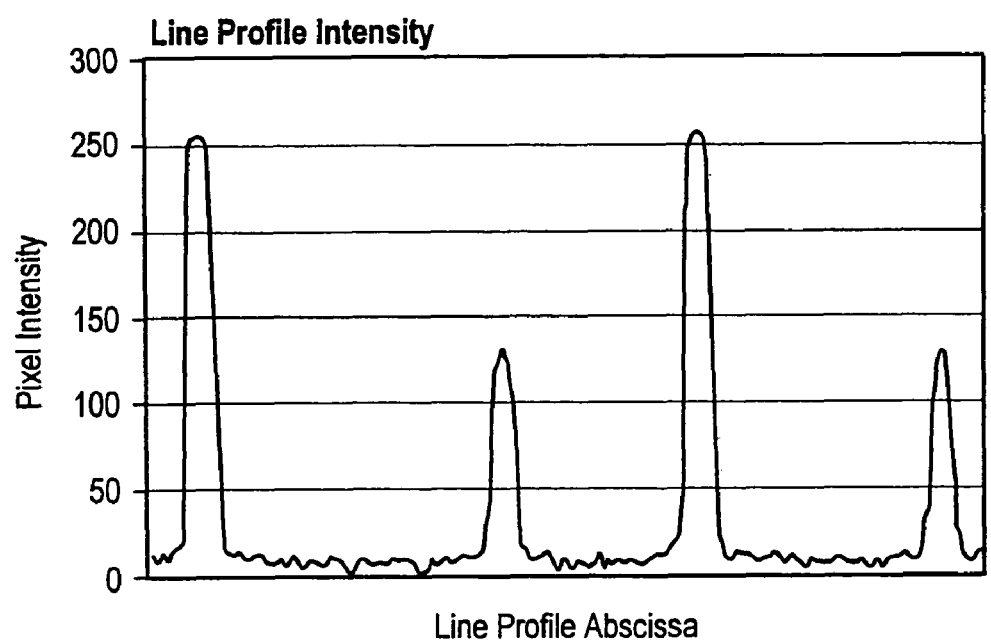

FIG. 58A-B depicts populations of polystyrene particles that are defined by size and by fluorescence signal intensity. FIG. 58A shows an image of particles captured on a membrane according to an embodiment. In this case, two different populations of particles are shown. The particles in this image are of the same size, but each population of particles is coupled to different amounts of an internal red fluorescent dye. These two populations of particles were mixed together, captured on a membrane in a flow cell and imaged optically using a red dichroic filter. FIG. 58A shows a view of an embodiment where polystyrene particles of the same size are distinguished on the basis of red fluorescence intensity. Particles of high fluorescence intensity are shown as open circles, and particles of lower fluorescence intensity are shown as shaded circles. FIG. 58B shows a line profile analysis of the particles in the boxed area of FIG. 58A. In this case, fluorescence intensity (measured as pixel intensity) is depicted as a function of the line profile. Confirmation that only one size of particles is present in the mixed population of particles may be achieved by determining the width of each peak at half the maximal pixel intensity. Conversely, the presence of two populations of particles distinguished on the basis of fluorescence signal intensity may be demonstrated by the presence of two peak pixel intensities.

In embodiments where both the capturing receptor and the detecting receptor are antibodies, the method of analyte detection may be referred to as a "sandwich immunoassay." The detecting receptor may be directed to the same epitope on the analyte as the capturing receptor. Conversely, the detecting receptor may be directed to a different epitope on the analyte than the capturing receptor. As used herein, the term "epitope" generally refers to a region on a molecule that is recognized by and that binds to the antigen binding sites of an antibody. In an embodiment, the detecting receptor may be coupled to a dye that distinguishes the detecting receptor from the size-and/or color-coded particle population. For example, in an embodiment, a detecting antibody that binds to an analyte captured by a capturing antibody on the surface of first color fluorescent particles may be coupled to a second colored fluorescent dye. In such an embodiment, a positive test for the presence of an analyte would occur when a population of particles appears having the first color when imaged optically using a first color filter, and the second color when imaged using a second color filter. Conversely, particles that have the first color, but do not appear to have the second color would indicate that the analyte is not present in the solution. In an embodiment, the concentration of an analyte in a solution may also be determined by measuring the fluorescence intensity of the second dye. In an alternate embodiment, the fluorescent dye that defines the population of particles may be coupled to the capturing receptor rather than being coupled to the particles.

FIG. 59A-C schematically depicts an assay for the detection of cytokine Tumor Necrosis Factor (TNF-α in a test fluid using a particle on membrane assay system. In FIG. 59A a sandwich-type immunocomplex between analyte-sensitized particles, the analyte of interest (e.g. TNF-α), and a second analyte-specific antibody is formed. In this embodiment, a population of 5.6 μm polystyrene red fluorescent particles is coupled to a TNF-α-specific capturing antibody. If TNF-α is present in the test fluid, the capturing antibody coupled to the population of TNF-αspecific particles captures it. The sandwich-type immunocomplex is formed when the detecting antibody, depicted in FIG. 59A as ALEXA FLUOR®488-Ab, which is also specific for TNF-α and is coupled to the green fluorescent dye ALEXA FLUOR® 488, binds to the complex.

FIG. 59B depicts the process involved in performing an assay according to an embodiment. Initially, an immunocomplex is formed in a solution containing TNF-α between the particle-coupled capturing antibody that binds to TNF-α, soluble TNF-α, and a detecting antibody that also binds to TNF-α and that is coupled to ALEXA FLUOR® 488. In this embodiment, particles belonging to the population of particles that are sensitized to detect TNF-α are depicted as closed circles, and particles belonging to populations of that do not detect TNF-α are depicted as open circles. This step may be referred to as the "immunoreaction" step. In an embodiment, the immunoreaction step may take place in vitro, such as in a test tube, for example. After the immunoreaction step, the fluid sample containing the immunocomplexes may be passed through a membrane-equipped flow cell and captured on the membrane equipped therewith. In an alternate embodiment, the immunoreaction step may occur on the surface of the membrane in the flow cell. In some embodiments, wash buffers, such as for example, phosphate buffered saline, or the like, may be passed through flow cell to remove any unbound detection antibody, or any other soluble components that may interfere with the imaging step.

Turning now to FIG. 59C, after the TNF-α-bound particles are captured on the membrane, the particles may be optically imaged using the appropriate combinations of dichroic filter sets. In this case, a red fluorescence signal identifies the particle population address, and green fluorescence signal identifies the population of particles that are bound to TNF-α. Particles belonging to the particle population that is defined by a different fluorescence intensity (shown as open circles in FIG. 59B-C) are not sensitized to capture TNF-α and do not emit a green fluorescence signal.

Figure 60:
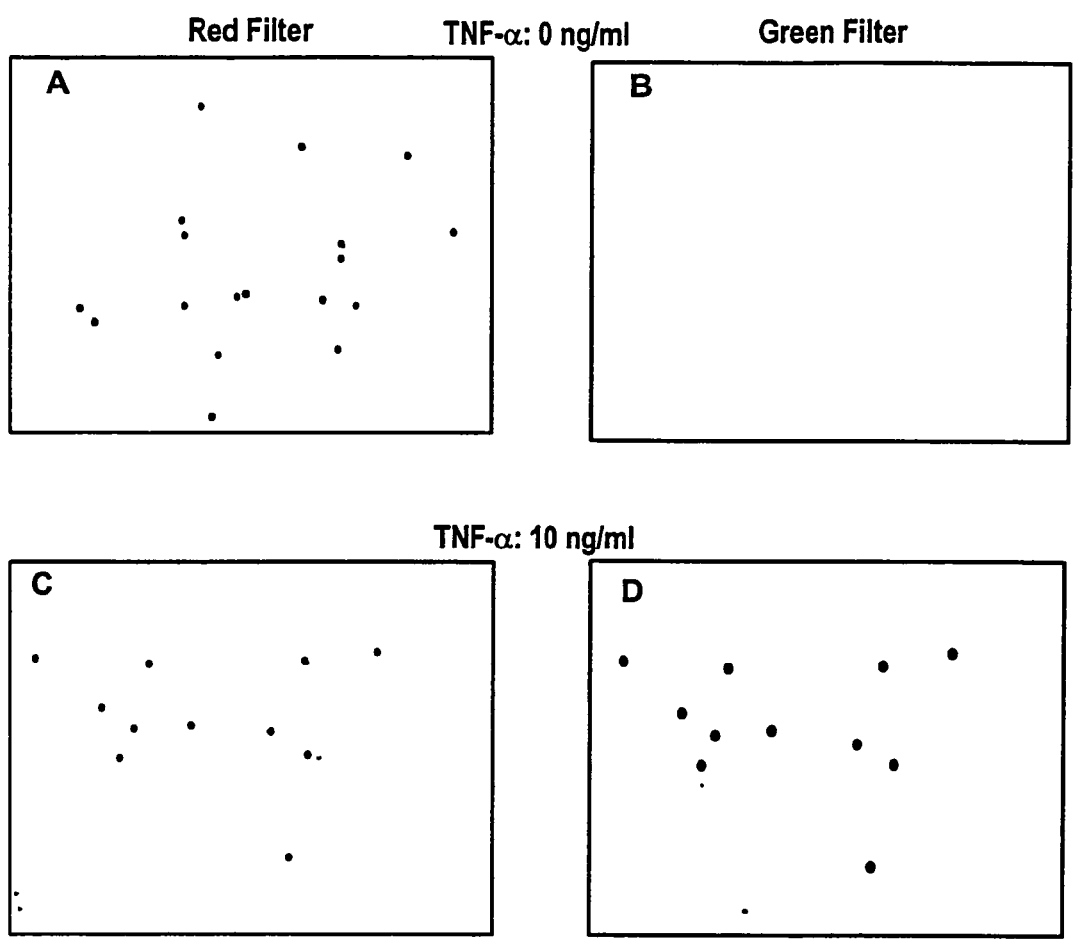
FIGS. 60A-D depicts the detection of TNF-α in a fluid according to an embodiment.

FIG. 60 depicts a proof of principle experiment using a particle on a membrane assay system to detect TNF-α in a fluid. In this embodiment, polystyrene particles were coated with a fluorescent red dye to designate particle address, and were coupled to an antibody directed against TNF-α. The particles were then added to a fluid containing no TNF-α (top panels), or to a fluid containing 10 ng/ml TNF-α (bottom panels). A detecting antibody that is coupled to ALEXA FLUOR® 188 and is also specific for TNF-α was added to both immunoreactions. The fluid containing the particles and any analyte captured thereon was then passed through a membrane-equipped flow cell and captured on the membrane residing therein. Captured particles were imaged using red (panels A and C) and green (panels B and D) dichroic filters. Panel A shows the particle address when the membrane is imaged using a red dichroic filter. However, since this sample contained no TNF-α, no immunocomplex was formed, and hence no green signal is detected when the membrane is imaged with a green dichroic filter, as shown in panel B. The sample that contained 10 ng/ml TNF-α emits a red signal from the particles when the membrane is imaged using a red dichroic filter as seen in panel C. In contrast to the sample that lacked TNF-α, in this case an immunocomplex formed between the capturing antibody, TNF-α, and the ALEXA FLUOR® 488-coupled detecting antibody, and thus a green signal is detected when the membrane is imaged using a green dichroic filter, as seen in panel D.

Figure 61:
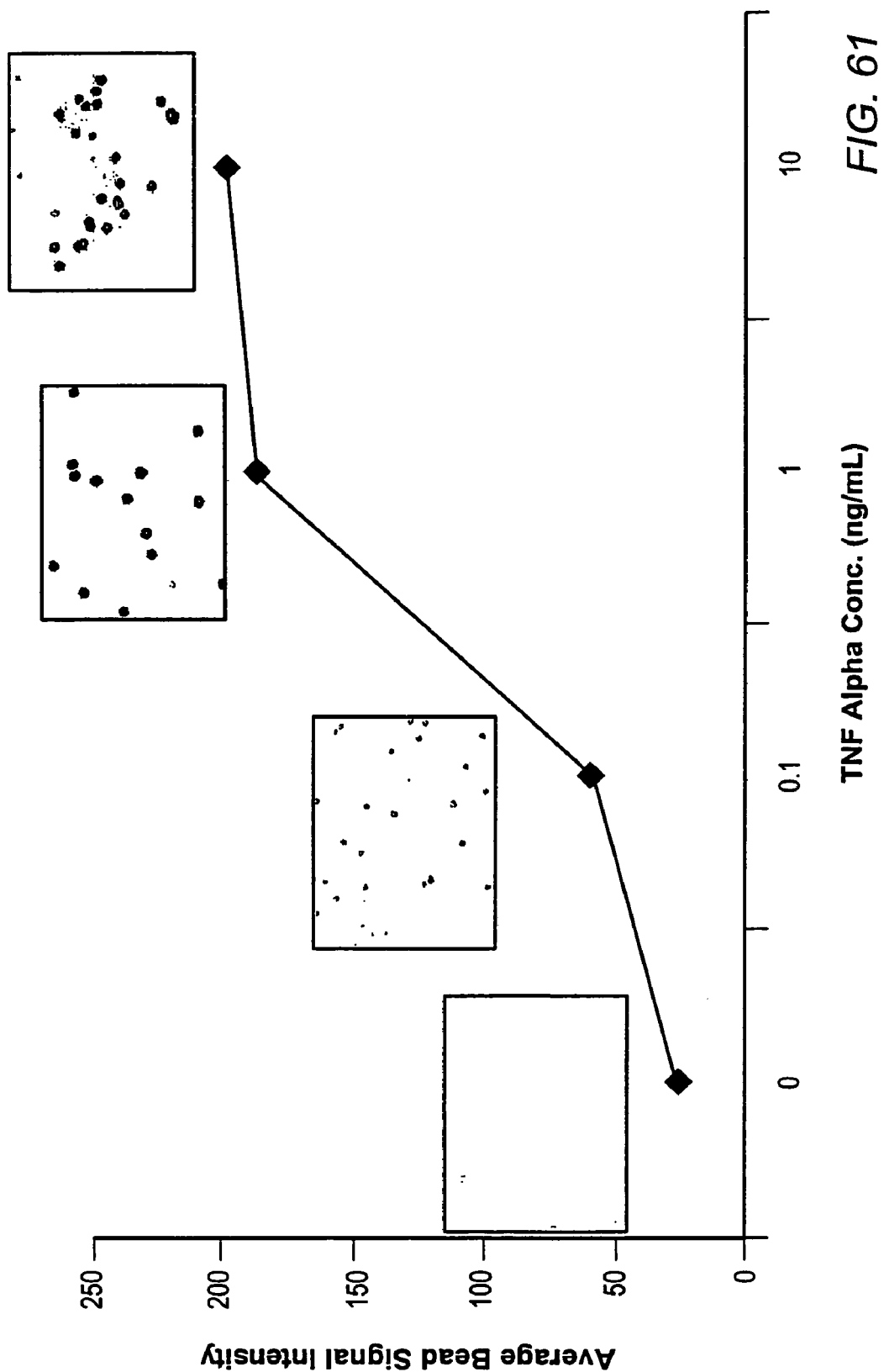
FIG. 61 depicts a dose response to TNF-α according to an embodiment.

FIG. 61 depicts a dose response curve to TNF-α according to an embodiment of a particle on a membrane assay system. In this case, fluorescent red polystyrene particles sensitized to detect TNF-α were exposed to either 0 ng/ml, 0.1 ng/ml, 1.0 ng/ml or 10 ng/ml TNF-α in a test fluid in the presence of ALEXA FLUOR® 188-coupled TNF-α-specific detecting antibody. The test fluids were then delivered to membrane-equipped flow cell, and the particles captured thereon were imaged optically by red and green fluorescence settings. In this case, the concentration of TNF-α in the test samples was determined by measuring green pixel intensity according to an embodiment. The results obtained are plotted as average particle signal intensity as a function of TNF-α concentration in the test fluid. Fluorescence images acquired using a green dichroic filter are provided in the box above each date point.

Certain embodiments of the particle on membrane assay system may be particularly suited to detecting evidence of one or more infectious agents in fluids derived from patients or test subjects. Suitable samples may be derived from body fluids, isolated, enriched or cultured cells, stool samples, swabs or aspirates taken from the nasopharyngeal, oral, genitourinary, or alimentary tracts, tissue homogenates, cell lysates, bronchoalveolar or gastric lavage, tissue aspirates or any other patient sample collected according to standard procedures in the art. Suitable body fluids may include, but are not limited to, whole blood, fractionated blood, blood plasma, serum, saliva, urine, mucous secretions, cerebrospinal fluid, lymphatic fluid, pulmonary or gastointestinal secretions or contents, semen, lacrimal secretions or combinations thereof. Non-limiting examples of infectious agents that may be detected according to some embodiments may include, viruses, bacteria, parasites, fungi, yeasts, prions, or combinations thereof.

In an embodiment, the particle on membrane assay system may be used to detect and diagnose viral infections and diseases caused by viruses. Examples of viral infections and diseases caused by viruses that may be diagnosed according to some embodiments may include, but are not limited to, retroviruses, human immunodeficiency virus (HIV), Acquired Immunodeficiency Syndrome (AIDS), hepatitis viruses, adenovirus, poliovirus, Epstein-Barr virus, mononucleosis, cytomegalovirus, influenza, viral encephalitis, viral meningitis, varicella-zoster virus, herpes simplex viruses, chickenpox, smallpox, Coxsackie virus, enteroviruses, Dengue fever, coronavirus, Severe Acute Respiratory Syndrome (SARS), Ebola, viral hemorrhagic fevers, measles, flaviviruses, yellow fever, paramyxoviruses, West-Nile virus, rabies, or any other virus or viral disease for which natural, synthetic or recombinant polypeptide or nucleic acid capturing and detecting receptors may be available.

In an embodiment, performing an HIV test on a test fluid by detecting HIV specific antibodies may include mixing one or more populations of particles coupled to HIV proteins with the test fluid. Suitable test fluids may include fluids containing blood or serum, saliva, urine or any other fluid or body fluid described previously. In an embodiment, the mixture may be passed across a porous membrane disposed in an analyte detection device, and the particles in the mixture captured thereon. In an embodiment, excess or residual test fluid may be evacuated from the flow cell device by flushing the chamber with an appropriate volume of wash buffer. In an embodiment, an indicator-coupled detecting antibody such as, for example, an ALEXA FLUOR® 488-coupled anti-human IgG antibody may be provided to the chamber. Optical imaging and analysis of the membrane-captured particles may then proceed according to embodiments described above.

In an alternate embodiment, viruses may be detected in a test fluid by coupling nucleic acids, such as DNA or RNA, whose nucleic acid sequences are complementary to and hybridize with at least a portion of the viral genome. In these embodiments, detecting receptors may include enzyme, chromophore or fluorophore-coupled nucleic acids whose nucleic acid sequences are homologous to and hybridize with the same or with different portions of the viral genome as the capturing receptor or proteins that bind to sequences within the viral genome. Embodiments in which nucleic acids are employed as capturing receptors may be used either alone or in combination with other nucleic acid hybridization or amplification techniques commonly used in the art, such as, for example, PCR.

In some cases, infectious agents, such as viruses, may be present at levels too low to be detected directly. In such cases, it may be preferable to detect antibodies that are specific for an infectious agent, and that may be present in test fluids derived from patients or test subjects. In such embodiments, a positive test for an infectious agent would include a positive test for the presence of antibodies specific for the infectious agent. In an embodiment, a purified or recombinant polypeptide molecule, or a synthetic oligopeptide, or derivatives or combinations thereof, whose polypeptide sequence substantially corresponds to at least a portion of the polypeptide sequence of a protein that is expressed by an infectious agent, may be coupled to a population of particles and function as capturing receptor. The particles may then be mixed with a test fluid derived from a patient or test subject. If the patient or test subject has been exposed to the infectious agent, or is infected with the infectious agent, and has mounted at least an humoral immune response against the infectious agent, then antibodies present in the test fluid would bind to their respective epitopes on the capturing receptor. The particles may then be passed though an analyte detection device and captured on a porous membrane, according to an embodiment. In an embodiment, an indicator-coupled detecting receptor that recognizes and binds to antibodies may be used to detect antibodies that are bound to particles. Suitable detecting receptors that bind specifically to antibodies are well known in the art and may include, but are not limited to, antibodies whose epitopes are the heavy or light chains of antibodies (e.g. anti-IgG, anti-IgE, anti-IgA, anti-IgD or anti-IgM antibodies), *Staphylococcus* protein A, *Streptococcus* protein G, chimeric protein AG, complement proteins, recombinant or purified FcR immunoglobulin receptors, or the like.

In an embodiment, the particle on membrane assay system may be used to detect and diagnose HIV infection. Populations of particles may be coupled to HIV proteins and used to detect antibodies specific to HIV that may be present in a body fluid derived from a patient suspected of being seropositive. Suitable HIV proteins that may be used include, but are not limited to, HIV coat proteins and glycoproteins, capsid proteins, structural proteins, nucleoplasmic proteins, viral enzymes, or the like. Non-limiting examples of HIV proteins that may be suitable for use in the embodiments presented herein include the HIV gag proteins p53, p24, p17, p7, p6, p2 or p1, the HIV env glycoproteins gp120, gp41 or gp160, HIV enzymes including integrase (p31), reverse transcriptase (p51 or p66), RNase H (p 15), protease (p10), the HIV nef proteins (p25/p27), the HIV vif protein p23, HIV rev protein p19, HIV vpr protein (p12/p10), HIV vpu protein (p16) or HIV tat proteins (p16/p14). These embodiments may include coupling the fill-length protein or derivatives, portions or combinations thereof to particles. Antibodies to multiple HIV proteins may be detected simultaneously in a patient sample according to an embodiment. By testing for antibodies to multiple HIV proteins present in a single sample, the likelihood of a false positive result may be reduced.

In an embodiment, performing an HIV test on a test fluid by detecting HIV specific antibodies may include mixing one or more populations of particles coupled to HIV proteins with the test fluid. Suitable test fluids may include fluids containing blood or serum, saliva, urine or any other fluid or body fluid described previously. In an embodiment, the mixture may be passed across a porous membrane disposed in an analyte detection device, and the particles in the mixture captured thereon. In an embodiment, excess or residual test fluid may be evacuated from the flow cell device by flushing the chamber with an appropriate volume of wash buffer. In an embodiment, an indicator-coupled detecting antibody such as, for example, an ALEXA FLUOR® 488-coupled anti-human IgG antibody may be provided to the chamber. Optical imaging and analysis of the membrane-captured particles may then proceed according to embodiments described above.

In a further embodiment, HIV virions or proteins may be detected in fluid samples, tissue homogenates or cell lysates. In an embodiment, antibodies that recognize HIV proteins may be used as capturing antibodies to perform a sandwich immunoassay as described in detail above. Detecting antibodies may be specific for the same or different HIV proteins as the capturing antibodies. For example, HIV virions may be detected in a fluid by coupling a capturing antibody whose epitope is one or more regions of the HIV env protein gp120. In this embodiment, a suitable detecting antibody may include the same antibody as the capturing antibody that is coupled to an indicator rather than to particles. Alternatively, the detecting antibody may include an indicator-coupled antibody whose epitope is a different region of gp120. In yet further embodiments, a capturing antibody may include an indicator-coupled antibody that binds to an epitope on a different protein such as, for example, p24 or gp41. In yet another embodiment, capturing and detecting receptors that may be used to detect HIV virions may include those cellular receptors that bind to HIV proteins. Non-limiting examples of cellular receptors that bind to HIV proteins may include, for example, CD4, chemokine receptors CCR5 or CXCR4, or combinations thereof.

In some embodiments, an instrument may include one or more disposable cartridges. Such an instrument may portable. In some embodiments, a cartridge may be designed such that the cartridge is removably positionable in an instrument. A cartridge may include one or more detection systems. Light from an optical platform of the instrument may pass onto a detection region and a detector in the optical platform may acquire images (e.g., visual or fluorescent) of the sample, and/or of sample-modulated particles.

Figure 62:
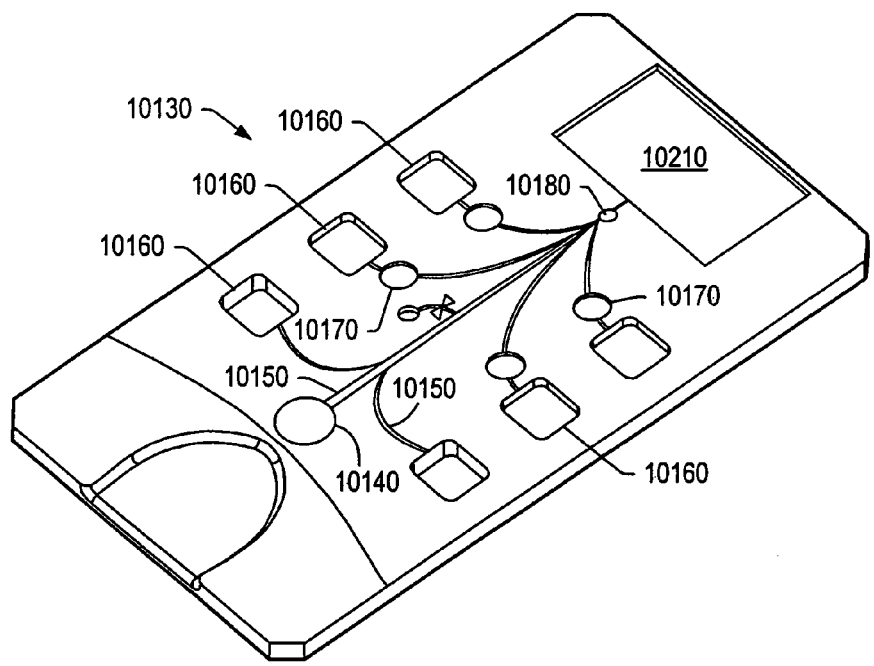
FIG. 62 depicts an embodiment of a cartridge that includes a sensor array.
Figure 63:
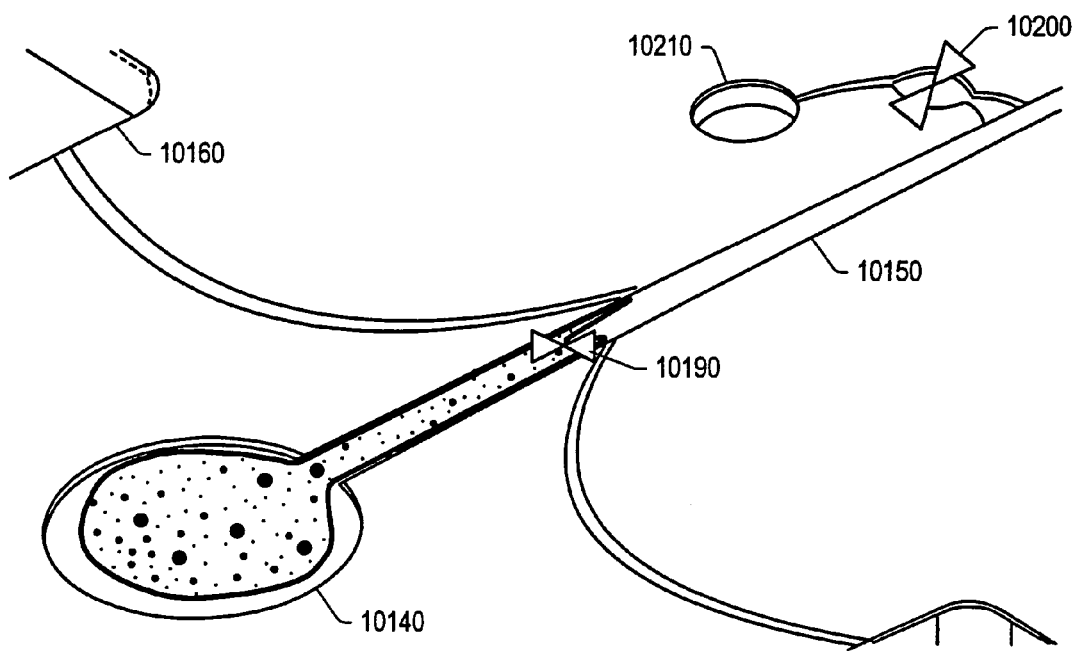
FIG. 63 depicts an embodiment of a portion of the cartridge depicted in FIG. 63.

FIG. 62 depicts an embodiment of a cartridge. FIG. 63 depicts an embodiment of a portion of the cartridge of FIG. 63. A cartridge 10130 may include a sample collection device 10140, as depicted in FIGS. 62 and 63. A sample may be delivered to the sample collection device 10140. In an embodiment, a sample collection device may include a sample pick-up pad. A sample may be introduced into the sample collection device. In one embodiment, a sample may be introduced into a sample collection device using a syringe or a pipette. Alternately, a sample may be introduced from a person directly to the sample collection device. For example, human blood may be introduced by forming a small incision in portion of a human body. The portion of the human body may be brought close to the sample pick-up pad such that blood flows from the incision in the human body to the sample pick-up pad.

Sample from the sample collection device 10140 may flow into one or more microfluidic channels 10150 coupled to the sample collection device. Capillary action may allow a sample to flow into a channel. A valve 10190 may restrict flow of sample from the sample collection device 10140. A valve 10190 proximate a sample collection device 10140 and a valve 10200 proximate an overflow reservoir 10210 in channel 10150 may be opened such that a predetermined amount of sample may be measured. During use the sample flows into channel 10150 until it fills the channel. The channel may hold a predetermined amount of fluid. An amount of sample greater than the predetermined amount may flow through valve 10200 into an overflow reservoir 10210. After a predetermined amount of sample is measured in channel 10150, valve 10190 and valve 10200 may be closed. Closing a valve 10190 proximate a sample reservoir may inhibit sample greater than a predetermined amount from flowing towards a detection region 10180. Closing a valve 10200 proximate an overflow reservoir 10210 may inhibit the predetermined amount of sample from flowing towards the overflow reservoir.

Figure 64:
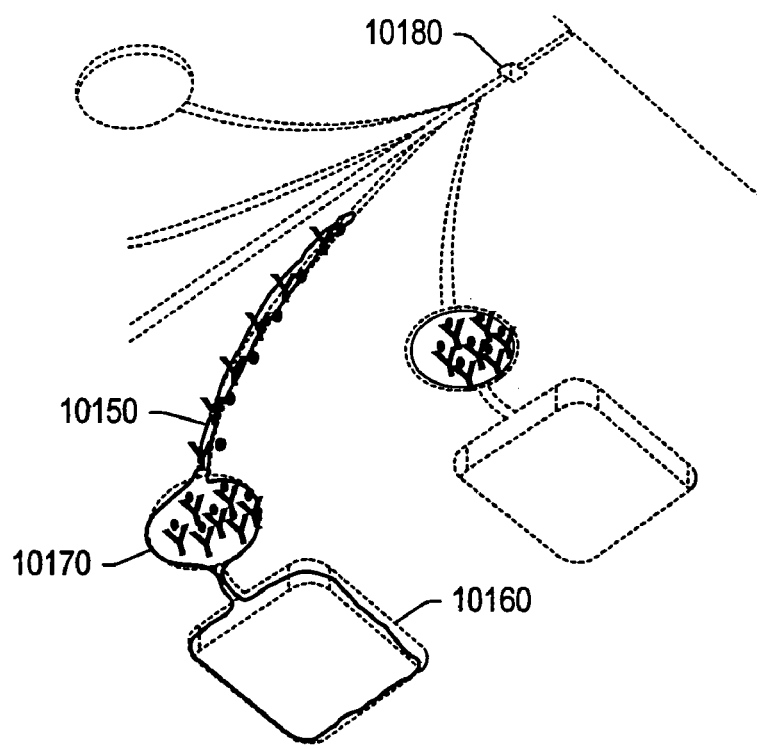
FIG. 64 depicts an embodiment of a reagent reservoir and reagent pack in the cartridge depicted in FIG. 63.

In some embodiments, a reservoir 10160 containing buffer and/or reagents may be coupled to a channel 10150. Fluid from the reservoir 10160 may push the predetermined sample towards a detection region. A buffer may be released from a buffer reservoir 10160 coupled by a channel to the channel containing the sample. In one embodiment, a buffer may be released from a reservoir 10160 by an actuator. Fluid from a reservoir may push the sample towards a mixing region or a detection region. A sample may mix and/or react with the fluid in a mixing region prior to flowing to a detection region. In certain embodiments, a reagent pick up pad 10170 may be positioned on a cartridge 10130 such that fluid from a reservoir 10160 may be able to flow over the reagent pick-up pad towards the detection region 10180. As depicted in FIG. 64, fluid from a reservoir 10160 may transfer reagents on a reagent pick-up pad 10170 into channel 10150. In some embodiments, reagents may be in a dehydrated or lyophilized state. Fluid from the reservoir may reconstitute and transfer the reagents as the fluid passes over the regent pick up pad 10170. Fluid from the reservoir 10160 containing reagents may be coupled to a detection region 10180 through a channel 10150. Detection region may include a particle based sensor array or a membrane-based system. Fluids in the cartridge 10130 may be collected in a waste reservoir 10190 after flowing past a detection region 10180, as depicted in FIG. 62. By containing all fluids within the cartridge, a user's exposure to reagents and sample may be substantially minimized.

Figure 65A:
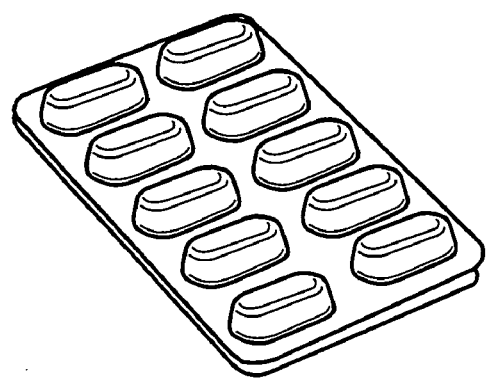
FIG. 65A depicts an embodiment of a blister pack containing reagents.
Figure 65B:
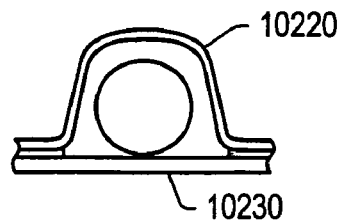
FIG. 65B depicts a cross-sectional view of a blister of a blister pack.

In some embodiments, one or more reagents may be contained in a reservoir positioned on a cartridge. A reagent reservoir may include a blister pack, as depicted in FIG. 65A. FIG. 65B depicts a cross-sectional view of an embodiment of a blister pack. A blister pack may include one or more reagents in a sealed reservoir. A sealed reservoir may substantially contain reagents in the reservoir until needed. Pressure applied to a blister pack may break one or more surfaces of the blister pack such that reagent is released from the blister pack. In an embodiment, a blister of a blister pack may be formed of a first material 10220 and a second materials 10230, where a second material is configured to rupture or break prior to the first material when pressure is applied to the blister. In an embodiment, a blister may include a first material configured not to break when pressure is applied to a blister and a second material configured to break when pressure is applied to a blister. A blister may be made of polyvinyl chloride (PVC); polyvinylidene chloride (PVDC); polyethylene (PE); polypropylene (PP); polyacrylonitrile (PAN); cyclic olefin copolymer (COC); fluoropolymer films; foil such as aluminum foil or plastic foil; and/or combinations thereof. A wall of a blister may be formed of layers of polypropylene, cyclic olefin copolymer. For example, a blister wall may be formed from a layer of cyclic olefin copolymer in between two layers of polypropylene. A wall of a blister may be formed of layers of polypropylene, cyclic olefin copolymer, and polyacrylonitrile. In an embodiment, a wall of a blister may be formed of layers of polyvinyl chloride, cyclic olefin copolymer, and polyvinylidene chloride.

Figure 66:
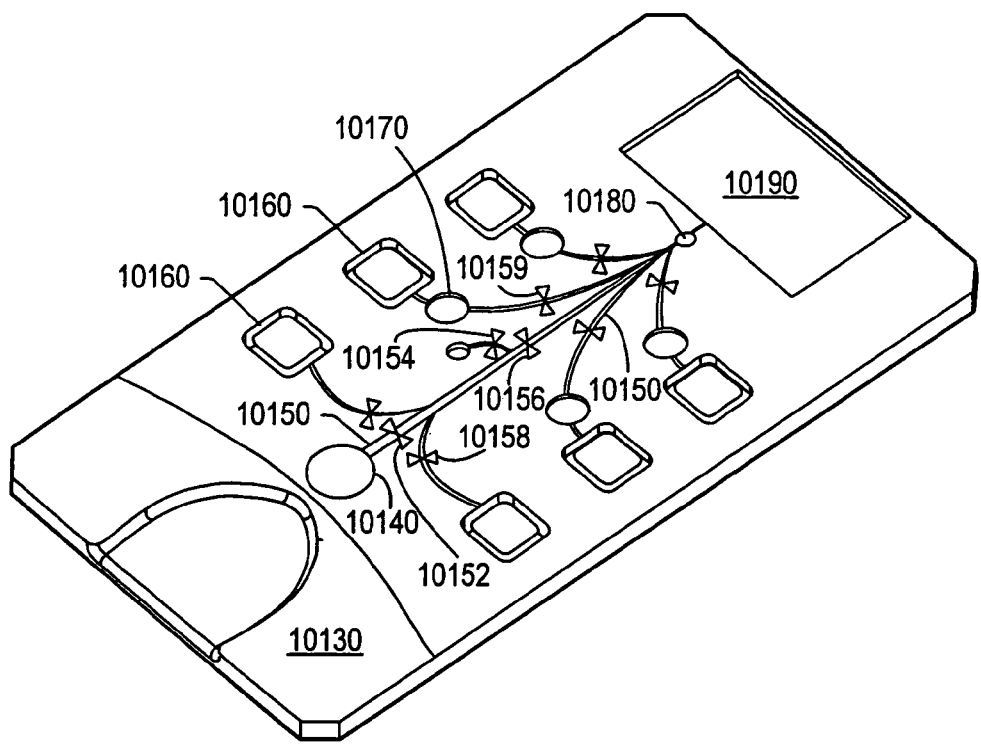
FIG. 66 depicts an embodiment of valves positioned in the cartridge depicted in FIG. 63.

In some embodiments, one or more valves may be coupled to channels in the cartridge. FIG. 66 depicts an embodiment of valve placement in channels on a cartridge. Valves may direct flow of a fluid through a channel. One or more valves coupled to microfluidic channels 10150 may allow a predetermined amount of sample from a sample reservoir 10140 to be analyzed. In one embodiment, a cartridge 10130 may include a first valve 10152 which may allow control of the introduction of sample into a portion of channel 10150. A first valve 10152 may be closed during sample collection to inhibit sample from flowing towards the detection region. A first valve 10152 may be opened to allow a predetermined amount of sample to flow into a microfluidic channel 10150 coupled to the detection region 10180. One or more other valves in the cartridge may be closed to direct a flow of sample in the cartridge.

In certain embodiments, a predetermined amount of sample may be measured into channel 10150. In one embodiment, sample is introduced into channel 10150 by opening of valve 10152. Sample is block from detection region 10180 by closing of valve 10156. As sample fills channel 10150, a predetermined amount of sample may be collected by allowing sample exceeding the predetermined amount to enter an overflow reservoir or region. A second valve 10154 proximate an overflow region may be opened as sample enters channel 10150 to allow sample exceeding the predetermined amount to flow into an overflow region and/or waste reservoir 10190. After a predetermined amount of sample is measured in a channel 10150, first valve 10152 and second valve 10154 are closed to prevent sample from the sample collection region and the overflow region from flowing to a detection region 10180. A third valve 10156 may be opened to allow a sample to flow towards a detection region 10180. A fourth valve 10158 may be opened to allow buffer from a buffer reservoir 10160 to push the measured sample towards the detection region 10180. One or more valves in a fifth set of valves 10159 may be opened to allow one or more reagents to flow towards a mixing chamber and/or detection region 10180. One or more reagent reservoirs 10160 may be actuated such that reagent may flow to the detection region. Reagents may mix with a sample in a mixing chamber and/or mixing region. Reagents from a reagent reservoir 10160 may flow over one or more reagent pick-up pads 10170 and reconstitute one or more reagents on the reagent pick-up pad. In one embodiment, a buffer solution may be passed over a reagent pick-up pad and flow towards a mixing region and/or detection region 10180. A sample may be analyzed in a detection region, such as a particle-based or a membrane-based detection region and/or platform. A cartridge may be flushed during or after analysis by buffer from one or more reservoirs contained in the cartridge. Fluids may flow from a detection region to a waste reservoir.

Figures 67A, 67B, 67C:
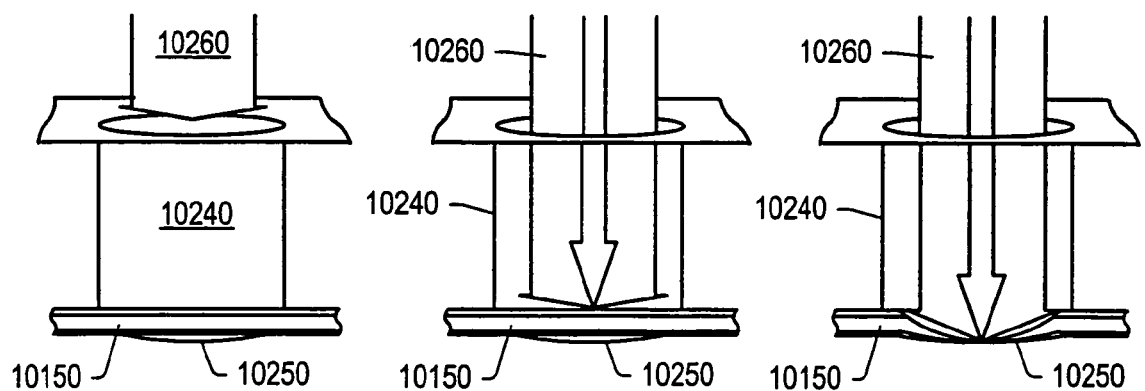
FIGS. 67A-67C depict views of the operation of a pinch valve.

Valves may include valves configured for microfluidic channels, such as gate valves, check valves, passive microvalves, and/or pinch valves. In one embodiment, pinch valves may be used in a cartridge to control flow in microfluidic channels. Fluids such as a sample, reagents, and/or buffers may flow through channels in a cartridge and valves may control the direction of the flow. A pinch valve may include an opening 10240 in a cartridge, as depicted in FIG. 67A. A channel 10150 may be accessed through the opening 10240. The opening may have a concave lower surface 10250. When a cartridge is loaded in an instrument, openings 10240 in the cartridge may be aligned with actuators 10260 coupled to the instrument.

Figure 68:
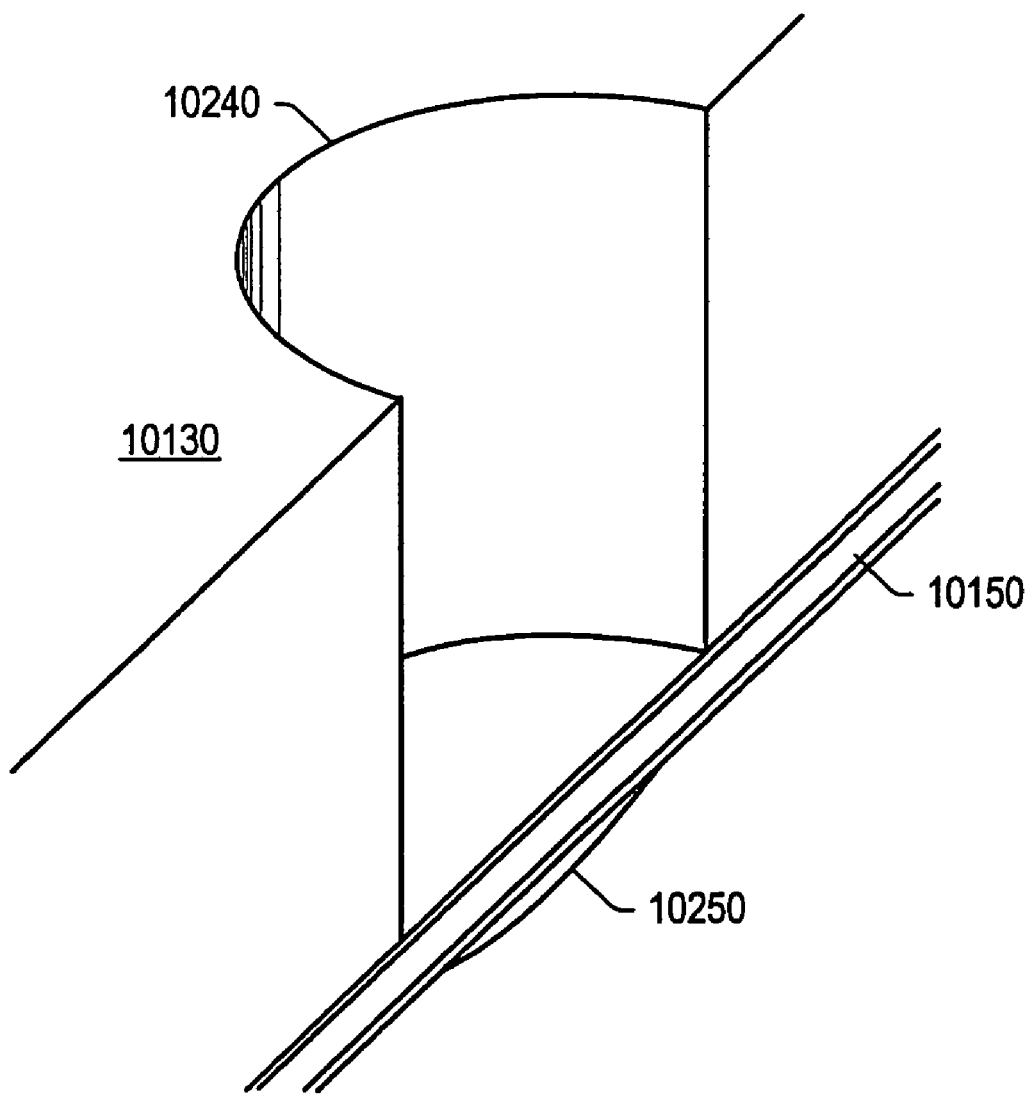
FIG. 68 depicts a cross-sectional view of a pinch valve.

In some embodiments, an actuator 10260 may be positioned in an opening 10240 of a cartridge above a channel 10150 after a cartridge is positioned in an instrument, as depicted in FIG. 67B. A lower surface 10250 of the opening 10240 may have a shape such that a bottom surface of an actuator 10260 fits in the lower surface of the opening. As depicted in FIG. 67C, an actuator 10260 may apply pressure on the channel 10150 such that fluid is inhibited from flowing through the channel. When pressure is applied to the channel 10150 to restrict flow through the channel, the valve is closed. In an embodiment, a lower surface 10250 of the opening may have a depth substantially equal to the diameter of the channel exposed in the opening. FIG. 68 depicts a cross-sectional view of an embodiment of a pinch valve in a cartridge. A pinch valve may include an opening 10240 in a cartridge 10130 that allows access to a channel 10150. A channel 10150 may be positioned above a lower surface 10250 of the opening 10240.

FIG. 69A depicts an exploded view of an embodiment of a cartridge. A cartridge may include a top seal layer 10270, a top microchannel layer 10280, a center layer 10290, a bottom microchannel layer 10300, and/or a bottom seal layer 10310. Layers of a cartridge may be coupled together. Layers of a cartridge may be sealed together. Creating a cartridge from several layers may facilitate fabrication. A top seal layer 10270 may include access 10320 to a sample collection device 10140 or sample collection pick-up pad. Top 10280 and/or bottom 10300 microchannel layers may create a system of microchannels through the cartridge. A center layer 10290 may include reservoirs 10160 containing buffer and/or reagents, a portion of a sample collection device 10140, and/or a waste reservoir 10190. FIG. 69B depicts a top view of an embodiment of a cartridge. FIG. 69C depicts a perspective view of an embodiment of a cartridge. FIG. 69D depicts a bottom view of an embodiment of a cartridge.

Figure 70:
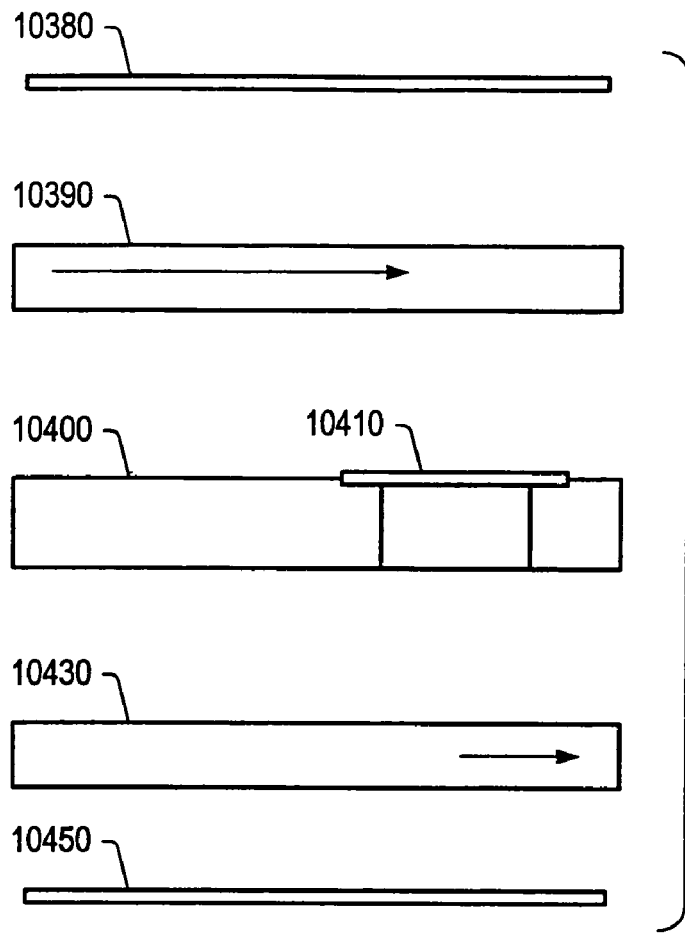
FIG. 70 depicts an exploded side view of an embodiment of a cartridge.

FIG. 70 depicts an exploded side view of an embodiment of a cartridge. Top 10380 and bottom 10450 seal layers may substantially contain fluid in the top 10390 and bottom 10430 microchannel layers. In an embodiment a fluid may flow from a top microchannel layer 10390 through a detection region 10410 in the center layer 10400 to a bottom microchannel layer 10430. Fluid may flow through the bottom microchannel layer 10430 to a waste reservoir.

Figure 71:
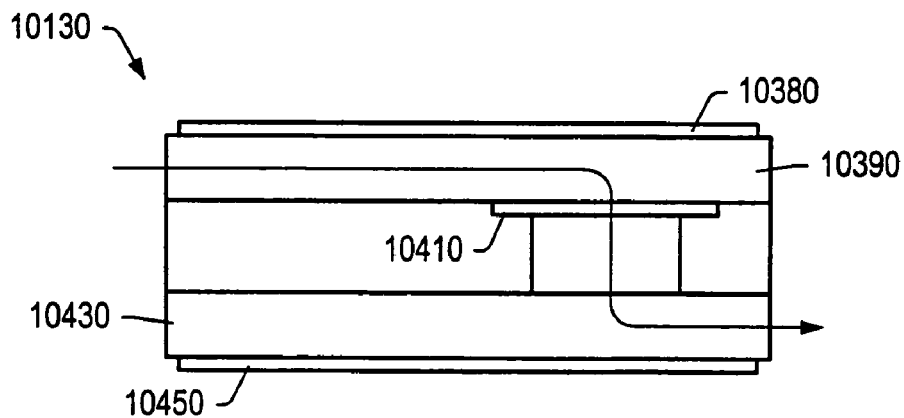
FIG. 71 depicts a side view of an embodiment of a cartridge.

FIG. 71 depicts a side view of an embodiment of a cartridge 10130. In some embodiments, fluid may flow from a top microchannel layer 10390 through a detection region 10410. Fluid may pass from the detection region 10410 through the bottom microchannel layer 10430 to a waste reservoir. Top 10380 and bottom 10450 seal layers may substantially retain fluid in microchannel layers.

FIG. 72A depicts an exploded view of another embodiment of a cartridge. An opening 10320 in the top seal layer 10270 may allow sample to be deposited in a sample collection device 10140 on the cartridge. When a sample is deposited in the cartridge one or more valves in a channel 10150 may inhibit a sample from flowing towards a detection region 10180. FIG. 72B depicts an embodiment of an arrangement of valves prior to and during deposition of a sample on the cartridge. During deposition of a sample, first 10330, second 10340, third 10350, and fourth 10360 valves may be closed to inhibit flow of sample through the cartridge.

In some embodiments, after a sample is deposited on the cartridge, an amount of sample may flow from the sample collection device 10140 through a channel 10150 via capillary action, as depicted in FIG. 73A. FIG. 73B depicts an arrangement of valves that allows sample to flow into a channel. A first valve 10330 may be open to allow a sample to flow into a microchannel. Second 10340 and third 10350 valves may be closed to control a flow of the sample. Closing a second valve 10340 may inhibit sample from flowing towards a buffer reservoir. Closing a third valve 10350 may allow a predetermined amount of sample to be measured. A fourth valve may be opened to allow sample in the channel to flow into an overflow reservoir.

Figure 74A:
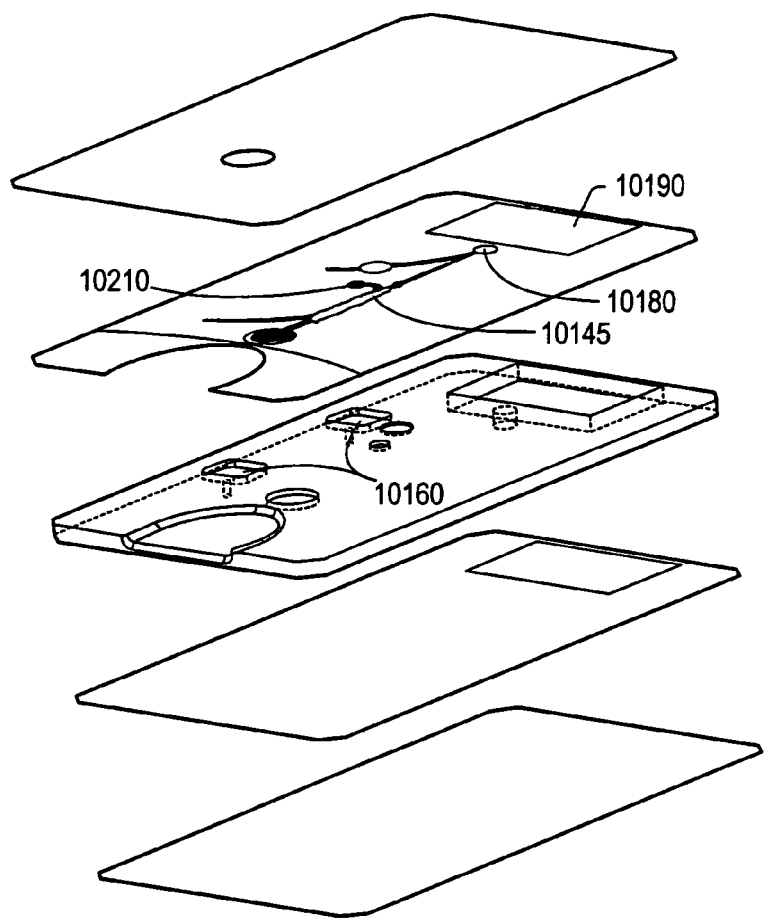
FIG. 74A depicts an exploded view of an embodiment of the cartridge depicted in FIG. 72A after the sample is introduced into the channel.
Figure 74B:
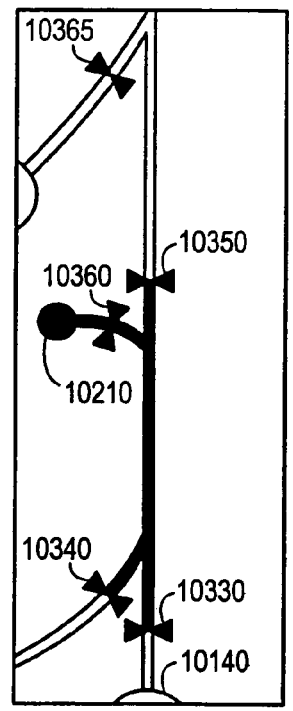
FIG. 74B depicts an embodiment of an arrangement of valves in a cartridge after the sample is introduced into the channel.

FIG. 74A depicts an embodiment of sample flow in a cartridge. In some embodiments, it may be desirable to allow a portion of sample to flow over a detection region 10180. A predetermined amount of sample 10145 may be measured and allowed to flow towards the detection region 10180. A predetermined amount of sample may be measured by allowing sample in excess of a predetermined amount to flow into an overflow region 10210. An overflow region 10210 may be coupled to a waste reservoir 10190. Valves in the cartridge may inhibit sample in a main channel from flowing into channels coupled to reservoirs 10160. After a predetermined amount of sample is measured, valves may be closed to inhibit additional sample from flowing into the channel containing the predetermined amount of sample. For example, as depicted in FIG. 74B, a first valve 10330 may be closed to inhibit additional sample from a sample collection device 10140 from entering a channel. Second 10340 and third 10350 valves may remain closed. A fourth valve 10360 may be closed to prevent sample from the overflow region 10210 from flowing into the channel.

Figures 75A, 75B:
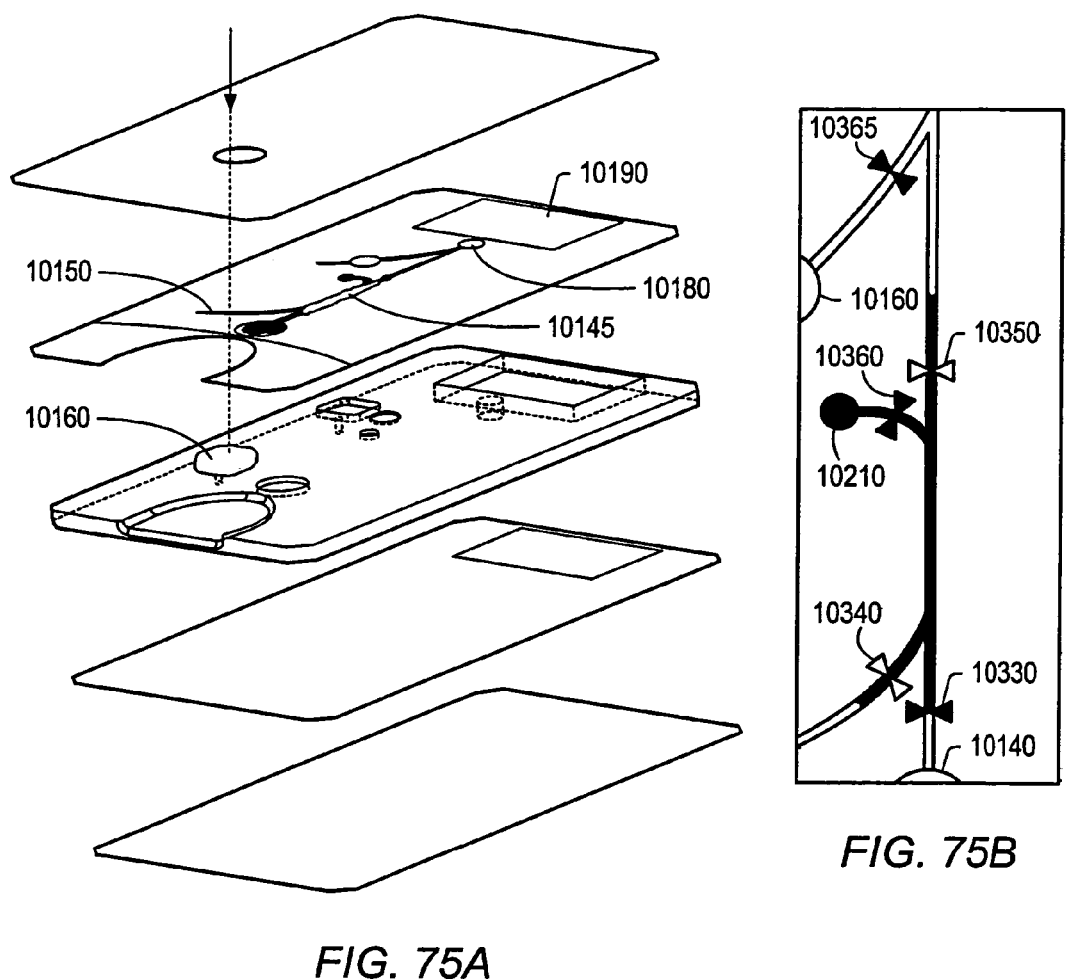
FIG. 75A depicts an exploded view of an embodiment of the cartridge of FIG. 72A in which a reservoir is being actuated.
FIG. 75B depicts an embodiment of an arrangement of valves in a cartridge that allows a sample to be pushed towards a detection region using buffer released from a reservoir.

After a predetermined amount of sample is measured, a reservoir 10160 may be actuated, as depicted in FIG. 75A. A reservoir may contain buffer and/or reagents. An actuator may release buffer from a reservoir. A buffer reservoir may be similar to a blister pack. As depicted in FIG. 75B, a third valve 10350 may be opened to allow fluid to flow towards a detection region. Actuation a buffer reservoir 10160 may cause buffer to be released from a reservoir into a microchannel. A reservoir 10160 may be coupled to the cartridge so that fluid from the reservoir may flow from the reservoir towards the detection region 10180. A reservoir 10160 may be positioned in the cartridge so that buffer from a reservoir may push a predetermined amount of sample 10145 towards a detection region 10180. In an embodiment, a buffer may flow from a reservoir 10160 over a membrane in a detection region 10180 to wash the membrane after the sample flows over the membrane. The buffer may then pass over the membrane and into the waste reservoir 10190.

FIG. 75B depicts an arrangement of valves in an embodiment of a cartridge that may allow a buffer to push a sample through a microchannel and towards a detection region. A first valve 10330 may be closed so that a sample may be inhibited from reentering a sample collection device 10140 or sample pick-up pad. A second valve 10340 may be opened to allow fluid from a buffer reservoir to flow towards a detection region. A fourth valve 10360 may be closed such that fluid may be inhibited from flowing into the overflow reservoir 10210. A third valve 10350 may be open such that fluid may flow towards a detection region.

Figure 76:
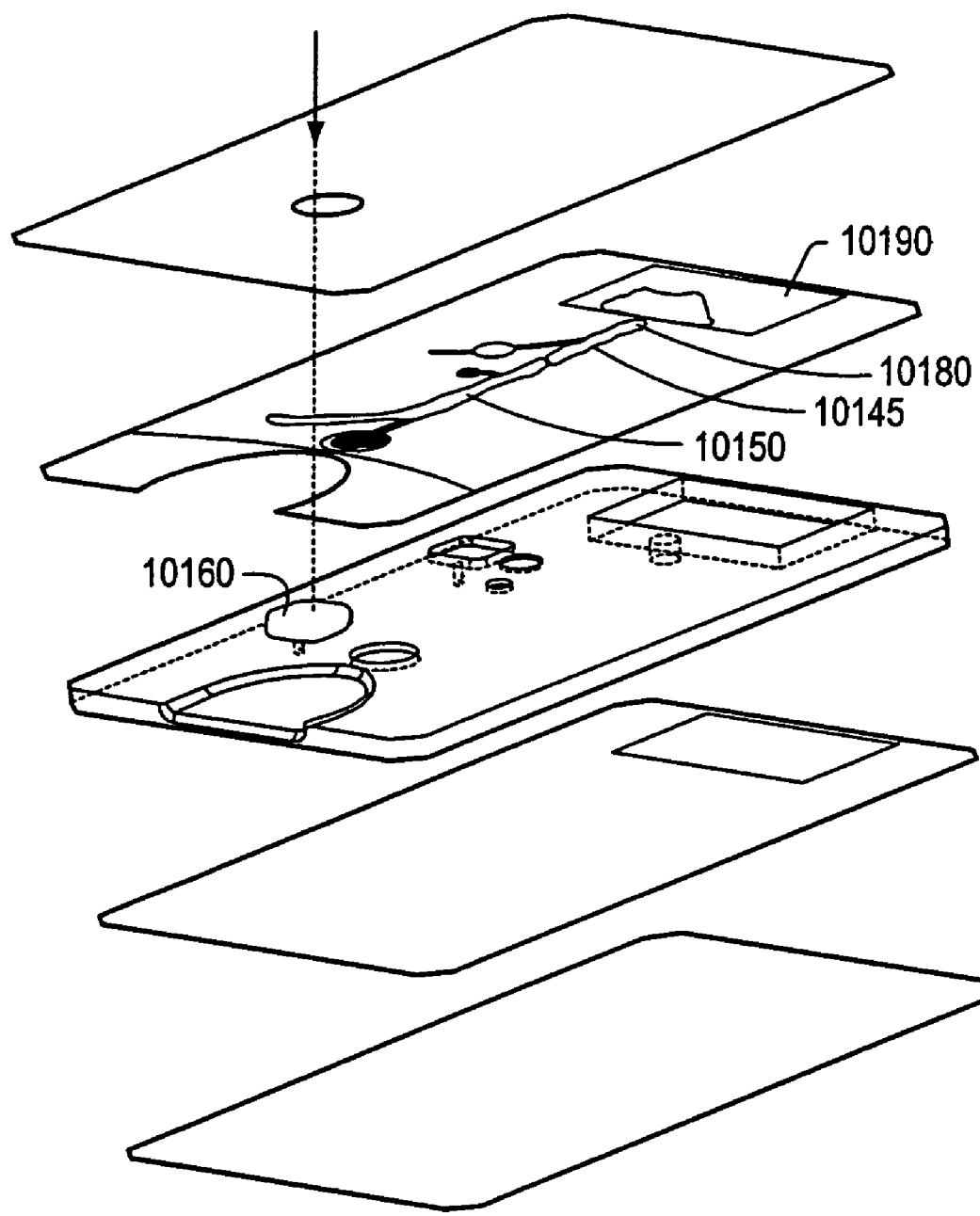
FIG. 76 depicts an embodiment of buffer pushing sample towards a detection region.
Figure 77:
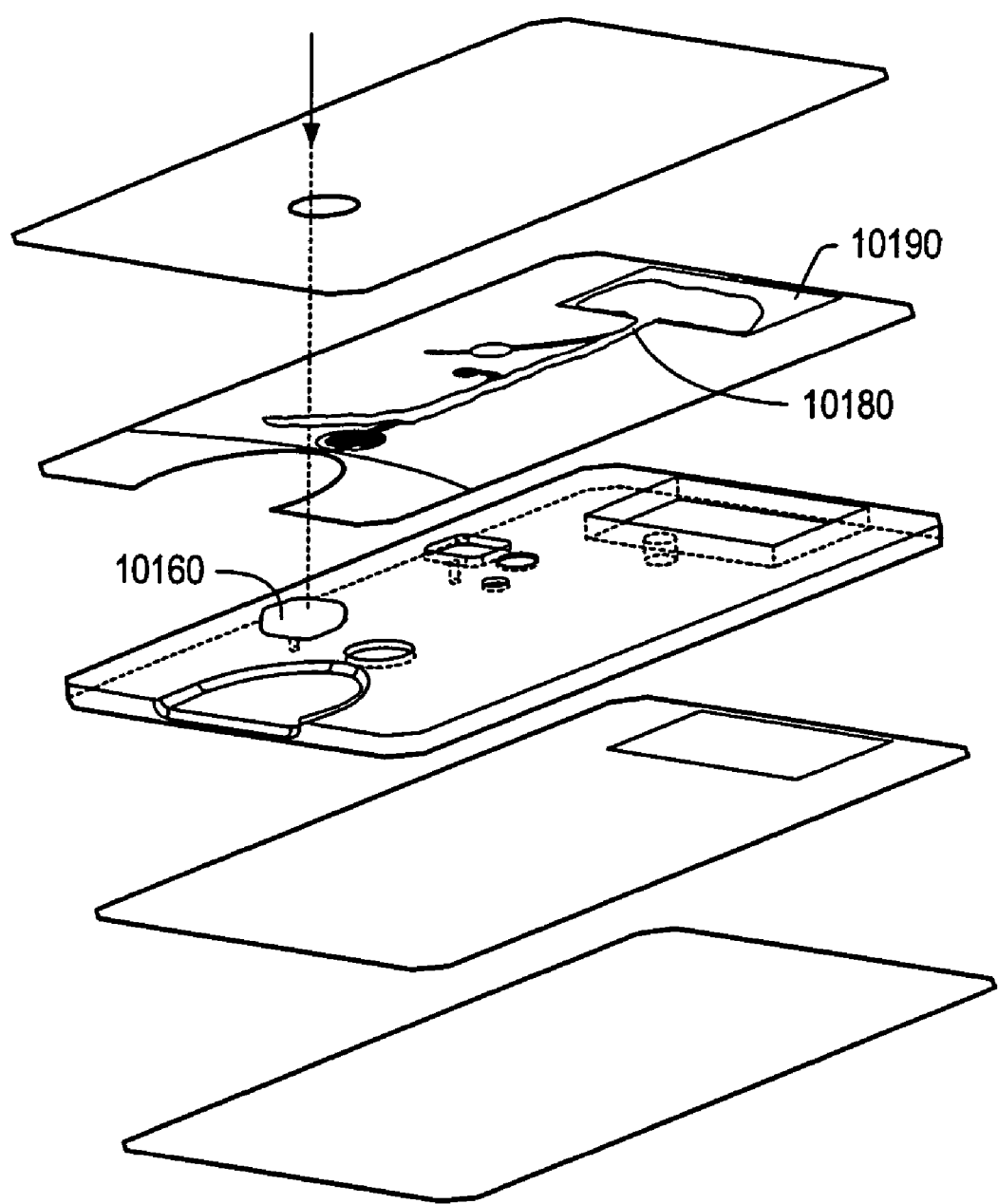
FIG. 77 depicts an embodiment of buffer pushing sample towards a detection region.

As the reservoir 10160 is actuated, buffer is released into a channel 10150 that couples the reservoir to a main channel containing the measured sample 10145. A main channel may couple a sample collection device 10140 to a detection region 10180 and/or waste reservoir 10190. The released buffer may push the predetermined amount or measured amount of sample 10145 towards a detection region 10180, as depicted in FIG. 76. Sample may pass over a detection region 10180, such as a membrane, and into a waste reservoir 10190. As depicted in FIG. 77, a buffer reservoir 10160 may be activated and buffer may be released such that the substantially all of the measured amount of sample and/or buffer flows over the detection region 10180. Fluid (e.g., sample and/or buffer) that passes through the detection region 10180 may flow into a waste reservoir 10190.

A reservoir 10370 containing reagents and/or buffer may be actuated to release reagents and/or buffer into channels in the cartridge, as depicted in FIG. 78A. FIG. 78B depicts an embodiment of valves in a cartridge. A first valve 10330 may be closed to prevent fluids from entering a sample collection device 10140. A second valve 10340 may be closed after buffer is released from a reservoir to push sample towards a detection region. Third 10350 and fourth 10360 valves may be closed to substantially inhibit fluid from flowing into an overflow region 10210 and/or away from a detection region. A fifth valve 10360 proximate a reservoir 10160 containing buffer and/or reagents may be opened to allow buffer and/or reagents to flow over a detection region.

Actuating a reservoir 10370 may push fluids from a reservoir over a reagent pad towards a detection region 10180 and/or waste reservoir 10190. A reservoir 10370 may include buffer and/or reagents. Reagents on a reagent pack may be reconstituted as the fluid from the reservoir 10370 passes over the reagent pack. A reservoir 10370 may be coupled to a detection region 10180 and/or a waste reservoir 10190 via one or more channels. One or more reagents may react with the sample in the detection region. In some embodiments, reagents from one or more reagent reservoirs and/or reagent packs may mix with a sample in a mixing chamber. After a fluid containing reagents from a reagent pad and/or a reservoir 10370 pass over a detection region 10180. Reagents may react with a portion of the sample in the detection region 10180. Unreacted reagents, excess reagents, and/or buffer may flow from the detection region and into a waste reservoir 10190. A reservoir 10370 may be actuated until a predetermined amount of reagents and/or buffer pass over the detection region 10180 and into a waste reservoir 10190. In some embodiments, a reservoir may be actuated to push buffer from the reservoir over the detection region. In certain embodiments, after analysis of the detection region, a reservoir may be actuated to release buffer and wash the detection region. Analysis of the sample may be repeated after analysis of the detection region.

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes can be made in the elements described herein without departing from the spirit and scope of the invention as described in the following claims. In addition, it is to be understood that features described herein independently may, in certain embodiments, be combined.

What is claimed is:

1. A method of detecting at least one analyte in a fluid comprising:
    forming a mixture of one or more first particles with the fluid, wherein each particle comprises a receptor configured to interact with at least a first analyte, and wherein particles that interact with at least a first analyte undergo a detectable spectroscopic change;
    passing the mixture of first particles and fluid across a porous membrane and a particle-based sensor array disposed in an analyte detection device, wherein the analyte detection device is configured to capture the first particles on the porous membrane allowing at least a second analyte to flow through the membrane and contact a second particle, wherein the analyte detection device comprises:
        a first sensor comprising the porous membrane configured to capture the first particles, a top member positioned at a spaced distance above the porous membrane such that a first cavity is formed between the top member and the porous membrane, wherein the top member covers at least a portion of the porous membrane, and wherein the top member is substantially transparent to light, and a bottom member positioned below the porous membrane, wherein the bottom member is configured to receive fluid flowing through the porous membrane, and
        a second sensor in series comprising the particle-based sensor array, wherein the particle-based sensor array is integral with the porous membrane and comprises a plurality of wells fabricated in an ordered array, wherein at least the second particle is positioned within a well and is configured to interact with the second analyte during use to produce a spectroscopic signal;
    detecting spectroscopic signals produced by the first particles captured on the porous membrane and the second particles in the particle-based sensor array; and
    determining if one or more analyte is present based on the detected spectroscopic signals.

2. The method of claim 1, wherein each of the particles comprises an identification molecule, wherein the identification molecule coupled to each particle is specific for the analyte that interacts with the particle, the method further comprising determining if the analyte is present by determining the identity of the identification molecule on particles in which a spectroscopic signal has been detected.

3. The method of claim 1, wherein each of the particles comprises a predetermined size, wherein the size of each particle is specific for the analyte that interacts with the particle, the method further comprising determining if the analyte is present by determining the size of the particles in which a spectroscopic signal has been detected.

4. The method of claim 1, further comprising detecting additional analytes, wherein each analyte is detected by one or more particles that are configured to produce a spectroscopic signal when one or more particles interact with the additional analytes.

5. The method of claim 1, wherein forming a mixture of one or more particles with the fluid further comprises adding a detecting receptor to the fluid, wherein the particles are configured to produce a first signal, and wherein the detecting receptor is configured to produce a second signal, and wherein determining if the analyte is present comprises detecting the first and second signals.

6. The method of claim 1, wherein the analyte detection device further comprises a membrane support in contact with the porous membrane, and wherein the membrane support comprises pores that allow fluid to flow through the membrane support at a speed that is equal to or greater than the speed that fluid passes through the porous membrane.

7. The method of claim 1, wherein the analyte detection device further comprises a membrane support in contact with the porous membrane, and wherein the membrane support provides sufficient support of the porous membrane to inhibit sagging of the porous membrane.

8. The method of claim 1, wherein the top member comprises a fluid inlet configured to allow fluid to be introduced to the porous membrane through the top member.

9. The method of claim 1, wherein the bottom member comprises a fluid outlet configured to allow fluid to pass from the porous membrane out of the analyte detection device.

10. The method of claim 1, wherein the receptor comprises an antibody that binds to at least a portion of a virus.

11. The method of claim 1, wherein the receptor comprises an antibody that binds to at least a portion of the human immunodeficiency virus.

12. The method of claim 1, wherein the receptor comprises an antibody to the analyte.

13. The method of claim 1, further comprising adding a visualization agent to the particles.

14. The method of claim 1, further comprising passing a background fluid through the analyte detection device and detecting an image captured on the porous membrane prior to passing the fluid containing the analyte across the porous membrane.

15. The method of claim 1, further comprising washing the surface of the porous membrane.

* * * * *